(12) United States Patent
Ajjawi et al.

(10) Patent No.: US 10,689,676 B2
(45) Date of Patent: Jun. 23, 2020

(54) ALGAL MUTANTS WITH INCREASED LIPID PRODUCTIVITY

(71) Applicant: Synthetic Genomics, Inc., La Jolla, CA (US)

(72) Inventors: Imad Ajjawi, San Diego, CA (US); Leah Soriaga, San Diego, CA (US); Moena Aqui, San Diego, CA (US); Eric R. Moellering, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 15/341,998

(22) Filed: Nov. 2, 2016

(65) Prior Publication Data

US 2017/0121742 A1 May 4, 2017

Related U.S. Application Data

(60) Provisional application No. 62/249,834, filed on Nov. 2, 2015.

(51) Int. Cl.
| | |
|---|---|
| *C12N 1/13* | (2006.01) |
| *C12P 7/64* | (2006.01) |
| *C12N 15/113* | (2010.01) |
| *C07K 14/405* | (2006.01) |

(52) U.S. Cl.
CPC ............ *C12P 7/649* (2013.01); *C07K 14/405* (2013.01); *C12N 15/113* (2013.01); *C12N 2310/111* (2013.01); *C12N 2310/20* (2017.05); *Y02E 50/13* (2013.01)

(58) Field of Classification Search
None
See application file for complete search history.

(56) References Cited

U.S. PATENT DOCUMENTS

| | | | |
|---|---|---|---|
| 8,765,404 B2 | 7/2014 | Stephanopoulos et al. | |
| 2010/0021912 A1 | 1/2010 | Farese et al. | |
| 2010/0255550 A1 | 10/2010 | Benning et al. | |
| 2012/0151635 A1 | 6/2012 | Coruzzi et al. | |
| 2014/0106417 A1 | 4/2014 | Schneider et al. | |
| 2014/0162330 A1 | 6/2014 | Allen | |
| 2014/0220638 A1* | 8/2014 | Bailey | C12N 1/12 435/71.1 |
| 2016/0002566 A1 | 1/2016 | Vanhercke et al. | |
| 2016/0194649 A1* | 7/2016 | Yohn | C07K 14/405 800/298 |

FOREIGN PATENT DOCUMENTS

| | | | |
|---|---|---|---|
| WO | WO 2011/127118 A1 | 10/2011 | |
| WO | WO 2012/082731 A3 | 6/2012 | |
| WO | WO 2015/071726 A1 | 5/2015 | |

OTHER PUBLICATIONS

Jeon et al., Current status and perspectives of genome editing technology for microalgae, Biotechnol. Biofuels, 2017, 10, 267.*
Wang et al., Genome editing of model oleaginous microalgae *Nannochloropsis* spp. by CRISPR/Cas9, Plant J., 2016, 88, 1071-81.*
Wei et al., RNAi-based targeted gene knockdown in the model oleaginous microalgae Nannochloropsis oceanica, Plant J., 2017, 89 , 1236-50.*
Mujtaba et al., Structure and acetyl-lysine recognition of the bromodomain, Oncogene, 2007, 26, 5521-27.*
Fujisawa et al., Functions of bromodomain-containing proteins and their roles in homeostasis and cancer, Nature Reviews Mol. Cell Biol., 2017, 18, 246-62.*
Matthews et al., Zinc Fingers-Folds for many occasions, IUBMB Life, 2002, 54, 351-55.*
Xu et al., Small-molecule Nucleic-acid-based Gene-silencing Strategies, Chapter 8, Nucleic Acids-From Basic Aspects to Laboratory Tools, 2016, www.intechopen.com/books/nucleic-acids-from-basicaspects-to-laboratory-tools.*
Carpinelli, E. C. et al.: "*Chromosome Scale Genome Assembly and Transcriptome Profiling of Nannochloropsis gaditana in Nitrogen Depletion*"; Molecular Plant, Aug. 21, 2013; vol. 7, No. 2; pp. 323-335.
International Search Report dated May 8, 2017, regarding PCT/US2016/060126.
Stephens, et al.: "*Genetic Engineering for Microalgae Strain Improvement in Relation to Biocrude Production Systems*"; Biomass and Biofuels from Microalgae, Apr. 2015; pp. 191-249.
Beacham, et al.: "*Altered Lipid Accumulation in Nannochloropsis salina CCAP849/3 Following EMS and UV Induced Mutagenesis;*"Biotechnology Reports, 2015, vol. 7, pp. 87-94.
Boyle, et al.: "*Three Acyltransferases and Nitrogen-Responsive Regulator are Implicated in Nitrogen Starvation-Induced Triacylglycerol Accumulation in Chlamydomonas;*" J, Biol. Chem., May 4, 2012, vol. 287, No, 19, pp. 15811-15825.
Camacho, et al.: "*Continuous Culture of the Marine Microalga Tetraselmis sp.—Productivity Analysis;*"Aquaculture, 1990, vol. 90, pp. 75-84.
Del Rio, et al.: "*Continuous Culture Methodology for the Screening of Microalgae for Oil;*" J. Biotechnol., 2015, vol. 195, pp. 103-107.
D'Ippolito, et al.: "*Potential of Lipid Metabolism in Marine Diatoms for Biofuel Production;*" Biotechnol. for Biofuels, BioMed Central, 2015, pp. 1-10.
Davey, et al.: "*Triacylglyceride Production and Autophagous Responses in Chlamydomonas reinhardtii Depend on Resource Allocation and Carbon Source;*" Eukaryotic Cell, Mar. 2014, vol. 13, No. 3, pp. 392-400.

(Continued)

Primary Examiner — Robert B Mondesi
Assistant Examiner — Todd M Epstein
(74) Attorney, Agent, or Firm — DLA Piper LLP (US)

(57) ABSTRACT

The present invention provides mutant microorganism that have higher lipid productivity than the wild type microorganisms from which they are derived while producing biomass at levels that are at least 45% of wild type biomass productivity under nitrogen replete conditions. Particular mutants produce at least 50% as much FAME lipid as wild type while producing at least the amount of biomass produced by wild type cells under nitrogen replete conditions. Also provided are methods of producing lipid using the mutant strains.

18 Claims, 25 Drawing Sheets

Specification includes a Sequence Listing.

(56) References Cited

OTHER PUBLICATIONS

Fan, et al.: "Genomic Foundation of Starch-to-Lipid Switch in Oleaginous Chlorella spp.;" Plant Physiology, 2015, vol. 169, pp. 2444-2461.
Gargouri, et al,: "Identification of Regulatory Network Hubs that Control Lipid Metabolism in Chlamydomonas reinhardtii;"J. Exp. Botany, 2015, pp. 1-16.
Goncalves, et al.: "Metabolic Regulation of Triacylglycerol Accumulation in the Green Algae: Identification of Potential Targets for Engineering to Improve Oil Yield;"Plant Biotechnol. J., 2016, pp. 1-12.
Gonzalez and Gonzalez: "Signal Transduction by Heme-Containing PAS-Domain Proteins;" J. Appl. Physiol., 2004, vol. 96, pp. 774-783.
Hassan, et al.: "Selective Recognition of Acetylated Histones by Bromodomains in Transcriptional Co-Activators;" Biochem. J., 2007, vol. 402, pp. 125-133.
Haynes, et al.: "The Bromodomain: A Conserved Sequence Found in Human, Drosophila and Yeast Proteins;" Nucl. Acids Res., 1992, vol. 20, No. 10, p. 2603.
Hefti, et al,: "The PAS Fold, a Redefinition of the PAS Domain Based Upon Structural Prediction;" Eur. J. Biochem., 2004, vol. 271, pp. 1198-1208.
Heisel, et al.: "Mutations in Histone Acetyltransferase1 Affect Sugar Response and Gene Expression in Arabidopsis;" Frontiers in Plant Science, 2013, vol. 4, Art. 245, pp. 1-13.
Henry and Crosson: "Ligand Binding PAS Domains in a Genomic, Cellular, and Structural Context;" Annu. Rev. Microbiol., 2011, vol. 65, pp. 261-286.
Hu, et al.: "Genome-Wide Identification of Transcription Factors and Transcription-Factor Binding Sites in Oleaginous Microalgae Nannochloropsis;" Nature Scientific Reports, 2014, vol. 4, Art. 5454, pp. 1-11.
Jin, et al.: PlantTFDB 3.0: A Portal for the Functional and Evolutionary Study of Plant Transcription Factors; Nucl. Acids Res., 2014, vol. 42, pp. D1182-D1187.
Leverentz and Reece: "Phosphorylation of $Zn(II)_2Cys_6$ Proteins: A Cause or Effect of Transcriptional Activation?" Biochem. Soc. Transactions, 2006, vol. 34, No. 5, 794-797.
Levitan, et al.: An RNA Interference Knock-Down of Nitrate Reductase Enhances Lipid Biosynthesis in the Diatom Phaeodactylum tricornutum; Plant J., 2015, vol. 84, pp. 963-973.
Li, et al.: "Choreography of Transcriptomes and Lipidomes of Nannochloropsis Reveals the Mechanisms of Oil Synthesis in Microalgae;" Plant Cell, 2014, vol. 26, pp. 1645-1665.
Macpherson, et al.: "A Fungal Family of Transcriptional Regulators: the Zinc Cluster Proteins;" Microbiol. Molecular Biol. Reviews, 2006, vol. 70, No. 3, pp. 583-604.
Mandadi, et al.: "BT2, a BTB Protein, Mediates Multiple Responses to Nutrients, Stresses, and Hormones in Arabidopsis;" Plant Physiol., 2009, vol. 150, pp. 1930-1939.
Marchetti, et al.: "Optimizing Conditions for the Continuous Culture of Isochrysis affinis galbana Relevant to Commercial Hatcheries;"Aquaculture, 2012, vol. 326-329, pp. 106-115.
Misra, A.: "The Bromodomain Proteins GTE9 and GTE11 Associate with BT2-Based E3 Ligase Complex and Mediate Responses to Multiple Signals in Arabidopsis thaliana;" Dissertation for Molecular and Environmental Plant Sciences, Texas A&M University, 2011, pp. 1-104.
Naar and Thakur: "Nuclear Receptor-Like Transcription Factors in Fungi;"Genes Dev., 2009, vol. 23, pp. 419-432.
Ngan, et al.: "Lineage-Specific Chromatin Signatures Reveal a Regulator of Lipid Mtabolism in Microalgae;" Nature Plants, 2015, Art. 15107, pp. 1-11.
Perez-Rodriguez, et al,: "PlnTFDB: Updated Content and New Features of the Plant Transcription Factor Database;" Nucl. Acids Res., 2010, vol. 38, pp. D822-D827.
Pistorius, et al.: "Monitoring of Biomass Composition from Microbiological Sources by Means of FT-IR Spectroscopy;" Biotechnol. Bioeng., 2009, vol. 103, No. 1, pp. 123-129.
Ponting and Aravind: "PAS: A Multifunctional Domain Family Comes to Light;" Curr. Biol., 1997, vol. 7, No. 11, pp. R674-R677.
Radakovits, et al.: "Draft Genome Sequence and Genetic Transformation of the Oleaginous Alga Nannochloropsis gaditana;" Nature Commun., 2012, Art. 686, pp. 1-10.
Supplementary Information for: Radakovits, et al.: "Draft Genome Sequence and Genetic Transformation of the Oleaginous Alga Nannochloropsis gaditana;" Nature Commun., 2013, vol. 3, Art. 686, pp. 1-10.
Sananurak, et al.: "Development of a Closed-Recirculating, Continuous Culture System for Microalga (Tetraselmis suecica) and Rotifer (Brachionus plicatilis) Production;" ScienceAsia, 2009, vol. 35, pp. 118-124.
Siaut, et al.: "Oil Accumulation in the Model Green Alga Chlamydomonas reinhardtii: Characterization, Variability Between Common Laboratory Strains and Relationship with Starch Reserves," BMC Biotechnol., 2011, vol. 7, No. 7, pp. 1-15.
Slocombe, et al.: "Comparison of Screening Methods for High-Throughput Determination of Oil Yields in Micro-Algal Biofuel Strains;" J. Appl. Phycol., 2013, vol. 25, pp. 961-972.
Taylor and Zhulin: "PAS Domains: Internal Sensors of Oxygen, Redox Potential, and Light;" Microbiol. Molecular Biol. Rev., 1999, vol. 63, No. 2, pp. 479-506.
Thakur, et al.: "Mediator Subunit Gal11p/MED15 is Required for Fatty Acid-Dependent Gene Activation by Yeast Transcription Factor Oaf1p;" J. Biol. Chem., 2009, vol. 284, No. 7, pp. 4422-4428.
Trentacoste, et al.: "Metabolic Engineering of Lipid Catabolism Increases Microalgal Lipid Accumulation Without Compromising Growth;" PNAS, 2013, vol. 110, No. 49, pp. 19748-19753.
Supporting Information for: Trentacoste, et al.: "Metabolic Engineering of Lipid Catabolism Increases Microalgal Lipid Accumulation Without Compromising Growth;" PNAS, 2013, vol. 110, No. 49, pp. 19748-19753.
Wang, et al.: "Algal Lipid Bodies: Stress Induction, Purification and Biochemical Characterization in Wild-Type and Starchless Chlamydomonas reinhardtii;" Eukaryotic Cell, 2009, vol. 8, No. 12, pp. 1856-1868.
Weyman, et al.: "Inactivation of Phaeodactylum tricornutum Urease Gene using Transcription Activator-Like Effector Nuclease-Based Targeted Mutagenesis;" Plant Biotechnol. J., 2014, pp. 1-11.
Yuan, et al.: "Nit-4, a Pathway-Specific Regulatory Gene of Neurospora crassa, Encodes a Protein with a Putative Binuclear Zinc DNA-Binding Domain;" Molecular Cellular Biol., 1991, vol. 11, No. 11, pp. 5735-5745.
Yuan and Marmorstein: "Histone Acetyltransferases: Rising Ancient Counterparts to Protein Kinases;" Biopolymers, 2013, vol. 99, No. 2, pp. 98-111.
Zetsche, et al.: "Cpf1 is a Single RNA-Guided Endonuclease of a Class 2 CRISPR-Cas System;" Cell, 2015, vol. 163, pp. 1-13.
Extended European Search Report dated May 29, 2019, regarding EP 16 86 2883.
Rack, Johannes G. M. et al.: "The PHD finger of p300 Influences Its Ability to Acetylate Histone and Non-Histone Targets", J Mol. Biol., Aug. 23, 2014, vol. 426, No. 24, 23, pp. 3960-3972.

* cited by examiner

```
SEQ_ID_NO_8    1  MDSNAQTTSGTVVESTASNGEASAPAPMLSSSLPSPSFESGPDPPPQLARRVPGNVPLDP
SEQ_ID_NO_6    1  MDSNAQTTSGTVVESTASNGEASAPAPMLSSSLPSPSFESGPDPPPQLARRVPGNVPLDP
SEQ_ID_NO_2    1  MDSNAQTTSGTVVESTASNGEASAPAPMLSSSLPSPSFESGPDPPPQLARRVPGNVPLDP
SEQ_ID_NO_4    1  MDSNAQTTSGTVVESTASNGEASAPAPMLSSSLPSPSFESGPDPPPQLARRVPGNVPLDP

SEQ_ID_NO_8   61  SAADVDDKDRASSAYGDEPPLPLPLLTSTSMTASEASSGQGGEAGAAPGVPSLASSPAFA
SEQ_ID_NO_6   61  SAADVDDKDRASSAYGDEPPLPLPLLTSTSMTASEASSGQGGEAGAAPGVPSLASSPAFA
SEQ_ID_NO_2   61  SAADVDDKDRASSAYGDEPPLPLPLLTSTSMTASEASSGQGGEAGAAPGVPSLASSPAFA
SEQ_ID_NO_4   61  SAADVDDKDRASSAYGDEPPLPLPLLTSTSMTASEASSGQGGEAGAAPGVPSLASSPAFA

SEQ_ID_NO_8  121  PAATGLSPSHSAGSGMSVLIQVPQNGPSEALSPLPLPTTALDTPLDTRSSTPRPAPAPAP
SEQ_ID_NO_6  121  PAATGLSPSHSAGSGMSVLIQVPQNGPSEALSPLPLPTTALDTPLDTRSSTPRPAPAPAP
SEQ_ID_NO_2  121  PAATGLSPSHSAGSGMSVLIQVPQNGPSEALSPLPLPTTALDTPLDTRSSTPRPAPAPAP
SEQ_ID_NO_4  121  PAATGLSPSHSAGSGMSVLIQVPQNGPSEALSPLPLPTTALDTPLDTRSSTPRPAPAPAP

SEQ_ID_NO_8  181  PSPYQTVGGLHGGERSFLPPVSTEGLAPPAMGTGEGGLEGGDGGSVGFYPPLAQSQTQLA
SEQ_ID_NO_6  181  PSPYQTVGGLHGGERSFLPPVSTEGLAPPAMGTGEGGLEGGDGGSVGFYPPLAQSQTQLA
SEQ_ID_NO_2  181  PSPYQTVGGLHGGERSFLPPVSTEGLAPPAMGTGEGGLEGGDGGSVGFYPPLAQSQTQLA
SEQ_ID_NO_4  181  PSPYQTVGGLHGGERSFLPPVSTEGLAPPAMGTGEGGLEGGDGGS--------------

SEQ_ID_NO_8  241  PLPGPPPPQAQDSLQYKPASVPEPTRMMEGSSDPPFHSSETPRAMGIGRGGNSQMVAPA
SEQ_ID_NO_6  241  PLPGPPPPQAQDSLQYKPASVPEPTRMMEGSSDPPFHSSETPRAMGIGRGGNSQMVAPA
SEQ_ID_NO_2  241  PLPGPPPPQAQDSLQYKPASVPEPTRMMEGSSDPPFHSSETPRAMGIGRGGNSQMVAPA
SEQ_ID_NO_4  227  ------------------------------------------DGDRLGGNSQMVAPA
```

```
SEQ_ID_NO_8   901  SSAHPMPQLGQGVADADGGEGGGSGVQQQQQQQQQQQQQQQQQQQQQ-LVAQSNQRTQ
SEQ_ID_NO_6   901  SSAHPMPQLGQGVADADGGEGGGSGVQQQQQQQQQQQQQQQQQQQQQQLVAQSNQRTQ
SEQ_ID_NO_2   901  SSAHPMPQLGQGVADADGGEGGGSGVQQQQQQQQQQQQQQQQQQQQQQLVAQSNQRTQ
SEQ_ID_NO_4   843  SSAHPMPQLGQGVADADGGEGGGSGVQQQQQQQQQQQQQQQQQQQQQQLVAQSNQRTQ

SEQ_ID_NO_8   960  QQQMLIAQQPPR------------RLPGRLPTRHDWLPEWPGWEGRRLAGGGTS
SEQ_ID_NO_6   961  QQQMLIAQQPPPAGMGGGRVGGMTGALANGGRGGRVGGRARGRGGQVVLPQQVAAGGRGI
SEQ_ID_NO_2   961  QQQMLIAQQPPPAGMGGGRVGGMTGALANGGRGGRVGGRARGRGGQVVLPQQVAAGGRGI
SEQ_ID_NO_4   903  QQQMLIAQQPPPAGMGGGRVGGMTGALANGGRGGRVGGRARGRGGQVVLPQQVAAGGRGI

SEQ_ID_NO_8  1006  SRASSPGPRGAGNRRSECRWKMEPATIAATAPTAAPTAAPAAAAAATPTKVPPRA
SEQ_ID_NO_6  1021  GGQNVGGSGMNQQRLQQQQQQQQQQQQQQQQQQQRPQNMASVPVPGVGRGGGGVRA
SEQ_ID_NO_2  1021  GGQNVGGSGMNQQRLQQQQQQQQQQQQQQQQQQQRPQNMASVPVPGVGRGGGGVRA
SEQ_ID_NO_4   963  GGQNVGGSGMNQQRLQQQQQQQQQQQQQQQQQQQRPQNMASVPVPGVGRGGGGVRA

SEQ_ID_NO_8  1066  GSWRTWGRFSWRGSPRLGHC--------------------WSGQQTWGPERPG
SEQ_ID_NO_6  1081  GGEALALGTAGGAGSKPGARSGSGRMPVVAKTPNGLMIQFETHGWVPVEPTKNGGYRPLV
SEQ_ID_NO_2  1081  GGEALALGTAGGAGSKPGARSGSGRMPVVAKTPNGLMIQFETHGWVPVEPTKNGGYRPLV
SEQ_ID_NO_4  1023  GGEALALGTAGGAGSKPGARSGSGRMPVVAKTPNGLMIQFETHGWVPVEPTKNGGYRPLV

SEQ_ID_NO_8  1103  ENASRSCDSEWPHDPDCVQMGCPPHEKRPLFSPGASPGLRSKLLLGCRRGWRGRTSW
SEQ_ID_NO_6  1141  PLPGSGQSFSQAAGGAGAGGRPGGVGRGVPGVPAPPSAAALQRFEDSVSLVNSFTDAQIK
SEQ_ID_NO_2  1141  PLPGSGQSFSQAAGGAGAGGRPGGVGRGVPGVPAPPSAAALQRFEDSVSLVNSFTDAQIK
SEQ_ID_NO_4  1083  PLPGSGQSFSQAAGGAGAGGRPGGVGRGVPGVPAPPSAAALQRFEDSVSLVNSFTDAQIK

SEQ_ID_NO_8  1163  RWERGAPRTCPTPRGSVAAPRLPLPGELPRGRTN---------
SEQ_ID_NO_6  1201  AHMASLRSGGGFWTPAKLKLVRSRLSTEPTVSLLVSEPTPRFHYAPPYIPAALSSPLTC
SEQ_ID_NO_2  1201  AHMASLRSGGGFWTPAKLKLVLPLVVKQLKSEYGWIFEEPVDPVKLGLPDYFDVIKHPM
SEQ_ID_NO_4  1143  AHMASLRSGGGFWTPAKLKLVLPLVVKQLKSEYGWIFEEPVDPVKLGLPDYFDVIKHPM

SEQ_ID_NO_8       ---------------------------------------
SEQ_ID_NO_6  1261  PLPLSPSFSPSG-----------------------
SEQ_ID_NO_2  1261  DLGTVIRLSGRG-----------------------GRPELEGKLNPNGQL
SEQ_ID_NO_4  1203  DLGTVIRRLENGSYTELEKVAADVKLSFDNAILYRFPGQEIHKVTDEPPLCKGGRSRLDE

SEQ_ID_NO_8       ---------------------------------------
SEQ_ID_NO_6       ---------------------------------------
SEQ_ID_NO_2  1288  SVLRGPLSEETDRLQELL-----------------
SEQ_ID_NO_4  1263  RALLEVSRPRLTLPADRSNGWFYDERMDGSTTKMK
```

Figure 2C

FAME production, mg/L

| DAY | 1 | 2 | 3 | 4 | 5 | 6 | 7 | 8 | 9 | 10 | Average | increase |
|---|---|---|---|---|---|---|---|---|---|---|---|---|
| GE-13027 (BASH-1) | 77.42 (1.57) | 73.44 (1.22) | 72.44 (1.85) | 66.27 (3.47) | 69.21 (5.38) | 71.59 (3.93) | 70.87 (6.03) | 68.90 (7.89) | 71.49 (6.7) | 70.59 (7.24) | 71.22 | 54% |
| GE-13030 (BASH-4) | 63.17 (5.10) | 60.48 (6.04) | 64.79 (6.79) | 57.94 (10.45) | 59.59 (10.11) | 63.47 (8.55) | 61.08 (9.58) | 60.04 (10.94) | 62.21 (10.23) | 59.91 (8.88) | 61.27 | 32% |
| GE-13032 (BASH-5) | 75.87 (2.43) | 71.22 (1.29) | 73.77 (0.21) | 68.11 (2.50) | 69.78 (3.13) | 71.07 (5.53) | 68.19 (4.64) | 66.01 (5.01) | 67.91 (4.11) | 68.38 (2.40) | 70.03 | 51% |
| WT-03730 | 44.90 (1.71) | 46.77 (1.15) | 48.13 (4.01) | 44.07 (4.25) | 46.92 (4.45) | 49.40 (5.89) | 44.55 (3.70) | 45.28 (4.80) | 47.15 (3.08) | 46.47 (3.64) | 46.36 | |

Figure 8A

TOC production

| average | 1 | 2 | 3 | 4 | 5 | 6 | 7 | 8 | 9 | 10 | Av | % diff |
|---|---|---|---|---|---|---|---|---|---|---|---|---|
| BASH-1 | 219.63 (8.16) | 182.67 (12.62) | 171.4 (5.47) | 149.23 (15.77) | 152.13 (17.57) | 149.35 (11.53) | 150.07 (20.38) | 138.27 (15.90) | 133.33 (16.11) | 131.27 (17.91) | 157.74 | -2.68 |
| BASH-4 | 199.23 (25.55) | 172.3 (21.64) | 174.5 (19.05) | 156.67 (27.65) | 157.7 (28.44) | 155.27 (11.21) | 169.83 (8.28) | 167.67 (10.52) | 147.77 (19.95) | 146.13 (23.15) | 164.71 | 1.62 |
| BASH-5 | 179.33 (21.27) | 158.97 (19.66) | 162.83 (19.25) | 148.1 (23.72) | 154.2 (33.81) | 132.65 (0.071) | 164.5 (31.16) | 176.67 (10.53) | 150.77 (26.90) | 141.7 (32.37) | 156.97 | -3.16 |
| WT | 162.75 (5.56) | 153.68 (8.76) | 165.03 (15.37) | 156.1 (20.26) | 169.73 (21.44) | 154.18 (25.05) | 155.73 (32.55) | 168.25 (13.18) | 169.55 (10.88) | 165.9 (15.33) | 162.09 | |

Figure 8C

| average FAME/TOC | 1 | 2 | 3 | 4 | 5 | 6 | 7 | 8 | 9 | 10 | ave | % diff |
|---|---|---|---|---|---|---|---|---|---|---|---|---|
| GE-13027 | 0.35 (0.01) | 0.40 (0.02) | 0.42 (0.02) | 0.45 (0.02) | 0.46 (0.02) | 0.49 (0.01) | 0.48 (0.07) | 0.50 (0.01) | 0.54 (0.01) | 0.49 () | 0.50 | 72% |
| GE-13030 | 0.32 (0.05) | 0.36 (0.05) | 0.37 (0.05) | 0.37 (0.05) | 0.38 (0.05) | 0.41 (0.04) | 0.36 (0.06) | 0.39 (0.06) | 0.42 (0.03) | 0.39 () | 0.39 | 33% |
| GE-13032 | 0.43 (0.06) | 0.45 (0.07) | 0.43 (0.04) | 0.47 (0.06) | 0.46 (0.07) | 0.55 (0.04) | 0.43 (0.12) | 0.37 (0.02) | 0.46 (0.06) | 0.45 () | 0.42 | 43% |
| WT-3730 | 0.27 (0.02) | 0.30 (0.01) | 0.29 (0.01) | 0.28 (0.00) | 0.28 (0.01) | 0.34 (0.09) | 0.33 (0.09) | 0.27 (0.02) | 0.28 (0.01) | 0.30 () | 0.29 | 0% |

Figure 8E

SEQUENCE LISTING

```
<160> NUMBER OF SEQ ID NOS: 78

<210> SEQ ID NO 1
<211> LENGTH: 3921
<212> TYPE: DNA
<213> ORGANISM: Nannochloropsis gaditana
<220> FEATURE:
<221> NAME/KEY: misc_feature
<223> OTHER INFORMATION: Bromo-1091 gene transcript a
<220> FEATURE:
<221> NAME/KEY: misc_feature
<223> OTHER INFORMATION: encodes the polypeptide of SEQ ID NO:2

<400> SEQUENCE: 1
atggattcga acgcgcaaac caccagtggc accgtcgttg aaagcacggc tagcaatgga      60
gaggcttctg cgcccgcgcc catgctttcg tcctcccttc cttctccaag ctttgagtcc     120
ggcccagacc cccccccca gttagcaagg cgggtccccg ggaacgtgcc gcttgacccc     180
```

-continued

```
tcggccgccg acgtggacga caaggaccgc gcctccagcg cctacggaga cgaacctccc      240
ctccccctcc ccctcctcac gtccacctcg atgacagcct cagaagcgag cagcggtcaa      300
ggagggaag ctggggccgc cccaggggtg ccctcccttg cttcctcccc tgccttcgcc       360
cccgcagcta ccgcctgtc cccgtctcac tccgccggtt ccggcatgtc agtgctgatc       420
caagtgcctc aaaacgggcc cagcgaggct ctgtcgcctt tgcccttgcc gaccactgcc      480
ttggatactc ccttggacac ccggtcgtcc accccccgcc ccgcgcccgc ccagccccg       540
ccttctcctt accagactgt tggaggcctc cacggcgggg agcactcgtt ccttcctccc      600
gtcagtacgg aagggctggc ccctccggcg atgggcacgg ggaaggagg gcttgagggc       660
ggggatggag ggtcggtagg tttttatccc ccccttgccc agtcgcagac gcaactcgcg      720
ccgttgccgg gcccaccgcc tccgcaggcg caagattcgc tgcagtacaa gcctgcttcg      780
gtaccggagc cgactaggat gatggaaggg tccagtgatc ctccttttca ttcgtcggag      840
acgcccaggg cgatgggat cggccggggg ggagggaatt cgcagatggt tgcacctgcc       900
cccgcgccat cgttgcaaca gtcggcgccg ttgcaacaac gtcagcaatt gcaacctcaa      960
cagcaccaac agttccattc gcgctcccac ccacaagtag cgccactcca ggtgcagcaa     1020
cggcagcaac cgcgggcact ggtgccaggg ccccagcagc agcagcagca tcagcagcag     1080
caagctctct atgcatcttc gcaacagcag cagcaacagc agcagcagca acagcagcaa     1140
catcagcagc agcagcagca gcagcagcag caacagcagc agagacatca cccgcaccca     1200
cagcaactgc agcaacaaca gcgacacaac cagcagcagc cactccagca tccacaagca     1260
cagcatcgag tcccacccca gggcatgcct cagcaccagc acgtccgggc gccacagcaa     1320
cagcggcagc agcaactcct ccctcttcca accgcgggca atgccgtccc aggcggccag     1380
gcaaccggca ccccgcacgc gtcgcaactg cctcacgccc agctctccca acaacaacaa     1440
cccgcgcatt ccttgcccca acggcagggc ctgggcgcgc agcccctcaa cccacaggac     1500
actgccttgc ggcccggaat ggtcaagaac atcatggtct tgctccaaca acgcaaaccc     1560
gccgccgatc cttccaaacc cttggtggaa actcggttga aggagatggc gatccggctg     1620
gaggactacc tgtggaaacg ctcgtccacg ttggcggagt actcggatct gagcaccctc     1680
aaacaccgcc tgcagtgttt ggcagtctac atgggcaagc accagcagcg ggtcaaact      1740
gtaccggcgg cgcaagggg cagaggggga gggatgccga atcaagcgcc ccagccacag      1800
gggggggggc tctctgggaa cacgaaccaa ctgcaacgtt tggtgcctac cgccaatgcc      1860
agcaatattc acctgcccaa ccctcatccc ggaggtcttt cggtggaat gggggcggga      1920
ggcgcgcgtg tgggagggcg gggcagtggg atcggcggag gggggttgat catgcaacct     1980
gggagtgcca tccacggaca tcccccgggg ccccagttgc ggggcagctc tctccccac      2040
caagggcaag tgcaaccgac ctcgcagcag ggaagtcagc aaagaagggt gggaacgggt     2100
ctggcgcctg cgcctggcac acaacccgcg tttttaccac aggaacaaac gcaaatgcaa     2160
ggtcggcggg tagggggggg agggatgctg cccgtaaatg ggggtaacag ccaccctcct     2220
cccgcgccag gtcctccaca aggccatctg cagccgccgc agcagtcatc aggacagggg     2280
caagccgctc ccttgaacgt gatggggggg gcacagcaag tgggggggg cggtaatgcg       2340
aaccgagggc tccctatgcc tttatcttca ggccccgggg gtaccgcctc cgccagtcag     2400
aagaaacgcg tccagcacac gcccgaacaa cgtcagcaaa tcttgcacca gcagcagcag    2460
cggctgcttt acttgcgcca tgcgtccaag tgcattcatg tggacggccg ctgtcccag      2520
gggtacccga actgcatcgg gatgaaggag ctttggaagc acatcgcctc ctgtagggaa     2580
```

```
caacggtgca agttccccca ctgcgtgtcc tcgagatacg tcctgtccca ctaccacaaa    2640
tgtaaggaca cgcagtgccc ggtgtgcgga cccgtacgaa acacgatccg atcttctcgc    2700
tcctcggcgc atcccatgcc gcaacttggt cagggtgtgg cagacgccga cggaggaggc    2760
gagggaggcg gatctggagt ccagcagcag cagcagcagc agcaacaaca acaacaacaa    2820
caacaacaac aacagcaaca caacagcaa ttggtagcac agagtaatca acgcacgcag    2880
cagcaacaaa tgttgatcgc ccagcagccc cccccgcag ggatggggggg agggaggtc    2940 ggaggcatga ctggggcct ggcgaatgga ggcaggggtg ggagggtcgg agggagggcg    3000
cggggcaggg ggggtcaagt cgtgcttcct cagcaggttg cggccggggg cggggaata    3060 ggcggtcaga atgtaggtgg aagtggaatg aaccagcaac gattgcagca acagcaacaa    3120
cagcagcagc aacaacaaca gcagcagcag cagcagcagc agcagcagca gcaacgccca    3180
caaaatatgg cttccgtgcc ggttcctggg gtaggacgtg ggggaggagg ggtgcgagct    3240
ggcggggaag ccctcgcctt gggcactgcg ggtggagcgg gcagcaaacc tggggccccgg   3300 agcggttcgg ggaaaatgcc agtcgtagcc aagactccga atggcctcat gatccagacg    3360
gaaacgcatg gatgggtgcc ggtagagccc acgaaaaacg cggctaccg tccctggtg    3420 cctctgcccg gctccggtca agcttctca caggctgccg gcggggctgg cgcgggcgga    3480
cgtcctggcg gcgttgggag aggggtgccc ggcgtacctg ccccaccttc gcggcagcg    3540 ttgcagcggt tcgaagactc cgtgtccttg gtgaactcct tcacgacgc acaaattaag    3600 gcgcacatgg cctctctgcg ttcaggggga gggttttgga ctcccgccaa gttgaaactt    3660
aaggttctcc ccctcgtggt aaaacagctg aaatcggagt atggatggat ttttgaagaa    3720
cccgtggacc ccgtgaagct cgggctcccg gattacttcg atgtgatcaa gcaccctatg    3780
gacttgggca ctgtacgtcg gcttgtgggg aggggagggc gaagagaggc gggagggaaa    3840
gacaatccca atggacaact gtcagtcgac gacaagggag aattggagga ggaggtcgac    3900
ggacttcagg aacttctttg a                                              3921
```

<210> SEQ ID NO 2
<211> LENGTH: 1306
<212> TYPE: PRT
<213> ORGANISM: Nannochloropsis gaditana
<220> FEATURE:
<221> NAME/KEY: misc_feature
<223> OTHER INFORMATION: Bromo-1091 polypeptide, isoform a

<400> SEQUENCE: 2

```
Met Asp Ser Asn Ala Gln Thr Thr Ser Gly Thr Val Val Glu Ser Thr
1               5                   10                  15

Ala Ser Asn Gly Glu Ala Ser Ala Pro Ala Pro Met Leu Ser Ser
            20                  25                  30

Leu Pro Ser Pro Ser Phe Glu Ser Gly Pro Asp Pro Pro Gln Leu
        35                  40                  45

Ala Arg Arg Val Pro Gly Asn Val Pro Leu Asp Pro Ser Ala Ala Asp
    50                  55                  60

Val Asp Asp Lys Asp Arg Ala Ser Ser Ala Tyr Gly Asp Glu Pro Pro
65                  70                  75                  80

Leu Pro Leu Pro Leu Leu Thr Ser Thr Ser Met Thr Ala Ser Glu Ala
                85                  90                  95

Ser Ser Gly Gln Gly Gly Glu Ala Gly Ala Ala Pro Gly Val Pro Ser
            100                 105                 110
```

-continued

Leu Ala Ser Ser Pro Ala Phe Ala Pro Ala Ala Thr Gly Leu Ser Pro
            115                 120                 125

Ser His Ser Ala Gly Ser Gly Met Ser Val Leu Ile Gln Val Pro Gln
        130                 135                 140

Asn Gly Pro Ser Glu Ala Leu Ser Pro Leu Pro Leu Pro Thr Thr Ala
145                 150                 155                 160

Leu Asp Thr Pro Leu Asp Thr Arg Ser Ser Thr Pro Arg Pro Ala Pro
                165                 170                 175

Ala Pro Ala Pro Pro Ser Pro Tyr Gln Thr Val Gly Leu His Gly
            180                 185                 190

Gly Glu His Ser Phe Leu Pro Pro Val Ser Thr Glu Gly Leu Ala Pro
        195                 200                 205

Pro Ala Met Gly Thr Gly Glu Gly Gly Leu Glu Gly Gly Asp Gly Gly
    210                 215                 220

Ser Val Gly Phe Tyr Pro Pro Leu Ala Gln Ser Gln Thr Gln Leu Ala
225                 230                 235                 240

Pro Leu Pro Gly Pro Pro Pro Gln Ala Gln Asp Ser Leu Gln Tyr
                245                 250                 255

Lys Pro Ala Ser Val Pro Glu Pro Thr Arg Met Met Glu Gly Ser Ser
            260                 265                 270

Asp Pro Pro Phe His Ser Ser Glu Thr Pro Arg Ala Met Gly Ile Gly
        275                 280                 285

Arg Gly Gly Asn Ser Gln Met Val Ala Pro Ala Pro Ala Pro Ser
    290                 295                 300

Leu Gln Gln Ser Ala Pro Leu Gln Gln Arg Gln Gln Leu Gln Pro Gln
305                 310                 315                 320

Gln His Gln Gln Phe His Ser Arg Ser His Pro Gln Val Ala Pro Leu
                325                 330                 335

Gln Val Gln Gln Arg Gln Pro Arg Ala Leu Val Pro Gly Pro Gln
            340                 345                 350

Gln Gln Gln Gln His Gln Gln Gln Ala Leu Tyr Ala Ser Ser Gln
        355                 360                 365

Gln Gln Gln Gln Gln Gln Gln Gln Gln Gln His Gln Gln Gln
    370                 375                 380

Gln Gln Gln Gln Gln Gln Gln Gln Arg His His Pro His Pro
385                 390                 395                 400

Gln Gln Leu Gln Gln Gln Arg His Asn Gln Gln Pro Leu Gln
                405                 410                 415

His Pro Gln Ala Gln His Arg Val Pro Pro Gln Gly Met Pro Gln His
            420                 425                 430

Gln His Val Arg Ala Pro Gln Gln Gln Arg Gln Gln Leu Leu Pro
        435                 440                 445

Leu Pro Thr Ala Gly Asn Ala Val Pro Gly Gly Gln Ala Thr Gly Thr
    450                 455                 460

Pro His Ala Ser Gln Leu Pro His Ala Gln Leu Ser Gln Gln Gln Gln
465                 470                 475                 480

Pro Ala His Ser Leu Pro Gln Arg Gln Gly Leu Gly Ala Gln Pro Leu
                485                 490                 495

Asn Pro Gln Asp Thr Ala Leu Arg Pro Gly Met Val Lys Asn Ile Met
            500                 505                 510

Val Leu Leu Gln Gln Arg Lys Pro Ala Ala Asp Pro Ser Lys Pro Leu
        515                 520                 525

Val Glu Thr Arg Leu Lys Glu Met Ala Ile Arg Leu Glu Asp Tyr Leu

```
                530             535             540
Trp Lys Arg Ser Ser Thr Leu Ala Glu Tyr Ser Asp Leu Ser Thr Leu
545                 550             555             560

Lys His Arg Leu Gln Cys Leu Ala Val Tyr Met Gly Lys His Gln Gln
                565             570             575

Arg Gly Gln Thr Val Pro Ala Gly Ala Arg Gly Arg Gly Gly Gly Met
                580             585             590

Pro Asn Gln Ala Pro Gln Pro Gln Gly Gly Leu Ser Gly Asn Thr
            595             600             605

Asn Gln Leu Gln Arg Leu Val Pro Thr Ala Asn Ala Ser Asn Ile His
            610             615             620

Leu Pro Asn Pro His Pro Gly Gly Leu Ser Gly Met Gly Ala Gly
625             630             635             640

Gly Ala Arg Val Gly Gly Arg Gly Ser Gly Ile Gly Gly Gly Leu
                645             650             655

Ile Met Gln Pro Gly Ser Ala Ile His Gly His Pro Pro Gly Pro Gln
                660             665             670

Leu Arg Gly Ser Ser Leu Pro His Gln Gly Gln Val Gln Pro Thr Ser
            675             680             685

Gln Gln Gly Ser Gln Gln Arg Val Gly Thr Gly Leu Ala Pro Ala
            690             695             700

Pro Gly Thr Gln Pro Ala Phe Leu Pro Gln Glu Gln Thr Gln Met Gln
705             710             715             720

Gly Arg Arg Val Gly Gly Gly Met Leu Pro Val Asn Gly Gly Asn
                725             730             735

Ser His Pro Pro Pro Ala Pro Gly Pro Pro Gln Gly His Leu Gln Pro
            740             745             750

Pro Gln Gln Ser Ser Gly Gln Gly Gln Ala Ala Pro Leu Asn Val Met
            755             760             765

Gly Gly Ala Gln Gln Val Gly Gly Gly Asn Ala Asn Arg Gly Leu
                770             775             780

Pro Met Pro Leu Ser Ser Gly Pro Gly Gly Thr Ala Ser Ala Ser Gln
785             790             795             800

Lys Lys Arg Val Gln His Thr Pro Glu Gln Arg Gln Ile Leu His
                805             810             815

Gln Gln Gln Gln Arg Leu Leu Tyr Leu Arg His Ala Ser Lys Cys Ile
            820             825             830

His Val Asp Gly Arg Cys Pro Gln Gly Tyr Pro Asn Cys Ile Gly Met
            835             840             845

Lys Glu Leu Trp Lys His Ile Ala Ser Cys Arg Glu Gln Arg Cys Lys
850             855             860

Phe Pro His Cys Val Ser Ser Arg Tyr Val Leu Ser His Tyr His Lys
865             870             875             880

Cys Lys Asp Thr Gln Cys Pro Val Cys Gly Pro Val Arg Asn Thr Ile
            885             890             895

Arg Ser Ser Arg Ser Ser Ala His Pro Met Pro Gln Leu Gly Gln Gly
            900             905             910

Val Ala Asp Ala Asp Gly Gly Gly Glu Gly Gly Gly Ser Gly Val Gln
            915             920             925

Gln Gln Gln Gln Gln Gln Gln Gln Gln Gln Gln Gln Gln Gln
            930             935             940

Gln Gln Gln Gln Gln Gln Leu Val Ala Gln Ser Asn Gln Arg Thr Gln
945             950             955             960
```

```
Gln Gln Gln Met Leu Ile Ala Gln Gln Pro Pro Ala Gly Met Gly
            965                 970                 975

Gly Gly Arg Val Gly Gly Met Thr Gly Ala Leu Ala Asn Gly Gly Arg
        980                 985                 990

Gly Gly Arg Val Gly Gly Arg Ala Arg Gly Arg Gly Gly Gln Val Val
        995                1000                1005

Leu Pro Gln Gln Val Ala Ala Gly Gly Arg Gly Ile Gly Gly Gln
    1010                1015                1020

Asn Val Gly Gly Ser Gly Met Asn Gln Gln Arg Leu Gln Gln Gln
    1025                1030                1035

Gln Gln Gln Gln Gln Gln Gln Gln Gln Gln Gln Gln Gln Gln Gln
    1040                1045                1050

Gln Gln Gln Gln Gln Arg Pro Gln Asn Met Ala Ser Val Pro Val
    1055                1060                1065

Pro Gly Val Gly Arg Gly Gly Gly Val Arg Ala Gly Gly Glu
    1070                1075                1080

Ala Leu Ala Leu Gly Thr Ala Gly Gly Ala Gly Ser Lys Pro Gly
    1085                1090                1095

Ala Arg Ser Gly Ser Gly Lys Met Pro Val Val Ala Lys Thr Pro
    1100                1105                1110

Asn Gly Leu Met Ile Gln Thr Glu Thr His Gly Trp Val Pro Val
    1115                1120                1125

Glu Pro Thr Lys Asn Gly Gly Tyr Arg Pro Leu Val Pro Leu Pro
    1130                1135                1140

Gly Ser Gly Gln Ser Phe Ser Gln Ala Ala Gly Gly Ala Gly Ala
    1145                1150                1155

Gly Gly Arg Pro Gly Gly Val Gly Arg Gly Val Pro Gly Val Pro
    1160                1165                1170

Ala Pro Pro Ser Ala Ala Ala Leu Gln Arg Phe Glu Asp Ser Val
    1175                1180                1185

Ser Leu Val Asn Ser Phe Thr Asp Ala Gln Ile Lys Ala His Met
    1190                1195                1200

Ala Ser Leu Arg Ser Gly Gly Gly Phe Trp Thr Pro Ala Lys Leu
    1205                1210                1215

Lys Leu Lys Val Leu Pro Leu Val Val Lys Gln Leu Lys Ser Glu
    1220                1225                1230

Tyr Gly Trp Ile Phe Glu Glu Pro Val Asp Pro Val Lys Leu Gly
    1235                1240                1245

Leu Pro Asp Tyr Phe Asp Val Ile Lys His Pro Met Asp Leu Gly
    1250                1255                1260

Thr Val Arg Arg Leu Val Gly Arg Gly Gly Arg Glu Ala Gly
    1265                1270                1275

Gly Lys Asp Asn Pro Asn Gly Gln Leu Ser Val Asp Asp Lys Gly
    1280                1285                1290

Glu Leu Glu Glu Glu Val Asp Gly Leu Gln Glu Leu Leu
    1295                1300                1305

<210> SEQ ID NO 3
<211> LENGTH: 3894
<212> TYPE: DNA
<213> ORGANISM: Nannochloropsis gaditana
<220> FEATURE:
<221> NAME/KEY: misc_feature
<223> OTHER INFORMATION: Bromo-1091 gene transcript b
<220> FEATURE:
```

<221> NAME/KEY: misc_feature
<223> OTHER INFORMATION: encodes the polypeptide of SEQ ID NO:4

<400> SEQUENCE: 3

| | | | | | |
|---|---|---|---|---|---|
| atggattcga | acgcgcaaac | caccagtggc | accgtcgttg | aaagcacggc | tagcaatgga | 60 |
| gaggcttctg | cgcccgcgcc | catgctttcg | tcctcccttc | cttctccaag | ctttgagtcc | 120 |
| ggcccagacc | cccccccca | gttagcaagg | cgggtcccg | ggaacgtgcc | gcttgacccc | 180 |
| tcggccgccg | acgtggacga | caaggaccgc | gcctccagcg | cctacggaga | cgaacctccc | 240 |
| ctcccctcc | ccctcctcac | gtccacctcg | atgacagcct | cagaagcgag | cagcggtcaa | 300 |
| ggagggaag | ctggggccgc | ccaggggtg | ccctcccttg | cttcctcccc | tgccttcgcc | 360 |
| cccgcagcta | ccggcctgtc | cccgtctcac | tccgccggtt | ccggcatgtc | agtgctgatc | 420 |
| caagtgcctc | aaaacgggcc | cagcgaggct | ctgtcgcctt | tgcccttgcc | gaccactgcc | 480 |
| ttggatactc | ccttggacac | ccggtcgtcc | accccccgcc | ccgcgcccgc | ccagccccg | 540 |
| ccttctcctt | accagactgt | tggaggcctc | acggcgggg | agcactcgtt | ccttcctccc | 600 |
| gtcagtacgg | aagggctggc | ccctccggcg | atgggcacgg | gggaaggagg | gcttgagggc | 660 |
| ggggatggag | ggtcgggcga | tggggatcgg | ccgggggag | ggaattcgca | gatggttgca | 720 |
| cctgccccg | cgccatcgtt | gcaacagtcg | cgccgttgc | aacaacgtca | gcaattgcaa | 780 |
| cctcaacagc | accaacagtt | ccattcgcgc | tcccacccac | aagtagcgcc | actccaggtg | 840 |
| cagcaacggc | agcaaccgcg | ggcactggtg | ccagggcccc | agcagcagca | gcagcatcag | 900 |
| cagcagcaag | ctctctatgc | atcttcgcaa | cagcagcagc | aacagcagca | gcagcaacag | 960 |
| cagcaacatc | agcagcagca | gcagcagcag | cagcagcaac | agcagcagag | acatcacccg | 1020 |
| cacccacagc | aactgcagca | caacagcga | cacaaccagc | agcagccact | ccagcatcca | 1080 |
| caagcacagc | atcgagtccc | accccagggc | atgcctcagc | accagcacgt | ccgggcgcca | 1140 |
| cagcaacagc | ggcagcagca | actcctccct | cttccaaccg | cgggcaatgc | cgtcccaggc | 1200 |
| ggccaggcaa | ccggcacccc | gcacgcgtcg | caactgcctc | acgcccagct | ctcccaacaa | 1260 |
| caacaacccg | cgcattcctt | gccccaacg | cagggcctgg | gcgcgcagcc | cctcaaccca | 1320 |
| caggacactg | ccttgcggcc | cggaatggtc | aagaacatca | tggtcttgct | ccaacaacgc | 1380 |
| aaacccgccg | ccgatccttc | caaacccttg | gtggaaactc | ggttgaagga | gatggcgatc | 1440 |
| cggctggagg | actacctgtg | gaaacgctcg | tccacgttgg | cggagtactc | ggatctgagc | 1500 |
| accctcaaac | accgcctgca | gtgtttggca | gtctacatgg | gcaagcacca | gcagcgggt | 1560 |
| caaactgtac | cggcgggcgc | aaggggcaga | ggggagggga | tgccgaatca | agcgccccag | 1620 |
| ccacagggg | gggggctctc | tgggaacacg | aaccaactgc | aacgtttggt | gcctaccgcc | 1680 |
| aatgccagca | atattcacct | gcccaaccct | catcccggag | tctttcggg | tggaatgggg | 1740 |
| gcgggaggcg | cgcgtgtggg | agggcgggc | agtgggatcg | gcggaggggg | gttgatcatg | 1800 |
| caacctggga | gtgccatcca | cggacatccc | ccgggcccc | agttgcgggg | cagctctctc | 1860 |
| ccccaccaag | ggcaagtgca | accgacctcg | cagcagggaa | gtcagcaaag | aagggtggga | 1920 |
| acgggtctgg | cgcctgcgcc | tggcacacaa | cccgcgtttt | taccacagga | acaaacgcaa | 1980 |
| atgcaaggtc | ggcgggtagg | gggggaggg | atgctgcccg | taatggggg | taacagccac | 2040 |
| cctcctcccg | cgccaggtcc | tccacaaggc | catctgcagc | cgccgcagca | gtcatcagga | 2100 |
| caggggcaag | ccgctccctt | gaacgtgatg | ggggggcac | agcaagtggg | ggggcggt | 2160 |
| aatgcgaacc | gagggctccc | tatgccttta | tcttcaggcc | ccggggtac | cgcctccgcc | 2220 |

-continued

```
agtcagaaga aacgcgtcca gcacacgccc gaacaacgtc agcaaatctt gcaccagcag    2280
cagcagcggc tgctttactt cgccatgcg tccaagtgca ttcatgtgga cggccgctgt     2340 ccccagggt  acccgaactg catcgggatg aaggagcttt ggaagcacat cgcctcctgt    2400
agggaacaac ggtgcaagtt cccccactgc gtgtcctcga gatacgtcct gtcccactac    2460
cacaaatgta aggacacgca gtgcccggtg tgcggacccg tacgaaacac gatccgatct    2520
tctcgctcct cggcgcatcc catgccgcaa cttggtcagg gtgtggcaga cgccgacgga    2580
ggaggcgagg gaggcggatc tggagtccag cagcagcagc agcagcagca acaacaacaa    2640
caacaacaac aacaacaaca gcaacaacaa cagcaattgg tagcacagag taatcaacgc    2700
acgcagcagc aacaaatgtt gatcgcccag cagccccccc ccgcagggat ggggggaggg    2760
agggtcggag gcatgactgg ggccctggcg aatggaggca ggggtgggag ggtcggaggg    2820
agggcgcggg gcagggggg  tcaagtcgtg cttcctcagc aggttgcggc cggggggcgg    2880
ggaataggcg gtcagaatgt aggtggaagt ggaatgaacc agcaacgatt gcagcaacag    2940
caacaacagc agcagcaaca acagcagcag cagcagcagc agcagcagca gcagcagcaa    3000
cgcccacaaa atatggcttc cgtgccggtt cctggggtag gacgtggggg aggaggggtg    3060
cgagctggcg gggaagccct cgccttgggc actgcgggtg gagcgggcag caaacctggg    3120
gcccggagcg gttcggggaa aatgccagtc gtagccaaga ctccgaatgg cctcatgatc    3180
cagacggaaa cgcatggatg ggtgccggta gagcccacga aaaacggcgg ctaccgtccc    3240
ctggtgcctc tgcccggctc cggtcaaagc ttctcacagg ctgccggcgg ggctggcgcg    3300
ggcggacgtc ctggcggcgt tgggagaggg gtgcccggcg tacctgcccc accttccgcg    3360
gcagcgttgc agcggttcga agactccgtg tccttggtga actccttcac ggacgcacaa    3420
attaaggcgc acatggcctc tctgcgttca gggggagggt tttggactcc cgccaagttg    3480
aaacttaagg ttctcccct  cgtggtaaaa cagctgaaat cggagtatgg atggattttt    3540
gaagaacccg tggaccccgt gaagctcggg ctcccggatt acttcgatgt gatcaagcac    3600
cctatggact tgggcactgt gaagcgtcgt ttggaaaacg gctcctacac agagctggaa    3660
aaggtggcgg cggacgtgaa gctcaccttc gacaatgcca tcctttacaa ccccccgggg    3720
caagaaatcc acaaggtaac ggacgaaaaa cgggcgggaa aagggggcag gtcaaggctg    3780
gatgaagagg cagacgagga ggttgaaaga gagaggctcg tgctagggc  ggaccggagc    3840 aatggatggt tctacgacga aaaaatggat ggttccacga cgaaaatgaa gtga         3894
```

<210> SEQ ID NO 4
<211> LENGTH: 1297
<212> TYPE: PRT
<213> ORGANISM: Nannochloropsis gaditana
<220> FEATURE:
<221> NAME/KEY: misc_feature
<223> OTHER INFORMATION: Bromo-1091 polypeptide, isoform b

<400> SEQUENCE: 4

```
Met Asp Ser Asn Ala Gln Thr Thr Ser Gly Thr Val Val Glu Ser Thr
1               5                   10                  15

Ala Ser Asn Gly Glu Ala Ser Ala Pro Ala Pro Met Leu Ser Ser Ser
            20                  25                  30

Leu Pro Ser Pro Ser Phe Glu Ser Gly Pro Asp Pro Pro Gln Leu
        35                  40                  45

Ala Arg Arg Val Pro Gly Asn Val Pro Leu Asp Pro Ser Ala Ala Asp
    50                  55                  60
```

-continued

Val Asp Asp Lys Asp Arg Ala Ser Ser Ala Tyr Gly Asp Glu Pro Pro
 65                  70                  75                  80

Leu Pro Leu Pro Leu Leu Thr Ser Thr Ser Met Thr Ala Ser Glu Ala
             85                  90                  95

Ser Ser Gly Gln Gly Gly Glu Ala Gly Ala Ala Pro Gly Val Pro Ser
            100                 105                 110

Leu Ala Ser Ser Pro Ala Phe Ala Pro Ala Ala Thr Gly Leu Ser Pro
            115                 120                 125

Ser His Ser Ala Gly Ser Gly Met Ser Val Leu Ile Gln Val Pro Gln
            130                 135                 140

Asn Gly Pro Ser Glu Ala Leu Ser Pro Leu Pro Leu Pro Thr Thr Ala
145                 150                 155                 160

Leu Asp Thr Pro Leu Asp Thr Arg Ser Ser Thr Pro Arg Pro Ala Pro
                165                 170                 175

Ala Pro Ala Pro Pro Ser Pro Tyr Gln Thr Val Gly Leu His Gly
            180                 185                 190

Gly Glu His Ser Phe Leu Pro Pro Val Ser Thr Glu Gly Leu Ala Pro
            195                 200                 205

Pro Ala Met Gly Thr Gly Glu Gly Leu Glu Gly Gly Asp Gly Gly
            210                 215                 220

Ser Gly Asp Gly Asp Arg Pro Gly Gly Asn Ser Gln Met Val Ala
225                 230                 235                 240

Pro Ala Pro Ala Pro Ser Leu Gln Gln Ser Ala Pro Leu Gln Gln Arg
                245                 250                 255

Gln Gln Leu Gln Pro Gln Gln His Gln Gln Phe His Ser Arg Ser His
            260                 265                 270

Pro Gln Val Ala Pro Leu Gln Val Gln Gln Arg Gln Gln Pro Arg Ala
            275                 280                 285

Leu Val Pro Gly Pro Gln Gln Gln Gln His Gln Gln Gln Gln Ala
            290                 295                 300

Leu Tyr Ala Ser Ser Gln Gln Gln Gln Gln Gln Gln Gln Gln Gln Gln
305                 310                 315                 320

Gln Gln His Gln Gln Gln Gln Gln Gln Gln Gln Gln Gln Gln Gln
            325                 330                 335

Arg His His Pro His Pro Gln Gln Leu Gln Gln Gln Arg His Asn
            340                 345                 350

Gln Gln Gln Pro Leu Gln His Pro Gln Ala Gln His Arg Val Pro Pro
            355                 360                 365

Gln Gly Met Pro Gln His Gln His Val Arg Ala Pro Gln Gln Gln Arg
            370                 375                 380

Gln Gln Gln Leu Leu Pro Leu Pro Thr Ala Gly Asn Ala Val Pro Gly
385                 390                 395                 400

Gly Gln Ala Thr Gly Thr Pro His Ala Ser Gln Leu Pro His Ala Gln
            405                 410                 415

Leu Ser Gln Gln Gln Pro Ala His Ser Leu Pro Arg Gln Gly
            420                 425                 430

Leu Gly Ala Gln Pro Leu Asn Pro Gln Asp Thr Ala Leu Arg Pro Gly
            435                 440                 445

Met Val Lys Asn Ile Met Val Leu Leu Gln Gln Arg Lys Pro Ala Ala
            450                 455                 460

Asp Pro Ser Lys Pro Leu Val Glu Thr Arg Leu Lys Glu Met Ala Ile
465                 470                 475                 480

Arg Leu Glu Asp Tyr Leu Trp Lys Arg Ser Ser Thr Leu Ala Glu Tyr

-continued

```
                485                 490                 495
Ser Asp Leu Ser Thr Leu Lys His Arg Leu Gln Cys Leu Ala Val Tyr
            500                 505                 510

Met Gly Lys His Gln Gln Arg Gly Gln Thr Val Pro Ala Gly Ala Arg
            515                 520                 525

Gly Arg Gly Gly Gly Met Pro Asn Gln Ala Pro Gln Pro Gln Gly Gly
            530                 535                 540

Gly Leu Ser Gly Asn Thr Asn Gln Leu Gln Arg Leu Val Pro Thr Ala
545                 550                 555                 560

Asn Ala Ser Asn Ile His Leu Pro Asn Pro His Pro Gly Gly Leu Ser
            565                 570                 575

Gly Gly Met Gly Ala Gly Ala Arg Val Gly Gly Arg Gly Ser Gly
            580                 585                 590

Ile Gly Gly Gly Leu Ile Met Gln Pro Gly Ser Ala Ile His Gly
            595                 600                 605

His Pro Pro Gly Pro Gln Leu Arg Gly Ser Ser Leu Pro His Gln Gly
            610                 615                 620

Gln Val Gln Pro Thr Ser Gln Gln Gly Ser Gln Gln Arg Arg Val Gly
625                 630                 635                 640

Thr Gly Leu Ala Pro Ala Pro Gly Thr Gln Pro Ala Phe Leu Pro Gln
                    645                 650                 655

Glu Gln Thr Gln Met Gln Gly Arg Arg Val Gly Gly Gly Met Leu
            660                 665                 670

Pro Val Asn Gly Gly Asn Ser His Pro Pro Ala Pro Gly Pro Pro
            675                 680                 685

Gln Gly His Leu Gln Pro Gln Gln Ser Ser Gly Gln Gly Gln Ala
            690                 695                 700

Ala Pro Leu Asn Val Met Gly Gly Ala Gln Val Gly Gly Gly Gly
705                 710                 715                 720

Asn Ala Asn Arg Gly Leu Pro Met Pro Leu Ser Ser Gly Pro Gly Gly
                    725                 730                 735

Thr Ala Ser Ala Ser Gln Lys Lys Arg Val Gln His Thr Pro Glu Gln
            740                 745                 750

Arg Gln Gln Ile Leu His Gln Gln Gln Arg Leu Leu Tyr Leu Arg
            755                 760                 765

His Ala Ser Lys Cys Ile His Val Asp Gly Arg Cys Pro Gln Gly Tyr
            770                 775                 780

Pro Asn Cys Ile Gly Met Lys Glu Leu Trp Lys His Ile Ala Ser Cys
785                 790                 795                 800

Arg Glu Gln Arg Cys Lys Phe Pro His Cys Val Ser Ser Arg Tyr Val
                    805                 810                 815

Leu Ser His Tyr His Lys Cys Lys Asp Thr Gln Cys Pro Val Cys Gly
            820                 825                 830

Pro Val Arg Asn Thr Ile Arg Ser Ser Arg Ser Ser Ala His Pro Met
            835                 840                 845

Pro Gln Leu Gly Gln Gly Val Ala Asp Ala Asp Gly Gly Gly Glu Gly
            850                 855                 860

Gly Gly Ser Gly Val Gln Gln Gln Gln Gln Gln Gln Gln Gln Gln Gln
865                 870                 875                 880

Gln Gln Gln Gln Gln Gln Gln Gln Gln Gln Gln Leu Val Ala Gln
                    885                 890                 895

Ser Asn Gln Arg Thr Gln Gln Gln Met Leu Ile Ala Gln Gln Pro
            900                 905                 910
```

```
Pro Pro Ala Gly Met Gly Gly Arg Val Gly Gly Met Thr Gly Ala
        915                 920                 925

Leu Ala Asn Gly Gly Arg Gly Arg Val Gly Gly Arg Ala Arg Gly
        930                 935                 940

Arg Gly Gly Gln Val Val Leu Pro Gln Gln Val Ala Ala Gly Arg
945                 950                 955                 960

Gly Ile Gly Gly Gln Asn Val Gly Gly Ser Gly Met Asn Gln Arg
            965                 970                 975

Leu Gln Gln Gln Gln Gln Gln Gln Gln Gln Gln Gln Gln Gln Gln
        980                 985                 990

Gln Gln Gln Gln Gln Gln Gln Arg Pro Gln Asn Met Ala Ser Val
        995                 1000                1005

Pro Val Pro Gly Val Gly Arg Gly Gly Gly Gly Val Arg Ala Gly
    1010                1015                1020

Gly Glu Ala Leu Ala Leu Gly Thr Ala Gly Gly Ala Gly Ser Lys
    1025                1030                1035

Pro Gly Ala Arg Ser Gly Ser Gly Lys Met Pro Val Val Ala Lys
    1040                1045                1050

Thr Pro Asn Gly Leu Met Ile Gln Thr Glu Thr His Gly Trp Val
    1055                1060                1065

Pro Val Glu Pro Thr Lys Asn Gly Gly Tyr Arg Pro Leu Val Pro
    1070                1075                1080

Leu Pro Gly Ser Gly Gln Ser Phe Ser Gln Ala Ala Gly Gly Ala
    1085                1090                1095

Gly Ala Gly Gly Arg Pro Gly Gly Val Gly Arg Gly Val Pro Gly
    1100                1105                1110

Val Pro Ala Pro Pro Ser Ala Ala Ala Leu Gln Arg Phe Glu Asp
    1115                1120                1125

Ser Val Ser Leu Val Asn Ser Phe Thr Asp Ala Gln Ile Lys Ala
    1130                1135                1140

His Met Ala Ser Leu Arg Ser Gly Gly Gly Phe Trp Thr Pro Ala
    1145                1150                1155

Lys Leu Lys Leu Lys Val Leu Pro Leu Val Val Lys Gln Leu Lys
    1160                1165                1170

Ser Glu Tyr Gly Trp Ile Phe Glu Glu Pro Val Asp Pro Val Lys
    1175                1180                1185

Leu Gly Leu Pro Asp Tyr Phe Asp Val Ile Lys His Pro Met Asp
    1190                1195                1200

Leu Gly Thr Val Lys Arg Arg Leu Glu Asn Gly Ser Tyr Thr Glu
    1205                1210                1215

Leu Glu Lys Val Ala Ala Asp Val Lys Leu Thr Phe Asp Asn Ala
    1220                1225                1230

Ile Leu Tyr Asn Pro Pro Gly Gln Glu Ile His Lys Val Thr Asp
    1235                1240                1245

Glu Lys Arg Ala Gly Lys Gly Gly Arg Ser Arg Leu Asp Glu Glu
    1250                1255                1260

Ala Asp Glu Glu Val Glu Arg Glu Arg Leu Val Leu Gly Ala Asp
    1265                1270                1275

Arg Ser Asn Gly Trp Phe Tyr Asp Glu Lys Met Asp Gly Ser Thr
    1280                1285                1290

Thr Lys Met Lys
    1295
```

<210> SEQ ID NO 5
<211> LENGTH: 4722
<212> TYPE: DNA
<213> ORGANISM: Nannochloropsis gaditana
<220> FEATURE:
<221> NAME/KEY: misc_feature
<223> OTHER INFORMATION: Bromo-1091 gene transcript c (HAT-B2)
<220> FEATURE:
<221> NAME/KEY: misc_feature
<223> OTHER INFORMATION: encodes the polypeptide of SEQ ID NO:6

<400> SEQUENCE: 5

| | | | | | |
|---|---|---|---|---|---|
| atggattcga | acgcgcaaac | caccagtggc | accgtcgttg | aaagcacggc | tagcaatgga | 60 |
| gaggcttctg | cgcccgcgcc | catgctttcg | tcctcccttc | cttctccaag | ctttgagtcc | 120 |
| ggcccagacc | cccccccca | gttagcaagg | cgggtcccg | ggaacgtgcc | gcttgacccc | 180 |
| tcggccgccg | acgtggacga | caaggaccgc | gcctccagcg | cctacggaga | cgaacctccc | 240 |
| ctccccctcc | ccctcctcac | gtccacctcg | atgacagcct | cagaagcgag | cagcggtcaa | 300 |
| ggagggaag | ctggggccgc | cccagggtg | ccctcccttg | cttcctcccc | tgccttcgcc | 360 |
| cccgcagcta | ccggcctgtc | ccgtctcac | tccgccggtt | ccggcatgtc | agtgctgatc | 420 |
| caagtgcctc | aaaacgggcc | cagcgaggct | ctgtcgcctt | gcccttgcc | gaccactgcc | 480 |
| ttggatactc | ccttggacac | ccggtcgtcc | accccccgcc | ccgcgcccgc | ccagccccg | 540 |
| ccttctcctt | accagactgt | tggaggcctc | acggcgggg | agcactcgtt | ccttcctccc | 600 |
| gtcagtacgg | aagggctggc | ccctccggcg | atgggcacgg | gggaaggagg | gcttgagggc | 660 |
| ggggatggag | ggtcggtagg | tttttatccc | cccttgccc | agtcgcagac | gcaactcgcg | 720 |
| ccgttgccgg | gcccaccgcc | tccgcaggcg | caagattcgc | tgcagtacaa | gcctgcttcg | 780 |
| gtaccggagc | cgactaggat | gatggaaggg | tccagtgatc | ctccttttca | ttcgtcggag | 840 |
| acgcccaggg | cgatggggat | cggccgggg | ggagggaatt | cgcagatggt | tgcacctgcc | 900 |
| cccgcgccat | cgttgcaaca | gtcggcgccg | ttgcaacaac | gtcagcaatt | gcaacctcaa | 960 |
| cagcaccaac | agttccattc | gcgctcccac | ccacaagtag | cgccactcca | ggtgcagcaa | 1020 |
| cggcagcaac | cgcgggcact | ggtgccaggg | ccccagcagc | agcagcagca | tcagcagcag | 1080 |
| caagctctct | atgcatcttc | gcaacagcag | cagcaacagc | agcagcagca | acagcagcaa | 1140 |
| catcagcagc | agcagcagca | gcagcagcag | caacagcagc | agagacatca | cccgcaccca | 1200 |
| cagcaactgc | agcaacaaca | gcgacacaac | cagcagcagc | cactccagca | tccacaagca | 1260 |
| cagcatcgag | tcccacccca | gggcatgcct | cagcaccagc | acgtccgggc | gccacagcaa | 1320 |
| cagcggcagc | agcaactcct | ccctcttcca | accgcgggca | atgccgtccc | aggcggccag | 1380 |
| gcaaccggca | cccgcacgc | gtcgcaactg | cctcacgccc | agctctccca | acaacaacaa | 1440 |
| cccgcgcatt | ccttgcccca | acggcagggc | ctgggcgcgc | agcccctcaa | cccacaggac | 1500 |
| actgccttgc | ggcccggaat | ggtcaagaac | atcatggtct | tgctccaaca | acgcaaaccc | 1560 |
| gccgccgatc | cttccaaacc | cttggtggaa | actcggttga | aggagatggc | gatccggctg | 1620 |
| gaggactacc | tgtggaaacg | ctcgtccacg | ttggcggagt | actcggatct | gagcaccctc | 1680 |
| aaacaccgcc | tgcagtgttt | ggcagtctac | atgggcaagc | accagcagcg | gggtcaaact | 1740 |
| gtaccggcgg | gcgcaagggg | cagaggggga | gggatgccga | atcaagcgcc | ccagccacag | 1800 |
| gggggggggc | tctctgggaa | cacgaaccaa | ctgcaacgtt | tggtgcctac | cgccaatgcc | 1860 |
| agcaatattc | acctgcccaa | ccctcatccc | ggaggtctt | cggtggaat | ggggcggga | 1920 |
| ggcgcgcgtg | tgggagggcg | ggcagtggg | atcggcggag | gggggttgat | catgcaacct | 1980 |

```
gggagtgcca tccacggaca tcccccgggg ccccagttgc ggggcagctc tctccccac    2040 caagggcaag tgcaaccgac ctcgcagcag ggaagtcagc aaagaagggt gggaacgggt    2100
ctggcgcctg cgcctggcac acaacccgcg tttttaccac aggaacaaac gcaaatgcaa    2160
ggtcggcggg tagggggggg agggatgctg cccgtaaatg ggggtaacag ccaccctcct    2220
cccgcgccag gtcctccaca aggccatctg cagccgccgc agcagtcatc aggacagggg    2280
caagccgctc ccttgaacgt gatggggggg gcacagcaag tggggggggg cggtaatgcg    2340
aaccgagggc tccctatgcc tttatcttca ggccccgggg gtaccgcctc cgccagtcag    2400
aagaaacgcg tccagcacac gcccgaacaa cgtcagcaaa tcttgcacca gcagcagcag    2460
cggctgcttt acttgcgcca tgcgtccaag tgcattcatg tggacggccg ctgtccccag    2520
gggtacccga actgcatcgg gatgaaggag ctttggaagc acatcgcctc ctgtagggaa    2580
caacggtgca agttccccca ctgcgtgtcc tcgagatacg tcctgtccca ctaccacaaa    2640
tgtaaggaca cgcagtgccc ggtgtgcgga cccgtacgaa acacgatccg atcttctcgc    2700
tcctcggcgc atcccatgcc gcaacttggt cagggtgtgg cagacgccga cggaggaggc    2760
gagggaggcg gatctggagt ccagcagcag cagcagcagc agcaacaaca acaacaacaa    2820
caacaacaac aacagcaaca caacagcaa ttggtagcac agagtaatca acgcacgcag    2880
cagcaacaaa tgttgatcgc ccagcagccc cccccgcag ggatgggggg agggagggtc    2940
ggaggcatga ctggggccct ggcgaatgga ggcagggggtg ggagggtcgg agggagggcg    3000
cggggcaggg ggggtcaagt cgtgcttcct cagcaggttg cggccggggg gcggggaata    3060
ggcggtcaga atgtaggtgg aagtggaatg aaccagcaac gattgcagca acagcaacaa    3120
cagcagcagc aacaacagca gcagcagcag cagcagcagc agcagcagca gcaacgccca    3180
caaaatatgg cttccgtgcc ggttcctggg gtaggacgtg ggggaggagg ggtgcgagct    3240
ggcggggaag ccctcgcctt gggcactgcg ggtggagcgg gcagcaaacc tggggcccgg    3300
agcggttcgg ggaaaatgcc agtcgtagcc aagactccga atggcctcat gatccagacg    3360
gaaacgcatg gatgggtgcc ggtagagccc acgaaaaacg gcggctaccg tccctggtg    3420 cctctgcccg gctccggtca aagcttctca caggctgccg gcggggctgg gcgcgggcgga    3480 cgtcctggcg gcgttgggag aggggtgccc ggcgtacctg ccccaccttc cgcggcagcg    3540
ttgcagcggt tcgaagactc cgtgtccttg gtgaactcct tcacgacgc acaaattaag    3600 gcgcacatgg cctctctgcg ttcagggga gggttttgga ctcccgccaa gttgaaactt    3660
aaggtgcgtt caaggatatc taccgagcca acggtctctt tgttagtctc tcccttttgtt    3720 ccccgctttc attacgctcc tgcatacctg gatgccgcgc tttcttctcc tctcacatgc    3780
cctgtccccc cctttcccc taggttctcc ccctcggggt aaaacagctg aaatcggagt    3840
agggatggat ttttgaagaa cccggggacc ccgtgaagct cgggctcccg gattacttcg    3900
atgtgatcaa gcaccctatg gacttggcca ctgtacgtcg gcttgtgtcg aggcgctttc    3960
cctcagaatc gtctccccc ccccccccc ccaatgacca gtgctgctgg tcgcatcatg    4020
tcttctactt tccctccatc ttttttttc ttttcgtct atgcctcttc ttcttccca    4080 cctctttttt taaaacggac attgcccgtt gttggtcaag ttggccttgc ctcccagcc    4140 cgtgctgacc atggctttcc gtcgtccctc cgttcttcct cgatcaggtg aagcgtcgtt    4200
tggaaaacgg ctcctacaca gagctggaaa ggtggcggcg gacgtgaagc tcaccttcga    4260
caatgccatc ctttacaacc cccgggggca agaaatccac aaggtaacgg acgaaaaacg    4320
```

```
ggcgggaaaa gggggcaggt caaggctgga tgaagaggca gacgaggagg ttgaaagaga    4380
gaggctcgtg ctaggggcgg accggagcaa tggatggttc tacgacgaaa aaatggatgg    4440
ttccacgacg aaaatgaagt gacgggcagg ggggaaaggg gggacacgga aacgacattg    4500
cgggatacag aagtctgttg ggtgggccat ccctccctct caccctccct ccctcgttgc    4560
tggcccctac agatggccaa ggacatgcgg gacagtttct tcaaggactt caggcagctg    4620
gaggaggagg ttaagaggga acagcagctg actgtcaaca ggtaacccta acagaaaggg    4680
agggcggaga gaagcgggag ggaaggggga ggggagggg ga                       4722
```

<210> SEQ ID NO 6
<211> LENGTH: 1273
<212> TYPE: PRT
<213> ORGANISM: Nannochloropsis gaditana
<220> FEATURE:
<221> NAME/KEY: misc_feature
<223> OTHER INFORMATION: Bromo-1091 polypeptide, isoform c (HAT-B2)

<400> SEQUENCE: 6

```
Met Asp Ser Asn Ala Gln Thr Thr Ser Gly Thr Val Val Glu Ser Thr
1               5                   10                  15

Ala Ser Asn Gly Glu Ala Ser Ala Pro Ala Pro Met Leu Ser Ser Ser
            20                  25                  30

Leu Pro Ser Pro Ser Phe Glu Ser Gly Pro Asp Pro Pro Gln Leu
        35                  40                  45

Ala Arg Arg Val Pro Gly Asn Val Pro Leu Asp Pro Ser Ala Ala Asp
    50                  55                  60

Val Asp Asp Lys Asp Arg Ala Ser Ser Ala Tyr Gly Asp Glu Pro Pro
65                  70                  75                  80

Leu Pro Leu Pro Leu Leu Thr Ser Thr Ser Met Thr Ala Ser Glu Ala
                85                  90                  95

Ser Ser Gly Gln Gly Gly Glu Ala Gly Ala Ala Pro Gly Val Pro Ser
            100                 105                 110

Leu Ala Ser Ser Pro Ala Phe Ala Pro Ala Ala Thr Gly Leu Ser Pro
        115                 120                 125

Ser His Ser Ala Gly Ser Gly Met Ser Val Leu Ile Gln Val Pro Gln
    130                 135                 140

Asn Gly Pro Ser Glu Ala Leu Ser Pro Leu Pro Leu Pro Thr Thr Ala
145                 150                 155                 160

Leu Asp Thr Pro Leu Asp Thr Arg Ser Ser Thr Pro Arg Pro Ala Pro
                165                 170                 175

Ala Pro Ala Pro Pro Ser Pro Tyr Gln Thr Val Gly Gly Leu His Gly
            180                 185                 190

Gly Glu His Ser Phe Leu Pro Pro Val Ser Thr Glu Gly Leu Ala Pro
        195                 200                 205

Pro Ala Met Gly Thr Gly Glu Gly Gly Leu Glu Gly Gly Asp Gly Gly
    210                 215                 220

Ser Val Gly Phe Tyr Pro Pro Leu Ala Gln Ser Gln Thr Gln Leu Ala
225                 230                 235                 240

Pro Leu Pro Gly Pro Pro Pro Gln Ala Gln Asp Ser Leu Gln Tyr
                245                 250                 255

Lys Pro Ala Ser Val Pro Glu Pro Thr Arg Met Met Glu Gly Ser Ser
            260                 265                 270

Asp Pro Pro Phe His Ser Ser Glu Thr Pro Arg Ala Met Gly Ile Gly
        275                 280                 285
```

-continued

Arg Gly Gly Gly Asn Ser Gln Met Val Ala Pro Ala Pro Ala Pro Ser
290                 295                 300

Leu Gln Gln Ser Ala Pro Leu Gln Gln Arg Gln Gln Leu Gln Pro Gln
305                 310                 315                 320

Gln His Gln Gln Phe His Ser Arg Ser His Pro Gln Val Ala Pro Leu
                325                 330                 335

Gln Val Gln Gln Arg Gln Gln Pro Arg Ala Leu Val Pro Gly Pro Gln
                340                 345                 350

Gln Gln Gln Gln His Gln Gln Gln Ala Leu Tyr Ala Ser Ser Gln
        355                 360                 365

Gln Gln Gln Gln Gln Gln Gln Gln Gln Gln His Gln Gln
370                 375                 380

Gln Gln Gln Gln Gln Gln Gln Gln Arg His His Pro His Pro
385                 390                 395                 400

Gln Gln Leu Gln Gln Gln Arg His Asn Gln Gln Pro Leu Gln
            405                 410                 415

His Pro Gln Ala Gln His Arg Val Pro Pro Gly Met Pro Gln His
                420                 425                 430

Gln His Val Arg Ala Pro Gln Gln Arg Gln Gln Leu Leu Pro
            435                 440                 445

Leu Pro Thr Ala Gly Asn Ala Val Pro Gly Gln Ala Thr Gly Thr
    450                 455                 460

Pro His Ala Ser Gln Leu Pro His Ala Gln Leu Ser Gln Gln Gln
465                 470                 475                 480

Pro Ala His Ser Leu Pro Gln Arg Gln Gly Leu Gly Ala Gln Pro Leu
                485                 490                 495

Asn Pro Gln Asp Thr Ala Leu Arg Pro Gly Met Val Lys Asn Ile Met
            500                 505                 510

Val Leu Leu Gln Gln Arg Lys Pro Ala Ala Asp Pro Ser Lys Pro Leu
        515                 520                 525

Val Glu Thr Arg Leu Lys Glu Met Ala Ile Arg Leu Glu Asp Tyr Leu
    530                 535                 540

Trp Lys Arg Ser Ser Thr Leu Ala Glu Tyr Ser Asp Leu Ser Thr Leu
545                 550                 555                 560

Lys His Arg Leu Gln Cys Leu Ala Val Tyr Met Gly Lys His Gln Gln
                565                 570                 575

Arg Gly Gln Thr Val Pro Ala Gly Ala Arg Gly Arg Gly Gly Met
            580                 585                 590

Pro Asn Gln Ala Pro Gln Pro Gln Gly Gly Leu Ser Gly Asn Thr
        595                 600                 605

Asn Gln Leu Gln Arg Leu Val Pro Thr Ala Asn Ala Ser Asn Ile His
610                 615                 620

Leu Pro Asn Pro His Pro Gly Gly Leu Ser Gly Gly Met Gly Ala Gly
625                 630                 635                 640

Gly Ala Arg Val Gly Gly Arg Gly Ser Gly Ile Gly Gly Gly Leu
            645                 650                 655

Ile Met Gln Pro Gly Ser Ala Ile His Gly His Pro Pro Gly Pro Gln
                660                 665                 670

Leu Arg Gly Ser Ser Leu Pro His Gln Gly Gln Val Gln Pro Thr Ser
            675                 680                 685

Gln Gln Gly Ser Gln Gln Arg Arg Val Gly Thr Gly Leu Ala Pro Ala
        690                 695                 700

Pro Gly Thr Gln Pro Ala Phe Leu Pro Gln Glu Gln Thr Gln Met Gln

```
                705                 710                 715                 720
Gly Arg Arg Val Gly Gly Gly Met Leu Pro Val Asn Gly Gly Asn
                    725                 730                 735
Ser His Pro Pro Ala Pro Gly Pro Pro Gln Gly His Leu Gln Pro
                    740                 745                 750
Pro Gln Gln Ser Ser Gly Gly Gln Ala Ala Pro Leu Asn Val Met
                    755                 760                 765
Gly Gly Ala Gln Gln Val Gly Gly Gly Asn Ala Asn Arg Gly Leu
                    770                 775                 780
Pro Met Pro Leu Ser Ser Gly Pro Gly Thr Ala Ser Ala Ser Gln
785                 790                 795                 800
Lys Lys Arg Val Gln His Thr Pro Glu Gln Arg Gln Ile Leu His
                    805                 810                 815
Gln Gln Gln Gln Arg Leu Leu Tyr Leu Arg His Ala Ser Lys Cys Ile
                    820                 825                 830
His Val Asp Gly Arg Cys Pro Gln Gly Tyr Pro Asn Cys Ile Gly Met
                    835                 840                 845
Lys Glu Leu Trp Lys His Ile Ala Ser Cys Arg Glu Gln Arg Cys Lys
850                 855                 860
Phe Pro His Cys Val Ser Ser Arg Tyr Val Leu Ser His Tyr His Lys
865                 870                 875                 880
Cys Lys Asp Thr Gln Cys Pro Val Cys Gly Pro Val Arg Asn Thr Ile
                    885                 890                 895
Arg Ser Ser Arg Ser Ser Ala His Pro Met Pro Gln Leu Gly Gln Gly
                    900                 905                 910
Val Ala Asp Ala Asp Gly Gly Gly Glu Gly Gly Gly Ser Gly Val Gln
                    915                 920                 925
Gln Gln Gln Gln Gln Gln Gln Gln Gln Gln Gln Gln Gln Gln Gln
930                 935                 940
Gln Gln Gln Gln Gln Gln Leu Val Ala Gln Ser Asn Gln Arg Thr Gln
945                 950                 955                 960
Gln Gln Gln Met Leu Ile Ala Gln Gln Pro Pro Pro Ala Gly Met Gly
                    965                 970                 975
Gly Gly Arg Val Gly Gly Met Thr Gly Ala Leu Ala Asn Gly Gly Arg
                    980                 985                 990
Gly Gly Arg Val Gly Gly Arg Ala Arg Gly Arg Gly Gln Val Val
                    995                 1000                1005
Leu Pro Gln Gln Val Ala Ala Gly Gly Arg Gly Ile Gly Gly Gln
    1010                1015                1020
Asn Val Gly Gly Ser Gly Met Asn Gln Gln Arg Leu Gln Gln Gln
    1025                1030                1035
Gln Gln Gln Gln Gln Gln Gln Gln Gln Gln Gln Gln Gln Gln Gln
    1040                1045                1050
Gln Gln Gln Gln Gln Arg Pro Gln Asn Met Ala Ser Val Pro Val
    1055                1060                1065
Pro Gly Val Gly Arg Gly Gly Gly Val Arg Ala Gly Gly Glu
    1070                1075                1080
Ala Leu Ala Leu Gly Thr Ala Gly Gly Ala Gly Ser Lys Pro Gly
    1085                1090                1095
Ala Arg Ser Gly Ser Gly Lys Met Pro Val Val Ala Lys Thr Pro
    1100                1105                1110
Asn Gly Leu Met Ile Gln Thr Glu Thr His Gly Trp Val Pro Val
    1115                1120                1125
```

| | | | | | | | | | | |
|---|---|---|---|---|---|---|---|---|---|---|
| Glu | Pro 1130 | Thr | Lys | Asn | Gly 1135 | Gly | Tyr | Arg | Pro 1140 | Leu | Val | Pro | Leu | Pro |

Glu Pro Thr Lys Asn Gly Gly Tyr Arg Pro Leu Val Pro Leu Pro
    1130            1135              1140

Gly Ser Gly Gln Ser Phe Ser Gln Ala Ala Gly Gly Ala Gly Ala
    1145            1150              1155

Gly Gly Arg Pro Gly Gly Val Gly Arg Gly Val Pro Gly Val Pro
    1160            1165              1170

Ala Pro Pro Ser Ala Ala Ala Leu Gln Arg Phe Glu Asp Ser Val
    1175            1180              1185

Ser Leu Val Asn Ser Phe Thr Asp Ala Gln Ile Lys Ala His Met
    1190            1195              1200

Ala Ser Leu Arg Ser Gly Gly Gly Phe Trp Thr Pro Ala Lys Leu
    1205            1210              1215

Lys Leu Lys Val Arg Ser Arg Ile Ser Thr Glu Pro Thr Val Ser
    1220            1225              1230

Leu Leu Val Ser Pro Phe Val Pro Arg Phe His Tyr Ala Pro Ala
    1235            1240              1245

Tyr Leu Asp Ala Ala Leu Ser Ser Pro Leu Thr Cys Pro Val Pro
    1250            1255              1260

Pro Leu Ser Pro Arg Phe Ser Pro Ser Gly
    1265            1270

```
<210> SEQ ID NO 7
<211> LENGTH: 4429
<212> TYPE: DNA
<213> ORGANISM: Nannochloropsis gaditana
<220> FEATURE:
<221> NAME/KEY: misc_feature
<223> OTHER INFORMATION: Bromo-1091 gene transcript d (HAT-B10)
<220> FEATURE:
<221> NAME/KEY: misc_feature
<223> OTHER INFORMATION: encodes the polypeptide of SEQ ID NO:8

<400> SEQUENCE: 7
atggattcga acgcgcaaac caccagtggc accgtcgttg aaagcacggc tagcaatgga      60
gaggcttctg cgcccgcgcc catgctttcg tcctcccttc cttctccaag ctttgagtcc     120
ggcccagacc ccccccccca gttagcaagg cgggtccccg gaacgtgcc gcttgacccc      180 tcggccgccg acgtggacga caaggaccgc gcctccagcg cctacggaga cgaacctccc     240 ctcccccctcc cctcctcac gtccacctcg atgacagcct cagaagcgag cagcggtcaa      300
ggaggggaag ctggggccgc cccaggggtg ccctcccttg cttcctcccc tgccttcgcc     360
cccgcagcta ccggcctgtc cccgtctcac tccgccggtt ccggcatgtc agtgctgatc     420
caagtgcctc aaaacgggcc cagcgaggct ctgtcgcctt gcccttgcc gaccactgcc      480 ttggatactc ccttggacac ccggtcgtcc acccccgcc ccgcgcccgc ccagccccg      540 ccttctcctt accagactgt tggaggcctc cacgcgggg agcactcgtt ccttcctccc     600
gtcagtacgg aagggctggc ccctccggcg atgggcacgg ggaaggagg gcttgagggc     660 ggggatggag ggtcggtagg tttttatccc ccccttgccc agtcgcagac gcaactcgcg     720
ccgttgccgg cccaccgcc tccgcaggcg caagattcgc tgcagtacaa gcctgcttcg     780
gtaccggagc cgactaggat gatggaaggg tccagtgatc tccttttca ttcgtcggag     840 acgcccaggg cgatggggat cggccggggg ggagggaatt cgcagatggt tgcacctgcc     900
cccgcgccat cgttgcaaca gtcggcgccg ttgcaacaac gtcagcaatt gcaacctcaa     960
cagcaccaac agttccattc gcgctcccac ccacaagtag cgccactcca ggtgcagcaa    1020
```

-continued

```
cggcagcaac cgcgggcact ggtgccaggg ccccagcagc agcagcagca tcagcagcag    1080
caagctctct atgcatcttc gcaacagcag cagcaacagc agcagcagca acagcagcaa    1140
catcagcagc agcagcagca gcagcagcag caacagcagc agagacatca cccgcaccca    1200
cagcaactgc agcaacaaca gcgacacaac cagcagcagc cactccagca tccacaagca    1260
cagcatcgag tcccacccca gggcatgcct cagcaccagc acgtccgggc gccacagcaa    1320
cagcggcagc agcaactcct ccctcttcca accgcgggca atgccgtccc aggcggccag    1380
gcaaccggca cccgcacgc gtcgcaactg cctcacgccc agctctccca acaacaacaa    1440
cccgcgcatt ccttgcccca acggcagggc ctgggcgcgc agcccctcaa cccacaggac    1500
actgccttgc ggcccggaat ggtcaagaac atcatggtct tgctccaaca acgcaaaccc    1560
gccgccgatc cttccaaacc cttggtggaa actcggttga aggagatggc gatccggctg    1620
gaggactacc tgtggaaacg ctcgtccacg ttggcggagt actcggatct gagcaccctc    1680
aaacaccgcc tgcagtgttt ggcagtctac atgggcaagc accagcagcg gggtcaaact    1740
gtaccggcgg gcgcaagggg cagaggggga gggatgccga tcaagcgcc ccagccacag    1800 gggggggggc tctctgggaa cacgaaccaa ctgcaacgtt tggtgcctac cgccaatgcc    1860
agcaatattc acctgcccaa ccctcatccc ggaggtcttt cgggtggaat gggggcggga    1920
ggcgcgcgtg tgggagggcg gggcagtggg atcggcggag gggggttgat catgcaacct    1980
gggagtgcca tccacggaca tccccccggg ccccagttgc ggggcagctc tctccccac    2040 caagggcaag tgcaaccgac ctcgcagcag ggaagtcagc aaagaagggt gggaacgggt    2100
ctggcgcctg cgcctggcac acaacccgcg tttttaccac aggaacaaac gcaaatgcaa    2160
ggtcggcggg tagggggggg agggatgctg cccgtaaatg ggggtaacag ccaccctcct    2220
cccgcgccag gtcctccaca aggccatctg cagccgccgc agcagtcatc aggacagggg    2280
caagccgctc ccttgaacgt gatggggggg gcacagcaag tggggggggg cggtaatgcg    2340
aaccgagggc tccctatgcc tttatcttca ggccccgggg gtaccgcctc cgccagtcag    2400
aagaaacgcg tccagcacac gcccgaacaa cgtcagcaaa tcttgcacca gcagcagcag    2460
cggctgcttt acttgcgcca tgcgtccaag tgcattcatg tggacggccg ctgtccccag    2520
gggtacccga actgcatcgg gatgaaggag ctttggaagc acatcgcctc ctgtagggaa    2580
caacggtgca agttccccca ctgcgtgtcc tcgagatacg tcctgtccca ctaccacaaa    2640
tgtaaggaca cgcagtgccc ggtgtgcgga cccgtacgaa acacgatccg atcttctcgc    2700
tcctcggcgc atcccatgcc gcaacttggt cagggtgtgg cagacgccga cggaggaggc    2760
gagggaggcg gatctggagt ccagcagcag cagcagcagc aacaacaaca acaacaacaa    2820
caacaacaac agcaacaaca acagcaattg gtagcacaga gtaatcaacg cacgcagcag    2880
caacaaatgt tgatcgccca gcagccccc ccccgcaggg atggggggag ggagggtcgg    2940
aggcatgact gggggccctgg cgaatggagg caggggtggg agggtcggag ggagggcgcg    3000 gggcagggg ggtcaagtcg tgcttcctca gcaggttgcg gccggggggc ggggaatagg    3060
cggtcagaat gtaggtggaa gtggaatgaa ccagcaacga ttgcagcaac agcaacaaca    3120
gcagcagcaa caacagcagc agcagcagca gcagcagcag cagcagcaac gcccacaaaa    3180
tatggcttcc gtgccggttc ctggggtagg acgtggggga ggaggggtgc gagctggcgg    3240
ggaagccctc gccttgggca ctgcgggtgg agcggcagc aaacctgggg cccggagcgg    3300
ttcggggaaa atgccagtcg tagccaagac tccgaatgcc ctcatgatcc agacggaaac    3360
gcatggatgg gtgccggtag agcccacgaa aaacggcggc taccgtcccc tggtgcctct    3420
```

-continued

```
gcccggctcc ggtcaaagct tctcacaggc tgccggcggg gctggcgcgg cggacgtcc    3480 tggcggcgtt gggagagggg tgcccggcgt acctgcccca ccttccgcgg cagcgttgca    3540
gcggttcgaa gactccgtgt ccttggtgaa ctccttcacg gacgcacaaa ttaaggcgca    3600
catggtctct ctgcgttcag ggggagggtt ttgaactccc gccaagttga aacttaaggt    3660
gcgttcaagg atatctaccg agccaacggt ctctttgttt gtctctccct ttgttccccg    3720 cttcattac gctcctgcat acctggatgc cgcgctttct tctcctctca catgccctgt     3780 ccccccctt tccctaggt tctcccctc gtggtaaaac agctgaaatc ggagtatgga       3840
tggatttttg aagaacccgt ggaccccgtg aagctcgggc tcccggatta cttcgatgtg    3900
atcaagcacc ctatggactt gggcactgta cgtcggcttg tgtcgaggcg ctttccctca    3960
gaatcgtctc cttccccccc cccccccaat gaccagtgct gctggtcgca tcatgtcttc    4020
tactttccct ccatctttt tttctttttc gtctatgcct cttcttcttc cccacctctt     4080 ttttaaaac ggacattgcc cgttgttggt caagttggcc ttgcctcccc agcccgtgct     4140
gaccatggct ttccgtcgtc cctccgttct tcctcgatca ggtgaagcgt cgtttggaaa    4200
acggctccta cacagagctg gaaaaggtgg cggcggacgt gaagctcacc ttcgacaatg    4260
ccatccttta caacccccg ggcaagaaa tccacaaggt aacggacgaa aaacgggcgg      4320
gaaaaggggg caggtcaagg ctggatgaag aggcagacga ggaggttgaa agagagaggc    4380
tcgtgctagg ggcggaccgg agcaatggat ggttctacga cgaaaaaat                4429
```

<210> SEQ ID NO 8
<211> LENGTH: 1197
<212> TYPE: PRT
<213> ORGANISM: Nannochloropsis gaditana
<220> FEATURE:
<221> NAME/KEY: misc_feature
<223> OTHER INFORMATION: Bromo-1091 polypeptide, isoform d (HAT-B10)

<400> SEQUENCE: 8

```
Met Asp Ser Asn Ala Gln Thr Thr Ser Gly Thr Val Val Glu Ser Thr
1               5                   10                  15

Ala Ser Asn Gly Glu Ala Ser Ala Pro Ala Pro Met Leu Ser Ser Ser
            20                  25                  30

Leu Pro Ser Pro Ser Phe Glu Ser Gly Pro Asp Pro Pro Gln Leu
        35                  40                  45

Ala Arg Arg Val Pro Gly Asn Val Pro Leu Asp Pro Ser Ala Ala Asp
    50                  55                  60

Val Asp Asp Lys Asp Arg Ala Ser Ser Ala Tyr Gly Asp Glu Pro Pro
65                  70                  75                  80

Leu Pro Leu Pro Leu Leu Thr Ser Thr Ser Met Thr Ala Ser Glu Ala
                85                  90                  95

Ser Ser Gly Gln Gly Gly Glu Ala Gly Ala Ala Pro Gly Val Pro Ser
            100                 105                 110

Leu Ala Ser Ser Pro Ala Phe Ala Pro Ala Ala Thr Gly Leu Ser Pro
        115                 120                 125

Ser His Ser Ala Gly Ser Gly Met Ser Val Leu Ile Gln Val Pro Gln
    130                 135                 140

Asn Gly Pro Ser Glu Ala Leu Ser Pro Leu Pro Leu Pro Thr Thr Ala
145                 150                 155                 160

Leu Asp Thr Pro Leu Asp Thr Arg Ser Ser Thr Pro Arg Pro Ala Pro
                165                 170                 175
```

```
Ala Pro Ala Pro Pro Ser Pro Tyr Gln Thr Val Gly Gly Leu His Gly
            180                 185                 190

Gly Glu His Ser Phe Leu Pro Val Ser Thr Glu Gly Leu Ala Pro
        195                 200                 205

Pro Ala Met Gly Thr Gly Glu Gly Leu Glu Gly Gly Asp Gly Gly
        210                 215                 220

Ser Val Gly Phe Tyr Pro Pro Leu Ala Gln Ser Gln Thr Gln Leu Ala
225                 230                 235                 240

Pro Leu Pro Gly Pro Pro Pro Gln Ala Gln Asp Ser Leu Gln Tyr
            245                 250                 255

Lys Pro Ala Ser Val Pro Glu Pro Thr Arg Met Met Glu Gly Ser Ser
            260                 265                 270

Asp Pro Pro Phe His Ser Ser Glu Thr Pro Arg Ala Met Gly Ile Gly
            275                 280                 285

Arg Gly Gly Gly Asn Ser Gln Met Val Ala Pro Ala Pro Ala Pro Ser
            290                 295                 300

Leu Gln Gln Ser Ala Pro Leu Gln Gln Arg Gln Gln Leu Gln Pro Gln
305                 310                 315                 320

Gln His Gln Gln Phe His Ser Arg Ser His Pro Gln Val Ala Pro Leu
            325                 330                 335

Gln Val Gln Gln Arg Gln Pro Arg Ala Leu Val Pro Gly Pro Gln
            340                 345                 350

Gln Gln Gln Gln His Gln Gln Gln Ala Leu Tyr Ala Ser Ser Gln
            355                 360                 365

Gln Gln Gln Gln Gln Gln Gln Gln Gln Gln His Gln Gln Gln
            370                 375                 380

Gln Gln Gln Gln Gln Gln Gln Gln Arg His His Pro His Pro
385                 390                 395                 400

Gln Gln Leu Gln Gln Gln Arg His Asn Gln Gln Pro Leu Gln
            405                 410                 415

His Pro Gln Ala Gln His Arg Val Pro Pro Gly Met Pro Gln His
            420                 425                 430

Gln His Val Arg Ala Pro Gln Gln Gln Arg Gln Gln Gln Leu Leu Pro
            435                 440                 445

Leu Pro Thr Ala Gly Asn Ala Val Pro Gly Gly Gln Ala Thr Gly Thr
450                 455                 460

Pro His Ala Ser Gln Leu Pro His Ala Gln Leu Ser Gln Gln Gln Gln
465                 470                 475                 480

Pro Ala His Ser Leu Pro Gln Arg Gln Gly Leu Gly Ala Gln Pro Leu
            485                 490                 495

Asn Pro Gln Asp Thr Ala Leu Arg Pro Gly Met Val Lys Asn Ile Met
            500                 505                 510

Val Leu Leu Gln Gln Arg Lys Pro Ala Ala Asp Pro Ser Lys Pro Leu
            515                 520                 525

Val Glu Thr Arg Leu Lys Glu Met Ala Ile Arg Leu Glu Asp Tyr Leu
            530                 535                 540

Trp Lys Arg Ser Ser Thr Leu Ala Glu Tyr Ser Asp Leu Ser Thr Leu
545                 550                 555                 560

Lys His Arg Leu Gln Cys Leu Ala Val Tyr Met Gly Lys His Gln Gln
            565                 570                 575

Arg Gly Gln Thr Val Pro Ala Gly Ala Arg Gly Arg Gly Gly Met
            580                 585                 590

Pro Asn Gln Ala Pro Gln Pro Gln Gly Gly Gly Leu Ser Gly Asn Thr
```

-continued

```
              595                 600                 605
Asn Gln Leu Gln Arg Leu Val Pro Thr Ala Asn Ala Ser Asn Ile His
    610                 615                 620

Leu Pro Asn Pro His Pro Gly Gly Leu Ser Gly Gly Met Gly Ala Gly
625                 630                 635                 640

Gly Ala Arg Val Gly Arg Gly Ser Gly Ile Gly Gly Gly Gly Gly Leu
                645                 650                 655

Ile Met Gln Pro Gly Ser Ala Ile His Gly His Pro Pro Gly Pro Gln
                660                 665                 670

Leu Arg Gly Ser Ser Leu Pro His Gln Gly Gln Val Gln Pro Thr Ser
            675                 680                 685

Gln Gln Gly Ser Gln Gln Arg Arg Val Gly Thr Gly Leu Ala Pro Ala
        690                 695                 700

Pro Gly Thr Gln Pro Ala Phe Leu Pro Gln Glu Gln Thr Gln Met Gln
705                 710                 715                 720

Gly Arg Arg Val Gly Gly Gly Met Leu Pro Val Asn Gly Gly Asn
                725                 730                 735

Ser His Pro Pro Pro Ala Pro Gly Pro Pro Gln Gly His Leu Gln Pro
            740                 745                 750

Pro Gln Gln Ser Ser Gly Gln Gly Gln Ala Ala Pro Leu Asn Val Met
        755                 760                 765

Gly Gly Ala Gln Gln Val Gly Gly Gly Asn Ala Asn Arg Gly Leu
    770                 775                 780

Pro Met Pro Leu Ser Ser Gly Pro Gly Gly Thr Ala Ser Ala Ser Gln
785                 790                 795                 800

Lys Lys Arg Val Gln His Thr Pro Glu Gln Arg Gln Ile Leu His
                805                 810                 815

Gln Gln Gln Gln Arg Leu Leu Tyr Leu Arg His Ala Ser Lys Cys Ile
            820                 825                 830

His Val Asp Gly Arg Cys Pro Gln Gly Tyr Pro Asn Cys Ile Gly Met
        835                 840                 845

Lys Glu Leu Trp Lys His Ile Ala Ser Cys Arg Glu Gln Arg Cys Lys
    850                 855                 860

Phe Pro His Cys Val Ser Ser Arg Tyr Val Leu Ser His Tyr His Lys
865                 870                 875                 880

Cys Lys Asp Thr Gln Cys Pro Val Cys Gly Pro Val Arg Asn Thr Ile
                885                 890                 895

Arg Ser Ser Arg Ser Ser Ala His Pro Met Pro Gln Leu Gly Gln Gly
            900                 905                 910

Val Ala Asp Ala Asp Gly Gly Gly Glu Gly Gly Gly Ser Gly Val Gln
        915                 920                 925

Gln Gln Gln Gln Gln Gln Gln Gln Gln Gln Gln Gln Gln Gln Gln Gln
    930                 935                 940

Gln Gln Gln Gln Gln Leu Val Ala Gln Ser Asn Gln Arg Thr Gln Gln
945                 950                 955                 960

Gln Gln Met Leu Ile Ala Gln Pro Pro Arg Arg Asp Gly Gly
                965                 970                 975

Arg Glu Gly Arg Arg His Asp Trp Gly Pro Gly Glu Trp Arg Gln Gly
            980                 985                 990

Trp Glu Gly Arg Arg Glu Gly Ala Gly Gln Gly Gly Ser Ser Arg Ala
        995                 1000                1005

Ser Ser Ala Gly Cys Gly Arg Gly Ala Gly Asn Arg Arg Ser Glu
    1010                1015                1020
```

```
Cys Arg Trp Lys Trp Asn Glu Pro Ala Thr Ile Ala Ala Thr Ala
    1025                1030                1035

Thr Thr Ala Ala Ala Thr Thr Ala Ala Ala Ala Ala Ala Ala Ala
    1040                1045                1050

Ala Ala Ala Thr Pro Thr Lys Tyr Gly Phe Arg Ala Gly Ser Trp
    1055                1060                1065

Gly Arg Thr Trp Gly Arg Arg Gly Ala Ser Trp Arg Gly Ser Pro
    1070                1075                1080

Arg Leu Gly His Cys Gly Trp Ser Gly Gln Gln Thr Trp Gly Pro
    1085                1090                1095

Glu Arg Phe Gly Glu Asn Ala Ser Arg Ser Gln Asp Ser Glu Trp
    1100                1105                1110

Pro His Asp Pro Asp Gly Asn Ala Trp Met Gly Ala Gly Arg Ala
    1115                1120                1125

His Glu Lys Arg Arg Leu Pro Ser Pro Gly Ala Ser Ala Arg Leu
    1130                1135                1140

Arg Ser Lys Leu Leu Thr Gly Cys Arg Arg Gly Trp Arg Gly Arg
    1145                1150                1155

Thr Ser Trp Arg Arg Trp Glu Arg Gly Ala Arg Arg Thr Cys Pro
    1160                1165                1170

Thr Phe Arg Gly Ser Val Ala Ala Val Arg Arg Leu Arg Val Leu
    1175                1180                1185

Gly Glu Leu Leu His Gly Arg Thr Asn
    1190                1195
```

<210> SEQ ID NO 9
<211> LENGTH: 66
<212> TYPE: PRT
<213> ORGANISM: Nannochloropsis gaditana
<220> FEATURE:
<221> NAME/KEY: misc_feature
<223> OTHER INFORMATION: TAZ zinc finger domain (PF02135), amino acids
      769-833 of SEQ ID NO:4

<400> SEQUENCE: 9

```
His Ala Ser Lys Cys Ile His Val Asp Gly Arg Cys Pro Gln Gly Tyr
1               5                   10                  15

Pro Asn Cys Ile Gly Met Lys Glu Leu Trp Lys His Ile Ala Ser Cys
                20                  25                  30

Arg Glu Gln Arg Cys Lys Phe Pro His Cys Val Ser Ser Arg Tyr Val
            35                  40                  45

Leu Ser His Tyr His Lys Cys Lys Asp Thr Gln Cys Pro Val Cys Gly
        50                  55                  60

Pro Val
65
```

<210> SEQ ID NO 10
<211> LENGTH: 43
<212> TYPE: PRT
<213> ORGANISM: Nannochloropsis gaditana
<220> FEATURE:
<221> NAME/KEY: misc_feature
<223> OTHER INFORMATION: Bromo domain (PF00439), amino acids 1165-1245
      of SEQ ID NO:4

<400> SEQUENCE: 10

```
Leu Pro Leu Val Val Lys Gln Leu Lys Ser Glu Tyr Gly Trp Ile Phe
1               5                   10                  15
```

```
Glu Glu Pro Val Asp Pro Val Lys Leu Gly Leu Pro Asp Tyr Phe Asp
            20                  25                  30

Val Ile Lys His Pro Met Asp Leu Gly Thr Val
            35                  40
```

<210> SEQ ID NO 11
<211> LENGTH: 639
<212> TYPE: DNA
<213> ORGANISM: Nannochloropsis oceanica
<220> FEATURE:
<221> NAME/KEY: misc_feature
<223> OTHER INFORMATION: encodes polypeptide of SEQ ID NO:12

<400> SEQUENCE: 11

```
atgaataata acgtcagtac caataacagc aacataggca atattaacac caatcgaaat      60
cagccaccca tgccgctccc tactggccct ggcggcggtc ctcccacttc gcagcagcaa     120
cggatgcagc acaccccccga gcagcgccag cagatcctgc accagcagca gcagcggttg     180
ttatacctaa gacatgcatc caagtgtatc cacgtggatg gtaggtgtcc ccaggggtac     240
cccaactgca aaggaatgaa ggagctctgg aagcacattg catcgtgccg agagcaacgg     300
tgtcaatttc cccactgcgt ctcgtcaaga tacgtcctct cccactatca aagtgcaag    360
gacacgaact gcccggtgtg tggacccgtg cgcaacacca tccggtcctc ccgcaacgca     420
tcccaaccca tgcctcagct gaatcaagga ggagtgggag gagtgatgcc ggtaccagga     480
cagccgcagc cgcagccgca gcagcaatca acaacaacaa caacaacaca acaacaacaa     540
caacagatgt acattccgca acagcaacag cagcaattac agcaagggat gggtggagga     600
agagggggc gtggatgccg atccaagcgc agccgttga                              639
```

<210> SEQ ID NO 12
<211> LENGTH: 212
<212> TYPE: PRT
<213> ORGANISM: Nannochloropsis oceanica
<220> FEATURE:
<221> NAME/KEY: misc_feature
<223> OTHER INFORMATION: Partial sequence, Bromo-1091 ortholog

<400> SEQUENCE: 12

```
Met Asn Asn Asn Val Ser Thr Asn Asn Ser Asn Ile Gly Asn Ile Asn
1               5                   10                  15

Thr Asn Arg Asn Gln Pro Pro Met Pro Leu Pro Thr Gly Pro Gly Gly
            20                  25                  30

Gly Pro Pro Thr Ser Gln Gln Gln Arg Met Gln His Thr Pro Glu Gln
            35                  40                  45

Arg Gln Gln Ile Leu His Gln Gln Gln Arg Leu Leu Tyr Leu Arg
    50                  55                  60

His Ala Ser Lys Cys Ile His Val Asp Gly Arg Cys Pro Gln Gly Tyr
65                  70                  75                  80

Pro Asn Cys Lys Gly Met Lys Glu Leu Trp Lys His Ile Ala Ser Cys
                85                  90                  95

Arg Glu Gln Arg Cys Gln Phe Pro His Cys Val Ser Ser Arg Tyr Val
            100                 105                 110

Leu Ser His Tyr His Lys Cys Lys Asp Thr Asn Cys Pro Val Cys Gly
        115                 120                 125

Pro Val Arg Asn Thr Ile Arg Ser Ser Arg Asn Ala Ser Gln Pro Met
    130                 135                 140

Pro Gln Leu Asn Gln Gly Gly Val Gly Gly Val Met Pro Val Pro Gly
145                 150                 155                 160
```

```
Gln Pro Gln Pro Gln Pro Gln Gln Ser Gln Gln Gln Gln Gln
            165                 170                 175
Gln Gln Gln Gln Gln Gln Met Tyr Ile Pro Gln Gln Gln Gln Gln
        180                 185                 190
Leu Gln Gln Gly Met Gly Gly Gly Arg Gly Gly Arg Gly Cys Arg Ser
        195                 200                 205
Lys Arg Ser Arg
    210

<210> SEQ ID NO 13
<211> LENGTH: 4305
<212> TYPE: DNA
<213> ORGANISM: Cyclotella sp.
<220> FEATURE:
<221> NAME/KEY: misc_feature
<223> OTHER INFORMATION: encodes polypeptide of SEQ ID NO:14

<400> SEQUENCE: 13
```

| | | | | | |
|---|---|---|---|---|---|
| atggtccgaa | acgcgagtag | taggttgcct | ctcatggcga | aaaagctcga | agaacacctt | 60 |
| tacaggtcag | cacaaaccaa | ggaagaatat | atggatcttt | cttcgctcaa | acgacgtctt | 120 |
| catctcattg | caaggcggt | aggagttcct | aagtttggct | atcagagtga | actccgagca | 180 |
| cccgttctg | ctgtaaacaa | tgcagtgaga | acaaacatga | atgaaaatgt | catgcaaccg | 240 |
| actgatgctg | tcaatctcaa | taatggtatg | caacgaaata | atgtcatgca | gccttttaac | 300 |
| gacatgcaaa | ccaacaacgc | cgttcagctt | agcaatggta | tgcaagctaa | caacaccatg | 360 |
| cagtctcaaa | ataatgctat | gcagcccttc | ggtacgggta | gtcaagaagc | cagtgggccg | 420 |
| aatccccaac | agactaagtc | tcaattgtca | cagctgcaac | agataaggga | aaatgtgcag | 480 |
| aatagcaccc | caagcagcgc | cttcgtctcg | tcagagcaga | tgcttagcga | ccaatccttc | 540 |
| gttgcagccg | caccagatag | ctcccatagc | aacgacacgg | atacaggctc | aatcgatcca | 600 |
| cgagccgaga | agaagaacct | tgttctccag | cagcaacagc | gccgtctatt | gttactgcgt | 660 |
| cattctaaat | tatgccgcat | tggacctaac | tgtgacacga | aattctgccc | tcaaatggtg | 720 |
| attctttgga | agcatttgaa | gtattgtcgg | ggcaaaacat | gccctgttcc | ccattgcgtc | 780 |
| tcctcacgtt | gtgtcttgag | ccaccatcgc | aattgtaaac | gtagaggtct | ttctgccaca | 840 |
| tgcgagattt | gttatccggt | cgcgaagtat | attcgtcgac | tgactggaga | cacagacggt | 900 |
| gatcattgga | acgacgattg | ggataatttc | tctgttttcg | aggcggacgg | ggacggggat | 960 |
| ggggacattg | atttgtccac | gagtactgca | gacaacataa | tgtccaactc | cagcgggctc | 1020 |
| gtccatggtg | aaatggcagc | atcaggcttg | atgcctcaac | cgcaaatacc | gcataacgaa | 1080 |
| tctgcctccg | tgaatgttat | tcgagcttta | caaaatgaaa | tcgagcagaa | gcagacagtc | 1140 |
| cttgcgcaaa | ttcgtcgcca | gaagggaacg | ctttttagtc | agaataaatt | gcttctagaa | 1200 |
| cagttatctg | catctaatga | ggctgacaat | tcgacacagc | tccagaatca | gataaatctt | 1260 |
| ctgcaacacc | tcaatgcaca | atttgaacga | caagaattgt | tacttgacag | agaaatcagc | 1320 |
| cgtcaatccc | gggagctcca | acaaatgcga | caatcgcagt | caggggagaa | ccagagcttg | 1380 |
| agtgccccat | cacttcctca | tagctcgggt | gctccaccac | taccgcctca | gactaccgag | 1440 |
| aaagaaagtg | cagagtcacc | gaagctaaag | ccgaaagctg | ccaaaagccc | cacggctact | 1500 |
| gaatcttcaa | atgattactc | tcccccttc | atgtctgtgt | cgtcgtcgtg | tcatacggcg | 1560 |
| cttcctgctt | gttctacgtc | ctgtgcgtct | aaaaagagat | ctactgcgca | gaatgatagc | 1620 |
| tgccaggaag | atgacgacga | ctctcgcatt | cggaagttgt | ttaagcagga | tggcgcagtg | 1680 |

```
ctcacttcaa cactatatga agacggaaat gatgcttctt cgactgccac gcaaaacgaa    1740
agtataggtg taagccagga gccatccgca gacgtgaacc ctcgtagtgt gaacgacatc    1800
ctttcatcga tgccagttgc cgcaatcgag gaacaccttg attccctgct aaattgctgt    1860
cagttgacac ctcggtgcat tgcgagaaag tgcctcccaa taattaagaa attaatcaga    1920
catgagcacg gatgggtgtt aaagatccg gttgatcccg ttgagctcgg tttagatgat    1980
tattttgaga ttgttgaaca ccccatggat cttggattag tcgaaaaaaa actcgaaaat    2040
tgtgtttata aggacatcga atcattcgag cgtgacgcaa gacttgtctt tgagaatgct    2100
attttattca atggcgatga aaatgaaatc ggaatatggg caagacaact attggatatt    2160
ttcaacgacg aagtgaaatc tctcatgaaa ggactgggaa tgagcctgaa acggaagct    2220 gtagaggcct gcggaaacga ctctacatgt tccctgtgtg ggaaatttag gcttttattt    2280
gagccaccgg cactttactg cagtggagtt tgcggaatgc aaaaaatacg acgtaatggc    2340
ttttactaca ctgaccagta caagcaaaac cattggtgtg accgatgctt taccgggtta    2400
aaagaagatc aaacaatcca gcttgacgat ggtaaagaga ccaaaaagtc tcttctcgtt    2460
agaatgaaaa atgatttgac accagaagaa cagtgggtcc aatgtgatgt ctgtcacgag    2520
tggtgccatc aaatttgcgc cctttttaac gctagtcgaa caacccggc aaagacattt    2580 tcttgcccca agtgtgttgt tgcgaagccg aaaaaggagc agaacgaaaa gtttgagtac    2640
tcatcgttca agatgccag tgctctaccc gagtgcaagt taagtcgtgc aatagaatca    2700
ggcttgtttg atacgctttc ggaggaatac gaaaagatcg ccaatcagag aacatgtgat    2760
gtatcccaag tcgaaaaagc tgatggcctc tgtgttcgtg tagtattgtc acaggagaag    2820
aaacacaagg ttcgagaggg tatgcagtca aggtattcta acaagggatt ccttcagag    2880 ttcccagtaa cgtcaaaatg catcttgctg ttccaaaaaa ttcacggggc tgatgttctc    2940 cttttttggga tgtatgtcta cgaatatggc gacaaatgcc cagcaccaaa cagaagacga    3000
gtgtatattt cttacttgga ttcggttcac taccttcagc cttcattata taggactctt    3060
acctatcaga caatcatagt ggaataccct cgatttgtca gatctcgagg gtttcatact    3120
gcccatattt ggagctgccc accttctaaa ggcgacgagt atattttta ctgtcatcca    3180 ccacaacagt tgataccaaa ggatgatatg ttgtgcgcct ggtacgttga gactttgaag    3240
aaggcccaag aaaaaggcgt cgtcctagaa acaaggacac tctatgatga atacttcaaa    3300
gaccatggcg tcaaccctga gaccggtgaa ccgtttgatc aaccagcat accatatttc    3360 gacggcgact acattcctgg agagattgaa aagatcatca caattctcaa caaggacgaa    3420
acactgcgtg aaggagcgaa gtgccatgat tcccactcga gtcgaatgc tcccaatggc    3480 caaaagatag aaggtaaaag acgaggcact aggagcaacc caggcgactt agtaaatcag    3540
gatcgtgaca aagtgatgaa tcgtctagat ttggccttgt ccaggatgaa gcaaaatttc    3600
ttcgtcgctc aattgcttag tgataacttc atcaaagcag tcgagattgg tgttgatgtt    3660
tcccaatggg tcgaagaaat aaagtccgat tcgatgatta accatcaaa acagattggc    3720 aaaagcccag atcttctaga tttgcgaacg gttgatgcta ccgcaaagac cccgccgatt    3780
ccaccaacgt caagcgttca agtaataggc aacactgttg atgaagaccc ctcgatagaa    3840
caagaatgtc tcgatacacg catcgcgttt ttgaacttttt gccagaagaa ttactatcag    3900
tttgatgaat tacgccgtgc caagtacagt acaatgatgc ttctaagtga gttgcacgat    3960
cctcgtgcag agagggagca gcaattcaag gtgcatctac aagtaatcgc acatgcagcg    4020
```

```
tcttgtcaag gctgcgcatc caaaaattgc acacgaatga agtccctttt tgatcacgtc   4080
agaaagtgtg acgtaacata ccgacatgga tgcaaagttt gtgtgcgtct ttttatgcta   4140
ttgaccaaac acgcacgcga ttgtgtcaca gagggaacat gctgcattcc tttttgtgaa   4200
cgcatcaggg aaaggcacag aagactgttg agacagcagc agcttttgga cgacaggcga   4260
cgtgatgagc aaaataacag gcatcagcaa gaggaagcag tctaa                  4305
```

<210> SEQ ID NO 14
<211> LENGTH: 1434
<212> TYPE: PRT
<213> ORGANISM: Cyclotella sp.
<220> FEATURE:
<221> NAME/KEY: misc_feature
<223> OTHER INFORMATION: translation product 5091230

<400> SEQUENCE: 14

```
Met Val Arg Asn Ala Ser Ser Arg Leu Pro Leu Met Ala Lys Lys Leu
1               5                   10                  15

Glu Glu His Leu Tyr Arg Ser Ala Gln Thr Lys Glu Glu Tyr Met Asp
            20                  25                  30

Leu Ser Ser Leu Lys Arg Arg Leu His Leu Ile Ala Lys Ala Val Gly
        35                  40                  45

Val Pro Lys Phe Gly Tyr Gln Ser Glu Leu Arg Ala Pro Val Ser Ala
    50                  55                  60

Val Asn Asn Ala Val Arg Thr Asn Met Asn Glu Asn Val Met Gln Pro
65                  70                  75                  80

Thr Asp Ala Val Asn Leu Asn Asn Gly Met Gln Arg Asn Asn Val Met
                85                  90                  95

Gln Pro Phe Asn Asp Met Gln Thr Asn Asn Ala Val Gln Leu Ser Asn
            100                 105                 110

Gly Met Gln Ala Asn Asn Thr Met Gln Ser Gln Asn Asn Ala Met Gln
        115                 120                 125

Pro Phe Gly Thr Gly Ser Gln Glu Ala Ser Gly Pro Asn Pro Gln Gln
    130                 135                 140

Thr Lys Ser Gln Leu Ser Gln Leu Gln Gln Ile Arg Glu Asn Val Gln
145                 150                 155                 160

Asn Ser Thr Pro Ser Ser Ala Phe Val Ser Glu Gln Met Leu Ser
                165                 170                 175

Asp Gln Ser Phe Val Ala Ala Ala Pro Asp Ser Ser His Ser Asn Asp
            180                 185                 190

Thr Asp Thr Gly Ser Ile Asp Pro Arg Ala Glu Lys Lys Asn Leu Val
        195                 200                 205

Leu Gln Gln Gln Gln Arg Arg Leu Leu Leu Arg His Ser Lys Leu
    210                 215                 220

Cys Arg Ile Gly Pro Asn Cys Asp Thr Lys Phe Cys Pro Gln Met Val
225                 230                 235                 240

Ile Leu Trp Lys His Leu Lys Tyr Cys Arg Gly Lys Thr Cys Pro Val
                245                 250                 255

Pro His Cys Val Ser Ser Arg Cys Val Leu Ser His Arg Asn Cys
            260                 265                 270

Lys Arg Arg Gly Leu Ser Ala Thr Cys Glu Ile Cys Tyr Pro Val Ala
        275                 280                 285

Lys Tyr Ile Arg Arg Leu Thr Gly Asp Thr Gly Asp His Trp Asn
    290                 295                 300

Asp Asp Trp Asp Asn Phe Ser Val Phe Glu Ala Asp Gly Asp Gly Asp
```

-continued

```
305                 310                 315                 320
Gly Asp Ile Asp Leu Ser Thr Ser Thr Ala Asp Asn Ile Met Ser Asn
                325                 330                 335

Ser Ser Gly Leu Val His Gly Glu Met Ala Ala Ser Gly Leu Met Pro
                340                 345                 350

Gln Pro Gln Ile Gln His Asn Glu Ser Ala Ser Val Asn Val Ile Arg
                355                 360                 365

Ala Leu Gln Asn Glu Ile Glu Gln Lys Gln Thr Val Leu Ala Gln Ile
            370                 375                 380

Arg Arg Gln Lys Gly Thr Leu Phe Ser Gln Asn Lys Leu Leu Leu Glu
385                 390                 395                 400

Gln Leu Ser Ala Ser Asn Glu Ala Asp Asn Ser Thr Gln Leu Gln Asn
                405                 410                 415

Gln Ile Asn Leu Leu Gln His Leu Asn Ala Gln Phe Glu Arg Gln Glu
            420                 425                 430

Leu Leu Leu Asp Arg Glu Ile Ser Arg Gln Ser Arg Glu Leu Gln Gln
            435                 440                 445

Met Arg Gln Ser Gln Ser Gly Glu Asn Gln Ser Leu Ser Ala Pro Ser
        450                 455                 460

Leu Pro His Ser Ser Gly Ala Pro Pro Leu Pro Pro Gln Thr Thr Glu
465                 470                 475                 480

Lys Glu Ser Ala Glu Ser Pro Lys Leu Lys Pro Lys Ala Ala Lys Ser
                485                 490                 495

Pro Thr Ala Thr Glu Ser Ser Asn Asp Tyr Ser Pro Pro Phe Met Ser
            500                 505                 510

Val Ser Ser Cys His Thr Ala Leu Pro Ala Cys Ser Thr Ser Cys
            515                 520                 525

Ala Ser Lys Lys Arg Ser Thr Ala Gln Asn Asp Ser Cys Gln Glu Asp
        530                 535                 540

Asp Asp Asp Ser Arg Ile Arg Lys Leu Phe Lys Gln Asp Gly Ala Val
545                 550                 555                 560

Leu Thr Ser Thr Leu Tyr Glu Asp Gly Asn Asp Ala Ser Ser Thr Ala
                565                 570                 575

Thr Gln Asn Glu Ser Ile Gly Val Ser Gln Glu Pro Ser Ala Asp Val
            580                 585                 590

Asn Pro Arg Ser Val Asn Asp Ile Leu Ser Ser Met Pro Val Ala Ala
        595                 600                 605

Ile Glu Glu His Leu Asp Ser Leu Leu Asn Cys Cys Gln Leu Thr Pro
    610                 615                 620

Arg Cys Ile Ala Arg Lys Cys Leu Pro Ile Ile Lys Lys Leu Ile Arg
625                 630                 635                 640

His Glu His Gly Trp Val Phe Lys Asp Pro Val Asp Pro Val Glu Leu
                645                 650                 655

Gly Leu Asp Asp Tyr Phe Glu Ile Val Glu His Pro Met Asp Leu Gly
            660                 665                 670

Leu Val Glu Lys Lys Leu Glu Asn Cys Val Tyr Lys Asp Ile Glu Ser
        675                 680                 685

Phe Glu Arg Asp Ala Arg Leu Val Phe Glu Asn Ala Ile Leu Phe Asn
    690                 695                 700

Gly Asp Glu Asn Glu Ile Gly Ile Trp Ala Arg Gln Leu Leu Asp Ile
705                 710                 715                 720

Phe Asn Asp Glu Val Lys Ser Leu Met Lys Gly Leu Gly Met Ser Leu
                725                 730                 735
```

```
Lys Thr Glu Ala Val Glu Ala Cys Gly Asn Asp Ser Thr Cys Ser Leu
                740                 745                 750

Cys Gly Lys Phe Arg Leu Leu Phe Glu Pro Pro Ala Leu Tyr Cys Ser
            755                 760                 765

Gly Val Cys Gly Met Gln Lys Ile Arg Arg Asn Gly Phe Tyr Tyr Thr
        770                 775                 780

Asp Gln Tyr Lys Gln Asn His Trp Cys Asp Arg Cys Phe Thr Gly Leu
785                 790                 795                 800

Lys Glu Asp Gln Thr Ile Gln Leu Asp Asp Gly Lys Glu Thr Lys Lys
                805                 810                 815

Ser Leu Leu Val Arg Met Lys Asn Asp Leu Thr Pro Glu Glu Gln Trp
            820                 825                 830

Val Gln Cys Asp Val Cys His Glu Trp Cys His Gln Ile Cys Ala Leu
        835                 840                 845

Phe Asn Ala Ser Arg Asn Asn Pro Ala Lys Thr Phe Ser Cys Pro Lys
850                 855                 860

Cys Val Val Ala Lys Pro Lys Lys Glu Gln Asn Glu Lys Phe Glu Tyr
865                 870                 875                 880

Ser Ser Phe Lys Asp Ala Ser Ala Leu Pro Glu Cys Lys Leu Ser Arg
            885                 890                 895

Ala Ile Glu Ser Gly Leu Phe Asp Thr Leu Ser Glu Glu Tyr Glu Lys
        900                 905                 910

Ile Ala Asn Gln Arg Thr Cys Asp Val Ser Gln Val Glu Lys Ala Asp
            915                 920                 925

Gly Leu Cys Val Arg Val Val Leu Ser Gln Glu Lys His Lys Val
        930                 935                 940

Arg Glu Gly Met Gln Ser Arg Tyr Ser Asn Lys Gly Phe Pro Ser Glu
945                 950                 955                 960

Phe Pro Val Thr Ser Lys Cys Ile Leu Leu Phe Gln Lys Ile His Gly
                965                 970                 975

Ala Asp Val Leu Leu Phe Gly Met Tyr Val Tyr Glu Tyr Gly Asp Lys
            980                 985                 990

Cys Pro Ala Pro Asn Arg Arg Arg Val Tyr Ile Ser Tyr Leu Asp Ser
        995                 1000                1005

Val His Tyr Leu Gln Pro Ser Leu Tyr Arg Thr Leu Thr Tyr Gln
    1010                1015                1020

Thr Ile Ile Val Glu Tyr Leu Arg Phe Val Arg Ser Arg Gly Phe
    1025                1030                1035

His Thr Ala His Ile Trp Ser Cys Pro Pro Ser Lys Gly Asp Glu
    1040                1045                1050

Tyr Ile Phe Tyr Cys His Pro Pro Gln Gln Leu Ile Pro Lys Asp
    1055                1060                1065

Asp Met Leu Cys Ala Trp Tyr Val Glu Thr Leu Lys Lys Ala Gln
    1070                1075                1080

Glu Lys Gly Val Val Leu Glu Thr Arg Thr Leu Tyr Asp Glu Tyr
    1085                1090                1095

Phe Lys Asp His Gly Val Asn Pro Glu Thr Gly Glu Pro Phe Asp
    1100                1105                1110

Pro Thr Ser Ile Pro Tyr Phe Asp Gly Asp Tyr Ile Pro Gly Glu
    1115                1120                1125

Ile Glu Lys Ile Ile Thr Ile Leu Asn Lys Asp Glu Thr Leu Arg
    1130                1135                1140
```

Glu Gly Ala Lys Cys His Asp Ser His Ser Lys Ser Asn Ala Pro
    1145                1150                1155

Asn Gly Gln Lys Ile Glu Gly Lys Arg Arg Gly Thr Arg Ser Asn
    1160                1165                1170

Pro Gly Asp Leu Val Asn Gln Asp Arg Asp Lys Val Met Asn Arg
    1175                1180                1185

Leu Asp Leu Ala Leu Ser Arg Met Lys Gln Asn Phe Phe Val Ala
    1190                1195                1200

Gln Leu Leu Ser Asp Asn Phe Ile Lys Ala Val Glu Ile Gly Val
    1205                1210                1215

Asp Val Ser Gln Trp Val Glu Glu Ile Lys Ser Asp Ser Met Ile
    1220                1225                1230

Lys Pro Ser Lys Gln Ile Gly Lys Ser Pro Asp Leu Leu Asp Leu
    1235                1240                1245

Arg Thr Val Asp Ala Thr Ala Lys Thr Pro Pro Ile Pro Pro Thr
    1250                1255                1260

Ser Ser Val Gln Val Ile Gly Asn Thr Val Asp Glu Asp Pro Ser
    1265                1270                1275

Ile Glu Gln Glu Cys Leu Asp Thr Arg Ile Ala Phe Leu Asn Phe
    1280                1285                1290

Cys Gln Lys Asn Tyr Tyr Gln Phe Asp Glu Leu Arg Arg Ala Lys
    1295                1300                1305

Tyr Ser Thr Met Met Leu Leu Ser Glu Leu His Asp Pro Arg Ala
    1310                1315                1320

Glu Arg Glu Gln Gln Phe Lys Val His Leu Gln Val Ile Ala His
    1325                1330                1335

Ala Ala Ser Cys Gln Gly Cys Ala Ser Lys Asn Cys Thr Arg Met
    1340                1345                1350

Lys Ser Leu Phe Asp His Val Arg Lys Cys Asp Val Thr Tyr Arg
    1355                1360                1365

His Gly Cys Lys Val Cys Val Arg Leu Phe Met Leu Leu Thr Lys
    1370                1375                1380

His Ala Arg Asp Cys Val Thr Glu Gly Thr Cys Cys Ile Pro Phe
    1385                1390                1395

Cys Glu Arg Ile Arg Glu Arg His Arg Arg Leu Leu Arg Gln Gln
    1400                1405                1410

Gln Leu Leu Asp Asp Arg Arg Arg Asp Glu Gln Asn Asn Arg His
    1415                1420                1425

Gln Gln Glu Glu Ala Val
    1430

<210> SEQ ID NO 15
<211> LENGTH: 4647
<212> TYPE: DNA
<213> ORGANISM: Cyclotella sp.
<220> FEATURE:
<221> NAME/KEY: misc_feature
<223> OTHER INFORMATION: encodes polypeptide of SEQ ID NO:16

<400> SEQUENCE: 15
atgcttaata tctcgaagag ccagagccag tcatcagttt ttatgtttac cgtcttcatg     60
tcgctttcgt ggggacagcg agcaatcctt tgctgtggcc aaaaaactac cagttttctt    120
cacactccgg gctttggacc aggcctttct catcggttgg caacgaaagt tcaccgccgt    180
caaagcactc cattttacac aaaaacaatca ttgctgtttt catcaactgc gcccaacaag    240

```
aaagaggaag tcgatcataa ttatgacttt gaccgcatcc tcccgtttga caaacattct    300
cacaattcaa tcaaaatagc agtcccacag aacgagcaag cagatccgag tgaagatctt    360
tttgacagcg aaacattcct ctcgaaacta gaagccaccg tagccaccgc caaacaactc    420
cacaaaactg ccatttggat cactgtgccc atcacaagag ctggtctcat gaacatgca     480 cacaaatgtg ggttcacgtt tcaccacgcc gaaggaaaca cggccactct gagcaagtgg    540
ctatccgaag atgaagaaag ccgaatcccc acgtttgcta ctcaccaggt aggcgttggc    600
gccgtagtta tcaatcgcga aacggaggaa atactttgcg tgagagagaa acgaaacaac    660
taccgtccat ggaaaatgcc tggcggtctt gctgaactgg gcgaagactt ggatatcgca    720
gtgataagag aagtttacga agaaactgga attcaatgta ggtttctcag tgttcttggt    780
gtaagacata ctcatggatt acaattcggt cgaagtgact tatactttgt ctgtcgtttg    840
gagcctgtga ccgatgagag cgggaaagtt gcgcagccag tgccacaaga aggagaaatc    900
gaagcggctg catggattcc gctggatgag tacagagata tggtaaacaa ccctgatagt    960
aatattggac atccaatgat gcgtcacatt atgaggattg ttgatcaggg cgactgggac   1020
aagtttgaca ttcagagaac ggttcgtcaa aagactgcga atggtcagta cgcctcccaa   1080
cctcccccga ttcctcaaca gcaacaacaa ccggccaatc tacaacagcc ccagcaacct   1140
ccacctccgg caacgcaaca aattgtccct gcctcgggtc ctaaaattaa ggcagggtac   1200
gtgtacagtg gaggaaatcc tgtaccagca gcgtccaaac cgggtggtgt agccctctcg   1260
aatgggaagg ttcttgcagc cccatcgagt tctggtccca aacctcaaga agatcatacc   1320
ctcataaatt gttttaccct ggaacaaatc gaaacccaca tcaagtctct taacaagggt   1380
ctgcaactcc ccctagcaaa gttgaaaaca aaatgcggtg aattgctcaa gggcttacaa   1440
tctcatcagc atggatgggt atttaacagc cctgtggacc tgtagagct tggactacct   1500 gattatttcg aagtcataaa gaaccccatg gatttgggca cagtgaagaa acgcctcgac   1560
aacggattgt atcggagcat cagagaggtt gaggctgata ttaatctgac atttgataac   1620
gcaatgctct ataatcctga aggatcagta gtctggagca tggcgaagga gctcaaggat   1680
aaattcgaga cagattttgc tgcacttatg aaagtcctc acgaagagga ggaagagaag   1740
cgcaagaacg gtgatgcttg ttcactttgc ggatgtgaaa agctactttt tgaaccccct   1800
gtcttctatt gcaatgggtt gtcatgtcgt tccaagcgaa tcagaaggaa cagttactat   1860
tttgttgggg gaaataatca ataccattgg tgccaaccct gttatgagga actgaaggaa   1920
agccaagcaa ttgaactgcc agatatgact ctgaagaaaa gtcaactgga caagaagaag   1980
aataatgagg ttccagagga aagttgggtc caatgcgatc gatgtgagag atggattcat   2040
caaatttgtg ctctcttcaa tactaggcaa aataagaatc aacagtctga gtttgtctgc   2100
ccaagttgta caatcaatga taggaagaag aagggttcgt tgggaccaac atccactact   2160
cccatggcag aggatttgcc caggacaaaa ctttctgagc atctagaaaa gcatgtgaga   2220
gagaaattca gtctgaaat ggaacgtttg gcaaaggaaa gggcagaagc agagggcatc   2280
tccatggaag aagccatgcg aataacttcc gacggaggcg tgagattta cattcgacag   2340 gtgacttcaa tgagccgaac attggaagtc cgtgaacgaa tgcttaaacg ttactcattc   2400
aaaaactatc ccaatgagtt taagtaccgc tgcaaatgcg tcattgtctt ccaaaacctg   2460
gatggtgtgg atgtcattct tttggcctg tacgtctacg agcatgacga aaccaatgcc   2520 cccccccaatc agcgtgctgt ctatattcc tatctggaca gtgtctacta catgagacct   2580
cgcaagatgc gaactttcgt gtatcatgag ttattgattt cgtacatgga ctatgtccgt   2640
```

```
tgcaaaggct actccactgc gcacatttgg gcatgccctc cgctcaaagg cgatgactat    2700
attttgtttg caaagccgga ggaccagaaa actcctaaag acgatcgtct tcgccaatgg    2760
taccttgaca tgctgaagga ttgccaacga aggggcatcg tgggaaaggt caccaatgca    2820
tatgatttgt atttctcaga cccgaagaac gatgcatcag tactgcctta catggaggga    2880
gactatttcc cagctgagct tgaaaacatc atcaaagatc tagaggaagg caaaaatctt    2940
agcaagaaac cagacaaatc ggcttcaaag aagggaaaga agaaaagaa atccaagaca     3000 aagaaggcgg gcagtcgagg tggaactcgt tcagcaggct tggacgagga cgctcttgca    3060
gcaagtggta ttcttcaaga gggtgtggat atcaagagcc tccaagctgg tggaagagac    3120
gctgtaatga agaagcttgg agacactatt taccccatga aggagagttt ccttgttgca    3180
tttcttgatt gggatggagc gaaagaagag aaccgagttg tgccgaaaga cattatggaa    3240
tacagagagc agcatgggat tgttgtcagg aaggcttctg gcgtgcagga aagaaagac    3300 ggcgatagca ctaaacccgc agcagagtgt caaatcttc cagccataaa ggaagagagt     3360
ccgaaagagg tggcagaatc ctccattgaa aaagccgctg aatcaactgc gtctccatcc    3420
agctctgctc caaccaaaga agattctgca tcaaaggatg gtcttctgc tgtaaaagag     3480 gaatcagatc ttgctcctgc caacaaccca tctgagtcca ctccattgca tgatctggca    3540
tctggcagcg aggaaaagaa agaggaagtt aacagcgaaa atcccgatgg ggctaccaaa    3600
gaatccgagt ctgccccgac agaaggaagc agtgcaagcc cccaaggcgt agctgaaaag    3660
cctaatagag gcgaggctga aacggccaag ggtggtaacg gtgatgtcga atggaagac    3720 tccaagagtt cggagtcaaa agaagataat gggaaggaag ctgagacgaa aggtgttgaa    3780
gctactactg gagaggcacc aaaacaagca atagtagcca gggagggtaa attcgctgca    3840
atggagaaaa ttaaaaagga aatgaaagtg aacccgaac cggagccatc atcctcaacc     3900
tctgatcaaa ttgcttccaa gagtgtcacg aaagatagca agggacgact agttaaggtt    3960
atcgatgacg atgacgagga aatggattgc gagttcctca ataaccgcca gcttttcctg    4020 aaccttgcc aaggcaatca ctaccagttt gaccagctcc gtagagccaa acacacatcc     4080
atgatggttt tgtggcatct gcataacaga gatgcaccaa agtttgttca gcaatgtgct    4140
gtgtgctcac gtgaaatcct gcaaggaatg cgttaccatt gccccacttg tgctgactttt   4200 gatcagtgct acgaatgcat gtccaacccg aatgttcctc ggcatcagca tccactcaaa    4260
ccaataccag taggtagcca gcagagttcg ttgacacccg agcaaagaaa agaaaggcag    4320
cgtagcattc aactccacat gaccttgttg ttgcatgctg ccacgtgcaa atcgtctaaa    4380
tgtgcctctg caaactgtgc gaaaatgaaa ggtctattga agcatggttc ccaatgccaa    4440
attaaagctg ccggaggatg tcatgtctgt aaacgcattt gggccctcct ccaaattcat    4500
gcaaggcagt gcaaacaaga caactgtcca gtgcctaatt gtttagctat ccgagagcga    4560
ttccgacagt tgaatttgca gcagcaggca atggatgaca ggcgtcgcca gatgatgaac    4620
cagacttatc atcagcaggc gcgctga                                        4647
```

<210> SEQ ID NO 16
<211> LENGTH: 1548
<212> TYPE: PRT
<213> ORGANISM: Cyclotella sp.
<220> FEATURE:
<221> NAME/KEY: misc_feature
<223> OTHER INFORMATION: translation product 5092334

<400> SEQUENCE: 16

-continued

```
Met Leu Asn Ile Ser Lys Ser Gln Ser Gln Ser Ser Val Phe Met Phe
1               5                   10                  15

Thr Val Phe Met Ser Leu Ser Trp Gly Gln Arg Ala Ile Leu Cys Cys
                20                  25                  30

Gly Gln Lys Thr Thr Ser Phe Leu His Thr Pro Gly Phe Gly Pro Gly
            35                  40                  45

Leu Ser His Arg Leu Ala Thr Lys Val His Arg Arg Gln Ser Thr Pro
        50                  55                  60

Phe Tyr Thr Lys Gln Ser Leu Leu Phe Ser Ser Thr Ala Pro Asn Lys
65                  70                  75                  80

Lys Glu Glu Val Asp His Asn Tyr Asp Phe Asp Arg Ile Leu Pro Phe
                85                  90                  95

Asp Lys His Ser His Asn Ser Ile Lys Ile Ala Val Pro Gln Asn Glu
            100                 105                 110

Gln Ala Asp Pro Ser Glu Asp Leu Phe Asp Ser Glu Thr Phe Leu Ser
        115                 120                 125

Lys Leu Glu Ala Thr Val Ala Thr Ala Lys Gln Leu His Lys Thr Ala
            130                 135                 140

Ile Trp Ile Thr Val Pro Ile Thr Arg Ala Gly Leu Met Glu His Ala
145                 150                 155                 160

His Lys Cys Gly Phe Thr Phe His His Ala Glu Gly Asn Thr Ala Thr
                165                 170                 175

Leu Ser Lys Trp Leu Ser Glu Asp Glu Glu Ser Arg Ile Pro Thr Phe
            180                 185                 190

Ala Thr His Gln Val Gly Val Gly Ala Val Val Ile Asn Arg Glu Thr
        195                 200                 205

Glu Glu Ile Leu Cys Val Arg Glu Lys Arg Asn Asn Tyr Arg Pro Trp
210                 215                 220

Lys Met Pro Gly Gly Leu Ala Glu Leu Gly Glu Asp Leu Asp Ile Ala
225                 230                 235                 240

Val Ile Arg Glu Val Tyr Glu Glu Thr Gly Ile Gln Cys Arg Phe Leu
                245                 250                 255

Ser Val Leu Gly Val Arg His Thr His Gly Leu Gln Phe Gly Arg Ser
            260                 265                 270

Asp Leu Tyr Phe Val Cys Arg Leu Glu Pro Val Thr Asp Glu Ser Gly
        275                 280                 285

Lys Val Ala Gln Pro Val Pro Gln Glu Gly Glu Ile Glu Ala Ala Ala
    290                 295                 300

Trp Ile Pro Leu Asp Glu Tyr Arg Asp Met Val Asn Asn Pro Asp Ser
305                 310                 315                 320

Asn Ile Gly His Pro Met Met Arg His Ile Met Arg Ile Val Asp Gln
                325                 330                 335

Gly Asp Trp Asp Lys Phe Asp Ile Gln Arg Thr Val Arg Gln Lys Thr
            340                 345                 350

Ala Asn Gly Gln Tyr Ala Ser Gln Pro Pro Ile Pro Gln Gln Gln
        355                 360                 365

Gln Gln Pro Ala Asn Leu Gln Gln Pro Gln Gln Pro Pro Pro Ala
    370                 375                 380

Thr Gln Gln Ile Val Pro Ala Ser Gly Pro Lys Ile Lys Ala Gly Tyr
385                 390                 395                 400

Val Tyr Ser Gly Gly Asn Pro Val Pro Ala Ala Ser Lys Pro Gly Gly
                405                 410                 415
```

Val Ala Leu Ser Asn Gly Lys Val Leu Ala Ala Pro Ser Ser Gly
                420                 425                 430

Pro Lys Pro Gln Glu Asp His Thr Leu Ile Asn Cys Phe Thr Leu Glu
435                 440                 445

Gln Ile Glu Thr His Ile Lys Ser Leu Asn Lys Gly Leu Gln Leu Pro
            450                 455                 460

Leu Ala Lys Leu Lys Thr Lys Cys Gly Glu Leu Leu Lys Gly Leu Gln
465                 470                 475                 480

Ser His Gln His Gly Trp Val Phe Asn Ser Pro Val Asp Pro Val Glu
                485                 490                 495

Leu Gly Leu Pro Asp Tyr Phe Glu Val Ile Lys Asn Pro Met Asp Leu
            500                 505                 510

Gly Thr Val Lys Lys Arg Leu Asp Asn Gly Leu Tyr Arg Ser Ile Arg
        515                 520                 525

Glu Val Glu Ala Asp Ile Asn Leu Thr Phe Asp Asn Ala Met Leu Tyr
        530                 535                 540

Asn Pro Glu Gly Ser Val Val Trp Ser Met Ala Lys Glu Leu Lys Asp
545                 550                 555                 560

Lys Phe Glu Thr Asp Phe Ala Ala Leu Met Lys Val Leu His Glu Glu
            565                 570                 575

Glu Glu Glu Lys Arg Lys Asn Gly Asp Ala Cys Ser Leu Cys Gly Cys
                580                 585                 590

Glu Lys Leu Leu Phe Glu Pro Pro Val Phe Tyr Cys Asn Gly Leu Ser
            595                 600                 605

Cys Arg Ser Lys Arg Ile Arg Arg Asn Ser Tyr Tyr Phe Val Gly Gly
610                 615                 620

Asn Asn Gln Tyr His Trp Cys Gln Pro Cys Tyr Glu Glu Leu Lys Glu
625                 630                 635                 640

Ser Gln Ala Ile Glu Leu Pro Asp Met Thr Leu Lys Lys Ser Gln Leu
            645                 650                 655

Asp Lys Lys Lys Asn Asn Glu Val Pro Glu Glu Ser Trp Val Gln Cys
        660                 665                 670

Asp Arg Cys Glu Arg Trp Ile His Gln Ile Cys Ala Leu Phe Asn Thr
    675                 680                 685

Arg Gln Asn Lys Asn Gln Gln Ser Glu Phe Val Cys Pro Ser Cys Thr
690                 695                 700

Ile Asn Asp Arg Lys Lys Lys Gly Ser Leu Gly Pro Thr Ser Thr Thr
705                 710                 715                 720

Pro Met Ala Glu Asp Leu Pro Arg Thr Lys Leu Ser Glu His Leu Glu
            725                 730                 735

Lys His Val Arg Glu Lys Phe Lys Ser Glu Met Glu Arg Leu Ala Lys
                740                 745                 750

Glu Arg Ala Glu Ala Glu Gly Ile Ser Met Glu Glu Ala Met Arg Ile
        755                 760                 765

Thr Ser Asp Gly Gly Glu Ile Tyr Ile Arg Gln Val Thr Ser Met
    770                 775                 780

Ser Arg Thr Leu Glu Val Arg Glu Arg Met Leu Lys Arg Tyr Ser Phe
785                 790                 795                 800

Lys Asn Tyr Pro Asn Glu Phe Lys Tyr Arg Cys Lys Cys Val Ile Val
                805                 810                 815

Phe Gln Asn Leu Asp Gly Val Asp Val Ile Leu Phe Gly Leu Tyr Val
            820                 825                 830

Tyr Glu His Asp Glu Thr Asn Ala Pro Pro Asn Gln Arg Ala Val Tyr

```
                835                 840                 845
Ile Ser Tyr Leu Asp Ser Val Tyr Tyr Met Arg Pro Arg Lys Met Arg
    850                 855                 860
Thr Phe Val Tyr His Glu Leu Leu Ile Ser Tyr Met Asp Tyr Val Arg
865                 870                 875                 880
Cys Lys Gly Tyr Ser Thr Ala His Ile Trp Ala Cys Pro Pro Leu Lys
                885                 890                 895
Gly Asp Asp Tyr Ile Leu Phe Ala Lys Pro Glu Asp Gln Lys Thr Pro
            900                 905                 910
Lys Asp Asp Arg Leu Arg Gln Trp Tyr Leu Asp Met Leu Lys Asp Cys
        915                 920                 925
Gln Arg Arg Gly Ile Val Gly Lys Val Thr Asn Ala Tyr Asp Leu Tyr
    930                 935                 940
Phe Ser Asp Pro Lys Asn Asp Ala Ser Val Leu Pro Tyr Met Glu Gly
945                 950                 955                 960
Asp Tyr Phe Pro Ala Glu Leu Glu Asn Ile Ile Lys Asp Leu Glu Glu
                965                 970                 975
Gly Lys Asn Leu Ser Lys Lys Pro Asp Lys Ser Ala Ser Lys Lys Gly
            980                 985                 990
Lys Lys Glu Lys Lys Ser Lys Thr Lys Lys Ala Gly Ser Arg Gly Gly
        995                 1000                1005
Thr Arg Ser Ala Gly Leu Asp Glu Asp Ala Leu Ala Ala Ser Gly
    1010                1015                1020
Ile Leu Gln Glu Gly Val Asp Ile Lys Ser Leu Gln Ala Gly Gly
    1025                1030                1035
Arg Asp Ala Val Met Lys Lys Leu Gly Asp Thr Ile Tyr Pro Met
    1040                1045                1050
Lys Glu Ser Phe Leu Val Ala Phe Leu Asp Trp Asp Gly Ala Lys
    1055                1060                1065
Glu Glu Asn Arg Val Val Pro Lys Asp Ile Met Glu Tyr Arg Glu
    1070                1075                1080
Gln His Gly Ile Val Val Arg Lys Ala Ser Gly Val Gln Glu Lys
    1085                1090                1095
Lys Asp Gly Asp Ser Thr Lys Pro Ala Ala Glu Cys Ser Asn Leu
    1100                1105                1110
Pro Ala Ile Lys Glu Glu Ser Pro Lys Glu Val Ala Glu Ser Ser
    1115                1120                1125
Ile Glu Lys Ala Ala Glu Ser Thr Ala Ser Pro Ser Ser Ser Ala
    1130                1135                1140
Pro Thr Lys Glu Asp Ser Ala Ser Lys Asp Gly Ser Ser Ala Val
    1145                1150                1155
Lys Glu Glu Ser Asp Leu Ala Pro Ala Asn Asn Pro Ser Glu Ser
    1160                1165                1170
Thr Pro Leu His Asp Leu Ala Ser Gly Ser Glu Glu Lys Lys Glu
    1175                1180                1185
Glu Val Asn Ser Glu Asn Pro Asp Gly Ala Thr Lys Glu Ser Glu
    1190                1195                1200
Ser Ala Pro Thr Glu Gly Ser Ala Ser Pro Gln Gly Val Ala
    1205                1210                1215
Glu Lys Pro Asn Arg Gly Glu Ala Glu Thr Ala Lys Gly Gly Asn
    1220                1225                1230
Gly Asp Val Glu Met Glu Asp Ser Lys Ser Ser Glu Ser Lys Glu
    1235                1240                1245
```

| Asp | Asn | Gly | Lys | Glu | Ala | Glu | Thr | Lys | Gly | Val | Glu | Ala | Thr | Thr |
|-----|-----|-----|-----|-----|-----|-----|-----|-----|-----|-----|-----|-----|-----|-----|
|     | 1250 |     |     |     | 1255 |     |     |     |     | 1260 |     |     |     |     |

| Gly | Glu | Ala | Pro | Lys | Gln | Ala | Ile | Val | Ala | Arg | Glu | Gly | Lys | Phe |
|-----|-----|-----|-----|-----|-----|-----|-----|-----|-----|-----|-----|-----|-----|-----|
| 1265 |     |     |     |     | 1270 |     |     |     |     | 1275 |     |     |     |     |

| Ala | Ala | Met | Glu | Lys | Ile | Lys | Lys | Glu | Met | Lys | Val | Glu | Pro | Glu |
|-----|-----|-----|-----|-----|-----|-----|-----|-----|-----|-----|-----|-----|-----|-----|
| 1280 |     |     |     |     | 1285 |     |     |     |     | 1290 |     |     |     |     |

| Pro | Glu | Pro | Ser | Ser | Ser | Thr | Ser | Asp | Gln | Ile | Ala | Ser | Lys | Ser |
|-----|-----|-----|-----|-----|-----|-----|-----|-----|-----|-----|-----|-----|-----|-----|
| 1295 |     |     |     |     | 1300 |     |     |     |     | 1305 |     |     |     |     |

| Val | Thr | Lys | Asp | Ser | Lys | Gly | Arg | Leu | Val | Lys | Val | Ile | Asp | Asp |
|-----|-----|-----|-----|-----|-----|-----|-----|-----|-----|-----|-----|-----|-----|-----|
| 1310 |     |     |     |     | 1315 |     |     |     |     | 1320 |     |     |     |     |

| Asp | Asp | Glu | Glu | Met | Asp | Cys | Glu | Phe | Leu | Asn | Asn | Arg | Gln | Leu |
|-----|-----|-----|-----|-----|-----|-----|-----|-----|-----|-----|-----|-----|-----|-----|
| 1325 |     |     |     |     | 1330 |     |     |     |     | 1335 |     |     |     |     |

| Phe | Leu | Asn | Leu | Cys | Gln | Gly | Asn | His | Tyr | Gln | Phe | Asp | Gln | Leu |
|-----|-----|-----|-----|-----|-----|-----|-----|-----|-----|-----|-----|-----|-----|-----|
| 1340 |     |     |     |     | 1345 |     |     |     |     | 1350 |     |     |     |     |

| Arg | Arg | Ala | Lys | His | Thr | Ser | Met | Met | Val | Leu | Trp | His | Leu | His |
|-----|-----|-----|-----|-----|-----|-----|-----|-----|-----|-----|-----|-----|-----|-----|
| 1355 |     |     |     |     | 1360 |     |     |     |     | 1365 |     |     |     |     |

| Asn | Arg | Asp | Ala | Pro | Lys | Phe | Val | Gln | Gln | Cys | Ala | Val | Cys | Ser |
|-----|-----|-----|-----|-----|-----|-----|-----|-----|-----|-----|-----|-----|-----|-----|
| 1370 |     |     |     |     | 1375 |     |     |     |     | 1380 |     |     |     |     |

| Arg | Glu | Ile | Leu | Gln | Gly | Met | Arg | Tyr | His | Cys | Pro | Thr | Cys | Ala |
|-----|-----|-----|-----|-----|-----|-----|-----|-----|-----|-----|-----|-----|-----|-----|
| 1385 |     |     |     |     | 1390 |     |     |     |     | 1395 |     |     |     |     |

| Asp | Phe | Asp | Gln | Cys | Tyr | Glu | Cys | Met | Ser | Asn | Pro | Asn | Val | Pro |
|-----|-----|-----|-----|-----|-----|-----|-----|-----|-----|-----|-----|-----|-----|-----|
| 1400 |     |     |     |     | 1405 |     |     |     |     | 1410 |     |     |     |     |

| Arg | His | Gln | His | Pro | Leu | Lys | Pro | Ile | Pro | Val | Gly | Ser | Gln | Gln |
|-----|-----|-----|-----|-----|-----|-----|-----|-----|-----|-----|-----|-----|-----|-----|
| 1415 |     |     |     |     | 1420 |     |     |     |     | 1425 |     |     |     |     |

| Ser | Ser | Leu | Thr | Pro | Glu | Gln | Arg | Lys | Glu | Arg | Gln | Arg | Ser | Ile |
|-----|-----|-----|-----|-----|-----|-----|-----|-----|-----|-----|-----|-----|-----|-----|
| 1430 |     |     |     |     | 1435 |     |     |     |     | 1440 |     |     |     |     |

| Gln | Leu | His | Met | Thr | Leu | Leu | Leu | His | Ala | Ala | Thr | Cys | Lys | Ser |
|-----|-----|-----|-----|-----|-----|-----|-----|-----|-----|-----|-----|-----|-----|-----|
| 1445 |     |     |     |     | 1450 |     |     |     |     | 1455 |     |     |     |     |

| Ser | Lys | Cys | Ala | Ser | Ala | Asn | Cys | Ala | Lys | Met | Lys | Gly | Leu | Leu |
|-----|-----|-----|-----|-----|-----|-----|-----|-----|-----|-----|-----|-----|-----|-----|
| 1460 |     |     |     |     | 1465 |     |     |     |     | 1470 |     |     |     |     |

| Lys | His | Gly | Ser | Gln | Cys | Gln | Ile | Lys | Ala | Ala | Gly | Gly | Cys | His |
|-----|-----|-----|-----|-----|-----|-----|-----|-----|-----|-----|-----|-----|-----|-----|
| 1475 |     |     |     |     | 1480 |     |     |     |     | 1485 |     |     |     |     |

| Val | Cys | Lys | Arg | Ile | Trp | Ala | Leu | Leu | Gln | Ile | His | Ala | Arg | Gln |
|-----|-----|-----|-----|-----|-----|-----|-----|-----|-----|-----|-----|-----|-----|-----|
| 1490 |     |     |     |     | 1495 |     |     |     |     | 1500 |     |     |     |     |

| Cys | Lys | Gln | Asp | Asn | Cys | Pro | Val | Pro | Asn | Cys | Leu | Ala | Ile | Arg |
|-----|-----|-----|-----|-----|-----|-----|-----|-----|-----|-----|-----|-----|-----|-----|
| 1505 |     |     |     |     | 1510 |     |     |     |     | 1515 |     |     |     |     |

| Glu | Arg | Phe | Arg | Gln | Leu | Asn | Leu | Gln | Gln | Ala | Met | Asp | Asp |     |
|-----|-----|-----|-----|-----|-----|-----|-----|-----|-----|-----|-----|-----|-----|-----|
| 1520 |     |     |     |     | 1525 |     |     |     |     | 1530 |     |     |     |     |

| Arg | Arg | Arg | Gln | Met | Met | Asn | Gln | Thr | Tyr | His | Gln | Gln | Ala | Arg |
|-----|-----|-----|-----|-----|-----|-----|-----|-----|-----|-----|-----|-----|-----|-----|
| 1535 |     |     |     |     | 1540 |     |     |     |     | 1545 |     |     |     |     |

<210> SEQ ID NO 17
<211> LENGTH: 5346
<212> TYPE: DNA
<213> ORGANISM: Cyclotella sp.
<220> FEATURE:
<221> NAME/KEY: misc_feature
<223> OTHER INFORMATION: encodes polypeptide of SEQ ID NO:18

<400> SEQUENCE: 17

| atgagtccct acgagggaac cacgacgacc caacagccgt cctcgtcgtc tggttcttcc | 60 |
| cgccctcctc cccagggcaa catgcccaa atgccaccta acatggccgg cctctccggt | 120 |
| gtggggggcc ctcaacacca tcccggaatg gggaaccttct acggattcca acagcatcgg | 180 |
| ggaagcgcga gccagcagcc tcccatgaac atgatgatgg gcggggacaa cgtaggcaac | 240 |

```
ggcagcatgg gggcaggcgg gtttatgcag ccccccctcca acgtcagagg tgggggatg      300
caccccaacc atcccatgaa tatggggggg cagtttcaca acggcccgg gcacatgtcc       360
gggcagaatc ctatgtataa tcatggaaat tttaatggac agcagcagaa tcaaatgcag      420
catccctaca ataatcctca tgggggcaa cagtctcaac agcaacagcc gcagcatggg       480
ggatataatc accaccaagc tcagatgcag cataatatgc aacaacatct gcagcaacag      540
caacatggcg gaaatgtagg caacaatggg atggggcata gttcgcaata tcaaaatcac      600
cccatgcaac ggcaacattc aagtcatcag cataattatc attcgcaaca gcagctgcag      660
cagcagcagc agatgcaaca cgcccagcaa caaatgcaac accccaccca acaacaacaa      720
ggctacccctt ccaacaatta ccaccgtcaa ccttcgtcta ctcaccactc acattccaac     780
tctccctcca ccccgaatcc ccatgacgcc aatgatggag ggctactgtc ctacaaacaa      840
ccgcctaatt tttcggaagt catgggtttg gactttgagt tgggagagta tggtcaacag      900
tttttgccaa cgggattgaa tggggactgg cagagtgatc gggatatgac acataggaga      960
gagatgattc agcatattgt gaaacttctt aagcaaaagg acaagaatgc atctcctgag      1020
tggctaacca agttaccca aatggtaaaa caactcgaag tatcgctata ccgttctgcg      1080
ccgtcgttcg aatcctattc ggacatatcg acccttaaac atcgcttaca acaacttgct     1140
atggaaatcg cgagaaaaac ccagcaggcc aaagagagta gtggaaggtc atccaaatca     1200
cgctctgatc gcagagatcg tcttccctcc tcgtccgccg cccccaagc tccatctatc      1260
tccacccaaa accatgtcat gggtgggatg cgcttccaca gcaccaacga acgaagaggg     1320
ggcgacgacg gagaagatca catcagttcc cagcacggca atccaaacga tcctgaatgg     1380
aagattcgaa tccgtcacaa gcagcagcgc cttctcctcc ttcaccactc ctccaaatgc     1440
ccgtacgatg atggcaaatg caaggtcacc ccgtattgct ccgagatgaa gaagttgtgg     1500
aagcacatgg ctcgttgcat cgacaatgaa tgtcgagtgc cgcactgctt ttcaagtcga     1560
tctatattaa gccattaccg aaaatgcaag gatccgcgtt gtccagcgtg cggcccagtc     1620
agggaaacgg ttcgcaagac actgaagagc agctcgcaaa gaaggcctaa tgggatgccg     1680
ggcgagggac ctcattctgg cggagggcat gattcgatga atatgggtat aggttttgggt    1740
ggattgggta atgtcgaatt ggggcagggc gatcagccaa tgaataatag tatgatccca     1800
atgtctcgtg ggaacagtgg tagtgatagg aatcaagtga tgttcagga atgcagcag      1860
cagggaatgc aggaggcgaa ttcgcccatg ccttggtcgg gagaagttgc aagcatgccg     1920
tacaatgctc cactatcggg aagtaatggg ggtggaagac tatcatctca aggcggtaat     1980
gatgctttcc ccgaatctct ggtaaatagc aacggagcac aaaatggggc ttcgggagcg     2040
caaagggaag tcgcgatgc tgaatcgagc aagtcgaaac acaagcagca gcgtcttctc      2100
cttctcaggc atgcttccaa gtgtactgct ccctcgggaa gttgcactgt taccccacat     2160
tgcgccgaga tgaaagttct gtggaggcat attgcgaact gcaaagagcc tcagtgcaaa     2220
ataaaacact gtatgagcag ccgatacgtt ctcagtcact accgtagatg cagggatcct     2280
tattgtgaca tttgtgctcc agtgagggaa acgattaaga atggcaccgc tacctacatc     2340
catgacccaa catttaatcc gacggggag aacgcgacgc ccccccctgc taacactgaa       2400
ggccctcaaa cgaagaagca gaagactaca cacgactcga gcacaatgga cagcatgccg     2460
cctcctcaag accgaccggc tattcctgca gcgggaattt catcgtcttc cgatccgcat      2520
tcggcatcta cctctccgca tgttcccact tcggggggagg aaaacagagc taagtcgaag    2580
```

```
ccagacccaa cgaaatcagc aggaaaggga gcgtcttcct ccagctcatc ggaagaccat   2640
tctctcttgg agtgcttcac aacacagcaa gttaagactc acatcgagtc gttaaaaaag   2700
actgtccaag ttccaccggc taaattgaag ctcaagtgct tggaggtgtt gcgtgggctt   2760
caaacgcacg agcatgggtg ggtttttgcc accccgttg atcctgtcga acttggacta    2820
gcagattact ttgacatcat caaaaagcca atggatcttg aactatcca gaagaagctc    2880 gaagcaggat cctaccattc gtttggagaa ttcaagtccg atgtacgtct tacgtttgag   2940
aacgccatga atacaacga agaaaggaca gttgtgcatg aaatggctaa agagctcaag    3000
aagaagttcg acgttgacta caaaaagctc atcaagcaat tggaaaaaga gcatcaagag   3060
gactcaaaaa aggcacaggc ttgtgggctt tgcggttgcg agaagctcaa ttttgaaccc   3120
ccggtcttct tctgcaatgg cctcaactgt cctagtaaac gaatccgtcg caacacacac   3180
ttttacatca cctccgacaa gcaatatgct tggtgcaacc aatgctttaa tgagttgggc   3240
aatgaaattg accttggaac gtctaaactg aaaaaggtag agctgactaa acgcaagaac   3300
gacgaaaccc acgaagaaag ctgggttcaa tgtgacgact gcgagcgttg gattcaccaa   3360
atatgtggtc tttacaacac tcgccaggat aaagagaaca aaagcgccta ttcatgtcct   3420
ctctgtcttt acgaaagag aaagaaggac ggagatccaa aagagttgcc gaaggctccg     3480
tctgccaatg atattcctag acaaagctg tcggattggt tggaaaagga tgtcctgagg     3540
agagtgaatg atcgcctcaa cgagattgcg aaagagaaat ctgaaactga aacacatca    3600 cttgagaaag cctacaaaga ggtcgcttct ggcgggccgt tgattattcg acaagttacg   3660
tctaccgaca ggaagctgga agtgcgagaa cgaatgaaag cccgatatgc ccacaaaaac   3720
tatccagagg aattcccta ccgttgtaaa tgcattgttg tcttccagaa tatagacggt     3780
gtcgacgttc tgctctttgc tctgtatgta tatgagcatg gcgatgataa tccttttccct   3840 aacaaaaaga ctgtctacgt gtcttatctt gacagtgttc acttcatgaa gccaaggaaa    3900
gttaggacct tcatttatca tgaaattttg atatccatc tggactatgt gaggagaaag     3960
ggttatcacc aagccttcat ctgggcatgt cccccgctaa aaggcgatga ctacatcttc    4020
tacgcaaagc cagaagatca aaaaactccc aaagatgtta ggcttcgcca gtggtaccttt   4080 gacatgcttg cagaatgcca gagacgggat atcgtgggca agtctccaa tatgtacgac    4140 caatattttg ccaacaagaa gttggacgct gcatccgtgc cttactttga gggcgattat   4200
ttccctggag aagctgagaa cattatcaaa cttcttgaag aaggggatgg caaacgaaag    4260
agtgcatcag ggaagaaaaa gaaggactca tctaagagcc aacgctcaag cagtagtgga   4320
tgcgaagaag gggatagtga tgacaaggca tataaggagg gcggccgaga tcctgtcatg    4380
cagaagtttt gcgacgccat ccagggaatg aaagaaagtt tcatcgttgc attcctcaat    4440
tgtgagggtg ccgacccaga aaatctagtc gttcccaaag atcatggaa atatcgcgaa    4500 gcgaagttga agtctattga aggtgacaac caacgtgatg ataattgtca gaccagaaag   4560
cgtgatgcgg acgggaacga acttcagaaa tcggaagacc aggtggacag gaaaggacgt   4620
cccattaaag tgttggacga tgatgcagaa gaaattgact gtgaattttt taacactcgc    4680
caatgcttcc tggatctctg tcagggaac cactaccaat tcgatgagct aaggcgagca    4740
aagcacacat ccatgatggt tctttggcat cttcaaaatc gcgaagcacc caaatttgtg    4800
caacaatgct tttcgtgcaa tcgtgagatt gtctcaggta ttcgacacca ttgcaatgtt    4860
tgctctgact tcgatctatg tgacgagtgt ttccgaagtc cagatgccaa caggggaagt    4920
tgtaaccaca aacttgaagt gatcaaagtt gatacatcgc agagtggatc cagtggactt    4980
```

-continued

```
acggaggagc aacgtagaga acgtcagaga acattcaac tccatataac acttattgaa    5040
catgcatctc gttgtgtttc gtcaacgtgc aagtcctcga attgtcagaa aatgaagtct    5100
tacctcaagc acggagagac ttgcaaaatt aaagcatctg gtggatgcaa gatttgcaaa    5160
cgaatttgga ctttgctgcg aattcatgct caacaatgca agaacaataa ttgtcccata    5220
cctcagtgta ttgcaattaa gaagcgtctg cgtcagctac agcaaaagca acaagctatg    5280
gatgaccgca gacggcagga aatgaatagg cattatagga tgggtatgat gggtgataac    5340
aattga                                                               5346
```

<210> SEQ ID NO 18
<211> LENGTH: 1781
<212> TYPE: PRT
<213> ORGANISM: Cyclotella sp.
<220> FEATURE:
<221> NAME/KEY: misc_feature
<223> OTHER INFORMATION: translation product 5092336

<400> SEQUENCE: 18

```
Met Ser Pro Tyr Glu Gly Thr Thr Thr Gln Gln Pro Ser Ser Ser
1               5                  10                  15

Ser Gly Ser Ser Arg Pro Pro Pro Gln Gly Asn Met Pro Gln Met Pro
            20                  25                  30

Pro Asn Met Ala Gly Leu Ser Gly Val Gly Gly Pro Gln His His Pro
        35                  40                  45

Gly Met Gly Asn Leu Tyr Gly Phe Gln Gln His Arg Gly Ser Ala Ser
    50                  55                  60

Gln Gln Pro Pro Met Asn Met Met Met Gly Gly Asp Asn Val Gly Asn
65                  70                  75                  80

Gly Ser Met Gly Ala Gly Gly Phe Met Gln Pro Pro Ser Asn Val Arg
                85                  90                  95

Gly Gly Gly Met His Pro Asn His Pro Met Asn Met Gly Gly Gln Phe
            100                 105                 110

His Asn Gly Pro Gly His Met Ser Gly Gln Asn Pro Met Tyr Asn His
        115                 120                 125

Gly Asn Phe Asn Gly Gln Gln Gln Asn Gln Met Gln His Pro Tyr Asn
    130                 135                 140

Asn Pro His Gly Gly Gln Gln Ser Gln Gln Gln Pro Gln His Gly
145                 150                 155                 160

Gly Tyr Asn His His Gln Ala Gln Met Gln His Asn Met Gln His
                165                 170                 175

Leu Gln Gln Gln Gln His Gly Gly Asn Val Gly Asn Asn Gly Met Gly
            180                 185                 190

His Ser Ser Gln Tyr Gln Asn His Pro Met Gln Arg Gln His Ser Ser
        195                 200                 205

His Gln His Asn Tyr His Ser Gln Gln Gln Leu Gln Gln Gln Gln
    210                 215                 220

Met Gln His Ala Gln Gln Gln Met Gln His Pro Thr Gln Gln Gln
225                 230                 235                 240

Gly Tyr Pro Ser Asn Asn Tyr His Arg Gln Pro Ser Thr His His
                245                 250                 255

Ser His Ser Asn Ser Pro Ser Thr Pro Asn Pro His Asp Ala Asn Asp
            260                 265                 270

Gly Gly Leu Leu Ser Tyr Lys Gln Pro Pro Asn Phe Ser Glu Val Met
        275                 280                 285
```

```
Gly Leu Asp Phe Glu Leu Gly Glu Tyr Gly Gln Gln Phe Leu Pro Thr
    290                 295                 300
Gly Leu Asn Gly Asp Trp Gln Ser Asp Arg Asp Met Thr His Arg Arg
305                 310                 315                 320
Glu Met Ile Gln His Ile Val Lys Leu Leu Lys Gln Lys Asp Lys Asn
                325                 330                 335
Ala Ser Pro Glu Trp Leu Thr Lys Leu Pro Gln Met Val Lys Gln Leu
            340                 345                 350
Glu Val Ser Leu Tyr Arg Ser Ala Pro Ser Phe Glu Ser Tyr Ser Asp
        355                 360                 365
Ile Ser Thr Leu Lys His Arg Leu Gln Gln Leu Ala Met Glu Ile Ala
    370                 375                 380
Arg Lys Thr Gln Gln Ala Lys Glu Ser Ser Gly Arg Ser Ser Lys Ser
385                 390                 395                 400
Arg Ser Asp Arg Arg Asp Arg Leu Pro Ser Ser Ala Ala Pro Gln
                405                 410                 415
Ala Pro Ser Ile Ser Thr Gln Asn His Val Met Gly Met Arg Phe
            420                 425                 430
His Ser Thr Asn Glu Arg Arg Gly Gly Asp Asp Gly Glu Asp His Ile
        435                 440                 445
Ser Ser Gln His Gly Asn Pro Asn Asp Pro Glu Trp Lys Ile Arg Ile
    450                 455                 460
Arg His Lys Gln Gln Arg Leu Leu Leu Leu His His Ser Ser Lys Cys
465                 470                 475                 480
Pro Tyr Asp Asp Gly Lys Cys Lys Val Thr Pro Tyr Cys Ser Glu Met
                485                 490                 495
Lys Lys Leu Trp Lys His Met Ala Arg Cys Ile Asp Asn Glu Cys Arg
            500                 505                 510
Val Pro His Cys Phe Ser Ser Arg Ser Ile Leu Ser His Tyr Arg Lys
        515                 520                 525
Cys Lys Asp Pro Arg Cys Pro Ala Cys Gly Pro Val Arg Glu Thr Val
    530                 535                 540
Arg Lys Thr Leu Lys Ser Ser Gln Arg Arg Pro Asn Gly Met Pro
545                 550                 555                 560
Gly Glu Gly Pro His Ser Gly Gly His Asp Ser Met Asn Met Gly
                565                 570                 575
Ile Gly Leu Gly Gly Leu Gly Asn Val Glu Leu Gly Gln Gly Asp Gln
            580                 585                 590
Pro Met Asn Asn Ser Met Ile Pro Met Ser Arg Gly Asn Ser Gly Ser
        595                 600                 605
Asp Arg Asn Gln Val Met Leu Gln Glu Met Gln Gln Gly Met Gln
    610                 615                 620
Glu Ala Asn Ser Pro Met Pro Trp Ser Gly Glu Val Ala Ser Met Pro
625                 630                 635                 640
Tyr Asn Ala Pro Leu Ser Gly Ser Asn Gly Gly Arg Leu Ser Ser
                645                 650                 655
Gln Gly Gly Asn Asp Ala Phe Pro Glu Ser Leu Val Asn Ser Asn Gly
            660                 665                 670
Ala Gln Asn Gly Ala Ser Gly Ala Gln Arg Glu Gly Arg Asp Ala Glu
        675                 680                 685
Ser Ser Lys Ser Lys His Lys Gln Gln Arg Leu Leu Leu Leu Arg His
    690                 695                 700
```

-continued

```
Ala Ser Lys Cys Thr Ala Pro Ser Gly Ser Cys Thr Val Thr Pro His
705                 710                 715                 720

Cys Ala Glu Met Lys Val Leu Trp Arg His Ile Ala Asn Cys Lys Glu
            725                 730                 735

Pro Gln Cys Lys Ile Lys His Cys Met Ser Ser Arg Tyr Val Leu Ser
        740                 745                 750

His Tyr Arg Arg Cys Arg Asp Pro Tyr Cys Asp Ile Cys Ala Pro Val
    755                 760                 765

Arg Glu Thr Ile Lys Asn Gly Thr Ala Thr Tyr Ile His Asp Pro Thr
770                 775                 780

Phe Asn Pro Thr Gly Glu Asn Ala Thr Pro Pro Ala Asn Thr Glu
785                 790                 795                 800

Gly Pro Gln Thr Lys Lys Gln Lys Thr Thr His Asp Ser Ser Thr Met
                805                 810                 815

Asp Ser Met Pro Pro Gln Asp Arg Pro Ala Ile Pro Ala Ala Gly
                820                 825                 830

Ile Ser Ser Ser Ser Asp Pro His Ser Ala Ser Thr Ser Pro His Val
                835                 840                 845

Pro Thr Ser Gly Glu Glu Asn Arg Ala Lys Ser Lys Pro Asp Pro Thr
850                 855                 860

Lys Ser Ala Gly Lys Gly Ala Ser Ser Ser Ser Ser Glu Asp His
865                 870                 875                 880

Ser Leu Leu Glu Cys Phe Thr Thr Gln Gln Val Lys Thr His Ile Glu
                885                 890                 895

Ser Leu Lys Lys Thr Val Gln Val Pro Pro Ala Lys Leu Lys Leu Lys
                900                 905                 910

Cys Leu Glu Val Leu Arg Gly Leu Gln Thr His Glu His Gly Trp Val
                915                 920                 925

Phe Ala Thr Pro Val Asp Pro Val Glu Leu Gly Leu Ala Asp Tyr Phe
                930                 935                 940

Asp Ile Ile Lys Lys Pro Met Asp Leu Gly Thr Ile Gln Lys Lys Leu
945                 950                 955                 960

Glu Ala Gly Ser Tyr His Ser Phe Gly Glu Phe Lys Ser Asp Val Arg
                965                 970                 975

Leu Thr Phe Glu Asn Ala Met Lys Tyr Asn Glu Glu Arg Thr Val Val
                980                 985                 990

His Glu Met Ala Lys Glu Leu Lys Lys Lys Phe Asp Val Asp Tyr Lys
            995                 1000                1005

Lys Leu Ile Lys Gln Leu Glu Lys Glu His Gln Glu Asp Ser Lys
    1010                1015                1020

Lys Ala Gln Ala Cys Gly Leu Cys Gly Cys Glu Lys Leu Asn Phe
    1025                1030                1035

Glu Pro Pro Val Phe Phe Cys Asn Gly Leu Asn Cys Pro Ser Lys
    1040                1045                1050

Arg Ile Arg Arg Asn Thr His Phe Tyr Ile Thr Ser Asp Lys Gln
    1055                1060                1065

Tyr Ala Trp Cys Asn Gln Cys Phe Asn Glu Leu Gly Asn Glu Ile
    1070                1075                1080

Asp Leu Gly Thr Ser Lys Leu Lys Lys Val Glu Leu Thr Lys Arg
    1085                1090                1095

Lys Asn Asp Glu Thr His Glu Ser Trp Val Gln Cys Asp Asp
    1100                1105                1110

Cys Glu Arg Trp Ile His Gln Ile Cys Gly Leu Tyr Asn Thr Arg
```

```
                1115                1120                1125

Gln Asp Lys Glu Asn Lys Ser Ala Tyr Ser Cys Pro Leu Cys Leu
                1130                1135                1140

Tyr Glu Lys Arg Lys Lys Asp Gly Asp Pro Lys Glu Leu Pro Lys
                1145                1150                1155

Ala Pro Ser Ala Asn Asp Ile Pro Arg Thr Lys Leu Ser Asp Trp
                1160                1165                1170

Leu Glu Lys Asp Val Leu Arg Arg Val Asn Asp Arg Leu Asn Glu
                1175                1180                1185

Ile Ala Lys Glu Lys Ser Glu Thr Glu Asn Thr Ser Leu Glu Lys
                1190                1195                1200

Ala Tyr Lys Glu Val Ala Ser Gly Gly Pro Leu Ile Ile Arg Gln
                1205                1210                1215

Val Thr Ser Thr Asp Arg Lys Leu Glu Val Arg Glu Arg Met Lys
                1220                1225                1230

Ala Arg Tyr Ala His Lys Asn Tyr Pro Glu Glu Phe Pro Tyr Arg
                1235                1240                1245

Cys Lys Cys Ile Val Val Phe Gln Asn Ile Asp Gly Val Asp Val
                1250                1255                1260

Leu Leu Phe Ala Leu Tyr Val Tyr Glu His Gly Asp Asp Asn Pro
                1265                1270                1275

Phe Pro Asn Lys Lys Thr Val Tyr Val Ser Tyr Leu Asp Ser Val
                1280                1285                1290

His Phe Met Lys Pro Arg Lys Val Arg Thr Phe Ile Tyr His Glu
                1295                1300                1305

Ile Leu Ile Ser Tyr Leu Asp Tyr Val Arg Arg Lys Gly Tyr His
                1310                1315                1320

Gln Ala Phe Ile Trp Ala Cys Pro Pro Leu Lys Gly Asp Asp Tyr
                1325                1330                1335

Ile Phe Tyr Ala Lys Pro Glu Asp Gln Lys Thr Pro Lys Asp Val
                1340                1345                1350

Arg Leu Arg Gln Trp Tyr Leu Asp Met Leu Ala Glu Cys Gln Arg
                1355                1360                1365

Arg Asp Ile Val Gly Lys Val Ser Asn Met Tyr Asp Gln Tyr Phe
                1370                1375                1380

Ala Asn Lys Lys Leu Asp Ala Ala Ser Val Pro Tyr Phe Glu Gly
                1385                1390                1395

Asp Tyr Phe Pro Gly Glu Ala Glu Asn Ile Ile Lys Leu Leu Glu
                1400                1405                1410

Glu Gly Asp Gly Lys Arg Lys Ser Ala Ser Gly Lys Lys Lys Lys
                1415                1420                1425

Asp Ser Ser Lys Ser Gln Arg Ser Ser Ser Gly Cys Glu Glu
                1430                1435                1440

Gly Asp Ser Asp Asp Lys Ala Tyr Lys Glu Gly Arg Asp Pro
                1445                1450                1455

Val Met Gln Lys Phe Cys Asp Ala Ile Gln Gly Met Lys Glu Ser
                1460                1465                1470

Phe Ile Val Ala Phe Leu Asn Cys Glu Gly Ala Asp Pro Glu Asn
                1475                1480                1485

Leu Val Val Pro Lys Glu Ile Met Glu Tyr Arg Glu Ala Lys Leu
                1490                1495                1500

Lys Ser Ile Glu Gly Asp Asn Gln Arg Asp Asp Asn Cys Gln Thr
                1505                1510                1515
```

Arg Lys Arg Asp Ala Asp Gly Asn Glu Leu Gln Lys Ser Glu Asp
1520             1525                 1530

Gln Val Asp Arg Lys Gly Arg Pro Ile Lys Val Leu Asp Asp Asp
1535             1540                 1545

Ala Glu Glu Ile Asp Cys Glu Phe Phe Asn Thr Arg Gln Cys Phe
1550             1555                 1560

Leu Asp Leu Cys Arg Gly Asn His Tyr Gln Phe Asp Glu Leu Arg
1565             1570                 1575

Arg Ala Lys His Thr Ser Met Met Val Leu Trp His Leu Gln Asn
1580             1585                 1590

Arg Glu Ala Pro Lys Phe Val Gln Gln Cys Phe Ser Cys Asn Arg
1595             1600                 1605

Glu Ile Val Ser Gly Ile Arg His His Cys Asn Val Cys Ser Asp
1610             1615                 1620

Phe Asp Leu Cys Asp Glu Cys Phe Arg Ser Pro Asp Ala Asn Arg
1625             1630                 1635

Gly Ser Cys Asn His Lys Leu Glu Val Ile Lys Val Asp Thr Ser
1640             1645                 1650

Gln Ser Gly Ser Ser Gly Leu Thr Glu Glu Gln Arg Arg Glu Arg
1655             1660                 1665

Gln Arg Asn Ile Gln Leu His Ile Thr Leu Ile Glu His Ala Ser
1670             1675                 1680

Arg Cys Val Ser Ser Thr Cys Lys Ser Ser Asn Cys Gln Lys Met
1685             1690                 1695

Lys Ser Tyr Leu Lys His Gly Glu Thr Cys Lys Ile Lys Ala Ser
1700             1705                 1710

Gly Gly Cys Lys Ile Cys Lys Arg Ile Trp Thr Leu Leu Arg Ile
1715             1720                 1725

His Ala Gln Gln Cys Lys Asn Asn Asn Cys Pro Ile Pro Gln Cys
1730             1735                 1740

Ile Ala Ile Lys Lys Arg Leu Arg Gln Leu Gln Gln Lys Gln Gln
1745             1750                 1755

Ala Met Asp Asp Arg Arg Arg Gln Glu Met Asn Arg His Tyr Arg
1760             1765                 1770

Met Gly Met Met Gly Asp Asn Asn
1775             1780

<210> SEQ ID NO 19
<211> LENGTH: 4290
<212> TYPE: DNA
<213> ORGANISM: Fragilariopsis cylindrus
<220> FEATURE:
<221> NAME/KEY: misc_feature
<223> OTHER INFORMATION: encodes polypeptide of SEQ ID NO:20

<400> SEQUENCE: 19
atgggtagtc attccatgag caattcgatg gggaactcga tgaatggaat ggggaataca      60
atgaacaaca acaattctat gaacggtacg aacaccatga actcgtcgat gaataactct     120
atgagtaata atactatgaa tgctcctatg ggaggcaact cgatgaataa catgggtgga     180
aactcgacga acggaccaac taacaatggt gcgagttctt ctcgaggcaa taatgtgatg     240
aatccaagcg gtcgcaatag cgttagcaac agcgctagtg gtagtgttaa tggcagcgct     300
agtggtaatg gtagtggtag tggtagtggt acttctggat tgaatggaaa ctggcaaaca     360
gatagagata cacccccatag acgagaaatg attcagcaca tcgtaaaaat gctaaaaaaa     420

```
gataagactg gttccccgga atggcttagc aagctgccac aaatggctaa gcagctagag    480
gtatctcttt atcgaaacgc acgatctttt gacgcatatg tcgacatgaa tacactgaaa    540
cagcgcttac agcagattgc agtacaggta tctcagaaag cacgaggtca agaccatgga    600
cggcgtgatc ggcacagaga ttcacaacaa aattctaatg gaatacgtca agacgggagt    660
tcttcatcat acacaggcaa caacccgtcg aatcggaccg ataggaacag cacaataaat    720
aataacaacc cctctagtgg catgtcgaat gtatctacat tgccaatatc ttcaggagga    780
tatcaacaac gatcgatgag caacaccgcc tcatcaaatg ctggcacgca acaacagcag    840
cagcagcaat caagtatgcc accccttca acaaatggtg gttcggctaa tggtctgacg     900
ggatctgatt ttacgtcacc tgcactatcc cctacaggtg aagtcaaaa tcccaacaac     960
acctcattac catcgtcatc atctagaagg aacgactccg aatggcaaaa ggttcgtcac   1020
aaacagcaac gacttttgtt gctgaggcac gcctctcgtt gtcagcataa gggaacgaaa   1080
tgccctgtta cccctcattg tgcaagtatg aaaaaacttt gggaacacat tgctcactgt   1140
aaggatcaac attgtagtgt tgcgcattgt atgagcagtc gatacgtcct tagtcactat   1200
agaagatgca aggacccacg ctgtccagca tgtgggcctg tccgcgaaac tattcgaaaa   1260
agtcacgagc gagagcaaca gcaaggcaat cgccagccaa cgtcatctag ttcgactccc   1320
tttgataccg aagtacccgg accaagtagc tctcctgatg ctttgccagc cacgaaacgt   1380
cccagaatag atccaaatgc tagtaatatg ccccccaccaa atcctacaga cggacaacct   1440
aatcaaccgc tttctgcccc ctctgatgtt atagcaccac cgacaaattc caacgaaaag   1500
gtttcgaaac caccttcccc tacaccttct tcttcagcga ataaaggctc cgaagatcga   1560
tcgttgctgg atagtttcac tcttgatcag attgcattgc atcttgcatc tttgaatcga   1620
gcggccgacc tacccccgc gaaactaaaa caaaaatgcc tagaagtcct gaaggggttg    1680
caagctcacc aacatggatg ggtatttaac gtaccagttg atccagtaga actaggttta   1740
cctgactatt ttgaacttat caaaaagccg atggatcttg gaagtgtcca aaaaaaactt   1800
gaaaaaggcg aatatcacgc catcaaggat ttccaatcag acgtgaattt aagctttgag   1860
aacgccatga catacaacga acaaggttca gtggtttacg acatggccaa ggaactgaag   1920
actaagtttg agggcgattt caagaaatta gaacaacagc tggaatctga agatcgcgag   1980
agacgagaaa atgatagagc ttgtgtcctt tgcggatgcg agaaacgtct attcgaaccc   2040
ccagtattct tctgcaacgg tataaattgc gcgagtaaac gaattcgacg taatagtcac   2100
ttttacatcg gcgaaaacaa ccaatatttt tggtgtaacc agtgctacgg tgagcttgag   2160
gagaaatcac caatcgagtt gatcgacctg actgttaaaa agactgattt gaagaagaaa   2220
aagaatgacg aaattgtcga agagagttgg gtgcagtgcg atatttgcga agatggatt    2280
catcaaattt gcgggctttt caacacaaga cagaacaaag agcatcacag cgaatattgc   2340
tgccctttat gtctgttaga aaacgtaaa aagaaccctg taacaccgcc accgcgaccg    2400
gcggggcaa cagaattacc aaggacgaaa ttatctgaat ttatagagaa tcacgttagg    2460
aaaaaaatag aaaagagacg acgtaatgtg gcggaagaaa agtgtcgtat tgagaatatt   2520
tcaatggatg atgcgctgaa agacgctcgg gaaggaggta atgtgatcat acgtcaggtc   2580
acgtcaatgg ataggaaatt ggaagtgcgg gaaggaataa agaatagata cgctcataag   2640
aattatcctg atgagttttc gtttcgatgt aaatgtcttc tagtattcca ggaaattgat   2700
ggtgttgatg tggttctgtt tgctctttac ttatacgagc acggcgagga tagcccacgt   2760
```

```
ccaaataccc gttctatata tatatcttat ctcgacagtg tgcattatat gaggcctcga   2820
aaacttcgaa cctttgttta ccatgaaatt ctgatttctt actgtgatta tgctcgacag   2880
agggggtttg caacagttca tatctgggca tgcccaccgt taaagggtga tgactacatt   2940
ttctatgcaa agcctgaaga tcagaagact ccgagggatt caaggttgag acaatggtac   3000
attgatatgc ttgttgaatg ccagaatcgt ggcatagtcg gaagactgac caatatgtat   3060
gatttgtact ttgcgaacgc atctatcgat gctacggctg tgccttacca cgaaggcgat   3120
tacttccctg gagaagccga gaatatcatc aagatgcttg atgacgaggg aggaaaaaag   3180
aatggaagca gtgggaagaa gaagaaacag aagaaccaaa gcaagtcaaa gaaccgaggc   3240
gggactcgat cgacaggagt tgacgaggaa gcattacttg caagtggcat gatggatgga   3300
gtgaagaatt atgaagagtt ggatcgagat caagtaatgg tcaagttagg cgaagctatt   3360
caaccgatga aggagagttt tcttgttgct tttctgactt ggtctggtat caaggaagaa   3420
gacttagagg tgcctgaagc tatagcgaag tatcgagaag agcaccccga aaatgttgta   3480
cctttaccat cgggtaataa gcgtaatgcc gacggtcaaa cgaaagatga agttgtaccg   3540
ctggacgcag atggacaccc actaaaagtc ctagacgatg acgcggaaga tcttgactgc   3600
gagttcttaa ataatcgcca agctttcctt aacttatgtc gtggaaacca ctatcaattt   3660
gacgagttac gtcgtgctaa acacacatca atgatggtat tgtggcatct tcagaaccgt   3720
gacgctccta aatatgtaca gcagtgtgtt tcttgtagcc gcgaaattct tagtggaaag   3780
cgctatcatt gtaattcctg tccagactat gatctttgcg agacatgtta caaagacccg   3840
aagaccaatc gtggcacgtg tacacacaag cttcaagaaa ttaaggttga atccgaaggg   3900
caatctgatt caagtggatt gacagagact cagagaaagc agcgtcaacg caacttgatg   3960
ctgcacatcc aattaatcga acatgcttca agatgcacgt cgtcaacttg tcaatcaaag   4020
aactgtgcga agatgaaaga gtatctacag cacgcacgca cttgcaagac aaaagttgta   4080
ggtggatgca gaatatgcaa acgaatttgg acccttcttc ggatccatgc gcagaaatgt   4140
aaggaaccgg tttgtcctat cccgcaatgt atgattatta gagaaaagat gcgtgaacta   4200
cagaagcaac agcaagctat ggatgatcga cgtcgtcaag aaatgaatcg acattacggc   4260
cgaatgagca tgaccagcgg atcaggttaa                                    4290
```

<210> SEQ ID NO 20
<211> LENGTH: 1429
<212> TYPE: PRT
<213> ORGANISM: Fragilariopsis cylindrus

<400> SEQUENCE: 20

```
Met Gly Ser His Ser Met Ser Asn Ser Met Gly Asn Ser Met Asn Gly
1               5                   10                  15

Met Gly Asn Thr Met Asn Asn Asn Asn Ser Met Asn Gly Thr Asn Thr
            20                  25                  30

Met Asn Ser Ser Met Asn Asn Ser Met Ser Asn Asn Thr Met Asn Ala
        35                  40                  45

Pro Met Gly Gly Asn Ser Met Asn Asn Met Gly Gly Asn Ser Thr Asn
    50                  55                  60

Gly Pro Thr Asn Asn Gly Ala Ser Ser Ser Arg Gly Asn Asn Val Met
65                  70                  75                  80

Asn Pro Ser Gly Arg Asn Ser Val Ser Asn Ser Ala Ser Gly Ser Val
                85                  90                  95

Asn Gly Ser Ala Ser Gly Asn Gly Ser Gly Ser Gly Ser Gly Thr Ser
```

```
            100                 105                 110
Gly Leu Asn Gly Asn Trp Gln Thr Asp Arg Asp Thr Pro His Arg Arg
        115                 120                 125

Glu Met Ile Gln His Ile Val Lys Met Leu Lys Lys Asp Lys Thr Gly
        130                 135                 140

Ser Pro Glu Trp Leu Ser Lys Leu Pro Gln Met Ala Lys Gln Leu Glu
145                 150                 155                 160

Val Ser Leu Tyr Arg Asn Ala Arg Ser Phe Asp Ala Tyr Val Asp Met
                165                 170                 175

Asn Thr Leu Lys Gln Arg Leu Gln Gln Ile Ala Val Gln Val Ser Gln
                180                 185                 190

Lys Ala Arg Gly Gln Asp His Gly Arg Arg Asp Arg His Arg Asp Ser
                195                 200                 205

Gln Gln Asn Ser Asn Gly Ile Arg Gln Asp Gly Ser Ser Ser Ser Tyr
        210                 215                 220

Thr Gly Asn Asn Pro Ser Asn Arg Thr Asp Arg Asn Ser Thr Ile Asn
225                 230                 235                 240

Asn Asn Asn Pro Ser Ser Gly Met Ser Asn Val Ser Thr Leu Pro Ile
                245                 250                 255

Ser Ser Gly Gly Tyr Gln Gln Arg Ser Met Ser Asn Thr Ala Ser Ser
                260                 265                 270

Asn Ala Gly Thr Gln Gln Gln Gln Gln Gln Ser Ser Met Pro Pro
                275                 280                 285

Pro Ser Thr Asn Gly Gly Ser Ala Asn Gly Leu Thr Gly Ser Asp Phe
        290                 295                 300

Thr Ser Pro Ala Leu Ser Pro Thr Gly Gly Ser Gln Asn Pro Asn Asn
305                 310                 315                 320

Thr Ser Leu Pro Ser Ser Ser Arg Arg Asn Asp Ser Glu Trp Gln
                325                 330                 335

Lys Val Arg His Lys Gln Gln Arg Leu Leu Leu Arg His Ala Ser
                340                 345                 350

Arg Cys Gln His Lys Gly Thr Lys Cys Pro Val Thr Pro His Cys Ala
        355                 360                 365

Ser Met Lys Lys Leu Trp Glu His Ile Ala His Cys Lys Asp Gln His
        370                 375                 380

Cys Ser Val Ala His Cys Met Ser Ser Arg Tyr Val Leu Ser His Tyr
385                 390                 395                 400

Arg Arg Cys Lys Asp Pro Arg Cys Pro Ala Cys Gly Pro Val Arg Glu
                405                 410                 415

Thr Ile Arg Lys Ser His Glu Arg Glu Gln Gln Gln Gly Asn Arg Gln
                420                 425                 430

Pro Thr Ser Ser Ser Thr Pro Phe Asp Thr Glu Val Pro Gly Pro
        435                 440                 445

Ser Ser Ser Pro Asp Ala Leu Pro Ala Thr Lys Arg Pro Arg Ile Asp
450                 455                 460

Pro Asn Ala Ser Asn Met Pro Pro Asn Pro Thr Asp Gly Gln Pro
465                 470                 475                 480

Asn Gln Pro Leu Ser Ala Pro Ser Asp Val Ile Ala Pro Thr Asn
                485                 490                 495

Ser Asn Glu Lys Val Ser Lys Pro Pro Ser Pro Thr Pro Ser Ser Ser
                500                 505                 510

Ala Asn Lys Gly Ser Glu Asp Arg Ser Leu Leu Asp Ser Phe Thr Leu
                515                 520                 525
```

```
Asp Gln Ile Ala Leu His Leu Ala Ser Leu Asn Arg Ala Ala Asp Leu
            530                 535                 540

Pro Pro Ala Lys Leu Lys Gln Lys Cys Leu Glu Val Leu Lys Gly Leu
545                 550                 555                 560

Gln Ala His Gln His Gly Trp Val Phe Asn Val Pro Val Asp Pro Val
                565                 570                 575

Glu Leu Gly Leu Pro Asp Tyr Phe Glu Leu Ile Lys Lys Pro Met Asp
            580                 585                 590

Leu Gly Ser Val Gln Lys Lys Leu Glu Lys Gly Glu Tyr His Ala Ile
        595                 600                 605

Lys Asp Phe Gln Ser Asp Val Asn Leu Ser Phe Glu Asn Ala Met Thr
610                 615                 620

Tyr Asn Glu Gln Gly Ser Val Val Tyr Asp Met Ala Lys Glu Leu Lys
625                 630                 635                 640

Thr Lys Phe Glu Gly Asp Phe Lys Lys Leu Glu Gln Gln Leu Glu Ser
                645                 650                 655

Glu Asp Arg Glu Arg Arg Glu Asn Asp Arg Ala Cys Val Leu Cys Gly
            660                 665                 670

Cys Glu Lys Arg Leu Phe Glu Pro Pro Val Phe Phe Cys Asn Gly Ile
        675                 680                 685

Asn Cys Ala Ser Lys Arg Ile Arg Arg Asn Ser His Phe Tyr Ile Gly
690                 695                 700

Gly Asn Asn Gln Tyr Phe Trp Cys Asn Gln Cys Tyr Gly Glu Leu Glu
705                 710                 715                 720

Glu Lys Ser Pro Ile Glu Leu Ile Asp Leu Thr Val Lys Lys Thr Asp
                725                 730                 735

Leu Lys Lys Lys Lys Asn Asp Glu Ile Val Glu Glu Ser Trp Val Gln
            740                 745                 750

Cys Asp Ile Cys Glu Arg Trp Ile His Gln Ile Cys Gly Leu Phe Asn
        755                 760                 765

Thr Arg Gln Asn Lys Glu His His Ser Glu Tyr Cys Cys Pro Leu Cys
770                 775                 780

Leu Leu Glu Lys Arg Lys Lys Asn Pro Val Thr Pro Pro Arg Pro
785                 790                 795                 800

Ala Gly Ala Thr Glu Leu Pro Arg Thr Lys Leu Ser Glu Phe Ile Glu
                805                 810                 815

Asn His Val Arg Lys Lys Ile Glu Lys Arg Arg Asn Val Ala Glu
            820                 825                 830

Glu Lys Cys Arg Ile Glu Asn Ile Ser Met Asp Asp Ala Leu Lys Asp
        835                 840                 845

Ala Arg Glu Gly Gly Asn Val Ile Ile Arg Gln Val Thr Ser Met Asp
850                 855                 860

Arg Lys Leu Glu Val Arg Glu Gly Ile Lys Asn Arg Tyr Ala His Lys
865                 870                 875                 880

Asn Tyr Pro Asp Glu Phe Ser Phe Arg Cys Lys Cys Leu Leu Val Phe
                885                 890                 895

Gln Glu Ile Asp Gly Val Asp Val Val Leu Phe Ala Leu Tyr Leu Tyr
            900                 905                 910

Glu His Gly Glu Asp Ser Pro Arg Pro Asn Thr Arg Ser Ile Tyr Ile
        915                 920                 925

Ser Tyr Leu Asp Ser Val His Tyr Met Arg Pro Arg Lys Leu Arg Thr
930                 935                 940
```

```
Phe Val Tyr His Glu Ile Leu Ile Ser Tyr Cys Asp Tyr Ala Arg Gln
945                 950                 955                 960

Arg Gly Phe Ala Thr Val His Ile Trp Ala Cys Pro Pro Leu Lys Gly
            965                 970                 975

Asp Asp Tyr Ile Phe Tyr Ala Lys Pro Glu Asp Gln Lys Thr Pro Arg
            980                 985                 990

Asp Ser Arg Leu Arg Gln Trp Tyr Ile Asp Met Leu Val Glu Cys Gln
        995                 1000                1005

Asn Arg Gly Ile Val Gly Arg Leu Thr Asn Met Tyr Asp Leu Tyr
    1010                1015                1020

Phe Ala Asn Ala Ser Ile Asp Ala Thr Ala Val Pro Tyr His Glu
    1025                1030                1035

Gly Asp Tyr Phe Pro Gly Glu Ala Glu Asn Ile Ile Lys Met Leu
    1040                1045                1050

Asp Asp Glu Gly Gly Lys Lys Asn Gly Ser Ser Gly Lys Lys Lys
    1055                1060                1065

Lys Gln Lys Asn Gln Ser Lys Ser Lys Asn Arg Gly Gly Thr Arg
    1070                1075                1080

Ser Thr Gly Val Asp Glu Glu Ala Leu Leu Ala Ser Gly Met Met
    1085                1090                1095

Asp Gly Val Lys Asn Tyr Glu Glu Leu Asp Arg Asp Gln Val Met
    1100                1105                1110

Val Lys Leu Gly Glu Ala Ile Gln Pro Met Lys Glu Ser Phe Leu
    1115                1120                1125

Val Ala Phe Leu Thr Trp Ser Gly Ile Lys Glu Glu Asp Leu Glu
    1130                1135                1140

Val Pro Glu Ala Ile Ala Lys Tyr Arg Glu Glu His Pro Glu Asn
    1145                1150                1155

Val Val Pro Leu Pro Ser Gly Asn Lys Arg Asn Ala Asp Gly Gln
    1160                1165                1170

Thr Lys Asp Glu Val Val Pro Leu Asp Ala Asp Gly His Pro Leu
    1175                1180                1185

Lys Val Leu Asp Asp Asp Ala Glu Asp Leu Asp Cys Glu Phe Leu
    1190                1195                1200

Asn Asn Arg Gln Ala Phe Leu Asn Leu Cys Arg Gly Asn His Tyr
    1205                1210                1215

Gln Phe Asp Glu Leu Arg Arg Ala Lys His Thr Ser Met Met Val
    1220                1225                1230

Leu Trp His Leu Gln Asn Arg Asp Ala Pro Lys Tyr Val Gln Gln
    1235                1240                1245

Cys Val Ser Cys Ser Arg Glu Ile Leu Ser Gly Lys Arg Tyr His
    1250                1255                1260

Cys Asn Ser Cys Pro Asp Tyr Asp Leu Cys Glu Thr Cys Tyr Lys
    1265                1270                1275

Asp Pro Lys Thr Asn Arg Gly Thr Cys Thr His Lys Leu Gln Glu
    1280                1285                1290

Ile Lys Val Glu Ser Glu Gly Gln Ser Asp Ser Ser Gly Leu Thr
    1295                1300                1305

Glu Thr Gln Arg Lys Gln Arg Gln Arg Asn Leu Met Leu His Ile
    1310                1315                1320

Gln Leu Ile Glu His Ala Ser Arg Cys Thr Ser Ser Thr Cys Gln
    1325                1330                1335

Ser Lys Asn Cys Ala Lys Met Lys Glu Tyr Leu Gln His Ala Arg
```

```
               1340            1345            1350
Thr Cys Lys Thr Lys Val Val Gly Gly Cys Arg Ile Cys Lys Arg
       1355            1360            1365

Ile Trp Thr Leu Leu Arg Ile His Ala Gln Lys Cys Lys Glu Pro
       1370            1375            1380

Val Cys Pro Ile Pro Gln Cys Met Ile Ile Arg Glu Lys Met Arg
       1385            1390            1395

Glu Leu Gln Lys Gln Gln Gln Ala Met Asp Asp Arg Arg Arg Gln
       1400            1405            1410

Glu Met Asn Arg His Tyr Gly Arg Met Ser Met Thr Ser Gly Ser
       1415            1420            1425

Gly

<210> SEQ ID NO 21
<211> LENGTH: 3156
<212> TYPE: DNA
<213> ORGANISM: Fragilariopsis cylindrus
<220> FEATURE:
<221> NAME/KEY: misc_feature
<223> OTHER INFORMATION: Encodes polypeptide of SEQ ID NO:22

<400> SEQUENCE: 21
atgaaacgat tgtggaagca cattgccgaa tgcaaagatc aaaagtgttt agttcctcat      60
tgtgttagtt cacggtatgt tcttagtcac tatcatcgat gtaaggatgt tcgttgtccg     120
gtgtgcggtc ccgtaagaga ggctatacat cgaagtcacg agaagcagaa gcaaatgcaa     180
gcattgaaac aacgacatca acaggccgtc cagcaaaatc aaaatgaaga aaaaatacca     240
gcaggagcag ccttagcacc tcctccagta caacatcaac aggggtttgg atatccttca     300
aaaccacaac cgatgtctca acagcccgga gttccttcta cggcatcagt accaccgaag     360
atcaccgtcc ctcctatcgc tggtgtcaag tttgctaacg ggcaagttat tactccgaag     420
tttactggtc cgaaaccaca ggaagatcat actcttatca attgttttc ggtcgaacag      480 atcgaaacgc acattaagtc tttgaataag ggtttgcaac ttccacccct aaaactgaag     540
gtaaaatgtc tcgaggtact caaagtcctt caaggtcacc agcatggttg ggtgtttaat     600
agtcccgtgg atcctattga actcggtcta cctgattact tcgaagttat taagattcca     660
atggatcttg gaacgattcg aaagaaatta gagaatggat gctatcattc tttggattcc     720
tttcataccc atgttcatac aacatttgat aatgcaatgc tgtataatcc cgaagggtca     780
gttgtttaca atatggcgaa tgaaatgaag accaagttta acaagatttt gaaatcctc     840 atgaagcaac tgaatgccga tgaggatgta aagcgtcgaa atggcgaggc atgttcgttg     900
tgtggatgtg aaaaactctt gtttgagcca ccggtattt attgcaacgg tctcagttgt      960
ccctcgaaac gtattcgacg aaatagctat tattatgtgg ggggaaacaa tcaatatcat    1020
tggtgccatc aatgttttca gaacttaag gacaatcaac tactcgaact tgcagatgtt    1080
tcgattcgga aggagcaact cacgaagaaa agaacgacg aaacacacga agaaagttgg     1140
gtccaatgcg atcgttgcga gcgatgggtc catcagattt tgctcttt caacactcgt     1200 cagaacaaag accagcggtc agaatttgct tgtccccggt gtacaattga ggaacgcaag   1260
aagacaggaa ggctggaagc aacttcctcc actccaatgg ctgaagatct tcaacgtaca   1320
aaactctctg aatacgttga aacccatgtt cgcgtcaaga tggctgaaca tctgaaggaa   1380
cttgcagaag agaaagtact aaaggaaggt atggacctcg aggaagctaa agcttctgtt   1440
acaatgggtg gtactatcac aatccgtcaa gttacttcta tggatcgtaa actcgaagtg   1500
```

```
agagaacgta tgaagaagcg ctacgccttt aagaattatc ctgacgaatt tacctatcgg    1560
tgcaagtgtt ttgtagtttt ccaaaatctt gacggtgtag atgtgattct atttggactt    1620
tacgtctacg aacacgacga aagaatcct gcgccgaacc agcgagctgt atatgtatcg     1680
tatctcgata gtgttcatta catgcgacca agatctatga gaacgttcat ttatcacgag    1740
attctgatat cataccttga ttatgttcga cgacgtgggt tttctacagc tcatatctgg    1800
gcctgtccgc cactgaaagg tgatgattat attctatatg ctaaaccaga agatcaaaaa    1860
acaccgaagg atgatcgact tcgtcaatgg tacattgata tgctaattga ctgtcaaaaa    1920
cgcggcattg ttggtagact tactaacatg tacgacctat acttctcgag caagaaaat    1980 aacgcaacga tcgttccata tatggaaggt gactatttcc cagccgaggt tgaaaatatc    2040
atcaaggaca tcgaagaagg aaaagttggc aagaagactg gaggaaagga aggaaagaaa    2100
aagaaaggag ataagaaaca gaagaagaag ggcggacgag gtggaacgcg atcaagtgga    2160
atcgacgaag atgccctcaa agctagtggt attcaattcc caggtaaaga ccaaaagagt    2220
ctagaagagg gaggtcgaga ctatgtaatg gtaaagttgg gggaaactat tcaacctatg    2280
aaggagagtt ttatcgttgc ccatttagcc tggaagggtg ctaaaaagga aaatatggtt    2340
gtgcccagag ctattcaaga atacagggaa aaacataata tcaagattga agatgagaag    2400
gagaaagaaa cggaagccga acctgcacca gttatttacg tcttggacag caagggaaga    2460
cgagtgaagg ttatcgacga tgatgcagaa gagatggact gtgaatttct caacaatcgt    2520
caagcatttt tgaatttatg ccaaggaaat cactatcagt acgatcattt aagaagggcg    2580
aagcattctt caatgatggt tctttggcat ctacacaatc gggatgcacc gaagtttgtc    2640
caacaatgta caacttgttc cagagagatt ttgcagggct atcgcttcca ttgtccaatc    2700
tgtgctgact ttgatcaatg tcaagattgt gtacagaatc ctaatactcc tcggcatcct    2760
catcagttga aacctattgc agtagcaggt caacaaactg agttgacaga agctcaacgc    2820
aaggaacgcc aacgaagtat acagttacat atgactcttt tgcagcacgc cgcgacctgt    2880
aactcaacaa agtgtccatc cgccaattgt accaaaatga agggcctttt gaagcacggt    2940
tcgcagtgta ctgttaaggc cacgggtggc tgtaatgtat gcaaaaggat atgggctctt    3000
ctccagatcc acgctcgtca gtgtaaggca cagcaatgtc ctgtccctaa ttgtatggcg    3060
atccgagaac gggtacgcca gttgaagaaa cagcaacagg caatgacgaa ccgtcgtcgt    3120
caagaaatga acagagtta tagaggagcg cgatag                               3156
```

<210> SEQ ID NO 22
<211> LENGTH: 1051
<212> TYPE: PRT
<213> ORGANISM: Fragilariopsis cylindrus
<220> FEATURE:
<221> NAME/KEY: misc_feature
<223> OTHER INFORMATION: translation product 388115

<400> SEQUENCE: 22

```
Met Lys Arg Leu Trp Lys His Ile Ala Glu Cys Lys Asp Gln Lys Cys
1               5                   10                  15

Leu Val Pro His Cys Val Ser Ser Arg Tyr Val Leu Ser His Tyr His
            20                  25                  30

Arg Cys Lys Asp Val Arg Cys Pro Val Cys Gly Pro Val Arg Glu Ala
        35                  40                  45

Ile His Arg Ser His Glu Lys Gln Lys Gln Met Gln Ala Leu Lys Gln
    50                  55                  60
```

-continued

```
Arg His Gln Gln Ala Val Gln Gln Asn Gln Asn Glu Lys Ile Pro
 65                  70                  75                  80

Ala Gly Ala Ala Leu Ala Pro Pro Val Gln His Gln Gln Gly Phe
                 85                  90                  95

Gly Tyr Pro Ser Lys Pro Gln Pro Met Ser Gln Gln Pro Gly Val Pro
            100                 105                 110

Ser Thr Ala Ser Val Pro Pro Lys Ile Thr Val Pro Pro Ile Ala Gly
            115                 120                 125

Val Lys Phe Ala Asn Gly Gln Val Ile Thr Pro Lys Phe Thr Gly Pro
130                 135                 140

Lys Pro Gln Glu Asp His Thr Leu Ile Asn Cys Phe Ser Val Glu Gln
145                 150                 155                 160

Ile Glu Thr His Ile Lys Ser Leu Asn Lys Gly Leu Gln Leu Pro Pro
                165                 170                 175

Leu Lys Leu Lys Val Lys Cys Leu Glu Val Leu Lys Val Leu Gln Gly
                180                 185                 190

His Gln His Gly Trp Val Phe Asn Ser Pro Val Asp Pro Ile Glu Leu
                195                 200                 205

Gly Leu Pro Asp Tyr Phe Glu Val Ile Lys Ile Pro Met Asp Leu Gly
210                 215                 220

Thr Ile Arg Lys Lys Leu Glu Asn Gly Cys Tyr His Ser Leu Asp Ser
225                 230                 235                 240

Phe His Thr His Val His Thr Thr Phe Asp Asn Ala Met Leu Tyr Asn
                245                 250                 255

Pro Glu Gly Ser Val Val Tyr Asn Met Ala Asn Glu Met Lys Thr Lys
                260                 265                 270

Phe Lys Gln Asp Phe Glu Ile Leu Met Lys Gln Leu Asn Ala Asp Glu
                275                 280                 285

Asp Val Lys Arg Arg Asn Gly Glu Ala Cys Ser Leu Cys Gly Cys Glu
     290                 295                 300

Lys Leu Leu Phe Glu Pro Pro Val Phe Tyr Cys Asn Gly Leu Ser Cys
305                 310                 315                 320

Pro Ser Lys Arg Ile Arg Arg Asn Ser Tyr Tyr Tyr Val Gly Gly Asn
                325                 330                 335

Asn Gln Tyr His Trp Cys His Gln Cys Phe Gln Glu Leu Lys Asp Asn
                340                 345                 350

Gln Leu Leu Glu Leu Ala Asp Val Ser Ile Arg Lys Glu Gln Leu Thr
                355                 360                 365

Lys Lys Lys Asn Asp Glu Thr His Glu Glu Ser Trp Val Gln Cys Asp
                370                 375                 380

Arg Cys Glu Arg Trp Val His Gln Ile Cys Ala Leu Phe Asn Thr Arg
385                 390                 395                 400

Gln Asn Lys Asp Gln Arg Ser Glu Phe Ala Cys Pro Arg Cys Thr Ile
                405                 410                 415

Glu Glu Arg Lys Lys Thr Gly Arg Leu Glu Ala Thr Ser Ser Thr Pro
                420                 425                 430

Met Ala Glu Asp Leu Gln Arg Thr Lys Leu Ser Glu Tyr Val Glu Thr
                435                 440                 445

His Val Arg Val Lys Met Ala Glu His Leu Lys Glu Leu Ala Glu Glu
                450                 455                 460

Lys Val Leu Lys Glu Gly Met Asp Leu Glu Glu Ala Lys Ala Ser Val
465                 470                 475                 480
```

```
Thr Met Gly Gly Thr Ile Thr Ile Arg Gln Val Thr Ser Met Asp Arg
                485                 490                 495
Lys Leu Glu Val Arg Glu Arg Met Lys Lys Arg Tyr Ala Phe Lys Asn
            500                 505                 510
Tyr Pro Asp Glu Phe Thr Tyr Arg Cys Lys Cys Phe Val Val Phe Gln
        515                 520                 525
Asn Leu Asp Gly Val Asp Val Ile Leu Phe Gly Leu Tyr Val Tyr Glu
    530                 535                 540
His Asp Glu Lys Asn Pro Ala Pro Asn Gln Arg Ala Val Tyr Val Ser
545                 550                 555                 560
Tyr Leu Asp Ser Val His Tyr Met Arg Pro Arg Ser Met Arg Thr Phe
                565                 570                 575
Ile Tyr His Glu Ile Leu Ile Ser Tyr Leu Asp Tyr Val Arg Arg Arg
            580                 585                 590
Gly Phe Ser Thr Ala His Ile Trp Ala Cys Pro Pro Leu Lys Gly Asp
        595                 600                 605
Asp Tyr Ile Leu Tyr Ala Lys Pro Glu Asp Gln Lys Thr Pro Lys Asp
    610                 615                 620
Asp Arg Leu Arg Gln Trp Tyr Ile Asp Met Leu Ile Asp Cys Gln Lys
625                 630                 635                 640
Arg Gly Ile Val Gly Arg Leu Thr Asn Met Tyr Asp Leu Tyr Phe Ser
                645                 650                 655
Ser Lys Glu Asn Asn Ala Thr Ile Val Pro Tyr Met Glu Gly Asp Tyr
            660                 665                 670
Phe Pro Ala Glu Val Glu Asn Ile Ile Lys Asp Ile Glu Glu Gly Lys
        675                 680                 685
Val Gly Lys Lys Thr Gly Gly Lys Glu Gly Lys Lys Lys Gly Asp
    690                 695                 700
Lys Lys Gln Lys Lys Gly Arg Gly Gly Thr Arg Ser Ser Gly
705                 710                 715                 720
Ile Asp Glu Asp Ala Leu Lys Ala Ser Gly Ile Gln Phe Pro Gly Lys
                725                 730                 735
Asp Gln Lys Ser Leu Glu Glu Gly Gly Arg Asp Tyr Val Met Val Lys
            740                 745                 750
Leu Gly Glu Thr Ile Gln Pro Met Lys Glu Ser Phe Ile Val Ala His
        755                 760                 765
Leu Ala Trp Lys Gly Ala Lys Lys Glu Asn Met Val Val Pro Arg Ala
    770                 775                 780
Ile Gln Glu Tyr Arg Glu Lys His Asn Ile Lys Ile Glu Asp Glu Lys
785                 790                 795                 800
Glu Lys Glu Thr Glu Ala Glu Pro Ala Pro Val Ile Tyr Val Leu Asp
                805                 810                 815
Ser Lys Gly Arg Arg Val Lys Val Ile Asp Asp Ala Glu Glu Met
            820                 825                 830
Asp Cys Glu Phe Leu Asn Asn Arg Gln Ala Phe Leu Asn Leu Cys Gln
        835                 840                 845
Gly Asn His Tyr Gln Tyr Asp His Leu Arg Arg Ala Lys His Ser Ser
    850                 855                 860
Met Met Val Leu Trp His Leu His Asn Arg Asp Ala Pro Lys Phe Val
865                 870                 875                 880
Gln Gln Cys Thr Thr Cys Ser Arg Glu Ile Leu Gln Gly Tyr Arg Phe
                885                 890                 895
His Cys Pro Ile Cys Ala Asp Phe Asp Gln Cys Gln Asp Cys Val Gln
```

```
                900             905             910
Asn Pro Asn Thr Pro Arg His Pro His Gln Leu Lys Pro Ile Ala Val
            915             920             925

Ala Gly Gln Gln Thr Glu Leu Thr Glu Ala Gln Arg Lys Glu Arg Gln
        930             935             940

Arg Ser Ile Gln Leu His Met Thr Leu Leu Gln His Ala Ala Thr Cys
945             950             955             960

Asn Ser Thr Lys Cys Pro Ser Ala Asn Cys Thr Lys Met Lys Gly Leu
            965             970             975

Leu Lys His Gly Ser Gln Cys Thr Val Lys Ala Thr Gly Gly Cys Asn
        980             985             990

Val Cys Lys Arg Ile Trp Ala Leu Leu Gln Ile His Ala Arg Gln Cys
    995             1000            1005

Lys Ala Gln Gln Cys Pro Val Pro Asn Cys Met Ala Ile Arg Glu
    1010            1015            1020

Arg Val Arg Gln Leu Lys Lys Gln Gln Gln Ala Met Asp Asp Arg
    1025            1030            1035

Arg Arg Gln Glu Met Asn Arg Val Tyr Arg Gly Ala Arg
    1040            1045            1050
```

<210> SEQ ID NO 23
<211> LENGTH: 2598
<212> TYPE: DNA
<213> ORGANISM: Thalassiosira pseudonana
<220> FEATURE:
<221> NAME/KEY: misc_feature
<223> OTHER INFORMATION: encodes polypeptide of SEQ ID NO:24

<400> SEQUENCE: 23

```
atgaatgatg actgtgtgat atcagctgac agcgaagcca gtagtgttgc ccagaaagtc      60
acctcgattc ttccgtcaat gtcaattgca gctattcaac agcacgttga atctttggca    120
tccaatggtc agctgacacc tcggcttatc acccgaaaat gcctccctct cgttagaaag    180
ctatataacc acgaacacgg atgggtcttt aaggatccag ttgatcctgt ggagttgggc    240
attccagact actttgatat tgtgcagcat ccaatggatc ttgccttggt agagacgaag    300
cttgagaatg gagtgtacaa agatctagat tcttttgagc gtgatacaaa gctagtgttt    360
gagaacgcaa tccttttcaa tggtgagaag aatgatgttg gtggaatggc aaagcaactg    420
ttgtttatgt ttgacgagga tctcaaagct gtaatgaaag gtatggggtt ggttcacaaa    480
agtgagaagg aagaacccaa gaagaaggat gacacgtcat gcacactctg tgggaatcac    540
cgccgtctct ttgagccaac cactctctac tgcagtggtc agtgcggaat gcagaaaatc    600
cgtcgcaacg catcgtatta cactgacaga tatcgacaaa accaatggtg tgagaagtgc    660
tttgatgttt tgatggagga gaagccagtt ctgcttgatg atggaaagga gacgaagaag    720
tcgctactgg tgaaaatgaa gaatgactcg acaccagagg agaagtgggt tcaatgcgac    780
aattgtcata attgggctca tcagatttgt gctctcttca atgaggtgca aagtagcaat    840
gcgtttacgt gtcccaagtg tttcttgaaa cagcaagata gagcgactag tccagagctt    900
acttcgttca agatgcagc cgctttgccc cagtgtaaac tgagtactgt gatcgaagaa    960
ggtctggcga cgacactttc tgtcgaatac gaaaagattg caaaggaaag aggatgcacc   1020
gtagcccagg ttgaaaaggc agagggcctc tgcgttagag ttgtgtcaag tcttgagaaa   1080
aagcacaagg ttcgggatga gatgctgggt cgatattcaa agaagggata tccatcagag   1140
tttccagtga cctcaaagtg catcctattg ttccagaaga tccacggagt tgatgtgctt   1200
```

```
ctgtttggaa tgtatgtcta cgagtacggt gacaagtgtg cagctccgaa ccggcgacga    1260
gtctacattt catacttgga ttcagttcag tatcttgagc catcatcata caggacaacc    1320
acctaccagt ccatcattgt tgaatacctt cgatacgcaa ggatgcgtgg ctttcacact    1380
gctcacattt ggagttgccc tccgtcaaag ggcgatgagt acattttcta ctgccaccct    1440
tcctctcagc tcgttcccaa agacgacatg ctttgtgctt ggtacattga aactctcaaa    1500
aaagctcaag accagggcat cgtcttggaa acaaggacca tctacgacga gtattttaag    1560
aacaatggta tcaactcaga gaatggagag ccctttgatc caatgagcct cccttacttt    1620
gaaggcgact acatccccgg agagatagag aaaatcatta gagactttaa caaggatgag    1680
aatttgcgcg aagagaccaa gttaaaggaa ctcaagtctg ccctgctcc aacggctcat     1740 aagaaggaag gcaatcgtaa aggcactagg tccaacccgg gtgaattggt aaatcaagac    1800
cgcgacaaag tgatgattcg tcttgacttg gctttggcga aaatgaagca aaactttatc    1860
gtagcccagc ttcttagcga tgacttcatc aaggcggtgg agaagggtca cgatgtttcc    1920
tcatggatag aagatattga gccgcacgaa gtaaagcagc cgaagcaggt tggcaagaat    1980
ccgtgcgtcc ttgatgcacc gactgatatg tctgacaaaa tgagcgctga cggaaaagat    2040
ggagatgcca caagacacc tgcatccttg gtaattggta atactattga cgaagaccc     2100 ttgatggagc aggaattcat cgacactcgt cttcagttct tgaactactg tcaaaagaac    2160
aacctccagt ttgatgagtt gcgtcgtgcc aaacacacaa caatgatgct tctttgcaat    2220
ctgcacaatc ctcgggctga acgagagcag caagttaagg tgcacttgca gatcattgca    2280
catgcttcgt gttgcaatgg tcctccggct tgcatgtcta ccaactgtcg aaggatgaag    2340
caactattca gccacgtcag gggatgcgaa attacctaca aaagaggctg caagatgtgc    2400
gttcgtctat tcatgcttct taccaaacat gcccgcgatt gtgactctgc gggatcatgt    2460
gctattccgt tttgtgatcg tattaggag aggaataga  gaatgttgcg tcaacagcaa    2520
cttatggatg ataggcgaag gaatgctcag aatgatagc acaggaaga ggaagatgac      2580 gctcaagctc gtgtttga                                                   2598
```

<210> SEQ ID NO 24
<211> LENGTH: 865
<212> TYPE: PRT
<213> ORGANISM: Thalassiosira pseudonana
<220> FEATURE:
<221> NAME/KEY: misc_feature
<223> OTHER INFORMATION: translation product 324007

<400> SEQUENCE: 24

```
Met Asn Asp Asp Cys Val Ile Ser Ala Asp Ser Glu Ala Ser Val
1               5                   10                  15

Ala Gln Lys Val Thr Ser Ile Leu Pro Ser Met Ser Ile Ala Ala Ile
            20                  25                  30

Gln Gln His Val Glu Ser Leu Ala Ser Asn Gly Gln Leu Thr Pro Arg
        35                  40                  45

Leu Ile Thr Arg Lys Cys Leu Pro Leu Val Arg Lys Leu Tyr Asn His
    50                  55                  60

Glu His Gly Trp Val Phe Lys Asp Pro Val Pro Val Glu Leu Gly
65                  70                  75                  80

Ile Pro Asp Tyr Phe Asp Ile Val Gln His Pro Met Asp Leu Ala Leu
                85                  90                  95

Val Glu Thr Lys Leu Glu Asn Gly Val Tyr Lys Asp Leu Asp Ser Phe
```

-continued

```
              100                 105                 110
Glu Arg Asp Thr Lys Leu Val Phe Glu Asn Ala Ile Leu Phe Asn Gly
            115                 120                 125
Glu Lys Asn Asp Val Gly Gly Met Ala Lys Gln Leu Leu Phe Met Phe
            130                 135                 140
Asp Glu Asp Leu Lys Ala Val Met Lys Gly Met Gly Leu Val His Lys
145                 150                 155                 160
Ser Glu Lys Glu Pro Lys Lys Asp Asp Thr Ser Cys Thr Leu
            165                 170                 175
Cys Gly Asn His Arg Arg Leu Phe Glu Pro Thr Thr Leu Tyr Cys Ser
            180                 185                 190
Gly Gln Cys Gly Met Gln Lys Ile Arg Arg Asn Ala Ser Tyr Tyr Thr
            195                 200                 205
Asp Arg Tyr Arg Gln Asn Gln Trp Cys Glu Lys Cys Phe Asp Val Leu
            210                 215                 220
Met Glu Glu Lys Pro Val Leu Leu Asp Asp Gly Lys Glu Thr Lys Lys
225                 230                 235                 240
Ser Leu Leu Val Lys Met Lys Asn Asp Ser Thr Pro Glu Glu Lys Trp
                245                 250                 255
Val Gln Cys Asp Asn Cys His Asn Trp Ala His Gln Ile Cys Ala Leu
                260                 265                 270
Phe Asn Glu Val Gln Ser Ser Asn Ala Phe Thr Cys Pro Lys Cys Phe
            275                 280                 285
Leu Lys Gln Gln Asp Arg Ala Thr Ser Pro Glu Leu Thr Ser Phe Lys
            290                 295                 300
Asp Ala Ala Leu Pro Gln Cys Lys Leu Ser Thr Val Ile Glu Glu
305                 310                 315                 320
Gly Leu Ala Thr Thr Leu Ser Val Glu Tyr Lys Ile Ala Lys Glu
                325                 330                 335
Arg Gly Cys Thr Val Ala Gln Val Glu Lys Ala Glu Gly Leu Cys Val
                340                 345                 350
Arg Val Val Ser Ser Leu Glu Lys Lys His Lys Val Arg Asp Glu Met
            355                 360                 365
Leu Gly Arg Tyr Ser Lys Lys Gly Tyr Pro Ser Glu Phe Pro Val Thr
            370                 375                 380
Ser Lys Cys Ile Leu Leu Phe Gln Lys Ile His Gly Val Asp Val Leu
385                 390                 395                 400
Leu Phe Gly Met Tyr Val Tyr Glu Tyr Gly Asp Lys Cys Ala Ala Pro
                405                 410                 415
Asn Arg Arg Arg Val Tyr Ile Ser Tyr Leu Asp Ser Val Gln Tyr Leu
                420                 425                 430
Glu Pro Ser Ser Tyr Arg Thr Thr Tyr Gln Ser Ile Ile Val Glu
            435                 440                 445
Tyr Leu Arg Tyr Ala Arg Met Arg Gly Phe His Thr Ala His Ile Trp
            450                 455                 460
Ser Cys Pro Pro Ser Lys Gly Asp Glu Tyr Ile Phe Tyr Cys His Pro
465                 470                 475                 480
Ser Ser Gln Leu Val Pro Lys Asp Asp Met Leu Cys Ala Trp Tyr Ile
                485                 490                 495
Glu Thr Leu Lys Lys Ala Gln Asp Gln Gly Ile Val Leu Glu Thr Arg
                500                 505                 510
Thr Ile Tyr Asp Glu Tyr Phe Lys Asn Asn Gly Ile Asn Ser Glu Asn
            515                 520                 525
```

```
Gly Glu Pro Phe Asp Pro Met Ser Leu Pro Tyr Phe Glu Gly Asp Tyr
        530                 535                 540

Ile Pro Gly Glu Ile Glu Lys Ile Ile Arg Asp Phe Asn Lys Asp Glu
545                 550                 555                 560

Asn Leu Arg Glu Glu Thr Lys Leu Lys Glu Leu Lys Ser Ala Pro Ala
                565                 570                 575

Pro Thr Ala His Lys Lys Glu Gly Asn Arg Lys Gly Thr Arg Ser Asn
                580                 585                 590

Pro Gly Glu Leu Val Asn Gln Asp Arg Asp Lys Val Met Ile Arg Leu
                595                 600                 605

Asp Leu Ala Leu Ala Lys Met Lys Gln Asn Phe Ile Val Ala Gln Leu
                610                 615                 620

Leu Ser Asp Asp Phe Ile Lys Ala Val Glu Lys Gly His Asp Val Ser
625                 630                 635                 640

Ser Trp Ile Glu Asp Ile Glu Pro His Glu Val Lys Gln Pro Lys Gln
                645                 650                 655

Val Gly Lys Asn Pro Cys Val Leu Asp Ala Pro Thr Asp Met Ser Asp
                660                 665                 670

Lys Met Ser Ala Asp Gly Lys Asp Gly Asp Ala Thr Lys Thr Pro Ala
                675                 680                 685

Ser Leu Val Ile Gly Asn Thr Ile Asp Glu Asp Pro Leu Met Glu Gln
690                 695                 700

Glu Phe Ile Asp Thr Arg Leu Gln Phe Leu Asn Tyr Cys Gln Lys Asn
705                 710                 715                 720

Asn Leu Gln Phe Asp Glu Leu Arg Arg Ala Lys His Thr Thr Met Met
                725                 730                 735

Leu Leu Cys Asn Leu His Asn Pro Arg Ala Glu Arg Glu Gln Gln Val
                740                 745                 750

Lys Val His Leu Gln Ile Ile Ala His Ala Ser Cys Cys Asn Gly Pro
                755                 760                 765

Pro Ala Cys Met Ser Thr Asn Cys Arg Arg Met Lys Gln Leu Phe Ser
                770                 775                 780

His Val Arg Gly Cys Glu Ile Thr Tyr Lys Arg Gly Cys Lys Met Cys
785                 790                 795                 800

Val Arg Leu Phe Met Leu Leu Thr Lys His Ala Arg Asp Cys Asp Ser
                805                 810                 815

Ala Gly Ser Cys Ala Ile Pro Phe Cys Asp Arg Ile Arg Glu Arg Asn
                820                 825                 830

Arg Arg Met Leu Arg Gln Gln Leu Met Asp Asp Arg Arg Arg Arg Asn
                835                 840                 845

Ala Gln Asn Asp Arg His Arg Glu Glu Glu Asp Asp Ala Gln Ala Arg
                850                 855                 860

Val
865
```

<210> SEQ ID NO 25
<211> LENGTH: 5154
<212> TYPE: DNA
<213> ORGANISM: Thalassiosira pseudonana
<220> FEATURE:
<221> NAME/KEY: misc_feature
<223> OTHER INFORMATION: encodes polypeptide of SEQ ID NO:26

<400> SEQUENCE: 25
atgggtccct atgaaggcgc atcttcagcc caacaaaaca atggatcacg accccctcac    60

```
aatcagatgc aagggcatcc ctcccaacag caaccgccgc agcatggagg aggaggggt       120 caaatgcctc ccaacgggca tcatcaaatg ggcaatccgt atggaggata tcatccactt      180
aatatgcagc agggaggtca accgcagcag cagcagaatg aaagatggga ggcgggggag     240
gcgtaaccat gggggggattt aacatgcaag gcagtaacgg aggtatgtcc atgggtggga    300
ataatggtca acagcacagg gggatgcatc cgatgagtat gcaaagcggg ggaggtggga     360
gtcaatacgg aggaccggga ggaggagggg gtaacaacaa catgtacaat catcccaatt     420
ttaactctgg gaatcagcct gggggaggag gacatcatca tgggggatac aatccccatc     480
agcaacagat acagcagcaa cagcttggtg ggtacaatcc ccaaatgatg cgcagatgc      540 agcagtcaca caattcgcag tataatccga tgcaacagat gggtcaacgt tctatcaaca    600
acaacagcag catcagggtg gatatcatcc acagccacag atccccctc ctcaggccca     660 agcctacggc caacaacagc agcagttgca tccatccaac tcctacgcca gacaagcctc    720
ctctgcatcc atacattcat ctattgccgt ggccaacgac agcagtccct cacccctgga   780
caacatgcaa cttctttcat acaaggaggc tccaaacttt tcagaagtaa cgggagtcga   840 tatagggggat gaggattatg ggcagcaatt tttgcccacg gggttgaatg gggattggca   900
gagtgatcgg gatatgcatc acaggaggga gatgattcag cacattgtta agctgctgaa    960
gcagaaagac aagagcgctt cccccgagtg gctcaccaaa ctccctcaga tggtgaaaca   1020
actagaagtg tcactctacc gttcagctcc ctcctttgaa gcgtattccg acaccaacac   1080
cctcaagcat cgtctacaac aactggccat ggaaattgcg aggaagactc aacaggccaa   1140
ggcgagtgga aggtcgtcca gcaggggtga tcgtattcca ggaatgggca acatgcacta   1200
caaccctgtc aacatgggag caaacgagga aatagtcagc agtcaatacg gcaatccaaa   1260
tgatcccgaa tggaaggttc gtatccgtca caagcagcaa cgtctactgc tcttgcacca    1320
ctcctccaaa tgcccctacg acaatgacaa gtgcaaggtc actccctatt gcggcgagat    1380
gaagaaattg tggaaacaca tggcgcgttg cacagacaat gagtgtcgag tgcctcactg    1440
cttctccagt cgatctattt tgagtcattg tcgtaaatgc aaagatcctg gatgtcctgc    1500
ctgcggtcct gtcagagaga cggtgcgaaa gacgcaaaag agtaacgctg gtaagggtgt    1560
gaatgaaggt caaggtgatt ttggtgggat gggtccaaat agtggaattg ggttgggagg    1620
aatgggtaat gaaatgggcg gcggtggtgg cagtgggatg ggaggcaacg acatgatggg    1680
tggaatgcca atgatggggg gaaacatgaa tcaaatgcca agaggcagc cttctcagcc     1740 aatgccttgg aaaggggata tcaatagcat gccaaacttc ccaccgccga atataagaca    1800
gcagcaggat gactacatgg ctttcccgga gggtttccct gagggacagc aggtgctcaa    1860
tggaccgagc tctgggcaga gtgggaatcc agaatcgagc aaggctaggc ataagcagca   1920
acgtcttctc cttcttcgtc atgcatcaaa gtgtaatgca gagcctggtc gctgtaccac   1980
cactccacac tgtgctgaaa tgaaagtctt gtggaaacac atcgccaatt gcaaggatca   2040
gtattgcaag gtgaaacact gcatgagcag tcggtatgtt ctcagtcact atcgtcggtg    2100
caatgatccg ggatgtgaga tttgcggtcc ggtgagggag atttttaaga gtggcacgaa    2160
ccatttcatt catgatccgt cctttatgcc aggatcatca gcggctgatc tcatcactcc   2220
tcctctccca gagggaccac aaacgaagag gtcgaggact aacgatcctt caatgaatgg    2280
aatgcatcat accgcgcctg ctcggccagc cttccctcta agtgctccta catctggctc    2340
ggagaatcat gccaagttga agtcttcagc gaagccttcg tcatccaatg ccacggaaga   2400
```

-continued

```
gcactctttta ttggaatgtt ttacgacgga gcaggtcaag actcatatcc aatcactgaa    2460
gaagacgata gaagtgtcac ccgccaagtt gaagctcaag tgcgtggaaa tattgagaga    2520
actccaaatt cacgagcatg gttgggtgtt tgcaacgcct gttgatcccg tcgagctggg    2580
tcttgatgac tactttgacg ttatcaaaaa gccgatggat cttggaacta tcagtaggag    2640
gcttgacaac ggatcgtacc atgcctttga tgacttcaag tctgatgttc ggcttacttt    2700
tgagaacgct atgaaataca atgatgaaa ttcggtagtt cacgaaatgg caaaggagtt     2760
gaagaagaag tttgatactg actacaaaaa gctaatgaag cagctggaga aggagcaccg    2820
agagaactcc atgaggcagc aggcgtgcgg cctttgtggt tgcgaaaagc tcaactttga    2880
gcctcccgtg ttcttttgca acggtatgaa ctgtcccagt aagcgcatcc gtcgtaacac    2940
ccacttctac atcacggccg acaagcagta tgcttggtgc agccaatgtt acaatgagct    3000
tgggggagag attgacctcg gtacgtcagt cttgaagaag gtggaccttg cgaagaagaa    3060
gaacgacgag actcacgagg agagttgggt tcagtgtgac gattgtgagc gatggatcca    3120
tcagatttgt ggactctaca acacacgtca ggacaaggaa acaagagtg cctattcttg     3180 tccactatgc ctgctggata agaggaagaa agaaggagag cctaaaaagc tcccacctcc    3240
tcccgcagcg agcgacattc ccaggacaaa tctgtcagat tggcttgaaa gggatgttca    3300
caagaaggta aatcagcgtc tcaaagagct tgcgcaggag aaggccgata ctgagcacat    3360
tgcctttgaa aaggcgtatg ctgatctttc tgctggggg cctttgacca ttcggcaggt     3420
gacgtctact gaccgaaagt tggaagttcg cgatcaaatg aggcagcgat atgctcataa    3480
gaactatcct gaggagtttc cctaccgttg taaatgcatt gttgtcttcc agaacattga    3540
tggtgttgac gtggttcttt ttgcgttgta tgtttacgag catggagatg acaatcccTT    3600
ccccaaaaaa agacggtgta tgtgtcctac cttgacagtg tccacttcat gaagccaagg    3660
caaatgagga cgttccttta ccacgaaatc ttaatctcct accttgacta cgctcgtcag    3720
aaaggcttct tgcaggcctt catttgggcg tgcccaccgt tgaaggggga cgattacatc    3780
ttctacgcaa aaccagagga tcaaaagact cccaaagacg taagacttcg tcaatggtat    3840
cttgatatgc tggtggagtg ccagaaacgc aacatcgttg gtatggtctc caatatgtat    3900
gatcaatact ttgccaacaa gtctctggat gcagcgagtg tccccTactt tgacggagat    3960
tacttccctg gagaggctga aaatatcatc aaagacttgg aagaaagcaa cagtaagcgc    4020
aagggtggtg ctggcaagaa aaataaggat ccttcaaaga gcaaagctgc tccatctggt    4080
gatgcagagt ttgtgggtga aaagtgctac aaggagggtg gtcgtgatcc cgtgatgcag    4140
aagttctgcg acgccattca ggggatgaag gagagtttca tcgtcgcata cttgaacgca    4200
aaggacgcca agcctgagca tcttgtcgta ccgaagaaga ttatggagtt tagggaagca    4260
aacaaacttc tcatgatcga cgatgatcct aagaagaaga agaagatgg aacggaggag     4320 aagaaggatg acgaaaagcc tcagagcaag agcgcgatg ctgacggtta cgaagtcgcc     4380
gcctcggaaa agccaccggc taataagcaa ctcaatagca agggaaagcc tgtccgagta    4440
ttgaacgacg acgatgaaga aattgactgt gaattcttta acacgcgaca atgctttttg    4500
gatctctgcc gtggtaacca ctatcagttt gatgagttgc gacgggcaaa gcatacgtca    4560
atgatggttt tgtggcacct tcaaaatcgt gaagcgccaa aattcgttca gcagtgcatg    4620
gcatgcaacc gcgagatcgc gtctggcatt cgtcatcatt gcaacgtatg ctcagacttt    4680
gacctctgtg acgattgctt ccgagatcca gacaccaaca gaggcacgtg caatcataag    4740
cttgaggcaa ttaaagtgga tactgcccag agtgaaaaca gtggactcac cgaggagcaa    4800
```

-continued

```
cgaaaggagc gtcagcgaaa catccagctt catatcactc tcattgagca tgcatctcgt    4860
tgtaactcgt cttcctgcaa gtcttccaat tgtatgaaaa tgaaatccta cctcaagcac    4920
ggctcaacgt gcacggtcaa agcatcagga ggatgcaaga tttgcaagag aatctggacg    4980
ttgttgagga ttcacgcaca gcaatgcaag agctctagct gtgccatccc gcaatgtatc    5040
gcaattagaa agcgtatccg tcagcttcag ctcaagcagc aggctatgga cgaccgtaga    5100
aggcaagaaa tgaaccgaca ctaccgcatg ggaatgatgt cctctgataa ctga          5154
```

```
<210> SEQ ID NO 26
<211> LENGTH: 1718
<212> TYPE: PRT
<213> ORGANISM: Thalassiosira pseudonana
<220> FEATURE:
<221> NAME/KEY: misc_feature
<223> OTHER INFORMATION: Translation product 324378

<400> SEQUENCE: 26

Met Gly Pro Tyr Glu Gly Ala Ser Ser Ala Gln Gln Asn Asn Gly Ser
1               5                   10                  15

Arg Pro Pro His Asn Gln Met Gln Gly His Pro Ser Gln Gln Gln Pro
                20                  25                  30

Pro Gln His Gly Gly Gly Gly Gln Met Pro Pro Asn Gly His His
            35                  40                  45

Gln Met Gly Asn Pro Tyr Gly Gly Tyr His Pro Leu Asn Met Gln Gln
        50                  55                  60

Gly Gly Gln Pro Gln Gln Gln Asn Gly Met Met Gly Gly Gly Gly
65                  70                  75                  80

Gly Val Thr Met Gly Gly Phe Asn Met Gln Gly Ser Asn Gly Gly Met
                85                  90                  95

Ser Met Gly Gly Asn Asn Gly Gln Gln His Arg Gly Met His Pro Met
                100                 105                 110

Ser Met Gln Ser Gly Gly Gly Ser Gln Tyr Gly Gly Pro Gly Gly
            115                 120                 125

Gly Gly Gly Asn Asn Asn Met Tyr Asn His Pro Asn Phe Asn Ser Gly
        130                 135                 140

Asn Gln Pro Gly Gly Gly Gly His His His Gly Gly Tyr Asn Pro His
145                 150                 155                 160

Gln Gln Gln Ile Gln Gln Gln Leu Gly Gly Tyr Asn Pro Gln Met
                165                 170                 175

Met Ala Gln Met Gln Ser His Asn Ser Tyr Asn Pro Met Gln
            180                 185                 190

Gln Met Gly Gln Arg Ser His Gln Gln Gln Gln His Gln Gly Gly
        195                 200                 205

Tyr His Pro Gln Pro Gln Ile Pro Leu Pro Gln Ala Gln Ala Tyr Gly
210                 215                 220

Gln Gln Gln Gln Gln Leu His Pro Ser Asn Ser Tyr Ala Arg Gln Ala
225                 230                 235                 240

Ser Ser Ala Ser Ile His Ser Ser Ile Ala Val Ala Asn Asp Ser Ser
                245                 250                 255

Pro Ser Pro Ser Asp Asn Met Gln Leu Leu Ser Tyr Lys Glu Ala Pro
                260                 265                 270

Asn Phe Ser Glu Val Thr Gly Val Asp Ile Gly Asp Glu Asp Tyr Gly
            275                 280                 285

Gln Gln Phe Leu Pro Thr Gly Leu Asn Gly Asp Trp Gln Ser Asp Arg
```

```
            290                 295                 300

Asp Met His His Arg Arg Glu Met Ile Gln His Ile Val Lys Leu Leu
305                 310                 315                 320

Lys Gln Lys Asp Lys Ser Ala Ser Pro Glu Trp Leu Thr Lys Leu Pro
                325                 330                 335

Gln Met Val Lys Gln Leu Glu Val Ser Leu Tyr Arg Ser Ala Pro Ser
            340                 345                 350

Phe Glu Ala Tyr Ser Asp Thr Asn Thr Leu Lys His Arg Leu Gln Gln
        355                 360                 365

Leu Ala Met Glu Ile Ala Arg Lys Thr Gln Gln Ala Lys Ala Ser Gly
    370                 375                 380

Arg Ser Ser Ser Arg Gly Asp Arg Ile Pro Gly Met Gly Asn Met His
385                 390                 395                 400

Tyr Asn Pro Val Asn Met Gly Ala Asn Glu Glu Ile Val Ser Ser Gln
                405                 410                 415

Tyr Gly Asn Pro Asn Asp Pro Glu Trp Lys Val Arg Ile Arg His Lys
            420                 425                 430

Gln Gln Arg Leu Leu Leu Leu His Ser Ser Lys Cys Pro Tyr Asp
        435                 440                 445

Asn Asp Lys Cys Lys Val Thr Pro Tyr Cys Gly Glu Met Lys Lys Leu
    450                 455                 460

Trp Lys His Met Ala Arg Cys Thr Asp Asn Glu Cys Arg Val Pro His
465                 470                 475                 480

Cys Phe Ser Ser Arg Ser Ile Leu Ser His Cys Arg Lys Cys Lys Asp
                485                 490                 495

Pro Gly Cys Pro Ala Cys Gly Pro Val Arg Glu Thr Val Arg Lys Thr
            500                 505                 510

Gln Lys Ser Asn Ala Gly Lys Gly Val Asn Glu Gly Gln Gly Asp Phe
        515                 520                 525

Gly Gly Met Gly Pro Asn Ser Gly Ile Gly Leu Gly Gly Met Gly Asn
    530                 535                 540

Glu Met Gly Gly Gly Gly Ser Gly Met Gly Gly Asn Asp Met Met
545                 550                 555                 560

Gly Gly Met Pro Met Met Gly Gly Asn Met Asn Gln Met Pro Lys Arg
                565                 570                 575

Gln Pro Ser Gln Pro Met Pro Trp Lys Gly Asp Ile Asn Ser Met Pro
            580                 585                 590

Asn Phe Pro Pro Pro Asn Ile Arg Gln Gln Gln Asp Asp Tyr Met Ala
        595                 600                 605

Phe Pro Glu Gly Phe Pro Glu Gly Gln Gln Val Leu Asn Gly Pro Ser
    610                 615                 620

Ser Gly Gln Ser Gly Asn Pro Glu Ser Ser Lys Ala Arg His Lys Gln
625                 630                 635                 640

Gln Arg Leu Leu Leu Leu Arg His Ala Ser Lys Cys Asn Ala Glu Pro
                645                 650                 655

Gly Arg Cys Thr Thr Thr Pro His Cys Ala Glu Met Lys Val Leu Trp
            660                 665                 670

Lys His Ile Ala Asn Cys Lys Asp Gln Tyr Cys Lys Val Lys His Cys
        675                 680                 685

Met Ser Ser Arg Tyr Val Leu Ser His Tyr Arg Arg Cys Asn Asp Pro
    690                 695                 700

Gly Cys Glu Ile Cys Gly Pro Val Arg Glu Ile Phe Lys Ser Gly Thr
705                 710                 715                 720
```

```
Asn His Phe Ile His Asp Pro Ser Phe Met Pro Gly Ser Ser Ala Ala
            725                 730                 735

Asp Leu Ile Thr Pro Pro Leu Pro Glu Gly Pro Gln Thr Lys Arg Ser
            740                 745                 750

Arg Thr Asn Asp Pro Ser Met Asn Gly Met His His Thr Ala Pro Ala
            755                 760                 765

Arg Pro Ala Phe Pro Leu Ser Ala Pro Thr Ser Gly Ser Glu Asn His
770                 775                 780

Ala Lys Leu Lys Ser Ser Ala Lys Pro Ser Ser Ser Asn Ala Thr Glu
785                 790                 795                 800

Glu His Ser Leu Leu Glu Cys Phe Thr Thr Glu Gln Val Lys Thr His
            805                 810                 815

Ile Gln Ser Leu Lys Lys Thr Ile Glu Val Ser Pro Ala Lys Leu Lys
            820                 825                 830

Leu Lys Cys Val Glu Ile Leu Arg Glu Leu Gln Ile His Glu His Gly
            835                 840                 845

Trp Val Phe Ala Thr Pro Val Asp Pro Val Glu Leu Gly Leu Asp Asp
            850                 855                 860

Tyr Phe Asp Val Ile Lys Lys Pro Met Asp Leu Gly Thr Ile Ser Arg
865                 870                 875                 880

Arg Leu Asp Asn Gly Ser Tyr His Ala Phe Asp Asp Phe Lys Ser Asp
                885                 890                 895

Val Arg Leu Thr Phe Glu Asn Ala Met Lys Tyr Asn Asp Glu Asn Ser
            900                 905                 910

Val Val His Glu Met Ala Lys Glu Leu Lys Lys Lys Phe Asp Thr Asp
            915                 920                 925

Tyr Lys Lys Leu Met Lys Gln Leu Glu Lys Glu His Arg Glu Asn Ser
            930                 935                 940

Met Arg Gln Gln Ala Cys Gly Leu Cys Gly Cys Glu Lys Leu Asn Phe
945                 950                 955                 960

Glu Pro Pro Val Phe Phe Cys Asn Gly Met Asn Cys Pro Ser Lys Arg
                965                 970                 975

Ile Arg Arg Asn Thr His Phe Tyr Ile Thr Ala Asp Lys Gln Tyr Ala
            980                 985                 990

Trp Cys Ser Gln Cys Tyr Asn Glu Leu Gly Gly Glu Ile Asp Leu Gly
            995                 1000                1005

Thr Ser Val Leu Lys Lys Val Asp Leu Ala Lys Lys Lys Asn Asp
    1010                1015                1020

Glu Thr His Glu Glu Ser Trp Val Gln Cys Asp Asp Cys Glu Arg
    1025                1030                1035

Trp Ile His Gln Ile Cys Gly Leu Tyr Asn Thr Arg Gln Asp Lys
    1040                1045                1050

Glu Asn Lys Ser Ala Tyr Ser Cys Pro Leu Cys Leu Leu Asp Lys
    1055                1060                1065

Arg Lys Lys Glu Gly Glu Pro Lys Lys Leu Pro Pro Pro Pro Ala
    1070                1075                1080

Ala Ser Asp Ile Pro Arg Thr Asn Leu Ser Asp Trp Leu Glu Arg
    1085                1090                1095

Asp Val His Lys Lys Val Asn Gln Arg Leu Lys Glu Leu Ala Gln
    1100                1105                1110

Glu Lys Ala Asp Thr Glu His Ile Ala Phe Glu Lys Ala Tyr Ala
    1115                1120                1125
```

```
Asp Leu Ser Ala Gly Gly Pro Leu Thr Ile Arg Gln Val Thr Ser
    1130            1135            1140

Thr Asp Arg Lys Leu Glu Val Arg Asp Gln Met Arg Gln Arg Tyr
    1145            1150            1155

Ala His Lys Asn Tyr Pro Glu Glu Phe Pro Tyr Arg Cys Lys Cys
    1160            1165            1170

Ile Val Val Phe Gln Asn Ile Asp Gly Val Asp Val Val Leu Phe
    1175            1180            1185

Ala Leu Tyr Val Tyr Glu His Gly Asp Asp Asn Pro Phe Pro Asn
    1190            1195            1200

Lys Lys Thr Val Tyr Val Ser Tyr Leu Asp Ser Val His Phe Met
    1205            1210            1215

Lys Pro Arg Gln Met Arg Thr Phe Leu Tyr His Glu Ile Leu Ile
    1220            1225            1230

Ser Tyr Leu Asp Tyr Ala Arg Gln Lys Gly Phe Leu Gln Ala Phe
    1235            1240            1245

Ile Trp Ala Cys Pro Pro Leu Lys Gly Asp Asp Tyr Ile Phe Tyr
    1250            1255            1260

Ala Lys Pro Glu Asp Gln Lys Thr Pro Lys Asp Val Arg Leu Arg
    1265            1270            1275

Gln Trp Tyr Leu Asp Met Leu Val Glu Cys Gln Lys Arg Asn Ile
    1280            1285            1290

Val Gly Met Val Ser Asn Met Tyr Asp Gln Tyr Phe Ala Asn Lys
    1295            1300            1305

Ser Leu Asp Ala Ala Ser Val Pro Tyr Phe Asp Gly Asp Tyr Phe
    1310            1315            1320

Pro Gly Glu Ala Glu Asn Ile Ile Lys Asp Leu Glu Glu Ser Asn
    1325            1330            1335

Ser Lys Arg Lys Gly Gly Ala Gly Lys Lys Asn Lys Asp Pro Ser
    1340            1345            1350

Lys Ser Lys Ala Ala Pro Ser Gly Asp Ala Glu Phe Val Gly Glu
    1355            1360            1365

Lys Cys Tyr Lys Glu Gly Gly Arg Asp Pro Val Met Gln Lys Phe
    1370            1375            1380

Cys Asp Ala Ile Gln Gly Met Lys Glu Ser Phe Ile Val Ala Tyr
    1385            1390            1395

Leu Asn Ala Lys Asp Ala Lys Pro Glu His Leu Val Val Pro Lys
    1400            1405            1410

Lys Ile Met Glu Phe Arg Glu Ala Asn Lys Leu Leu Met Ile Asp
    1415            1420            1425

Asp Asp Pro Lys Lys Lys Lys Glu Asp Gly Thr Glu Glu Lys Lys
    1430            1435            1440

Asp Asp Glu Lys Pro Gln Ser Lys Lys Arg Asp Ala Asp Gly Tyr
    1445            1450            1455

Glu Val Ala Ala Ser Glu Lys Pro Pro Ala Asn Lys Gln Leu Asn
    1460            1465            1470

Ser Lys Gly Lys Pro Val Arg Val Leu Asn Asp Asp Asp Glu Glu
    1475            1480            1485

Ile Asp Cys Glu Phe Phe Asn Thr Arg Gln Cys Phe Leu Asp Leu
    1490            1495            1500

Cys Arg Gly Asn His Tyr Gln Phe Asp Glu Leu Arg Arg Ala Lys
    1505            1510            1515

His Thr Ser Met Met Val Leu Trp His Leu Gln Asn Arg Glu Ala
```

|  | 1520 |  | 1525 |  |  | 1530 |  |  |  |
|---|---|---|---|---|---|---|---|---|---|

Pro Lys Phe Val Gln Gln Cys Met Ala Cys Asn Arg Glu Ile Ala
    1535                      1540                      1545

Ser Gly Ile Arg His His Cys Asn Val Cys Ser Asp Phe Asp Leu
    1550                      1555                      1560

Cys Asp Asp Cys Phe Arg Asp Pro Asp Thr Asn Arg Gly Thr Cys
 1565                      1570                      1575

Asn His Lys Leu Glu Ala Ile Lys Val Asp Thr Ala Gln Ser Glu
    1580                      1585                      1590

Asn Ser Gly Leu Thr Glu Glu Gln Arg Lys Glu Arg Gln Arg Asn
    1595                      1600                      1605

Ile Gln Leu His Ile Thr Leu Ile Glu His Ala Ser Arg Cys Asn
    1610                      1615                      1620

Ser Ser Ser Cys Lys Ser Ser Asn Cys Met Lys Met Lys Ser Tyr
    1625                      1630                      1635

Leu Lys His Gly Ser Thr Cys Thr Val Lys Ala Ser Gly Gly Cys
    1640                      1645                      1650

Lys Ile Cys Lys Arg Ile Trp Thr Leu Leu Arg Ile His Ala Gln
    1655                      1660                      1665

Gln Cys Lys Ser Ser Ser Cys Ala Ile Pro Gln Cys Ile Ala Ile
 1670                      1675                      1680

Arg Lys Arg Ile Arg Gln Leu Gln Leu Lys Gln Gln Ala Met Asp
    1685                      1690                      1695

Asp Arg Arg Arg Gln Glu Met Asn Arg His Tyr Arg Met Gly Met
 1700                      1705                      1710

Met Ser Ser Asp Asn
    1715

```
<210> SEQ ID NO 27
<211> LENGTH: 7281
<212> TYPE: DNA
<213> ORGANISM: Phaeodactylum tricornutum
<220> FEATURE:
<221> NAME/KEY: misc_feature
<223> OTHER INFORMATION: encodes polypeptide of SEQ ID NO:28

<400> SEQUENCE: 27
atgcaatcca atagtggtgg gatgcctgga ggtagtatga acgcaacgtc gatgcaagac      60
atgcaacgtt tgcagctcca aatggcgcag tatcaacagc agcagcaaca acaacaacga     120
caggcgcccg tcggaaacca gctactcctt aacaatcaca acagtgtgtc aaacctaaat     180
atgcagcagc agtttcccag caacacaaac aacgcgccta ccgcatcatt tgtgaacctg     240
tcgacacaat ctggcgccgc aggtcgtatg agtaatccgg cgcttgccat gatgcaacaa     300
cagcagcagg gagttgtgac aggtagcaat ggcgcttcat tgatgaattc cggggtccc     360 aacgcggctt ccatgtttag ttggaatgga atgcagcagc acagcagggg tcagaacgcg     420
tcgtcgatgg acgccagcac cggaagtagt gctcgtctca tggctatggc taacatgaat     480
cgtatgagta taggggagg ggccggtact atttcagggc aggggaatag tatgaatccg     540
tctacgagca caatgccgaa tatgcagact ttacttcagc agcagcaggt gaacgcctct     600
catacaccaa atcagatggg cttcagcag cagcatcact tgtcgggtc tcagatggga     660 tcgtccacaa atacgaatca caccaacggt ggaggagcac agcagcttat gctacagcag     720
cagatcgcga gtttacagaa gcagatgcaa tttcaacatc aaggtggcat tggaaccgta     780
tcagctatgc agaatcctc tatatccaat gcaactgttg gcagtgcggg tccacgggcg     840
```

```
gcaaactcgc tgcaatctca ccagcagcaa cttctgcagc aaatacagca acaacagcat    900
gttgggcccg ggcctccttc tatgcctgcg caacaccagc aaccctatca acaacaccaa    960
atgtctgccg gaatgcagtc tctgcatcag caagactcga ctccacaaaa tatgatgaat   1020
atgcttcaac agcaacctca atctcacgcc agaaataatg ccatggctaa cgtgatgagt   1080
gatcaatcaa gtcagactct tagtcgaagt gggtccttaa atgagcaaca gttgcgaatt   1140
catcagcaga atctgctgcg tgcttcatcc gggcagcaaa ccacggtgtc ggatacgcaa   1200
gaagcggcga agtccgtaag atcgcagcag cagtcaccaa gtcaaccgtc caaacaacat   1260
ggaatgcatc cacaaaatgc aacgtcgtat caaccatcca acaatattgt acagggtcca   1320
tttggcggaa tgcatggctt gcccaatcag catagcatgc aaagtgtgtc caaccaacag   1380
ctaaacaatc atgggaaagc aatgccgatg cattccgatg gtagcactac tttaggcatg   1440
tcctcacatg gaacaatag catgtacagt gggcaaatga gtggtagtaa cgcttctcag    1500
cagcagggta gcgacgatcc aatttccatt tcacagcaca gtaatttaag tgctggtcag   1560
ctgtcacgca ctcatcaagc gagcagcaat gactctggac aaaagacttt tctggatggt   1620
agctttgctg ggggctggca atctaacgat gatctgccag atcgacgtcg cgttatattt   1680
agcattttag aggtgattcg gcagattcgg cccgacgata cgagcaaaat gtcaaacaaa   1740
ctacctcata tggcaaagag cctggaagag catttgtatc gatcggcaca cagcaaagac   1800
gaatacatgg attttcaac tctgaaggag cgtttgcaag caattgcgca tggacttgac   1860
ctgcacagag gttcctcttc gccaatggtt tccaagaatc atgatacgac gcacttgccc   1920
cagcaaagta gtaatccaag ctattcaaat attgagtctc agcagaattc tttgcaaatc   1980
ggctttccgc caagcttgac tgcatctggt ccgacaagtc agcagcatca aaatgcgggt   2040
tggacgggtc catatgatgt aagttccaag gatgtgatga aaattcaagg ccaaaacaac   2100
gccgacaatt tagttgtgca gagaaacgca gctagtcagc agagctttgg acgtattgct   2160
ggttcgaata gtcaacatgg aggcattatg tcgggatcaa ataccgctgg tccaaaccac   2220
aacagcggaa tttggccaac gaatatggga tcgtcggaaa gtttgggtca accgagcata   2280
gggaatgtgg caatgaacgg cggctcgcag catcaatcct caatgaatca agggatgaac   2340
gatatggcgt cgatgagtca gacttcgcaa cagaacgatt ttgctgggtc ttccctgttt   2400
attgatcctt gcaaggctt caattggcag agcggtttcc tttcggactc aaatatgcct   2460
cccctgtcg ggaatggtat agttaactcg gattatccaa atacacccaa gtaccaggat   2520
ccgggcgtag cgcagaagca gaaggtcata ttgcagcagc aacagcgatt gctgctactt   2580
cggcatgcca gtaaatgcaa ggcgggatca aactgtacga cgaagttctg ttctcagatg   2640
gtgaccttgt ggaagcatat gaagacttgc cgtgataaga attgtaagac ttctcattgc   2700
ttgagcagtc gttgtgtttt gaatcactac cgtatttgca aaatcaagg caagacgtcg   2760
acttgtgaag tatgcggtcc tgtgatggcg aaaatccgtc aacaggagcg cgacgatggt   2820
actggtgatc ccttggccac cgattcctct gccatgaact atcttcagcc aagcttgaat   2880
gctcttccaa atgtgattcc gacaaaacaa atcggtggtt tgtcacaggt tcgacggagc   2940
gataatattt tggaaaattc ttgtcaaagt gaacaggtcc agctgcagca attgcaggcg   3000
cagcaaatga aacttcaaac acagttggat tcattgaagc agcttcagaa acagcaagag   3060
caattgctcg agcagcagtc gagaatacag gagcaggcgc ataaggtcaa ggacccaagc   3120
tcccagcaag cacaacaatt gcaacaacag cagcttcttc tgcatcagct acagaaacga   3180
```

```
tgcgaacaac agcagcttca gctacaacaa gagattcagt cccaatcgag aacagctggt    3240
ttggcccaag ctcaggctca gcaattccaa gcggcagcac agtttcgtac aagtgtacaa    3300
gaggcccaga tgttgcagtc ttcatcacca attattcctg gatcctacgg ggaaccaaca    3360
gagtctaaga aaaagcggca tacggtaaca aaatccaaac gaatttcgtc gaaagggaag    3420
cgtggtggga agggaaagg acttcgggct gcggttgagg ttctatcatc ccatgatcca    3480
gccgaagata actttgatcc atatgcctcg ccaaaaaaga ggggtctgtc ttcttcttcg    3540
aagccagcgc aaaagaaaag gaaggcaact tccgataaag aggctgaccc aggcgaaagg    3600
gcgacaggaa ctgatattgt ggaagactcg acgctggcgt atgaaggcaa tacgtctttg    3660
cttccgttca tgagtctagt cagcgtcaga aaacatgtgg attctctgaa taaaaaaaca    3720
agtctttggt ctcgcatggt gacttacaag tgtcttccag tcattcaaga gctcattgac    3780
gaccagtttg ggtgggtttt ccacgacgcc gtcgatccaa ttgcacttgg cttgcccgac    3840
tactttgatg ttgtgaaaca tcccatgcat ctcgagcttg tgaagaaaaa actggaaaat    3900
gcgatctact gtgacacaga cagttttgcg catgacgttg agctagtttt tgagaatgct    3960
attttgtaca atgggaaaac cagtgaagtt ggagagctag cgaatagttt cttggtcaag    4020
tttgctcaga tatacgagaa gctcattgca ggaatcgagt cgccgcagca actcgtgaaa    4080
aagaatgggg aggcttgtgc tctctgtggt ctccaaaaga gacagcttga gccattatcg    4140
ctttattgtc atgggaactg tggtatgcag cctatcgaaa ggcattcatc ttactttacc    4200
gatcactcaa aatcaaatct ttggtgttta ttgtgttacg atcagttgca cgaagaaaaa    4260
atcatattgc tggacgacgg aagtgatatt agaaaaaagg attacaaga gttcaagaat    4320 gacacttgtc ctgaggaagc atggatcact tgtgacgagt gtaattctca agttcacgaa    4380
gtttgcgctc ttttcagcag gagaaacgag gcaaaagctt cgtacacctg cccaaactgc    4440
tatacctcga aatctttagc gtcgcaaagc acgaagtctg tggccaagtt tgtaaagggg    4500
gctgattatt taccacactg taaaatgagt attgatatcg aaaagggact tcatagaacg    4560
ctccaagatc tctatgatgc caaagcgaaa gatgaaaaat tgggggccgg ccaaactgag    4620
caagcggagg gtctcactgt tagagtgcta tcaaatgtag aaaagaaaca atctgtagga    4680
gcgaggatgc aacgctgttt ttccgaaaag gggtacccct tagagtttcc tgtacgctcg    4740 aaaatgcattg ccctctcttca aaaaatccac ggtgttgaca cccttctttt ttcagtctat    4800
gtgtatgaat acgggcaaga atgtccagct ccgaacaaaa gaagggtgta catttcttgc    4860
ttagattctg ttcaatatt tgagcccagc tgctaccgta aagcggctta ccaggcaatc    4920
attgtcgaat atctgcgtta cgtaaaggag cgaggcttcc atacggctca tatatggagc    4980
tgtcctctga cgcccgaaga cggatacatt ttctattgtc acccatcgca ccaacttata    5040
ccgcgagaag atatgcttca gtcatggtat catcagctac tagaaaaggc gaagtcaagt    5100
ggtgttgcta ttagcaccac cacgctctat cacgagtatt ttgaaggtgg ggctgattct    5160
acgaaaattg agcaacaaag gttgccgacc tgtctcccat atttttgaagg tgactacata    5220 cctggtgaaa tcgagaatat cctggaaaca attgatgaaa agaaaatca gagtagtgtc    5280 cagaaactga tcatgtccct gcttgggcag aggatcatga agatgaaaga caatttcctc    5340
gttgttcatt tacacaatga tggtgttgct gcggctagcg agcaaagcga agacgtttca    5400
aaagggtgtg acggctgcga cgagaaaata gtgctcagca agatcaag tacaactgaa    5460 ccgggtttga tgcggatcga tgtaagggac gatgatgtag caatgacgga agctgacgct    5520
tttcctgccc gggaggatcc tactgtattg aaaacagctg ctccaccgaa gaaggtaaat    5580
```

-continued

```
actccggaga aagctacacg ttcaatggga gaggcaacat ccaaatctga aaaaactgaa    5640
gacaagagtg ttccaacacc tggtatgttg ctatttgaaa agcctgggag cgacacaagt    5700
cttgttgatt cagctaaaga cgcagcaaat gagggtgtgg ccccaatatc agtttcaatg    5760
ggagaaccaa cagccgaatc tgaaaagagg aaagatagat atgtttcgac agctattgtt    5820
tgtgagaagc ctaggagtaa cttcagtctg attgaatcaa cgaaagatac agcagaaacc    5880
gctgcggccc ccgattcaat ttcgatagta gattcaaaag ttgattccaa agacacggct    5940
tattcaacaa ctggcgcttt gctttgtggt aagcctggga gcgacataag cccgattgat    6000
tcagccgata acgtcaaaaa tgaaattgag cttcctggtg taagagtagc tggagtgaaa    6060
gaagaaagtg aagcgaggg  attgcgggag aaagtcagcc ttgcgcatac tgtttgcgtt    6120
gtagaattaa aagctaacga tgaacctccg ctagaagaat cgggcggtaa cggaggcctg    6180
acaaacgaaa gcgatggggt cgctgcttca ctcatagaga aacaagctac catccagata    6240
gctggaggga atctttccga aacccaaacg gagccaatcg attcggagga tggatgtatc    6300
gacgattctg tcaacactgc agtccaatct ggcgagttgg atgaaaagga gggaagtgca    6360
acagaacaaa atcgggatga agtgattgcc accatcgaca agaaagcgag caaaaggctt    6420
atggacagcg cgatctcaac ccacactgaa cccaccgaat cttcgagtga aatttcgaca    6480
aaaagtgctc tggcgagcag aagccctctc gtcaatagaa agaggccgct gaattcggtt    6540
gaatccaaca catgggatga agatgctccc attgaaaatg ctttgtttga accccacag    6600 catttcttaa attttgtaa  aacaaagcac tttcagtttg atgagcttcg acgagccaaa    6660
cactccactt tgtcgatact ctttcagctg cacaatccta tggcttcaca cgttcttcag    6720
cagtgcggat cgtgctaccg agatataacc tgcgatgcca ggtaccattg caatgtttgc    6780
tccaacttcg acttgtgcca agaatgctac agctcagtaa tgaagaagga gtttgttctg    6840
aatgactccc gcttcgctca tgacacgagc cacacgtttt ctcccattga tacgaaaatg    6900
cttgaagaaa cgaaaacacg cgaagaacgt cagaaatcct taacggcgca tgttgaactc    6960
ctggagcacg ctgtaccttg ccaaggccca ccagcatgct ctctggagaa ctgccagcgc    7020
atgaaaaaac tcgtcgagca cgtgggaact tgtatgatcc aaccaaagaa ggactgcaag    7080
atttgcagtc gactcctgtc gctatgtaca atacattcgc gtttgtgcgc tattcgcgga    7140
ccttgtccga ttcccttttg tgaccgaatc cgagagcgca acaaacgact acgccagcag    7200
caagatcttg tggacgaccg cgccgacaa  gctcaaaatg aattgtacca atcctctgaa    7260
gagccatcta taacaacttg a                                              7281
```

<210> SEQ ID NO 28
<211> LENGTH: 2426
<212> TYPE: PRT
<213> ORGANISM: Phaeodactylum tricornutum
<220> FEATURE:
<221> NAME/KEY: misc_feature
<223> OTHER INFORMATION: Translation product 332250

<400> SEQUENCE: 28

```
Met Gln Ser Asn Ser Gly Gly Met Pro Gly Gly Ser Met Asn Ala Thr
1               5                   10                  15

Ser Met Gln Asp Met Gln Arg Leu Gln Leu Gln Met Ala Gln Tyr Gln
                20                  25                  30

Gln Gln Gln Gln Gln Gln Gln Arg Gln Ala Pro Val Gly Asn Gln Leu
            35                  40                  45
```

```
Leu Leu Asn Asn His Asn Ser Val Ser Asn Leu Asn Met Gln Gln Gln
 50                  55                  60

Phe Pro Ser Asn Thr Asn Asn Ala Pro Thr Ala Ser Phe Val Asn Leu
 65                  70                  75                  80

Ser Thr Gln Ser Gly Ala Ala Gly Arg Met Ser Asn Pro Ala Leu Ala
                 85                  90                  95

Met Met Gln Gln Gln Gln Gly Val Val Thr Gly Ser Asn Gly Ala
            100                 105                 110

Ser Leu Met Asn Ser Gly Gly Pro Asn Ala Ala Ser Met Phe Ser Trp
            115                 120                 125

Asn Gly Met Gln Gln Pro Gln Gln Gly Gln Asn Ala Ser Ser Met Asp
    130                 135                 140

Ala Ser Thr Gly Ser Ser Ala Arg Leu Met Ala Met Ala Asn Met Asn
145                 150                 155                 160

Arg Met Ser Ile Gly Gly Ala Gly Thr Ile Ser Gly Gln Gly Asn
                165                 170                 175

Ser Met Asn Pro Ser Thr Ser Thr Met Pro Asn Met Gln Thr Leu Leu
            180                 185                 190

Gln Gln Gln Gln Val Asn Ala Ser His Thr Pro Asn Gln Met Gly Phe
        195                 200                 205

Gln Gln Gln His His Leu Ser Gly Ser Gln Met Gly Ser Ser Thr Asn
    210                 215                 220

Thr Asn His Thr Asn Gly Gly Ala Gln Gln Leu Met Leu Gln Gln
225                 230                 235                 240

Gln Ile Ala Ser Leu Gln Lys Gln Met Gln Phe Gln His Gln Gly Gly
                245                 250                 255

Ile Gly Thr Val Ser Ala Met Gln Asn Pro Ser Ile Ser Asn Ala Thr
            260                 265                 270

Val Gly Ser Ala Gly Pro Arg Ala Ala Asn Ser Leu Gln Ser His Gln
        275                 280                 285

Gln Gln Leu Leu Gln Gln Ile Gln Gln Gln His Val Gly Pro Gly
    290                 295                 300

Pro Pro Ser Met Pro Ala Gln His Gln Gln Pro Tyr Gln Gln His Gln
305                 310                 315                 320

Met Ser Ala Gly Met Gln Ser Leu His Gln Gln Asp Ser Thr Pro Gln
                325                 330                 335

Asn Met Met Asn Met Leu Gln Gln Gln Pro Gln Ser His Ala Arg Asn
            340                 345                 350

Asn Ala Met Ala Asn Val Met Ser Asp Gln Ser Ser Gln Thr Leu Ser
        355                 360                 365

Arg Ser Gly Ser Leu Asn Glu Gln Gln Leu Arg Ile His Gln Gln Asn
    370                 375                 380

Leu Leu Arg Ala Ser Ser Gly Gln Gln Thr Thr Val Ser Asp Thr Gln
385                 390                 395                 400

Glu Ala Ala Lys Ser Val Arg Ser Gln Gln Ser Pro Ser Gln Pro
                405                 410                 415

Ser Lys Gln His Gly Met His Pro Gln Asn Ala Thr Ser Tyr Gln Pro
            420                 425                 430

Ser Asn Asn Ile Val Gln Gly Pro Phe Gly Met His Gly Leu Pro
        435                 440                 445

Asn Gln His Ser Met Gln Ser Val Ser Asn Gln Leu Asn Asn His
    450                 455                 460

Gly Lys Ala Met Pro Met His Ser Asp Gly Ser Thr Thr Leu Gly Met
```

-continued

```
            465                 470                 475                 480
        Ser Ser His Gly Asn Asn Ser Met Tyr Ser Gly Gln Met Ser Gly Ser
                            485                 490                 495

Asn Ala Ser Gln Gln Gln Gly Ser Asp Asp Pro Ile Ser Ile Ser Gln
                            500                 505                 510

His Ser Asn Leu Ser Ala Gly Gln Leu Ser Arg Thr His Gln Ala Ser
                            515                 520                 525

Ser Asn Asp Ser Gly Gln Lys Thr Phe Leu Asp Gly Ser Phe Ala Gly
                            530                 535                 540

Gly Trp Gln Ser Asn Asp Asp Leu Pro Asp Arg Arg Arg Val Ile Phe
        545                 550                 555                 560

Ser Ile Leu Glu Val Ile Arg Gln Ile Arg Pro Asp Asp Thr Ser Lys
                            565                 570                 575

Met Ser Asn Lys Leu Pro His Met Ala Lys Ser Leu Glu Glu His Leu
                            580                 585                 590

Tyr Arg Ser Ala His Ser Lys Asp Glu Tyr Met Asp Phe Ser Thr Leu
                            595                 600                 605

Lys Glu Arg Leu Gln Ala Ile Ala His Gly Leu Asp Leu His Arg Gly
                            610                 615                 620

Ser Ser Ser Pro Met Val Ser Lys Asn His Asp Thr Thr His Leu Pro
        625                 630                 635                 640

Gln Gln Ser Ser Asn Pro Ser Tyr Ser Asn Ile Glu Ser Gln Gln Asn
                            645                 650                 655

Ser Leu Gln Ile Gly Phe Pro Pro Ser Leu Thr Ala Ser Gly Pro Thr
                            660                 665                 670

Ser Gln Gln His Gln Asn Ala Gly Trp Thr Gly Pro Tyr Asp Val Ser
                            675                 680                 685

Ser Lys Asp Val Met Lys Ile Gln Gly Gln Asn Asn Ala Asp Asn Leu
                            690                 695                 700

Val Val Gln Arg Asn Ala Ala Ser Gln Gln Ser Phe Gly Arg Ile Ala
        705                 710                 715                 720

Gly Ser Asn Ser Gln His Gly Gly Ile Met Ser Gly Ser Asn Thr Ala
                            725                 730                 735

Gly Pro Asn His Asn Ser Gly Ile Trp Pro Thr Asn Met Gly Ser Ser
                            740                 745                 750

Glu Ser Leu Gly Gln Pro Ser Ile Gly Asn Val Ala Met Asn Gly Gly
                            755                 760                 765

Ser Gln His Gln Ser Ser Met Asn Gln Gly Met Asn Asp Met Ala Ser
                            770                 775                 780

Met Ser Gln Thr Ser Gln Gln Asn Asp Phe Ala Gly Ser Ser Leu Phe
        785                 790                 795                 800

Ile Asp Pro Leu Gln Gly Phe Asn Trp Gln Ser Gly Phe Leu Ser Asp
                            805                 810                 815

Ser Asn Met Pro Pro Val Gly Asn Gly Ile Val Asn Ser Asp Tyr
                            820                 825                 830

Pro Asn Thr Pro Lys Tyr Gln Asp Pro Gly Val Ala Gln Lys Gln Lys
                            835                 840                 845

Val Ile Leu Gln Gln Gln Arg Leu Leu Leu Arg His Ala Ser
        850                 855                 860

Lys Cys Lys Ala Gly Ser Asn Cys Thr Thr Lys Phe Cys Ser Gln Met
        865                 870                 875                 880

Val Thr Leu Trp Lys His Met Lys Thr Cys Arg Asp Lys Asn Cys Lys
                            885                 890                 895
```

Thr Ser His Cys Leu Ser Ser Arg Cys Val Leu Asn His Tyr Arg Ile
                900                 905                 910
Cys Lys Asn Gln Gly Lys Thr Ser Thr Cys Glu Val Cys Gly Pro Val
                915                 920                 925
Met Ala Lys Ile Arg Gln Gln Glu Arg Asp Asp Gly Thr Gly Asp Pro
            930                 935                 940
Leu Ala Thr Asp Ser Ser Ala Met Asn Tyr Leu Gln Pro Ser Leu Asn
945                 950                 955                 960
Ala Leu Pro Asn Val Ile Pro Thr Lys Gln Ile Gly Gly Leu Ser Gln
                965                 970                 975
Val Arg Arg Ser Asp Asn Ile Leu Glu Asn Ser Cys Gln Ser Glu Gln
            980                 985                 990
Val Gln Leu Gln Gln Leu Gln Ala Gln Gln Met Lys Leu Gln Thr Gln
            995                 1000                1005
Leu Asp Ser Leu Lys Gln Leu Gln Lys Gln Gln Glu Gln Leu Leu
    1010                1015                1020
Glu Gln Gln Ser Arg Ile Gln Glu Gln Ala His Lys Val Lys Asp
    1025                1030                1035
Pro Ser Ser Gln Gln Ala Gln Gln Leu Gln Gln Gln Gln Leu Leu
    1040                1045                1050
Leu His Gln Leu Gln Lys Arg Cys Glu Gln Gln Gln Leu Gln Leu
    1055                1060                1065
Gln Gln Glu Ile Gln Ser Gln Ser Arg Thr Ala Gly Leu Ala Gln
    1070                1075                1080
Ala Gln Ala Gln Gln Phe Gln Ala Ala Ala Gln Phe Arg Thr Ser
    1085                1090                1095
Val Gln Glu Ala Gln Met Leu Gln Ser Ser Ser Pro Ile Ile Pro
    1100                1105                1110
Gly Ser Tyr Gly Glu Pro Thr Glu Ser Lys Lys Lys Arg His Thr
    1115                1120                1125
Val Thr Lys Ser Lys Arg Ile Ser Ser Lys Gly Lys Arg Gly Gly
    1130                1135                1140
Lys Gly Lys Gly Leu Arg Ala Ala Val Glu Val Leu Ser Ser His
    1145                1150                1155
Asp Pro Ala Glu Asp Asn Phe Asp Pro Tyr Ala Ser Pro Lys Lys
    1160                1165                1170
Arg Gly Leu Ser Ser Ser Ser Lys Pro Ala Gln Lys Lys Arg Lys
    1175                1180                1185
Ala Thr Ser Asp Lys Glu Ala Asp Pro Gly Glu Arg Ala Thr Gly
    1190                1195                1200
Thr Asp Ile Val Glu Asp Ser Thr Leu Ala Tyr Glu Gly Asn Thr
    1205                1210                1215
Ser Leu Leu Pro Phe Met Ser Leu Val Ser Val Arg Lys His Val
    1220                1225                1230
Asp Ser Leu Asn Lys Lys Thr Ser Leu Trp Ser Arg Met Val Thr
    1235                1240                1245
Tyr Lys Cys Leu Pro Val Ile Gln Glu Leu Ile Asp Asp Gln Phe
    1250                1255                1260
Gly Trp Val Phe His Asp Ala Val Asp Pro Ile Ala Leu Gly Leu
    1265                1270                1275
Pro Asp Tyr Phe Asp Val Val Lys His Pro Met His Leu Glu Leu
    1280                1285                1290

```
Val Lys Lys Lys Leu Glu Asn Ala Ile Tyr Cys Asp Thr Asp Ser
    1295                1300                1305

Phe Ala His Asp Val Glu Leu Val Phe Glu Asn Ala Ile Leu Tyr
    1310                1315                1320

Asn Gly Glu Thr Ser Glu Val Gly Glu Leu Ala Asn Ser Phe Leu
    1325                1330                1335

Val Lys Phe Ala Gln Ile Tyr Glu Lys Leu Ile Ala Gly Ile Glu
    1340                1345                1350

Ser Pro Gln Gln Leu Val Lys Lys Asn Gly Glu Ala Cys Ala Leu
    1355                1360                1365

Cys Gly Leu Gln Lys Arg Gln Leu Glu Pro Leu Ser Leu Tyr Cys
    1370                1375                1380

His Gly Asn Cys Gly Met Gln Pro Ile Glu Arg His Ser Ser Tyr
    1385                1390                1395

Phe Thr Asp His Ser Lys Ser Asn Leu Trp Cys Leu Leu Cys Tyr
    1400                1405                1410

Asp Gln Leu His Glu Glu Lys Ile Ile Leu Leu Asp Asp Gly Ser
    1415                1420                1425

Asp Ile Arg Lys Lys Asp Leu Gln Glu Phe Lys Asn Asp Thr Cys
    1430                1435                1440

Pro Glu Glu Ala Trp Ile Thr Cys Asp Glu Cys Asn Ser Gln Val
    1445                1450                1455

His Glu Val Cys Ala Leu Phe Ser Arg Arg Asn Glu Ala Lys Ala
    1460                1465                1470

Ser Tyr Thr Cys Pro Asn Cys Tyr Thr Ser Lys Ser Leu Ala Ser
    1475                1480                1485

Gln Ser Thr Lys Ser Val Ala Lys Phe Val Lys Gly Ala Asp Tyr
    1490                1495                1500

Leu Pro His Cys Lys Met Ser Ile Asp Ile Glu Lys Gly Leu His
    1505                1510                1515

Arg Thr Leu Gln Asp Leu Tyr Asp Ala Lys Ala Lys Asp Glu Lys
    1520                1525                1530

Leu Gly Ala Gly Gln Thr Glu Gln Ala Glu Gly Leu Thr Val Arg
    1535                1540                1545

Val Leu Ser Asn Val Glu Lys Lys Gln Ser Val Gly Ala Arg Met
    1550                1555                1560

Gln Arg Cys Phe Ser Glu Lys Gly Tyr Pro Leu Glu Phe Pro Val
    1565                1570                1575

Arg Ser Lys Cys Ile Ala Leu Phe Gln Lys Ile His Gly Val Asp
    1580                1585                1590

Thr Leu Leu Phe Ser Val Tyr Val Tyr Glu Tyr Gly Gln Glu Cys
    1595                1600                1605

Pro Ala Pro Asn Lys Arg Arg Val Tyr Ile Ser Cys Leu Asp Ser
    1610                1615                1620

Val Gln Tyr Phe Glu Pro Ser Cys Tyr Arg Lys Ala Ala Tyr Gln
    1625                1630                1635

Ala Ile Ile Val Glu Tyr Leu Arg Tyr Val Lys Glu Arg Gly Phe
    1640                1645                1650

His Thr Ala His Ile Trp Ser Cys Pro Leu Thr Pro Glu Asp Gly
    1655                1660                1665

Tyr Ile Phe Tyr Cys His Pro Ser His Gln Leu Ile Pro Arg Glu
    1670                1675                1680

Asp Met Leu Gln Ser Trp Tyr His Gln Leu Leu Glu Lys Ala Lys
```

```
            1685                1690                1695

Ser Ser Gly Val Ala Ile Ser Thr Thr Thr Leu Tyr His Glu Tyr
    1700                1705                1710

Phe Glu Gly Gly Ala Asp Ser Thr Lys Ile Glu Gln Gln Arg Leu
    1715                1720                1725

Pro Thr Cys Leu Pro Tyr Phe Glu Gly Asp Tyr Ile Pro Gly Glu
    1730                1735                1740

Ile Glu Asn Ile Leu Glu Thr Ile Asp Glu Lys Glu Asn Gln Ser
    1745                1750                1755

Ser Val Gln Lys Leu Ile Met Ser Leu Leu Gly Gln Arg Ile Met
    1760                1765                1770

Lys Met Lys Asp Asn Phe Leu Val Val His Leu His Asn Asp Gly
    1775                1780                1785

Val Ala Ala Ala Ser Glu Gln Ser Glu Asp Val Ser Lys Gly Cys
    1790                1795                1800

Asp Gly Cys Asp Glu Lys Ile Val Leu Ser Lys Arg Ser Ser Thr
    1805                1810                1815

Thr Glu Pro Gly Leu Met Arg Ile Asp Val Arg Asp Asp Val
    1820                1825                1830

Ala Met Thr Glu Ala Asp Ala Phe Pro Ala Arg Glu Asp Pro Thr
    1835                1840                1845

Val Leu Lys Thr Ala Ala Pro Pro Lys Lys Val Asn Thr Pro Glu
    1850                1855                1860

Lys Ala Thr Arg Ser Met Gly Glu Ala Thr Ser Lys Ser Glu Lys
    1865                1870                1875

Thr Glu Asp Lys Ser Val Pro Thr Pro Gly Met Leu Leu Phe Glu
    1880                1885                1890

Lys Pro Gly Ser Asp Thr Ser Leu Val Asp Ser Ala Lys Asp Ala
    1895                1900                1905

Ala Asn Glu Gly Val Ala Pro Ile Ser Val Ser Met Gly Glu Pro
    1910                1915                1920

Thr Ala Glu Ser Glu Lys Arg Lys Asp Arg Tyr Val Ser Thr Ala
    1925                1930                1935

Ile Val Cys Glu Lys Pro Arg Ser Asn Phe Ser Leu Ile Glu Ser
    1940                1945                1950

Thr Lys Asp Thr Ala Glu Thr Ala Ala Ala Pro Asp Ser Ile Ser
    1955                1960                1965

Ile Val Asp Ser Lys Val Asp Ser Lys Asp Thr Ala Tyr Ser Thr
    1970                1975                1980

Thr Gly Ala Leu Leu Cys Gly Lys Pro Gly Ser Asp Ile Ser Pro
    1985                1990                1995

Ile Asp Ser Ala Asp Asn Val Lys Asn Glu Ile Glu Leu Pro Gly
    2000                2005                2010

Val Arg Val Ala Gly Val Lys Glu Glu Ser Gly Ser Glu Gly Leu
    2015                2020                2025

Arg Glu Lys Val Ser Leu Ala His Thr Val Cys Val Val Glu Leu
    2030                2035                2040

Lys Ala Asn Asp Glu Pro Pro Leu Glu Glu Ser Gly Gly Asn Gly
    2045                2050                2055

Gly Leu Thr Asn Glu Ser Asp Gly Val Ala Ala Ser Leu Ile Glu
    2060                2065                2070

Lys Gln Ala Thr Ile Gln Ile Ala Gly Gly Asn Leu Ser Glu Thr
    2075                2080                2085
```

Gln Thr Glu Pro Ile Asp Ser Glu Asp Gly Cys Ile Asp Asp Ser
    2090            2095                2100

Val Asn Thr Ala Val Gln Ser Gly Glu Leu Asp Glu Lys Glu Gly
    2105            2110                2115

Ser Ala Thr Glu Gln Asn Arg Asp Glu Val Ile Ala Thr Ile Asp
    2120            2125                2130

Lys Lys Ala Ser Lys Arg Leu Met Asp Ser Ala Ile Ser Thr His
    2135            2140                2145

Thr Glu Pro Thr Glu Ser Ser Ser Glu Ile Ser Thr Lys Ser Ala
    2150            2155                2160

Leu Ala Ser Arg Ser Pro Leu Val Asn Arg Lys Arg Pro Leu Asn
    2165            2170                2175

Ser Val Glu Ser Asn Thr Trp Asp Glu Asp Ala Pro Ile Glu Asn
    2180            2185                2190

Ala Leu Phe Glu Thr Pro Gln His Phe Leu Asn Phe Cys Lys Thr
    2195            2200                2205

Lys His Phe Gln Phe Asp Glu Leu Arg Arg Ala Lys His Ser Thr
    2210            2215                2220

Leu Ser Ile Leu Phe Gln Leu His Asn Pro Met Ala Ser His Val
    2225            2230                2235

Leu Gln Gln Cys Gly Ser Cys Tyr Arg Asp Ile Thr Cys Asp Ala
    2240            2245                2250

Arg Tyr His Cys Asn Val Cys Ser Asn Phe Asp Leu Cys Gln Glu
    2255            2260                2265

Cys Tyr Ser Ser Val Met Lys Lys Glu Phe Val Leu Asn Asp Ser
    2270            2275                2280

Arg Phe Ala His Asp Thr Ser His Thr Phe Ser Pro Ile Asp Thr
    2285            2290                2295

Glu Met Leu Glu Glu Thr Lys Thr Arg Glu Arg Gln Lys Ser
    2300            2305                2310

Leu Thr Ala His Val Glu Leu Leu Glu His Ala Val Pro Cys Gln
    2315            2320                2325

Gly Pro Pro Ala Cys Ser Leu Glu Asn Cys Gln Arg Met Lys Lys
    2330            2335                2340

Leu Val Glu His Val Gly Thr Cys Met Ile Gln Pro Lys Lys Asp
    2345            2350                2355

Cys Lys Ile Cys Ser Arg Leu Leu Ser Leu Cys Thr Ile His Ser
    2360            2365                2370

Arg Leu Cys Ala Ile Arg Gly Pro Cys Pro Ile Pro Phe Cys Asp
    2375            2380                2385

Arg Ile Arg Glu Arg Asn Lys Arg Leu Arg Gln Gln Gln Asp Leu
    2390            2395                2400

Val Asp Asp Arg Arg Gln Ala Gln Asn Glu Leu Tyr Gln Ser
    2405            2410                2415

Ser Glu Glu Pro Ser Ile Thr Thr
    2420            2425

<210> SEQ ID NO 29
<211> LENGTH: 4812
<212> TYPE: DNA
<213> ORGANISM: Phaeodactylum tricornutum
<220> FEATURE:
<221> NAME/KEY: misc_feature
<223> OTHER INFORMATION: Encodes polypeptide of SEQ ID NO:30

```
<400> SEQUENCE: 29
atgcaagcct cgcaagccca actgcagcca caacaggcgc cgccggttgc cgccccgctt      60
ccgtcagcgg cggcgcaaca aggatcggcg gcggcgccgg cagtgtcgca ctactcatca     120
cagcacttgt cacaggtgcc ggctgcgcaa cccgtctggg cgccgcaatc gcaaggagtt     180
gttcatcaac agcgcccagt gtcgcaaggt ataaactata cgacgcaaac gtcacaatcg     240
cagacgccgg ctcagcagca ggctcccccg caacagcatt tccctcacca aggactcaac     300
ggcggatggc aaagcgataa ggactatcaa gagcgccgga aaatgatcgc caagattgtg     360
catctactgc aacagcgcaa gccgaatgct ccgcaggaat ggttgaagaa acttccgcaa     420
atggcgaaaa gattggaaga gtcgctgtat cgcacagcaa cgtcctttga agagtataac     480
gatgccaaca cgttgaagca tcgtttgcag cagttggcgg tgaacattgg ccaaaagacc     540
aagaagctgc aacaacagca ggcgttgttg gctcaacaga gactacagca gcagcaacaa     600
caacaacagg ttcggcagca gtctgataca actcagtaca ctccccaggt accgccatct     660
acttcacagc aagcattaat acagccgcag acgcagcaag gtctaatacc tcaagtgaag     720
agcgccgcgc cacctgcgtc acaagtacaa ggtcaacgga tggtaaacat gtcggaaatc     780
aacccgataa tgggacaacc gacccaacaa cagcaaagcg ccccagctcc acaaccgccg     840
cctctccagc aagtgcagta cacacaaaag ccgcccgtgg cccccatttc agcccccact     900
cctcaggctc ccgcaccggc cgcaaacggc cccaatggcc aggcttctgg tcgacaagtt     960
tcggatcgtc aacaggtgtt acgccatcaa cagcaacggc tgctgctact gcgacacgct    1020
gccaaatgtc agcatgaaga cggaaaatgc ccagtaacgc cgcattgcgc tgggatgaag    1080
agattgtgga agcatattgc cgaatgcaag gatcaaaaat gtcttgtacc gcattgcgtc    1140
agttcccggt acgtgttaag tcattatcac cgatgcaagg acgttcgttg tccagtgtgt    1200
ggcccagtaa gggaagccat tcatcgaagc cacgaaaagc agaaacagat gcaggcccta    1260
aaacagcgac atcagcaggc cgtacagcaa cagggccaac ctcagaatgc gacttcagcg    1320
cccgccgcta tcggtgcttt gccagtcccc gctcctcctg gacatagttt ggaacctgtt    1380
accaagaaac agcgcaccgc gcccattaca gctttgagag ctccgatcat gccagttcag    1440
cgacttcagc agccaccagg tactcgtccg gccgtttcgc atccaaccac agtaagacct    1500
ggatataccg gaagtcaacc tcccatcact tctggtcctg gtggtccacc ggttgcgcaa    1560
gtacctggcc tagcgtttgc gaacggacaa gtagtaatgc cgaaacattc aggaccaaag    1620
ccacaagaag atcacacttt gatcaactgc ttctctgtcc agcaaattga gacgcacata    1680
tcttccttga gcaatgggtt ggtcctgcct ccgcagaaat tgaaaacgaa aggattggac    1740
gctcttaaaa cgctgcagtc gcaccaacat gcgtgggtat tcaacactcc agtggatccc    1800
gtggaactcg gcttgccgga ctactttgag gtcatcaaaa aaccaatgga tctagggaca    1860
ataaggaaga gctcgaaaaa tggcgtttat cagaggctgg acgacttcaa agagcatgta    1920
ctgcttacat ttgataacgc catgatgtac aacccggagg gttcggttgt gtataacatg    1980
gctaatgaaa tgaaggtaaa gtttcagagc gacttcgtaa agctcatgga caactgaac     2040
gccgaagaag atgtcaagcg aaagaacggg gaggcctgtt gtttatgcgg atgtgaaaag    2100
ctgctatttg agcctcctgt attttattgc aacggaataa attgcccttc gaagcgaatt    2160
cggcgaaaca gttattacta cattggaggg aacaaccaat atcactgtgt caccagtgc     2220
tatcaagaac tccgcgacaa ttcaaccatt gatttaggcg acctttccgt taaaaaagaa    2280
agtctcgtga agaagaagaa tgacgaggtg cacgaagaga gctgggtaca atgcgatcgt    2340
```

```
tgtgaaagat gggttcatca gatttgtgct ttatttaaca ctcggcaaaa taaggatcag    2400
cgatccgaat acgcttgtcc gaagtgtaca attgacgaac gaaaggcaaa aggcgagctt    2460
gaggcaaaat cgtcaactcc gatggcagag gacctccctc gtaccaagct gtccgagtac    2520
ttggagaatc atgtgcgtga aaggtcgat gagttcgttg aacagaggtc gcaggatatg    2580
gttgttgctc aaggttgctc tattgaagaa gccagaagca aacttaagat gggaggtgca    2640
atcactatcc gacaggtaac ttccatggac agacgacttg aggtccgaga tagaatgaag    2700
caacgctatg cattcaaaaa ctacccggaa gaattcaatt ttcggtgtaa atgcatcgtt    2760
gtcttccaga atttggacgg cgttgatgtt gttttgtttg cctttacgt atacgagcat     2820
gatgagaaaa atcctgcccc caacaagcgg gccgtctatg tgtcctatct cgatagtgtt    2880
cattacatga gaccacgtga tatgcgtact ttcatttacc acgaaatttt aatatcttat    2940
cttgattacg tccggaggcg tggattttcg actgctcaca tttgggcttg tccgccgctt    3000
cgcggagacg actacatcct ttacgcaaaa ccagaggacc agaagacccc gaaagacgat    3060
cgattgcgtc agtggtacat agacatgctg attgaggccc aaaggcgagg gattgttggg    3120
aaacttacca acatgtacga cctctatttt tccaacgaga aaaacgatgc aacggttgtc    3180
ccctacatgg atggtgacta cttttcctgct gaggttgaga atatcatcaa ggatattgag    3240
gaaggcaaga cgggaaagaa aggcagttcg caaggcaaaa agaaaaaaga aaagccaaa     3300
cagaagaaga agtcaggtcg tggcggaact cggtctacgg gattggatga agacgctctt    3360
aaagcgagcg gatttctgcc acccggtact gattcaaaaa gtctagaaga aggcgctcga    3420
gactacgtca tggtgaaact tggtgagacc atccagccca tgaaggaaag tttcattgtg    3480
gctttcttag gctgggaagg ggcgaaagag ggagacatgg ttgttcccaa tgagatccaa    3540
gagcaccgtg acctgcatga gatcacttgg aaacttaaaa gcagtagcac caaagctgat    3600
acagtggaga ctatcgagaa cgaaagcgat aggcaacagg acgccgagat caaagattct    3660
agggataaaa aaggggacag ttcgataaag ttaaacggta ctacttcaaa gaagccggat    3720
gacacgtcct caagctcagg aaacatcgaa gacactgcca gcacacatag ggctcatgtt    3780
gacacaccga tggaagggat tgtaaaaaat gaatttaccg aaaccaatgg aattttgcaa    3840
tcctcacctc aagagaataa agactctgaa tccatcaacg ctcctgcgct tcgtgttgga    3900
actgaggcta ttgatcgccc ggatgctccg cagtccgcga taactgcagc accaaacact    3960
atttctatcc gagagggaaa attcgctgct atggcggccc ggaaacgtga tagagaaggg    4020
gagccgaaag agcccgagga ggtggaaagt acaagtgaga agacgaagga agaaaagctg    4080
acttccataa cagtgactga tagcaagggc cgtactgtga aagttttgga tgacgacgag    4140
gaggaacttg actgcgagtt tctaaacaat cgacaggcgt tcttaaatct atgtcaagga    4200
aatcactacc agtttgatca cctgcgccgc gcaaagcact cctccatgat ggttttgtgg    4260
caccttcaca acagggatgc accaaaattt gtgcagcaat gtgcgacttg ctccagagaa    4320
cttcttaccg gatatcgctt taattgtcct acatgtgggg atttcgatca gtgccaagac    4380
tgcatttcca acccgaaggt tcctcggcac ccgcatcagc tcaagcctat tccggtggcc    4440
aatgcgcaac aaaacgaatt gacggaagcg caacgcaagg aacgcagcg cagtatccag     4500
cttcatatga ctcttttgct gcatgctgct acgtgtagct cgccgaagtg tccgtcagcc    4560
aattgtacaa agatgaaggg tcttttaaag cacggcgcgc aatgccaagt gaaggccact    4620
ggcggttgca acgtatgcaa gagaatatgg gctttactgc aaattcatgc tcgtcagtgc    4680
```

-continued

```
aaagcgaagt cttgccctgt tccgaattgt atggcaatcc gtgaaagagt tcgccaattg    4740
aaaaagcaac aacaggcgat ggatgaccgt cgtcgccaag aaatgaatcg agcttacagg    4800
gggaagcgct aa                                                        4812
```

<210> SEQ ID NO 30
<211> LENGTH: 1603
<212> TYPE: PRT
<213> ORGANISM: Phaeodactylum tricornutum
<220> FEATURE:
<221> NAME/KEY: misc_feature
<223> OTHER INFORMATION: Translation product 332333

<400> SEQUENCE: 30

```
Met Gln Ala Ser Gln Ala Gln Leu Gln Pro Gln Gln Ala Pro Pro Val
 1               5                  10                  15

Ala Ala Pro Leu Pro Ser Ala Ala Gln Gln Gly Ser Ala Ala Ala
                20                  25                  30

Pro Ala Val Ser His Tyr Ser Ser Gln His Leu Ser Gln Val Pro Ala
            35                  40                  45

Ala Gln Pro Gly Leu Ala Pro Gln Ser Gln Gly Val Val His Gln Gln
        50                  55                  60

Arg Pro Val Ser Gln Gly Ile Asn Tyr Thr Thr Gln Thr Ser Gln Ser
 65                  70                  75                  80

Gln Thr Pro Ala Gln Gln Ala Pro Pro Gln Gln His Phe Pro His
                85                  90                  95

Gln Gly Leu Asn Gly Gly Trp Gln Ser Asp Lys Asp Tyr Gln Glu Arg
            100                 105                 110

Arg Lys Met Ile Ala Lys Ile Val His Leu Leu Gln Gln Arg Lys Pro
        115                 120                 125

Asn Ala Pro Gln Glu Trp Leu Lys Lys Leu Pro Gln Met Ala Lys Arg
    130                 135                 140

Leu Glu Glu Ser Leu Tyr Arg Thr Ala Thr Ser Phe Glu Glu Tyr Asn
145                 150                 155                 160

Asp Ala Asn Thr Leu Lys His Arg Leu Gln Gln Leu Ala Val Asn Ile
                165                 170                 175

Gly Gln Lys Thr Lys Lys Leu Gln Gln Gln Ala Leu Leu Ala Gln
            180                 185                 190

Gln Arg Leu Gln Gln Gln Gln Gln Gln Val Arg Gln Ser
        195                 200                 205

Asp Thr Thr Gln Tyr Thr Pro Gln Val Pro Ser Thr Ser Gln Gln
    210                 215                 220

Ala Leu Ile Gln Pro Gln Thr Gln Gln Gly Leu Ile Pro Gln Val Lys
225                 230                 235                 240

Ser Ala Ala Pro Pro Ala Ser Gln Val Gln Gly Gln Arg Met Val Asn
                245                 250                 255

Met Ser Glu Ile Asn Pro Ile Met Gly Gln Pro Thr Gln Gln Gln Gln
            260                 265                 270

Ser Ala Pro Ala Pro Gln Pro Pro Leu Gln Gln Val Gln Tyr Thr
        275                 280                 285

Gln Lys Pro Pro Val Ala Pro Ile Ser Ala Pro Thr Pro Gln Ala Pro
    290                 295                 300

Ala Pro Ala Ala Asn Gly Pro Asn Gly Gln Ala Ser Gly Arg Gln Val
305                 310                 315                 320

Ser Asp Arg Gln Gln Val Leu Arg His Gln Gln Gln Arg Leu Leu Leu
                325                 330                 335
```

Leu Arg His Ala Ala Lys Cys Gln His Glu Asp Gly Lys Cys Pro Val
            340                 345                 350

Thr Pro His Cys Ala Gly Met Lys Arg Leu Trp Lys His Ile Ala Glu
            355                 360                 365

Cys Lys Asp Gln Lys Cys Leu Val Pro His Cys Val Ser Ser Arg Tyr
370                 375                 380

Val Leu Ser His Tyr His Arg Cys Lys Asp Val Arg Cys Pro Val Cys
385                 390                 395                 400

Gly Pro Val Arg Glu Ala Ile His Arg Ser His Glu Lys Gln Lys Gln
            405                 410                 415

Met Gln Ala Leu Lys Gln Arg His Gln Gln Ala Val Gln Gln Gly
            420                 425                 430

Gln Pro Gln Asn Ala Thr Ser Ala Pro Ala Ala Ile Gly Ala Leu Pro
            435                 440                 445

Val Pro Ala Pro Pro Gly His Ser Leu Glu Pro Val Thr Lys Lys Gln
            450                 455                 460

Arg Thr Ala Pro Ile Thr Ala Leu Arg Ala Pro Ile Met Pro Val Gln
465                 470                 475                 480

Arg Leu Gln Gln Pro Pro Gly Thr Arg Pro Ala Val Ser His Pro Thr
            485                 490                 495

Thr Val Arg Pro Gly Tyr Thr Gly Ser Gln Pro Pro Ile Thr Ser Gly
            500                 505                 510

Pro Gly Gly Pro Pro Val Ala Gln Val Pro Gly Leu Ala Phe Ala Asn
            515                 520                 525

Gly Gln Val Val Met Pro Lys His Ser Gly Pro Lys Pro Gln Glu Asp
            530                 535                 540

His Thr Leu Ile Asn Cys Phe Ser Val Gln Gln Ile Glu Thr His Ile
545                 550                 555                 560

Ser Ser Leu Ser Asn Gly Leu Val Leu Pro Pro Gln Lys Leu Lys Thr
            565                 570                 575

Lys Gly Leu Asp Ala Leu Lys Thr Leu Gln Ser His Gln His Ala Trp
            580                 585                 590

Val Phe Asn Thr Pro Val Asp Pro Val Glu Leu Gly Leu Pro Asp Tyr
            595                 600                 605

Phe Glu Val Ile Lys Lys Pro Met Asp Leu Gly Thr Ile Arg Lys Lys
            610                 615                 620

Leu Glu Asn Gly Val Tyr Gln Arg Leu Asp Asp Phe Lys Glu His Val
625                 630                 635                 640

Leu Leu Thr Phe Asp Asn Ala Met Met Tyr Asn Pro Glu Gly Ser Val
            645                 650                 655

Val Tyr Asn Met Ala Asn Glu Met Lys Val Lys Phe Gln Ser Asp Phe
            660                 665                 670

Val Lys Leu Met Glu Gln Leu Asn Ala Glu Glu Asp Val Lys Arg Lys
            675                 680                 685

Asn Gly Glu Ala Cys Cys Leu Cys Gly Cys Glu Lys Leu Leu Phe Glu
            690                 695                 700

Pro Pro Val Phe Tyr Cys Asn Gly Ile Asn Cys Pro Ser Lys Arg Ile
705                 710                 715                 720

Arg Arg Asn Ser Tyr Tyr Tyr Ile Gly Gly Asn Asn Gln Tyr His Trp
            725                 730                 735

Cys His Gln Cys Tyr Gln Glu Leu Arg Asp Asn Ser Thr Ile Asp Leu
            740                 745                 750

```
Gly Asp Leu Ser Val Lys Lys Glu Ser Leu Val Lys Lys Asn Asp
         755                 760                 765

Glu Val His Glu Glu Ser Trp Val Gln Cys Asp Arg Cys Glu Arg Trp
770                 775                 780

Val His Gln Ile Cys Ala Leu Phe Asn Thr Arg Gln Asn Lys Asp Gln
785                 790                 795                 800

Arg Ser Glu Tyr Ala Cys Pro Lys Cys Thr Ile Asp Glu Arg Lys Ala
            805                 810                 815

Lys Gly Glu Leu Glu Ala Lys Ser Ser Thr Pro Met Ala Glu Asp Leu
                820                 825                 830

Pro Arg Thr Lys Leu Ser Glu Tyr Leu Glu Asn His Val Arg Glu Lys
            835                 840                 845

Val Asp Glu Phe Val Glu Gln Arg Ser Gln Asp Met Val Val Ala Gln
850                 855                 860

Gly Cys Ser Ile Glu Glu Ala Arg Ser Lys Leu Lys Met Gly Gly Ala
865                 870                 875                 880

Ile Thr Ile Arg Gln Val Thr Ser Met Asp Arg Arg Leu Glu Val Arg
                885                 890                 895

Asp Arg Met Lys Gln Arg Tyr Ala Phe Lys Asn Tyr Pro Glu Glu Phe
            900                 905                 910

Asn Phe Arg Cys Lys Cys Ile Val Phe Gln Asn Leu Asp Gly Val
    915                 920                 925

Asp Val Val Leu Phe Gly Leu Tyr Val Tyr Glu His Asp Glu Lys Asn
            930                 935                 940

Pro Ala Pro Asn Lys Arg Ala Val Tyr Val Ser Tyr Leu Asp Ser Val
945                 950                 955                 960

His Tyr Met Arg Pro Arg Asp Met Arg Thr Phe Ile Tyr His Glu Ile
                965                 970                 975

Leu Ile Ser Tyr Leu Asp Tyr Val Arg Arg Gly Phe Ser Thr Ala
            980                 985                 990

His Ile Trp Ala Cys Pro Pro Leu Arg Gly Asp Asp Tyr Ile Leu Tyr
            995                 1000                1005

Ala Lys Pro Glu Asp Gln Lys Thr Pro Lys Asp Asp Arg Leu Arg
    1010                1015                1020

Gln Trp Tyr Ile Asp Met Leu Ile Glu Ala Gln Arg Arg Gly Ile
    1025                1030                1035

Val Gly Lys Leu Thr Asn Met Tyr Asp Leu Tyr Phe Ser Asn Glu
    1040                1045                1050

Lys Asn Asp Ala Thr Val Val Pro Tyr Met Asp Gly Asp Tyr Phe
    1055                1060                1065

Pro Ala Glu Val Glu Asn Ile Ile Lys Asp Ile Glu Glu Gly Lys
    1070                1075                1080

Thr Gly Lys Lys Gly Ser Ser Gln Gly Lys Lys Lys Glu Lys
    1085                1090                1095

Ala Lys Gln Lys Lys Ser Gly Arg Gly Gly Thr Arg Ser Thr
    1100                1105                1110

Gly Leu Asp Glu Asp Ala Leu Lys Ala Ser Gly Phe Leu Pro Pro
    1115                1120                1125

Gly Thr Asp Ser Lys Ser Leu Glu Glu Gly Ala Arg Asp Tyr Val
    1130                1135                1140

Met Val Lys Leu Gly Glu Thr Ile Gln Pro Met Lys Glu Ser Phe
    1145                1150                1155

Ile Val Ala Phe Leu Gly Trp Glu Gly Ala Lys Glu Gly Asp Met
```

```
            1160                1165                1170
Val Val Pro Asn Glu Ile Gln Glu His Arg Asp Leu His Glu Ile
    1175                1180                1185

Thr Trp Lys Leu Lys Ser Ser Ser Thr Lys Ala Asp Thr Val Glu
    1190                1195                1200

Thr Ile Glu Asn Glu Ser Asp Arg Gln Gln Asp Ala Glu Ile Lys
    1205                1210                1215

Asp Ser Arg Asp Lys Lys Gly Asp Ser Ser Ile Lys Leu Asn Gly
    1220                1225                1230

Thr Thr Ser Lys Lys Pro Asp Thr Ser Ser Ser Gly Asn
    1235                1240                1245

Ile Glu Asp Thr Ala Ser Thr His Arg Ala His Val Asp Thr Pro
    1250                1255                1260

Met Glu Gly Ile Val Lys Asn Glu Phe Thr Glu Thr Asn Gly Ile
    1265                1270                1275

Leu Gln Ser Ser Pro Gln Glu Asn Lys Asp Ser Glu Ser Ile Asn
    1280                1285                1290

Ala Pro Ala Leu Arg Val Gly Thr Glu Ala Ile Asp Arg Pro Asp
    1295                1300                1305

Ala Pro Gln Ser Ala Ile Thr Ala Ala Pro Asn Thr Ile Ser Ile
    1310                1315                1320

Arg Glu Gly Lys Phe Ala Ala Met Ala Ala Arg Lys Arg Asp Arg
    1325                1330                1335

Glu Gly Glu Pro Lys Glu Pro Glu Glu Val Glu Ser Thr Ser Glu
    1340                1345                1350

Lys Thr Lys Glu Glu Lys Leu Thr Ser Ile Thr Val Thr Asp Ser
    1355                1360                1365

Lys Gly Arg Thr Val Lys Val Leu Asp Asp Asp Glu Glu Glu Leu
    1370                1375                1380

Asp Cys Glu Phe Leu Asn Asn Arg Gln Ala Phe Leu Asn Leu Cys
    1385                1390                1395

Gln Gly Asn His Tyr Gln Phe Asp His Leu Arg Arg Ala Lys His
    1400                1405                1410

Ser Ser Met Met Val Leu Trp His Leu His Asn Arg Asp Ala Pro
    1415                1420                1425

Lys Phe Val Gln Gln Cys Ala Thr Cys Ser Arg Glu Leu Leu Thr
    1430                1435                1440

Gly Tyr Arg Phe Asn Cys Pro Thr Cys Gly Asp Phe Asp Gln Cys
    1445                1450                1455

Gln Asp Cys Ile Ser Asn Pro Lys Val Pro Arg His Pro His Gln
    1460                1465                1470

Leu Lys Pro Ile Pro Val Ala Asn Ala Gln Gln Asn Glu Leu Thr
    1475                1480                1485

Glu Ala Gln Arg Lys Glu Arg Gln Arg Ser Ile Gln Leu His Met
    1490                1495                1500

Thr Leu Leu Leu His Ala Ala Thr Cys Ser Ser Pro Lys Cys Pro
    1505                1510                1515

Ser Ala Asn Cys Thr Lys Met Lys Gly Leu Leu Lys His Gly Ala
    1520                1525                1530

Gln Cys Gln Val Lys Ala Thr Gly Gly Cys Asn Val Cys Lys Arg
    1535                1540                1545

Ile Trp Ala Leu Leu Gln Ile His Ala Arg Gln Cys Lys Ala Lys
    1550                1555                1560
```

```
Ser Cys Pro Val Pro Asn Cys Met Ala Ile Arg Glu Arg Val Arg
    1565            1570                1575

Gln Leu Lys Lys Gln Gln Gln Ala Met Asp Asp Arg Arg Arg Gln
    1580            1585                1590

Glu Met Asn Arg Ala Tyr Arg Gly Lys Arg
    1595            1600
```

<210> SEQ ID NO 31
<211> LENGTH: 3171
<212> TYPE: DNA
<213> ORGANISM: Phaeodactylum tricornutum
<220> FEATURE:
<221> NAME/KEY: misc_feature
<223> OTHER INFORMATION: encodes polypeptide of SEQ ID NO:32

<400> SEQUENCE: 31

| | | |
|---|---|---|
| atgaagcgac tttggagaca tattgcaaat tgtaaggatc aggactgctc tgttcaacat | 60 |
| tgtcttagta gtcgcggcgt tctcagccat tatcgacggt gtaaagatgc gctctgtcct | 120 |
| gcatgtgggc ctgtccgaga actatacgg aaaagtcatg agatggaaag tcaaagcaat | 180 |
| ccacaagggg taccgtccga caatcggttt atgggtcgag atgattcgtt cggtcggtca | 240 |
| agttccgtta catcgccaac cgaacaggaa ccgaagcgta tgagaacaga catcgccct | 300 |
| agcgcggcgt ctataaaatc agcgcgctct acgcctgtga gcgcgcctcc tttgaagcaa | 360 |
| gaaccccctc gaagcatagg caaaggtgag aaagtagctc catctgctga aaaagattcg | 420 |
| aaaggaagtg tcgaccgatc actcctcgag agtttctcgg tgaaggagct cgaaactcat | 480 |
| ttgcgatcgc tggaacgaga gacccaactt cctccggcga agctcaagtc taaatgtctg | 540 |
| gatgtattaa agggtttaat ggctcaccaa cacggttggg ttttcaatgg tccagtcgat | 600 |
| ccagttgagc tcggtcttgt tgattatttt gaaattatca gaagcccat ggacctcggc | 660 |
| accattcaaa agcgtttgga agtagtgca taccactcca tcgatgactt aaaaacggat | 720 |
| atcttcttaa cttttgagaa tgcaatggtg tataatgagg atggttccgt tgtctacgac | 780 |
| atggcgaagc agctgaaggt taaagccgaa tctgacatga agagacttgt ggcacaactg | 840 |
| gaaacagaag accttgaaag acgccagaat gaacgcgcgt gcaccttgtg tggttcagag | 900 |
| aaactgttgt ttgaacctcc tgtttatttt tgtaacggaa ttaattgtca atcgcagcgg | 960 |
| atccgacgaa acagtcactt ctatatcgga ggaaacaacc aatactttg gtgtagcct | 1020 |
| tgctttaatg aacttgatga taaaattccg attgagcttg ccgacttgac agtcatgaaa | 1080 |
| aacaatctga agaagaaaa gaatgacgag attcacgagg agagctgggt acagtgtgac | 1140 |
| acttgcgaac ggtgggttca ccagatatgt ggacttttta acaccgtca gaataaagag | 1200 |
| caccacagcg agtactgttg tcctaaatgt ttgcttgaaa aacgcaaaac tgtttcaata | 1260 |
| actccagcgc cgaagccatt gctggctgcg acttgccgc ggactacttt atcggagtgg | 1320 |
| ctagaacgca gtgtcactaa gaaagtggaa aaaaggaaga gagaactggc cgaagagcgt | 1380 |
| tcgcagaatg aggggatatc tcttgaagaa gctttgcgac aggtagaaag tggcggccca | 1440 |
| ataataattc gtcaagttac cgcgatggat agaaagcttg aggttcgcga gctgatgaaa | 1500 |
| aagcgatatg cacacaagaa ttatcctgac gaatttccct ttcggtgcaa atcgattgtc | 1560 |
| gtttttcagc atcttgacgg agttgatgtc attctgtttg cgttgtatct ctacgaacac | 1620 |
| ggtgaagaca atcctccgcc caaccaacga accgtgtaca tctcatatct ggacagtgtt | 1680 |
| cactttatga ggcctcgcaa actccggacc tttgtgtacc atgagattct gattgcctat | 1740 |

-continued

```
ttggactacg ctaggcgacg gggatttgca actgctcata tttgggcatg cccacctttg      1800
aagggtgacg attacatttt ctacgctaaa ccagaagacc agaagactcc gagagattca      1860
cgactgcgcc tttggtacat tgacatgctc gtagaatgtc aaaaaaggag tatcgtcggc      1920
aaagtaacga atatgtacga tatttatttc gcagacccga atttggacgc cactgctgtt      1980
ccctatttgg agggcgacta ttttcctggt gaagcggaga atattataaa aatgctcgaa      2040
gaaggtggag gcaagaaact tgggtcagtg gggaaaaaga agaaaagcaa atcgtcgaaa      2100
gcgcagaaga ataagggagg aaatacgggt actagatcca ctggagtcga cgaagaagcg      2160
cttattgcga gtggtattct ggatggaacc aagagtttaa aggaccttga tcgtgatcag      2220
gtcatggtga agctgggtga acgattcag cctatgaagg aaagttttat agtagcgttc       2280
ttaaattgga agatgctcg cgaagaagat atgatagtcc cagaagaaat cgaaatggct       2340
aggattgaat acgcagcgaa aggtgatcca gagcttgttg aagcaaacg tgatgctgct       2400 ggaaacatga gagacgctac gtcgaagacg ggcgcgaatg gagagcctgt aaaggttatt      2460
gatgacgacg ctgaagatct agattgcgag tttttgaaca atcgccaagc attcttgaat      2520
ctttgtcgag gaaccatta tcaatttgac gagctccggc gagcaaagca tacttcattg       2580
atgctccttt ggcatctaca taacagagat gcaccaaaat tgtgcagca gtgcgtttct       2640 tgcagtcgcg aaatcctcag tggcaaacgt tttcactgcg cacgtgccc tgactatgat       2700 ctctgtcaag attgctacaa agaccctaag gcaaacagag taactgtac gcacgctctt       2760 aaaccactcg ccgttgaagc tgattccgga caggatcgca gtgggctatc agagcaagaa      2820
cgcatgcaac gccagcgaaa cctgttgtta cacattcaac ttatcgaaca cgcttcaagg      2880
tgttcctctc agacatgttc ttcattaaat tgcgcaaaaa tgaaaaaata tctgcagcat      2940
gctcgtgtct gcaaggttaa agtattagga gggtgcaaga tttgcaaaaa gatctggacc      3000
ttactccgaa ttcatgcgca gaaatgtaag gatacaaatt gccccattcc acaatgcaat      3060
gcgattcgtg agaagatgag gcaactgcaa aagcagcagc aggctatgga cgaccggcgc      3120
cgtctggaaa tgaatcgtca catgcgtttc tccaccgcag gaggctcttg a              3171
```

<210> SEQ ID NO 32
<211> LENGTH: 1056
<212> TYPE: PRT
<213> ORGANISM: Phaeodactylum tricornutum
<220> FEATURE:
<221> NAME/KEY: misc_feature
<223> OTHER INFORMATION: translation product 332603

<400> SEQUENCE: 32

```
Met Lys Arg Leu Trp Arg His Ile Ala Asn Cys Lys Asp Gln Asp Cys
1               5                   10                  15

Ser Val Gln His Cys Leu Ser Ser Arg Gly Val Leu Ser His Tyr Arg
            20                  25                  30

Arg Cys Lys Asp Ala Leu Cys Pro Ala Cys Gly Pro Val Arg Glu Thr
        35                  40                  45

Ile Arg Lys Ser His Glu Met Glu Ser Gln Ser Asn Pro Gln Gly Val
    50                  55                  60

Pro Ser Asp Asn Arg Phe Met Gly Arg Asp Ser Phe Gly Arg Ser
65                  70                  75                  80

Ser Ser Val Thr Ser Pro Thr Glu Gln Glu Pro Lys Arg Met Arg Thr
            85                  90                  95

Glu His Arg Pro Ser Ala Ala Ser Ile Lys Ser Ala Arg Ser Thr Pro
        100                 105                 110
```

```
Val Ser Ala Pro Pro Leu Lys Gln Glu Pro Pro Arg Ser Ile Gly Lys
            115                 120                 125

Gly Glu Lys Val Ala Pro Ser Ala Glu Lys Asp Ser Lys Gly Ser Val
            130                 135                 140

Asp Arg Ser Leu Leu Glu Ser Phe Ser Val Lys Glu Leu Glu Thr His
145                 150                 155                 160

Leu Arg Ser Leu Glu Arg Glu Thr Gln Leu Pro Pro Ala Lys Leu Lys
                165                 170                 175

Ser Lys Cys Leu Asp Val Leu Lys Gly Leu Met Ala His Gln His Gly
            180                 185                 190

Trp Val Phe Asn Gly Pro Val Asp Pro Val Glu Leu Gly Leu Val Asp
            195                 200                 205

Tyr Phe Glu Ile Ile Lys Lys Pro Met Asp Leu Gly Thr Ile Gln Lys
            210                 215                 220

Arg Leu Glu Ser Ser Ala Tyr His Ser Ile Asp Asp Phe Lys Thr Asp
225                 230                 235                 240

Ile Phe Leu Thr Phe Glu Asn Ala Met Val Tyr Asn Glu Asp Gly Ser
                245                 250                 255

Val Val Tyr Asp Met Ala Lys Gln Leu Lys Val Lys Ala Glu Ser Asp
            260                 265                 270

Met Lys Arg Leu Val Ala Gln Leu Glu Thr Glu Asp Leu Glu Arg Arg
            275                 280                 285

Gln Asn Glu Arg Ala Cys Thr Leu Cys Gly Ser Glu Lys Leu Leu Phe
            290                 295                 300

Glu Pro Pro Val Tyr Phe Cys Asn Gly Ile Asn Cys Gln Ser Gln Arg
305                 310                 315                 320

Ile Arg Arg Asn Ser His Phe Tyr Ile Gly Gly Asn Asn Gln Tyr Phe
                325                 330                 335

Trp Cys Ser Pro Cys Phe Asn Glu Leu Asp Asp Lys Ile Pro Ile Glu
            340                 345                 350

Leu Ala Asp Leu Thr Val Met Lys Asn Asn Leu Lys Lys Lys Lys Asn
            355                 360                 365

Asp Glu Ile His Glu Gly Ser Trp Val Gln Cys Asp Thr Cys Glu Arg
            370                 375                 380

Trp Val His Gln Ile Cys Gly Leu Phe Asn Thr Arg Gln Asn Lys Glu
385                 390                 395                 400

His His Ser Glu Tyr Cys Cys Pro Lys Cys Leu Leu Glu Lys Arg Lys
                405                 410                 415

Thr Val Ser Ile Thr Pro Ala Pro Lys Pro Leu Leu Ala Ala Asp Leu
            420                 425                 430

Pro Arg Thr Thr Leu Ser Glu Trp Leu Glu Arg Ser Val Thr Lys Lys
            435                 440                 445

Val Glu Lys Arg Lys Arg Glu Leu Ala Glu Glu Arg Ser Gln Asn Glu
            450                 455                 460

Gly Ile Ser Leu Glu Glu Ala Leu Arg Gln Val Glu Ser Gly Gly Pro
465                 470                 475                 480

Ile Ile Ile Arg Gln Val Thr Ala Met Asp Arg Lys Leu Glu Val Arg
                485                 490                 495

Glu Leu Met Lys Lys Arg Tyr Ala His Lys Asn Tyr Pro Asp Glu Phe
            500                 505                 510

Pro Phe Arg Cys Lys Ser Ile Val Val Phe Gln His Leu Asp Gly Val
            515                 520                 525
```

-continued

```
Asp Val Ile Leu Phe Ala Leu Tyr Leu Tyr Glu His Gly Glu Asp Asn
    530                 535                 540
Pro Pro Pro Asn Gln Arg Thr Val Tyr Ile Ser Tyr Leu Asp Ser Val
545                 550                 555                 560
His Phe Met Arg Pro Arg Lys Leu Arg Thr Phe Val Tyr His Glu Ile
                565                 570                 575
Leu Ile Ala Tyr Leu Asp Tyr Ala Arg Arg Arg Gly Phe Ala Thr Ala
            580                 585                 590
His Ile Trp Ala Cys Pro Pro Leu Lys Gly Asp Tyr Ile Phe Tyr
        595                 600                 605
Ala Lys Pro Glu Asp Gln Lys Thr Pro Arg Asp Ser Arg Leu Arg Leu
    610                 615                 620
Trp Tyr Ile Asp Met Leu Val Glu Cys Gln Lys Arg Ser Ile Val Gly
625                 630                 635                 640
Lys Val Thr Asn Met Tyr Asp Ile Tyr Phe Ala Asp Pro Asn Leu Asp
                645                 650                 655
Ala Thr Ala Val Pro Tyr Leu Glu Gly Asp Tyr Phe Pro Gly Glu Ala
            660                 665                 670
Glu Asn Ile Ile Lys Met Leu Glu Glu Gly Gly Lys Lys Leu Gly
        675                 680                 685
Ser Val Gly Lys Lys Lys Ser Lys Ser Ser Lys Ala Gln Lys Asn
    690                 695                 700
Lys Gly Gly Asn Thr Gly Thr Arg Ser Thr Gly Val Asp Glu Glu Ala
705                 710                 715                 720
Leu Ile Ala Ser Gly Ile Leu Asp Gly Thr Lys Ser Leu Lys Asp Leu
                725                 730                 735
Asp Arg Asp Gln Val Met Val Lys Leu Gly Glu Thr Ile Gln Pro Met
            740                 745                 750
Lys Glu Ser Phe Ile Val Ala Phe Leu Asn Trp Lys Asp Ala Arg Glu
        755                 760                 765
Glu Asp Met Ile Val Pro Glu Glu Ile Glu Met Ala Arg Ile Glu Tyr
    770                 775                 780
Ala Ala Lys Gly Asp Pro Glu Leu Val Gly Ser Lys Arg Asp Ala Ala
785                 790                 795                 800
Gly Asn Met Arg Asp Ala Thr Ser Lys Thr Gly Ala Asn Gly Glu Pro
                805                 810                 815
Val Lys Val Ile Asp Asp Ala Glu Asp Leu Asp Cys Glu Phe Leu
            820                 825                 830
Asn Asn Arg Gln Ala Phe Leu Asn Leu Cys Arg Gly Asn His Tyr Gln
        835                 840                 845
Phe Asp Glu Leu Arg Arg Ala Lys His Thr Ser Leu Met Leu Leu Trp
    850                 855                 860
His Leu His Asn Arg Asp Ala Pro Lys Phe Val Gln Cys Val Ser
865                 870                 875                 880
Cys Ser Arg Glu Ile Leu Ser Gly Lys Arg Phe His Cys Asp Thr Cys
                885                 890                 895
Pro Asp Tyr Asp Leu Cys Gln Asp Cys Tyr Lys Asp Pro Lys Ala Asn
            900                 905                 910
Arg Gly Asn Cys Thr His Ala Leu Lys Pro Leu Ala Val Glu Ala Asp
        915                 920                 925
Ser Gly Gln Asp Arg Ser Gly Leu Ser Glu Gln Glu Arg Met Gln Arg
    930                 935                 940
Gln Arg Asn Leu Leu Leu His Ile Gln Leu Ile Glu His Ala Ser Arg
```

```
                945               950               955               960
Cys Ser Ser Gln Thr Cys Ser Ser Leu Asn Cys Ala Lys Met Lys Lys
                    965               970               975
Tyr Leu Gln His Ala Arg Val Cys Lys Val Lys Val Leu Gly Gly Cys
                    980               985               990
Lys Ile Cys Lys Lys Ile Trp Thr Leu Leu Arg Ile His Ala Gln Lys
                    995               1000              1005
Cys Lys Asp Thr Asn Cys Pro Ile Pro Gln Cys Asn  Ala Ile Arg
        1010              1015              1020
Glu Lys Met Arg Gln Leu Gln  Lys Gln Gln Gln Ala  Met Asp Asp
        1025              1030              1035
Arg Arg Arg Leu Glu Met Asn  Arg His Met Arg Phe  Ser Thr Ala
        1040              1045              1050
Gly Gly Ser
    1055

<210> SEQ ID NO 33
<211> LENGTH: 4614
<212> TYPE: DNA
<213> ORGANISM: Navicula WT0229
<220> FEATURE:
<221> NAME/KEY: misc_feature
<223> OTHER INFORMATION: encodes polypeptide of SEQ ID NO:34

<400> SEQUENCE: 33
atgagtactc aacaacagca gccacccca cagcctcctc ctccgccaca agcacagggc       60
atgggcggtg ggagttggca aagtgatcgg gatatacctc accgaaggga aatgatacaa      120
cacattatta agttgctcaa gaaggataga agtgggtcac ctgaatcact gaacaggctt      180
ccacaaatgg cgaaacattt ggaagtatcg ctctatcgga acgctccgtc atttgaggct      240
ttcgtcgata tgtcaactct caagcagcgt ttgcaccgaa ttgctgccga ggtatcgcgg      300
cggtctcgct ctcaaaatga ttccagacgt gacgattcga tgcgacctca aagtgttgac      360
cattcgttac cgtcgtttag tcaaaacggt atgcgaggag ggtcgtcatc gccatatatg      420
ggtggaatga gtgctggcag tggacacatg aacagtggaa gcatgaacaa tggaagcatg      480
aacagtggaa gaatggtcaa catggaagat atcaacccga tgtctaatgg agtcagctcc      540
caggtctacc accagcagcc tcaaagaaac gatcgaatga ccagcatca gccgccgcca       600
cagcaaccgc agcagcgtcc aaacctgcag cctccggcga tgcaacctca aggtcaaaac      660
cgcaacgatc cggagtggaa acttaggata cgtcacaagc agcagcgttt attactgctt      720
catcattcag cgaagtgtag ccacaaaggc caatgtccag taacacctca ttgcgctgac      780
atgaaacggc tctggagaca catggagggc tgcaaagaca accaatgtcg tgttccgcac      840
tgttttcctc ccagagcaat tttaagtcac tacaggaaat gcaaagatcc tgcttgtcca      900
gcgtgtggac cggtgcgtga acagttcgt aagggccagc gacctggctc tagcgcgaat      960
gcaatgaacc ttataagaac atcatcgcct tctgttccta atcagcaacc gcagcaacaa     1020
atgatgcaag gtaccgacat ggtgcaaatg gcaattcgt cttttggtgg cggttcggtt     1080
cggtcaggca gtgggcattc tgtaatgccc cctccaagcg taccagtagg caataacgac     1140
atgcagtttt cttcgcagtt tcgatcaaac aatccggttc cctcaggcga ccaagtattc     1200
ttcggtagcg accagcagtc ctctgacgcc catggtactt cactttccgc caatacccaa     1260
tcttcgctga agatcatgc ttcgacaacg atcccaggag gtagcagacc gccaggtagt      1320
agtgaatcgg agtggcaaaa aattcgacac aagcaacagc gactccttct gttacggcat     1380
```

```
gcgtcaagat gccagcacga gatgggtaca tgcccagtaa cacctcactg cgctagcatg    1440
aaaaaattat gggaccatat tgctcactgc aaagaccagc agtgcaaagt tcagcactgt    1500
cttacaagtc gttacgtact cagtcattat cgtcgttgca agaacgcgcg atgcccctct    1560
tgtgggcctg tacgtgattc aattcgtagg tcggcgctaa aagaaaagca gcaacaaggg    1620
gctgtgatga gttcgatttc gttggatgac gatgttttca agactccagt ttcctcaccg    1680
cctcaacttg agccctctct gaccgaatcg tcgttacaac cagaacagaa gcgaagaagg    1740
aaaggagacg atgcatctga agccacgagt tccacgatgc ctatcagcaa tgaaacttta    1800
aaagtgccat ctgcacctgg ttcgtctctg gctgcgacgg tggattctaa attgcagtca    1860
gctcctccta cgaaagggga tatgaaaccg aaggacacca aaagtgctga tagatccttg    1920
ttgaatagct ttactttgac ggaacttgag acacacttgc agtctcttga ccggaaaacg    1980
cagctaccag ctgctaagct caagtctaaa tgctcagaag tgctgaaggg tttacaaaca    2040
caccagcacg gatgggtgtt taattgtcct gttgacccag ttgaacttgg ccttcccgac    2100
tattttgaga tcatcaaaaa accgatggac cttggaacta tccagaaaaa ggtggaaagt    2160
gggggcatcc attcaatcga ggaattcata gctctcgttc atctcacgtt tgataacgcg    2220
atggcgtaca acgagtctga atcggtagtg tacgaatgg cgaaagaatt gaagacaaaa     2280
ttcgagggtg atgtcaagaa gctaatgaaa acgctggaag aggaagacat ggagcggcga    2340
caaaatgatc gcgcatgcca tttgtgtgga tgcgaaaagc tgttgttcga gccacctgtt    2400 tactttgca acggaatgaa ttgcccgagt cagcgaattc gcaggaacaa taattttttac    2460 atcggaggca ataatcagta tttctggtgc agttcgtgct ttaatgaact tgacgacaag    2520
atccccatcg agttaattga catgacaata atgaaaagtg atcttgtcaa aaagagaaac    2580
gacgaagttc acgaggaaag ctgggtgcaa tgcgacacat gtgagaactg ggtgcatcag    2640
atttgtggct tatttaacac tcgccaaaac aaagagcacc atagcgagta taattgtccc    2700
agatgcattc gggataagcg ataacatgt ggtgatatac catttactag accaccaggc     2760
gcatccgatt tgccccgaac aacactatcg gagtgtcttg aacagcatat cgcgaatcgg    2820
atcgagaaga aaaagaggca gctcgcagaa gacaagcaaa gaaacgaggg aatttcatt    2880 gacgatgcgt tgaaatatgt cgagtccgga ggtccgatta tcatccgcca ggttacagca    2940
atggatcgaa agcttgaagt cagggatttg atgcgagagc gttatgcgca taagaattac    3000
ccagaagaat tccctttttcg gtgcaaatgc atcgttgtct tccagaagct tgacggagtc    3060
gataccatct tgttcgcgct ctatgtgtat gaacacggag agaacaatcc tccacccaac    3120
cagcgatgtg tttacatttc atacttggac agtgtgcatt tcatgcgacc gcgaaatttg    3180 aggactttttg tctatcacga gattctcata gcgtatctcg actacgcgcg ccagagaggt    3240
ttcgccactg ctcatatttg ggcatgtcca ccccttagag gcgacgatta catttttcttc    3300 gccaagccag aggaccagaa aacgccacgt gacaacaggc ttcgccaatg gtaccaagag    3360
atgttgatcg aagcccaaaa acgagggatt gttggaaagc ttacgaatat gtacgatctg    3420
tattttgcaa acgaatcact tgatgcgaca gctgttccct atatggaggg tgactatttt    3480
cccgcgaagc tgaaaatat cattaagctt cttcaagaag gtaaaggaaa gaaagccgga    3540
aacggaggga aaagaaaaa gagcaaggcc agcaaagggt ctactggtac gcggtcgaca    3600
ggtgttgacg aggaagcact tctcgccagc ggattcatgg acgacgcaaa gtcactgaaa    3660
gacttggacc gcgatcaggt gatggtgaaa cttggcgaaa caatccagcc catgaaagaa    3720
```

-continued

```
agtttcattg tagcttttct gaattggtcc ggcgcgaaag aagaggataa ggtcgtgccc    3780
gaggcgatga tcaaggcccg tgctgaatac gtggatgaga atctagaaag cgacgctgcc    3840
ggtagcaagc gcgatgctga agggcatacc gcaaatagct cgacccattc tgataaggtt    3900
attaatgacg acgaagagga tcttgattgt gagttcttga ataaccgcca agcttttctc    3960
aacctttgtc gaggtaatca ttatcagttc gacgagctca gacgctctaa gcacacgtcc    4020
atgatggtcc tttggcactt gcacaacaga gacgcgccca gtttgttca acaatgtgtg     4080 gcttgcagcc gagagattct cagtggtaag cgataccact gtagcacgtg ccctgactat    4140
gatctctgtc aagactgcta caaagacccg aaggttaata gaggaaactg cacccatact    4200
ttgactccaa tcgctgtcga tcctgatgcg aaccaggaac gcaatggcat ggacgacgcc    4260
gaacgacagg ctcgccagcg caatcttatg atgcacattc agctgatcga acacgcctcc    4320
ggatgtgtgt cgaagacatg cacttcgtcg aactgcgcca agatgaagaa ttatcttcac    4380
catgctagta tctgccgcgt gaaggttcaa ggcggatgta aaatctgtaa gaagatctgg    4440
actctcctga gaatccacgc ccagaaatgc agacaggcgc gatgtccgat cccgcaatgt    4500
aatgctattc gtgagaagat gcgacaacta cagaagcagc aacaggccat ggacgacaga    4560
cgtcgtctag agatgaaccg ccacatgcgt ttcggtggcg cagccccgtc ctaa          4614
```

<210> SEQ ID NO 34
<211> LENGTH: 1537
<212> TYPE: PRT
<213> ORGANISM: Navicula WT0229
<220> FEATURE:
<221> NAME/KEY: misc_feature
<223> OTHER INFORMATION: translation product 4241628

<400> SEQUENCE: 34

```
Met Ser Thr Gln Gln Gln Gln Pro Pro Gln Pro Pro Pro Pro Pro
 1               5                  10                  15

Gln Ala Gln Gly Met Gly Gly Gly Ser Trp Gln Ser Asp Arg Asp Ile
            20                  25                  30

Pro His Arg Arg Glu Met Ile Gln His Ile Ile Lys Leu Leu Lys Lys
        35                  40                  45

Asp Arg Ser Gly Ser Pro Glu Ser Leu Asn Arg Leu Pro Gln Met Ala
    50                  55                  60

Lys His Leu Glu Val Ser Leu Tyr Arg Asn Ala Pro Ser Phe Glu Ala
65                  70                  75                  80

Phe Val Asp Met Ser Thr Leu Lys Gln Arg Leu His Arg Ile Ala Ala
                85                  90                  95

Glu Val Ser Arg Arg Ser Arg Ser Gln Asn Asp Ser Arg Arg Asp Asp
            100                 105                 110

Ser Met Arg Pro Gln Ser Val Asp His Ser Leu Pro Ser Phe Ser Gln
        115                 120                 125

Asn Gly Met Arg Gly Gly Ser Ser Pro Tyr Met Gly Gly Met Ser
    130                 135                 140

Ala Gly Ser Gly His Met Asn Ser Gly Ser Met Asn Gly Ser Met
145                 150                 155                 160

Asn Ser Gly Arg Met Val Asn Met Glu Asp Ile Asn Pro Met Ser Asn
                165                 170                 175

Gly Val Ser Ser Gln Val Tyr His Gln Gln Pro Gln Arg Asn Asp Arg
            180                 185                 190

Met Ser Gln His Gln Pro Pro Gln Gln Pro Gln Gln Arg Pro Asn
        195                 200                 205
```

```
Leu Gln Pro Pro Ala Met Gln Pro Gln Gly Gln Asn Arg Asn Asp Pro
    210                 215                 220

Glu Trp Lys Leu Arg Ile Arg His Lys Gln Gln Arg Leu Leu Leu Leu
225                 230                 235                 240

His His Ser Ala Lys Cys Ser His Lys Gly Gln Cys Pro Val Thr Pro
                245                 250                 255

His Cys Ala Asp Met Lys Arg Leu Trp Arg His Met Glu Gly Cys Lys
            260                 265                 270

Asp Asn Gln Cys Arg Val Pro His Cys Phe Ser Ser Arg Ala Ile Leu
        275                 280                 285

Ser His Tyr Arg Lys Cys Lys Asp Pro Ala Cys Pro Ala Cys Gly Pro
    290                 295                 300

Val Arg Glu Thr Val Arg Lys Gly Gln Arg Pro Gly Ser Ser Ala Asn
305                 310                 315                 320

Ala Met Asn Leu Ile Arg Thr Ser Ser Pro Ser Val Pro Asn Gln Gln
                325                 330                 335

Pro Gln Gln Gln Met Met Gln Gly Thr Asp Met Val Gln Met Gly Asn
            340                 345                 350

Ser Ser Phe Gly Gly Gly Ser Val Arg Ser Gly Ser Gly His Ser Val
        355                 360                 365

Met Pro Pro Pro Ser Val Pro Val Gly Asn Asn Asp Met Gln Phe Ser
    370                 375                 380

Ser Gln Phe Arg Ser Asn Asn Pro Val Pro Ser Gly Asp Gln Val Phe
385                 390                 395                 400

Phe Gly Ser Asp Gln Gln Ser Ser Asp Ala His Gly Thr Ser Leu Ser
                405                 410                 415

Ala Asn Thr Gln Ser Ser Leu Lys Asp His Ala Ser Thr Thr Ile Pro
            420                 425                 430

Gly Gly Ser Arg Pro Pro Gly Ser Ser Glu Ser Glu Trp Gln Lys Ile
        435                 440                 445

Arg His Lys Gln Gln Arg Leu Leu Leu Leu Arg His Ala Ser Arg Cys
    450                 455                 460

Gln His Glu Met Gly Thr Cys Pro Val Thr His Cys Ala Ser Met
465                 470                 475                 480

Lys Lys Leu Trp Asp His Ile Ala His Cys Lys Asp Gln Gln Cys Lys
                485                 490                 495

Val Gln His Cys Leu Thr Ser Arg Tyr Val Leu Ser His Tyr Arg Arg
            500                 505                 510

Cys Lys Asn Ala Arg Cys Pro Ser Cys Gly Pro Val Arg Asp Ser Ile
        515                 520                 525

Arg Arg Ser Ala Leu Lys Glu Lys Gln Gln Gly Ala Val Met Ser
    530                 535                 540

Ser Ile Ser Leu Asp Asp Asp Val Phe Lys Thr Pro Val Ser Ser Pro
545                 550                 555                 560

Pro Gln Leu Glu Pro Ser Leu Thr Glu Ser Ser Leu Gln Pro Glu Gln
                565                 570                 575

Lys Arg Arg Arg Lys Gly Asp Asp Ala Ser Glu Ala Thr Ser Ser Thr
            580                 585                 590

Met Pro Ile Ser Asn Glu Thr Leu Lys Val Pro Ser Ala Pro Gly Ser
        595                 600                 605

Ser Leu Ala Ala Thr Val Asp Ser Lys Leu Gln Ser Ala Pro Pro Thr
    610                 615                 620
```

```
Lys Gly Asp Met Lys Pro Lys Asp Thr Lys Ser Ala Asp Arg Ser Leu
625                 630                 635                 640

Leu Asn Ser Phe Thr Leu Thr Glu Leu Glu Thr His Leu Gln Ser Leu
                645                 650                 655

Asp Arg Lys Thr Gln Leu Pro Ala Ala Lys Leu Lys Ser Lys Cys Ser
            660                 665                 670

Glu Val Leu Lys Gly Leu Gln Thr His Gln His Gly Trp Val Phe Asn
        675                 680                 685

Cys Pro Val Asp Pro Val Leu Gly Leu Pro Asp Tyr Phe Glu Ile
    690                 695                 700

Ile Lys Lys Pro Met Asp Leu Gly Thr Ile Gln Lys Val Glu Ser
705                 710                 715                 720

Gly Gly Ile His Ser Ile Glu Glu Phe Ile Ala Leu Val His Leu Thr
                725                 730                 735

Phe Asp Asn Ala Met Ala Tyr Asn Glu Ser Glu Ser Val Val Tyr Gly
                740                 745                 750

Met Ala Lys Glu Leu Lys Thr Lys Phe Glu Gly Asp Val Lys Lys Leu
            755                 760                 765

Met Lys Thr Leu Glu Glu Glu Asp Met Glu Arg Arg Gln Asn Asp Arg
770                 775                 780

Ala Cys His Leu Cys Gly Cys Glu Lys Leu Leu Phe Glu Pro Pro Val
785                 790                 795                 800

Tyr Phe Cys Asn Gly Met Asn Cys Pro Ser Gln Arg Ile Arg Arg Asn
                805                 810                 815

Asn Asn Phe Tyr Ile Gly Gly Asn Asn Gln Tyr Phe Trp Cys Ser Ser
                820                 825                 830

Cys Phe Asn Glu Leu Asp Asp Lys Ile Pro Ile Glu Leu Ile Asp Met
                835                 840                 845

Thr Ile Met Lys Ser Asp Leu Val Lys Lys Arg Asn Asp Glu Val His
850                 855                 860

Glu Glu Ser Trp Val Gln Cys Asp Thr Cys Glu Asn Trp Val His Gln
865                 870                 875                 880

Ile Cys Gly Leu Phe Asn Thr Arg Gln Asn Lys Glu His His Ser Glu
                885                 890                 895

Tyr Asn Cys Pro Arg Cys Ile Arg Asp Lys Arg Ile Thr Cys Gly Asp
                900                 905                 910

Ile Pro Phe Thr Arg Pro Pro Gly Ala Ser Asp Leu Pro Arg Thr Thr
                915                 920                 925

Leu Ser Glu Cys Leu Glu Gln His Ile Ala Asn Arg Ile Glu Lys Lys
            930                 935                 940

Lys Arg Gln Leu Ala Glu Asp Lys Gln Arg Asn Glu Gly Ile Ser Phe
945                 950                 955                 960

Asp Asp Ala Leu Lys Tyr Val Glu Ser Gly Gly Pro Ile Ile Arg
                965                 970                 975

Gln Val Thr Ala Met Asp Arg Lys Leu Glu Val Arg Asp Leu Met Arg
            980                 985                 990

Glu Arg Tyr Ala His Lys Asn Tyr Pro Glu Glu Phe Pro Phe Arg Cys
            995                 1000                1005

Lys Cys Ile Val Val Phe Gln Lys Leu Asp Gly Val Asp Thr Ile
    1010                1015                1020

Leu Phe Ala Leu Tyr Val Tyr Glu His Gly Glu Asn Asn Pro Pro
    1025                1030                1035

Pro Asn Gln Arg Cys Val Tyr Ile Ser Tyr Leu Asp Ser Val His
```

```
              1040                1045                1050

Phe Met Arg Pro Arg Asn Leu Arg Thr Phe Val Tyr His Glu Ile
    1055                1060                1065

Leu Ile Ala Tyr Leu Asp Tyr Ala Arg Gln Arg Gly Phe Ala Thr
    1070                1075                1080

Ala His Ile Trp Ala Cys Pro Pro Leu Arg Gly Asp Asp Tyr Ile
    1085                1090                1095

Phe Phe Ala Lys Pro Glu Asp Gln Lys Thr Pro Arg Asp Asn Arg
    1100                1105                1110

Leu Arg Gln Trp Tyr Gln Glu Met Leu Ile Glu Ala Gln Lys Arg
    1115                1120                1125

Gly Ile Val Gly Lys Leu Thr Asn Met Tyr Asp Leu Tyr Phe Ala
    1130                1135                1140

Asn Glu Ser Leu Asp Ala Thr Ala Val Pro Tyr Met Glu Gly Asp
    1145                1150                1155

Tyr Phe Pro Gly Glu Ala Glu Asn Ile Ile Lys Leu Leu Gln Glu
    1160                1165                1170

Gly Lys Gly Lys Lys Ala Gly Asn Gly Gly Lys Lys Lys Lys Ser
    1175                1180                1185

Lys Ala Ser Lys Gly Ser Thr Gly Thr Arg Ser Thr Gly Val Asp
    1190                1195                1200

Glu Glu Ala Leu Leu Ala Ser Gly Phe Met Asp Asp Ala Lys Ser
    1205                1210                1215

Leu Lys Asp Leu Asp Arg Asp Gln Val Met Val Lys Leu Gly Glu
    1220                1225                1230

Thr Ile Gln Pro Met Lys Glu Ser Phe Ile Val Ala Phe Leu Asn
    1235                1240                1245

Trp Ser Gly Ala Lys Glu Glu Asp Lys Val Val Pro Glu Ala Met
    1250                1255                1260

Ile Lys Ala Arg Ala Glu Tyr Val Asp Glu Asn Leu Glu Ser Asp
    1265                1270                1275

Ala Ala Gly Ser Lys Arg Asp Ala Glu Gly His Thr Ala Asn Ser
    1280                1285                1290

Ser Thr His Ser Asp Lys Val Ile Asn Asp Asp Glu Glu Asp Leu
    1295                1300                1305

Asp Cys Glu Phe Leu Asn Asn Arg Gln Ala Phe Leu Asn Leu Cys
    1310                1315                1320

Arg Gly Asn His Tyr Gln Phe Asp Glu Leu Arg Arg Ser Lys His
    1325                1330                1335

Thr Ser Met Met Val Leu Trp His Leu His Asn Arg Asp Ala Pro
    1340                1345                1350

Lys Phe Val Gln Gln Cys Val Ala Cys Ser Arg Glu Ile Leu Ser
    1355                1360                1365

Gly Lys Arg Tyr His Cys Ser Thr Cys Pro Asp Tyr Asp Leu Cys
    1370                1375                1380

Gln Asp Cys Tyr Lys Asp Pro Lys Val Asn Arg Gly Asn Cys Thr
    1385                1390                1395

His Thr Leu Thr Pro Ile Ala Val Asp Pro Asp Ala Asn Gln Glu
    1400                1405                1410

Arg Asn Gly Met Asp Asp Ala Glu Arg Gln Ala Arg Gln Arg Asn
    1415                1420                1425

Leu Met Met His Ile Gln Leu Ile Glu His Ala Ser Gly Cys Val
    1430                1435                1440
```

```
Ser Lys Thr Cys Thr Ser Ser Asn Cys Ala Lys Met Lys Asn Tyr
    1445              1450                1455

Leu His His Ala Ser Ile Cys Arg Val Lys Val Gln Gly Gly Cys
    1460              1465                1470

Lys Ile Cys Lys Lys Ile Trp Thr Leu Leu Arg Ile His Ala Gln
    1475              1480                1485

Lys Cys Arg Gln Ala Arg Cys Pro Ile Pro Gln Cys Asn Ala Ile
    1490              1495                1500

Arg Glu Lys Met Arg Gln Leu Gln Lys Gln Gln Ala Met Asp
    1505              1510                1515

Asp Arg Arg Arg Leu Glu Met Asn Arg His Met Arg Phe Gly Gly
    1520              1525                1530

Ala Ala Pro Ser
    1535

<210> SEQ ID NO 35
<211> LENGTH: 6698
<212> TYPE: DNA
<213> ORGANISM: Navicula WT0229
<220> FEATURE:
<221> NAME/KEY: misc_feature
<223> OTHER INFORMATION: encodes polypeptide of SEQ ID NO:36

<400> SEQUENCE: 35
tgaacgattc tgctgtacga tctcatccga gttcagtaaa cccaagacaa gacaatatca      60
ataatagcag tcaaagtgca aatggaagct cggatcagaa agcattcctt gacggaagct     120
ttgctggcgg ctggcagtct aacgcggacc ttcccgatcg acgtgaggtg atttttcgaa     180
ttctggaagt aatcaggcac atgagaccag atacggatcg tgtttcatca aagcttccgc     240
acatggcaaa aagtttagaa gagcacctct accggtcagc acagactaag gaagagtaca     300
tggattttgg aacactaagg cgccgcctcc aggcaatcgc acacggactc gaactccacc     360
ggccgtcttc ttctaccagt cagcaatcgg gagaccaatc caatcagacc cagcccgtgg     420
catctgggcg aaatcaaggc aggtcgtcat ttcaaactgc cagtagtacc gacagtggga     480
tgtattctag cgcaagtaat gccaatccgg ataatttgaa ctcgtcgatg acttccggaa     540
tgggtatggg ttccatcaac cagtcacaga taccctctaa tatgcaaaaa atgggcggac     600
aaatgaacca gtccgctagt tttgggagta atatgggtgt gaacacgtct gcgccttcca     660
gtatgggaaa cctttcgcag cgacagacat cttcgcaatt ccagaagaat agtaactggt     720
caaacagcgg aagtgcagac tacgcggca gtatggctgg tgattcgaac atgaccacta     780
tgccactaaa cgggggaatt ctaccgatgg gtggaatgag cctgccacaa cagcaacaga     840
tgcaaccttc aatgattcag caacagcagc ctatgtcgaa cattatgccg tctcagatgg     900
ggagtgctgc tggacaggct attaattcgt cacaggctgt tccacagaac tgggcttctc     960
agtcagcacc cttttgggat tcagccggtt caacgagtgg aatggactcg tcgatgcaaa    1020 agaaaaagt cattcttcag cagcagcaaa gacttctcct gctccgccat gccagtaaat    1080
gtacggctgg tgcggcatgt caaactagat tttgctccca gatggtgacg ctgtggcggc    1140
atatgaaggc ttgcagggat aaaaattgca aaacgcctca ttgcgtcagt agtcgctgcg    1200
ttcttaatca ttaccgtatt tgtaagagca acggaaacac agcgagctgc gaagtgtgtg    1260
gccctgtgat gatgaaaatt aaccaaaagg tactgaagc catggctggt gatcctctca    1320
cgagagatca agatctgtcg atgaagcaga cgcatcatcc atatcaacag caatctatgc    1380
```

```
tgcagccggg agggggggcag atgtcctcgg gattgatgaa ccaaaatatc atgcaaccac    1440
ttcctatgca acctatgcaa cagcagtcga ccatgcaacc agggtcttcg cagcacatgg    1500
tgaactcggt gtcggagggt atccaattgc aacaagctaa acaacagcag cagctgaaac    1560
tgaagcagca acttgagagc cttaagcaac tccaaaagaa gcaagaagaa ctcgaaaagc    1620
aacagaagcg acttgagatg cacgctcagc agattcagga tcctagctcg ccccaagcgc    1680
agcagctaca gcagcagcaa atgctcttac ggcacctcca gaaaaagtgt caacaacaac    1740
aactcatgct acagcaagaa gtaaaacttc ttatgacggg tggcggcaat ccgcaacaag    1800
accaaagtca gatatctcta caagctcaag ttcaacaaca gcaatttcag cagcagctta    1860
ttgcgcacca gcagggactg cagggcacca tgggattgtc agcgggcgcc gtacatggag    1920
ttcagtcttc cagtgcaatt gcggagggtc atatccaagg tccctcgccg cgtaagtccc    1980
ccgttccagc aaagccacga tatacggggg gcaaaggacg acgggagga aaagggaagt    2040 cgctaggtat aaattctgcc gtttcaaaga aaggctaag cgaaaccgag gacgattccc    2100
cccagtaccg aaaacgcgcg acaatcacaa aaccagaaac tgagctttcc gagactattg    2160
ccgtggaaag aaattcttca ctgggctctg ggcttgatga acatcgctg attcccttaa    2220 tgacgagaga tgagataatg aagcatctcg aatccttgaa caagcggttt tgtttgtcat    2280
ctcgaactgt gactcacaag tgcatgccta ttatacaagg tcttattgac gaccaatttg    2340 gatggtttt tcatgatcct gtcgatcctg taacgttggg tcttcctgat tactttgatg    2400
tagtgaaaac accaatgtgc ctcgaactcg ttaagaagaa gctggagaat gcagtttata    2460
acgacacgga atcatttgcc cgagatctca gtctggtttt tgaaaatgcc atcctgtata    2520
acggtgaaag cagtgaagta ggggagttag ccaaatccat gctggataaa tttcacacgg    2580
tttatcgcgc tttggttcaa gaacttgaat cttcctattt aagtttggag aagaaaggtg    2640
aactgtgttc gctttgtgga aatcagaata gaaaattcga gcctacaatt ctttactgtc    2700
aaggcgattg tgaaatgcag caaatcaagc ggcatgcgac ttacttcacg gatcgggcaa    2760
agcagaataa ctggtgcgag ggatgcttta agctccttca agatgaccag cctatcatgc    2820
ttgacgacgg caccgaagtg agaaaaagcg acctacagga atgtcaaaat gatgcgcttc    2880
cggaagaggg atgggtcaac tgcgatcact gcaactcatg ggtgcaccaa gtctgctcat    2940
tatttaacgg gcgagttaat aagtccggcg cgcggtacac atgccctaat tgttatctaa    3000
gcaaaggtag tatcgggaga gctttctcga agcaaataaa ggttgcggct gatctacctc    3060
attgcaagat gagtgaagcg atcgaacgtg gtcttttggc tacgcttgag aaagcctaca    3120
gagaccggtc aaatgaaatc ggagtggcca tcgacgatgt tgaaaaggca gaatccttga    3180
caattcgcgt cgtatcgaat attgaaaaga agcacatagt tggagaagag atgcttaaac    3240
ggtacaagga cgagggatgt gtaaaaggtt atcctgtccg tacaaagtgt atcgctctat    3300
ttcaaaagat acacgggggct gataccttc ttttcgccat gtacgtctac gaatatggtc    3360
acgaatgccc tgctcccaac cgcagacgag tgtacatatc ctatcttgat tctgtccaat    3420
attttgaacc caaatgctat cgaacacttg tttatcactc agttctggta gagtatctcc    3480
gctacgttaa agctcgcggt ttccacactg ctcattttttg gagctgtcca ccaacccccg    3540
gcgacgatta tatttttcat gtacacccat cgcaccagct ggtaccacgt gaagatatgc    3600
tcagagcttg gtatcatgat atgctagatc gcgccaaagc agagggtata gttattcgga    3660
caactaattt atacgacgag tactttgtga aaggcggcat ggactccgtg ccatgggcta    3720
cagggcgacc gacatgttta ccctatttttg aaggggacta tattcctggg gagatcgaaa    3780
```

```
ctatcataag atcggagcaa gaaaaattga cggatggctc ggagatggga gaagaagaca    3840
gagtgatggc gcgtctcggt ctaaatctcc gcaaaatgaa agacaatttc atcgtcgtgc    3900
acctcagaag taggcgtttt gctgcagcag tagaaagcgg tgatgatgta tctgatttca    3960
aagatgacag tgatgaagaa cttgtacgta acaagcgcgc gaagattagc ggcaaagaca    4020
caggttcatt atgtatgcaa gctgaacttc tcgaccaagc tgggtctgtt accttggaaa    4080
gagacccaac ggcacatact acaacggagg aacatgctag cggggcgtca tcggaaaatg    4140
agcaccctga gcgcagtcct gttggtgagg ttaaaaaggc agagccagtc tcagctttcg    4200
tggcaacgga aaccagccag tcaccatcca catcaacacg agatgaaagc gctaacaatg    4260
gaaggcatgt acaagatcaa gcattaccga taataggtga tgtccctacc gacgagatgg    4320
agtcgagtaa tggaagtcct agtccgcttg tcgaaaccat cgagacggtt gagtcgcatg    4380
acctgcccgc gtttgcttct cattatgacg aagagaaaag gaaccacgaa ctcagtgctg    4440
aaagggagcc aaccaaaacg acaacagctg agactagctc cgtcacttca gccctggtca    4500
agaaggacga tgataccgaa gaacgcgtga atacaccaaa cgtcgaagcc caggaccatg    4560
ttgaaaaaga accaccgtca cgcaacatta agttggatcc agacctacaa catggcggcc    4620
acgcagtcgc acaagacatt tcatctgaaa tagtcgagac tcaaaccaat caggaacagt    4680
caaatgattg cgccccaact gattctgttc tcttggataa taacaggccc gaggagattg    4740
aaaaaggagc ttcagacatt gatcatcgtt gtgcagacga ggccatcgaa tttaaacaag    4800
ttattgatga tgatgacaag gatgcttcca ggaaagtaaa cgagtgcaat cgtggtcgcg    4860
agataataga agagaaagtc ggtctaggtg acagaaacaa gaatactgac gaaatgccat    4920
taccgtatgc agccgacacc aataaagtga ctctcaacga cgaaacggcg gccactaaca    4980
gagaatcggt taatgatatc gctatgactg ccgattccgg aggaatgaac gaagacgaag    5040
cggttgccgt taatcatgaa attaccggag ctgaagttgt gatcgcagac ggactcgaag    5100
agaacaaaga tgaatctatg aaagggggatt ctgtgatcat gaacacagta aacgaggtta    5160
aagacagctc cttggtttct tccagagaag gcataaaaag tagtcttgag agtatgatcg    5220
ctaatccagc agaggcaaaa gacgcctcag aggttcctgg attggaaacc attgataatg    5280
gtgttgctgt gaacgcgaat ccctcaagag acaacacagt ccattcgcag acctctgatg    5340
aagcattgcc ggaaattaca ggtggagata gcaaggtgaa acctctgat cataatgcca    5400
gcaaaagtga tactgtgact gctgtttcag cgggggaaat tgcaagcacg accgatcgag    5460
tatgccaagt agactctgga aaacaggttt caacgccaga gaatgcacca aaaaatttgg    5520
gaccaggaca cgtgcttcta atgcctgaag cagctgcaac cacttcaagc gaccaagaat    5580
gtctcttccc tcaaagagga atttcagaca aattgagtca tgtctctgat gttgatgcta    5640
caatagccga tcaacagccc ccgaatgcac cagaagagtc tattgcaatt gcacgtccaa    5700
tcataatcaa taccgcctct gacgtagagg gtaaaaacat tagttcacag acagaagcag    5760
cagtcgaaaa gactgcttct gaccaagatg tcttgactcc accgcgtgat gccacggttt    5820
ttgttcaatt tcctgatggc caatcctcgg accaagcgac tgctgatcca agtttattta    5880
ctggcaacag ctcgcaagga ctgaagcgtg atattgatga agtcaagccg ctactttctc    5940
gtcatttcga cgaaatgaat cgacctctaa aatacgtaac ggatacagct gatcccgacg    6000
aaccgataga agttgagctt ttcgaatcgc ggcaaagatt tctcaattat tgccaaacta    6060
gccactgtca gttcgacgaa ttgcgacggg cgaagcactc gactatgatg gtcttatttc    6120
```

-continued

```
agcttcacaa ccctgcggcc ccgctgtttc tccagcaatg cggtgcttgt tacagagaca    6180
taacacacgg tgtccgatac agttgtaaca attgctctaa atttgatcta tgcgaggatt    6240
gctacaagcc tgttacttca ggtttgtggg ccaaaagaga ctctcgtttt gagcatgatc    6300
catcccacac atttacacct atcgacatgg aagtgtccac tgacagcgca atgagccaag    6360
aagatcggca gaaggcccta aaagcacatt gcgccttatt ggagcacgca ggtgactgtc    6420
aaggtccccc gacttgttct cttcaaaact gtcaaaaaat gaagaagctt tttaatcacg    6480
tgcgaagttg cgaaatcaag ccaaagagcg attgtagaat atgcactcgt ctcatttcgc    6540
tgtgtgcaat tcatgctcga acatgcaaaa tcgctgactc gtgcccagtt ccattctgtg    6600
atcgcatccg cgatagaaac gaaagacttc agcgacaaca acaactcatg gatgatcgcc    6660
gtcgtcaagc ccaaaacgat ttatatcaca cgtcttaa                           6698
```

<210> SEQ ID NO 36
<211> LENGTH: 2232
<212> TYPE: PRT
<213> ORGANISM: Navicula WT0229
<220> FEATURE:
<221> NAME/KEY: misc_feature
<223> OTHER INFORMATION: translation product 4244056

<400> SEQUENCE: 36

```
Met Asn Asp Ser Ala Val Arg Ser His Pro Ser Ser Val Asn Pro Arg
1               5                   10                  15

Gln Asp Asn Ile Asn Asn Ser Ser Gln Ser Ala Asn Gly Ser Ser Asp
            20                  25                  30

Gln Lys Ala Phe Leu Asp Gly Ser Phe Ala Gly Gly Trp Gln Ser Asn
        35                  40                  45

Ala Asp Leu Pro Asp Arg Arg Glu Val Ile Phe Arg Ile Leu Glu Val
    50                  55                  60

Ile Arg His Met Arg Pro Asp Thr Asp Arg Val Ser Ser Lys Leu Pro
65                  70                  75                  80

His Met Ala Lys Ser Leu Glu Glu His Leu Tyr Arg Ser Ala Gln Thr
                85                  90                  95

Lys Glu Glu Tyr Met Asp Phe Gly Thr Leu Arg Arg Arg Leu Gln Ala
            100                 105                 110

Ile Ala His Gly Leu Glu Leu His Arg Pro Ser Ser Ser Thr Ser Gln
        115                 120                 125

Gln Ser Gly Asp Gln Ser Asn Gln Thr Gln Pro Val Ala Ser Gly Arg
    130                 135                 140

Asn Gln Gly Arg Ser Ser Phe Gln Thr Ala Ser Ser Thr Asp Ser Gly
145                 150                 155                 160

Met Tyr Ser Ser Ala Ser Asn Ala Asn Pro Asp Asn Leu Asn Ser Ser
                165                 170                 175

Met Thr Ser Gly Met Gly Met Gly Ser Ile Asn Gln Ser Gln Ile Pro
            180                 185                 190

Ser Asn Met Gln Lys Met Gly Gly Gln Met Asn Gln Ser Ala Ser Phe
        195                 200                 205

Gly Ser Asn Met Gly Val Asn Thr Ser Ala Pro Ser Ser Met Gly Asn
    210                 215                 220

Leu Ser Gln Arg Gln Thr Ser Ser Gln Phe Gln Lys Asn Ser Asn Trp
225                 230                 235                 240

Ser Asn Ser Gly Ser Ala Asp Tyr Gly Gly Ser Met Ala Gly Asp Ser
                245                 250                 255
```

```
Asn Met Thr Thr Met Pro Leu Asn Gly Ile Leu Pro Met Gly Gly
            260                 265                 270

Met Ser Leu Pro Gln Gln Gln Met Gln Pro Ser Met Ile Gln Gln
        275                 280                 285

Gln Gln Pro Met Ser Asn Ile Met Pro Ser Gln Met Gly Ser Ala Ala
    290                 295                 300

Gly Gln Ala Ile Asn Ser Ser Gln Ala Val Pro Gln Asn Trp Ala Ser
305                 310                 315                 320

Gln Ser Ala Pro Phe Trp Asp Ser Ala Gly Ser Thr Ser Gly Met Asp
                325                 330                 335

Ser Ser Met Gln Lys Lys Val Ile Leu Gln Gln Gln Arg Leu
            340                 345                 350

Leu Leu Leu Arg His Ala Ser Lys Cys Thr Ala Gly Ala Cys Gln
        355                 360                 365

Thr Arg Phe Cys Ser Gln Met Val Thr Leu Trp Arg His Met Lys Ala
    370                 375                 380

Cys Arg Asp Lys Asn Cys Lys Thr Pro His Cys Val Ser Ser Arg Cys
385                 390                 395                 400

Val Leu Asn His Tyr Arg Ile Cys Lys Ser Asn Gly Asn Thr Ala Ser
                405                 410                 415

Cys Glu Val Cys Gly Pro Val Met Met Lys Ile Asn Gln Lys Asp Thr
                420                 425                 430

Glu Ala Met Ala Gly Asp Pro Leu Thr Arg Asp Gln Asp Leu Ser Met
            435                 440                 445

Lys Gln Thr His His Pro Tyr Gln Gln Gln Ser Met Leu Gln Pro Gly
    450                 455                 460

Gly Gly Gln Met Ser Ser Gly Leu Met Asn Gln Asn Ile Met Gln Pro
465                 470                 475                 480

Leu Pro Met Gln Pro Met Gln Gln Ser Thr Met Gln Pro Gly Ser
                485                 490                 495

Ser Gln His Met Val Asn Ser Val Ser Glu Gly Ile Gln Leu Gln Gln
                500                 505                 510

Ala Lys Gln Gln Gln Gln Leu Lys Leu Lys Gln Gln Leu Glu Ser Leu
    515                 520                 525

Lys Gln Leu Gln Lys Gln Glu Glu Leu Glu Lys Gln Gln Lys Arg
    530                 535                 540

Leu Glu Met His Ala Gln Gln Ile Gln Asp Pro Ser Ser Pro Gln Ala
545                 550                 555                 560

Gln Gln Leu Gln Gln Gln Met Leu Leu Arg His Leu Gln Lys Lys
            565                 570                 575

Cys Gln Gln Gln Gln Leu Met Leu Gln Gln Glu Val Lys Leu Leu Met
            580                 585                 590

Thr Gly Gly Gly Asn Pro Gln Gln Asp Gln Ser Gln Ile Ser Leu Gln
    595                 600                 605

Ala Gln Val Gln Gln Gln Phe Gln Gln Gln Leu Ile Ala His Gln
610                 615                 620

Gln Gly Leu Gln Gly Thr Met Gly Leu Ser Ala Gly Ala Val His Gly
625                 630                 635                 640

Val Gln Ser Ser Ser Ala Ile Ala Glu Gly His Ile Gln Gly Pro Ser
                645                 650                 655

Pro Arg Lys Ser Pro Val Pro Ala Lys Pro Arg Tyr Thr Gly Gly Lys
                660                 665                 670

Gly Arg Arg Gly Gly Lys Gly Lys Ser Leu Gly Ile Asn Ser Ala Val
```

-continued

```
            675                 680                 685
Ser Lys Lys Arg Leu Ser Glu Thr Glu Asp Ser Pro Gln Tyr Arg
690                 695                 700

Lys Arg Ala Thr Ile Thr Lys Pro Glu Thr Glu Leu Ser Glu Thr Ile
705                 710                 715                 720

Ala Val Glu Arg Asn Ser Ser Leu Gly Ser Gly Leu Asp Glu Thr Ser
                725                 730                 735

Leu Ile Pro Leu Met Thr Arg Asp Glu Ile Met Lys His Leu Glu Ser
                740                 745                 750

Leu Asn Lys Arg Phe Cys Leu Ser Ser Arg Thr Val Thr His Lys Cys
                755                 760                 765

Met Pro Ile Ile Gln Gly Leu Ile Asp Asp Gln Phe Gly Trp Val Phe
                770                 775                 780

His Asp Pro Val Asp Pro Val Thr Leu Gly Leu Pro Asp Tyr Phe Asp
785                 790                 795                 800

Val Val Lys Thr Pro Met Cys Leu Glu Leu Val Lys Lys Lys Leu Glu
                805                 810                 815

Asn Ala Val Tyr Asn Asp Thr Glu Ser Phe Ala Arg Asp Leu Ser Leu
                820                 825                 830

Val Phe Glu Asn Ala Ile Leu Tyr Asn Gly Glu Ser Ser Glu Val Gly
                835                 840                 845

Glu Leu Ala Lys Ser Met Leu Asp Lys Phe His Thr Val Tyr Arg Ala
850                 855                 860

Leu Val Gln Glu Leu Glu Ser Ser Tyr Leu Ser Leu Glu Lys Lys Gly
865                 870                 875                 880

Glu Leu Cys Ser Leu Cys Gly Asn Gln Asn Arg Lys Phe Glu Pro Thr
                885                 890                 895

Ile Leu Tyr Cys Gln Gly Asp Cys Glu Met Gln Gln Ile Lys Arg His
                900                 905                 910

Ala Thr Tyr Phe Thr Asp Arg Ala Lys Gln Asn Asn Trp Cys Glu Gly
                915                 920                 925

Cys Phe Lys Leu Leu Gln Asp Asp Gln Pro Ile Met Leu Asp Asp Gly
                930                 935                 940

Thr Glu Val Arg Lys Ser Asp Leu Gln Glu Cys Gln Asn Asp Ala Leu
945                 950                 955                 960

Pro Glu Glu Gly Trp Val Asn Cys Asp His Cys Asn Ser Trp Val His
                965                 970                 975

Gln Val Cys Ser Leu Phe Asn Gly Arg Val Asn Lys Ser Gly Ala Arg
                980                 985                 990

Tyr Thr Cys Pro Asn Cys Tyr Leu Ser Lys Gly Ser Ile Gly Arg Ala
                995                 1000                1005

Phe Ser Lys Gln Ile Lys Val Ala Ala Asp Leu Pro His Cys Lys
        1010                1015                1020

Met Ser Glu Ala Ile Glu Arg Gly Leu Leu Ala Thr Leu Glu Lys
        1025                1030                1035

Ala Tyr Arg Asp Arg Ser Asn Glu Ile Gly Val Ala Ile Asp Asp
        1040                1045                1050

Val Glu Lys Ala Glu Ser Leu Thr Ile Arg Val Val Ser Asn Ile
        1055                1060                1065

Glu Lys Lys His Ile Val Gly Glu Glu Met Leu Lys Arg Tyr Lys
        1070                1075                1080

Asp Glu Gly Cys Val Lys Gly Tyr Pro Val Arg Thr Lys Cys Ile
        1085                1090                1095
```

```
Ala Leu Phe Gln Lys Ile His Gly Ala Asp Thr Leu Leu Phe Ala
    1100            1105                1110

Met Tyr Val Tyr Glu Tyr Gly His Glu Cys Pro Ala Pro Asn Arg
    1115            1120                1125

Arg Arg Val Tyr Ile Ser Tyr Leu Asp Ser Val Gln Tyr Phe Glu
    1130            1135                1140

Pro Lys Cys Tyr Arg Thr Leu Val Tyr His Ser Val Leu Val Glu
    1145            1150                1155

Tyr Leu Arg Tyr Val Lys Ala Arg Gly Phe His Thr Ala His Phe
    1160            1165                1170

Trp Ser Cys Pro Pro Thr Pro Gly Asp Asp Tyr Ile Phe His Val
    1175            1180                1185

His Pro Ser His Gln Leu Val Pro Arg Glu Asp Met Leu Arg Ala
    1190            1195                1200

Trp Tyr His Asp Met Leu Asp Arg Ala Lys Ala Glu Gly Ile Val
    1205            1210                1215

Ile Arg Thr Thr Asn Leu Tyr Asp Glu Tyr Phe Val Lys Gly Gly
    1220            1225                1230

Met Asp Ser Val Pro Trp Ala Thr Gly Arg Pro Thr Cys Leu Pro
    1235            1240                1245

Tyr Phe Glu Gly Asp Tyr Ile Pro Gly Glu Ile Glu Thr Ile Ile
    1250            1255                1260

Arg Ser Glu Gln Glu Lys Leu Thr Asp Gly Ser Glu Met Gly Glu
    1265            1270                1275

Glu Asp Arg Val Met Ala Arg Leu Gly Leu Asn Leu Arg Lys Met
    1280            1285                1290

Lys Asp Asn Phe Ile Val Val His Leu Arg Ser Arg Arg Phe Ala
    1295            1300                1305

Ala Ala Val Glu Ser Gly Asp Asp Val Ser Asp Phe Lys Asp Asp
    1310            1315                1320

Ser Asp Glu Glu Leu Val Arg Asn Lys Arg Ala Lys Ile Ser Gly
    1325            1330                1335

Lys Asp Thr Gly Ser Leu Cys Met Gln Ala Glu Leu Leu Asp Gln
    1340            1345                1350

Ala Gly Ser Val Thr Leu Glu Arg Asp Pro Thr Ala His Thr Thr
    1355            1360                1365

Thr Glu Glu His Ala Ser Gly Ala Ser Ser Glu Asn Glu His Pro
    1370            1375                1380

Glu Arg Ser Pro Val Gly Glu Val Lys Lys Ala Glu Pro Val Ser
    1385            1390                1395

Ala Phe Val Ala Thr Glu Thr Ser Gln Ser Pro Ser Thr Ser Thr
    1400            1405                1410

Arg Asp Glu Ser Ala Asn Asn Gly Arg His Val Gln Asp Gln Ala
    1415            1420                1425

Leu Pro Ile Ile Gly Asp Val Pro Thr Asp Glu Met Glu Ser Ser
    1430            1435                1440

Asn Gly Ser Pro Ser Pro Leu Val Glu Thr Ile Glu Thr Val Glu
    1445            1450                1455

Ser His Asp Leu Pro Ala Phe Ala Ser His Tyr Asp Glu Glu Lys
    1460            1465                1470

Arg Asn His Glu Leu Ser Ala Glu Arg Glu Pro Thr Lys Thr Thr
    1475            1480                1485
```

```
Thr Ala Glu Thr Ser Ser Val Thr Ser Ala Leu Val Lys Lys Asp
    1490            1495            1500

Asp Asp Thr Glu Glu Arg Val Asn Thr Pro Asn Val Glu Ala Gln
    1505            1510            1515

Asp His Val Glu Lys Glu Pro Pro Ser Arg Asn Ile Lys Leu Asp
    1520            1525            1530

Pro Asp Leu Gln His Gly Gly His Ala Val Ala Gln Asp Ile Ser
    1535            1540            1545

Ser Glu Ile Val Glu Thr Gln Thr Asn Gln Glu Gln Ser Asn Asp
    1550            1555            1560

Cys Ala Pro Thr Asp Ser Val Leu Leu Asp Asn Asn Arg Pro Glu
    1565            1570            1575

Glu Ile Glu Lys Gly Ala Ser Asp Ile Asp His Arg Cys Ala Asp
    1580            1585            1590

Glu Ala Ile Glu Phe Lys Gln Val Ile Asp Asp Asp Lys Asp
    1595            1600            1605

Ala Ser Arg Lys Val Asn Glu Cys Asn Arg Gly Arg Glu Ile Ile
    1610            1615            1620

Glu Glu Lys Val Gly Leu Gly Asp Arg Asn Lys Asn Thr Asp Glu
    1625            1630            1635

Met Pro Leu Pro Tyr Ala Ala Asp Thr Asn Lys Val Thr Leu Asn
    1640            1645            1650

Asp Glu Thr Ala Ala Thr Asn Arg Glu Ser Val Asn Asp Ile Ala
    1655            1660            1665

Met Thr Ala Asp Ser Gly Gly Met Asn Glu Asp Glu Ala Val Ala
    1670            1675            1680

Val Asn His Glu Ile Thr Gly Ala Glu Val Val Ile Ala Asp Gly
    1685            1690            1695

Leu Glu Glu Asn Lys Asp Glu Ser Met Lys Gly Asp Ser Val Ile
    1700            1705            1710

Met Asn Thr Val Asn Glu Val Lys Asp Ser Ser Leu Val Ser Ser
    1715            1720            1725

Arg Glu Gly Ile Lys Ser Ser Leu Glu Ser Met Ile Ala Asn Pro
    1730            1735            1740

Ala Glu Ala Lys Asp Ala Ser Glu Val Pro Gly Leu Glu Thr Ile
    1745            1750            1755

Asp Asn Gly Val Ala Val Asn Ala Asn Pro Ser Arg Asp Asn Thr
    1760            1765            1770

Val His Ser Gln Thr Ser Asp Glu Ala Leu Pro Glu Ile Thr Gly
    1775            1780            1785

Gly Asp Ser Lys Gly Glu Thr Ser Asp His Asn Ala Ser Lys Ser
    1790            1795            1800

Asp Thr Val Thr Ala Val Ser Ala Gly Glu Ile Ala Ser Thr Thr
    1805            1810            1815

Asp Arg Val Cys Gln Val Asp Ser Gly Lys Gln Val Ser Thr Pro
    1820            1825            1830

Glu Asn Ala Pro Lys Asn Leu Gly Pro Gly His Val Leu Leu Met
    1835            1840            1845

Pro Glu Ala Ala Ala Thr Thr Ser Ser Asp Gln Glu Cys Leu Phe
    1850            1855            1860

Pro Gln Arg Gly Ile Ser Asp Lys Leu Ser His Val Ser Asp Val
    1865            1870            1875

Asp Ala Thr Ile Ala Asp Gln Gln Pro Pro Asn Ala Pro Glu Glu
```

```
                    1880            1885            1890
Ser Ile Ala Ile Ala Arg Pro Ile Ile Asn Thr Ala Ser Asp
    1895            1900            1905

Val Glu Gly Lys Asn Ile Ser Ser Gln Thr Glu Ala Ala Val Glu
    1910            1915            1920

Lys Thr Ala Ser Asp Gln Asp Val Leu Thr Pro Pro Arg Asp Ala
    1925            1930            1935

Thr Val Phe Val Gln Phe Pro Asp Gly Gln Ser Ser Asp Gln Ala
    1940            1945            1950

Thr Ala Asp Pro Ser Leu Phe Thr Gly Asn Ser Ser Gln Gly Leu
    1955            1960            1965

Lys Arg Asp Ile Asp Glu Val Lys Pro Leu Leu Ser Arg His Phe
    1970            1975            1980

Asp Glu Met Asn Arg Pro Leu Lys Tyr Val Thr Asp Thr Ala Asp
    1985            1990            1995

Pro Asp Glu Pro Ile Glu Val Glu Leu Phe Glu Ser Arg Gln Arg
    2000            2005            2010

Phe Leu Asn Tyr Cys Gln Thr Ser His Cys Gln Phe Asp Glu Leu
    2015            2020            2025

Arg Arg Ala Lys His Ser Thr Met Met Val Leu Phe Gln Leu His
    2030            2035            2040

Asn Pro Ala Ala Pro Leu Phe Leu Gln Gln Cys Gly Ala Cys Tyr
    2045            2050            2055

Arg Asp Ile Thr His Gly Val Arg Tyr Ser Cys Asn Asn Cys Ser
    2060            2065            2070

Lys Phe Asp Leu Cys Glu Asp Cys Tyr Lys Pro Val Thr Ser Gly
    2075            2080            2085

Leu Trp Ala Lys Arg Asp Ser Arg Phe Glu His Asp Pro Ser His
    2090            2095            2100

Thr Phe Thr Pro Ile Asp Met Glu Val Ser Thr Asp Ser Ala Met
    2105            2110            2115

Ser Gln Glu Asp Arg Gln Lys Ala Leu Lys Ala His Cys Ala Leu
    2120            2125            2130

Leu Glu His Ala Gly Asp Cys Gln Gly Pro Pro Thr Cys Ser Leu
    2135            2140            2145

Gln Asn Cys Gln Lys Met Lys Lys Leu Phe Asn His Val Arg Ser
    2150            2155            2160

Cys Glu Ile Lys Pro Lys Ser Asp Cys Arg Ile Cys Thr Arg Leu
    2165            2170            2175

Ile Ser Leu Cys Ala Ile His Ala Arg Thr Cys Lys Ile Ala Asp
    2180            2185            2190

Ser Cys Pro Val Pro Phe Cys Asp Arg Ile Arg Asp Arg Asn Glu
    2195            2200            2205

Arg Leu Gln Arg Gln Gln Leu Met Asp Asp Arg Arg Arg Gln
    2210            2215            2220

Ala Gln Asn Asp Leu Tyr His Thr Ser
    2225            2230
```

<210> SEQ ID NO 37
<211> LENGTH: 4665
<212> TYPE: DNA
<213> ORGANISM: Navicula WT0229
<220> FEATURE:
<221> NAME/KEY: misc_feature
<223> OTHER INFORMATION: encodes polypeptide of SEQ ID NO:38

<400> SEQUENCE: 37

```
atgcaaaccc atccgcagca gcccggctcg ggcggtgcca gctttcccca gcctcctact    60
cagcaacaac agcagcagca aatatttcca caccaaggac tcaacggcgg gtggcagagt   120
gacaaagatt atgaggatcg tcggaaaatg attgcgaaaa tcgtgcatct cttgcaacaa   180
cggaagccaa acgcgccgca agaatggcta agaagttgc ctcaaatggc gaaacgatta    240
gaagaatcat tgtacaggtc ggccaaatct ttcaatgagt ataatgatgc aaatacattg   300
aagcacagac tgcagcaact cgccgtaaat attggaatga aaacaaagaa actccagcaa   360
caacaggcga tgatgcaaca gcaaaagatg cagcagcagc aacaacaaca atcgcaacaa   420
ccagggataa atcagttttc acggtcgact atgccggcac aggcgcaaca agaacaaccc   480
cttgtcaagc tcaagcaca gcaaccaatt ccattatctg ctccacaagg caccaacggt    540
cagcagcaac agcaacgaat agtcaacatg gcggagataa atcctatgat gagttcccaa   600
acaactactc cctcgcagcc tcagcccccg gtacctgcac ctgcacctcc tctacaacaa   660
atccagtatg gtcagccggg gtctgctcca gtcccttccg cgcctcctgc ggcactgtca   720
ggtgcgcccg gtccaaattt atcagcagct gctagcaacg gaggacgaca aatagctaat   780
agacagcagg ttcttcgaca tcaacaacaa cgcctacttc ttttgcgcca cgcagccaag   840
tgccaatatg acgacggtcg atgcccagtg accccgcact cgcaggtat gaagcgatta     900
tggaaacata ttgcggaatg caagaaccag aaatgtcttg ttccccattg tgtgagctct   960
cgttacgttt tgagtcacta ccatcgttgc aaagacgtgc ggtgcccgt atgtggacct    1020
gtgcgtgaag ccattcatcg cagtcacgaa aagcagaagc acatgcaagc gctcaaacag   1080
cggcaccagc aagctgtgca acaaaatcaa acacaagaag gagctcagca acagcctgct   1140
gcactggctc ccactggagc tgcttctgta catccgaccc agccctgtc tgctgaacca    1200
ccaaacaaga agcaacggac tgctgggta ttgaccgctc catcattcca gtccaacaa     1260
cgacctttac agcacccggg agcgagaccg gtagcgcctg ggcaaaccca gtctggctac   1320
agtttatcgc agcaacagag tgcacaacag gcgggcccac agttatccca ccatcaagca   1380
ggccagcagc aaggatctcg cccagtcgtc gcatctacgc caggcttggc ttttttctaat   1440
ggacaggtga taactccaaa atattcgggt ccaaagcctc aggaggatca tactttgatc   1500
aactgtttct ccgttgaaca aattgaatct catatcgagt cgctgaacaa tggtctgcag   1560
ttgcctcctg cgaagctcaa agcgaaatgc ctcgacgtat tgagactatt acagtcgcat   1620
cagcatgcat gggtgtttaa tactccggtg gatcctgtgg agcttggctt acctgattat   1680
tttgaggtta tcaagacacc aatggactta gggaccatca ggaagaaact tgagaacggt   1740
gtttaccaga agattgaaga attcgagggg cacgttttat tgacattcga gaatgcgatg   1800
ctgtataatc ctgaagggtc agtggtgtac aatatggcaa agagatgaa agagaaattt    1860
gtgcgcgact atgccaaatt gatcgaaatt ctcaatgagg aagaagacgt taaaggaag    1920
aacggagaag catgcctact atgtggatgc gaaaagctac ttttcgagcc tcctgtcttc   1980
tattgtaacg gcatgaattg tccgtcgaag cgtatacgac gaaacagcca ttactatgtg   2040
ggtggcaaca accagtatca ctggtgccat caatgttacc aggatcttcg ggataattca   2100
acaatcgatc tagggggatat ccaagtaaag aaagagagct tgactaagaa aaagaatgat   2160
gaagtgcacg aggaaagttg ggtgcaatgt gatcgatgcg aacgatgggt gcaccaaatt   2220
tgtgctttgt ttaacacaag gcagaacaaa gaccagcgct ctgaatatgc ttgtcctcgt   2280
```

```
tgcacgattg aggaacgcat gaaaagaggc aacttagagg caatctcgtc ttcgccaatg    2340
gcggaagacc ttcctcgaac aaagatgtct gagtatcttg aatctcacgt tcgtcagaaa    2400
gtcgatgagt tcgtggagaa aaaatcgaag gcggtttcga tcgcagaaaa tattccgttc    2460
gaggaggcca agaagaagat tcaaatggga ggcgagataa cgattcgaca ggtaacctct    2520
atggacagga agttggaggt tagggaacgg atgaagagaa gatatgcctt caaaaactat    2580
cccgaagagt ttactttccg gtgcaagtgc tttgttgttt ttcagaatct cgacggggtg    2640
gacgttgttt tgttcggact ttacgtgtac gaacacgacg agaaaaaccc tttaccgaac    2700
agccgcactg tctacgtgtc gtacctagac agtgttcact acatgagacc gcgccaaatg    2760
cgaactttta tatatcatga gatacttatc tcctaccttg actacgtgcg gcgtcgagga    2820
ttttctacag ctcacatctg ggcctgtcct cctctgaaag gcgatgatta catcctttac    2880
gcgaaaccag aagatcagaa aactcctaga gacgatcgcc tcaaacagtg gtatatcgac    2940
atgctggtcg agtcacagag gcgaggaatt gttgggaaac tgacgaacat gtatgatctc    3000
tacttctcga acccgaagaa tgatgcgacc gtcgttccgt acatggatgg agattatttt    3060
cctgctgaag ctgagaacat catcaaagac attgaagaag ggaaaacggg gaagaagtcc    3120
agttctcagg gaaagaagaa agagaaggcg aagcagaaaa agaagtctgg gtctagccgt    3180
ggtggcacac ggtccacggg tttagatgaa gatgcattga aagctagcgg tattctacca    3240
ccaggtgcta atcagaaaag tctcgaggaa ggcggccgtg attttgtcat ggctaagttg    3300
ggagagacta tccagccaat gaaagaaagt ttcatagtgg cgtatcttgc ctggagcgga    3360
gcgaaggatg aggatatgca agttccgaaa gaaattgagg agtatcgtaa cgagcatggc    3420
atcacgtgga agatcaatga agaagcgtcg tctgagaaag gtgataaaga aaacccgaaa    3480
ccgacggagt cgattgagat ggagacgacg ccgactgaag tttcaactag cgtgaatgcg    3540
acagctgggg tcgccgaaaa caaagatccg gaaaaacaaa caggaaacga tggagacgag    3600
aagaatgcca caatgagcat ggacacaggc gcatccagcc tcgagccgaa aagtgatgac    3660
gcgtgtgacg attcgtcaaa ggccaagaca agcgctgaca atatggaatc ggacccggaa    3720
ataaaagtcg aatcacaaac caggtcacag cttgatacgc aggtggaaca aagttccgat    3780
tcagcgaatg catctcaacc taacgctgta aatatgagta ttcgagaagg aaagttcgct    3840
gccatggctg ctaggaaaag agatatcgat ggtgtcccaa agaaaagttc agagggtgaa    3900
gaatctacaa aagccaaaaa cgagccttca aagactgtta ccgtcaaaga tagtaaggga    3960
agaacggtga agttttggga cgacgatgaa gaggagcttg actgcgaatt cttaaacaat    4020
cggcaagcat ttttgaatct ttgccaggga aatcattacc agttcgatac gattcgccgc    4080
gcaaaacact cttcaatgat ggtactttgg cacctccata atcgtgacgc tcctaagttc    4140
gttcaacagt gcgctacgtg ctccagggaa atattgactg gtatgaggtt ccactgtcca    4200
acttgtgcgg actttgatca gtgtcaagat tgcgtctcca actcgaaaat accgagacat    4260
ccacatccat tgaaacctat agcagttggc aacggccaac aatctgactt gacagacgag    4320
cagcgcaagg agcgccagcg aagtattcag ttgcatatga cacttctgca gcatgctgcc    4380
acatgttcaa acgcgaaatg tccttccgcc aattgcacca aaatgaaggg tctattgaaa    4440
cacgggtcgc aatgccagat caaggcaaca ggcggatgca acgtatgcaa acgtatttgg    4500
gccctactgc aaatacatgc acgacagtgc aagacatcaa gttgtgcagt tcctaactgt    4560
atggcaattc gtgaacgatt tcgccaactc aaaaagcaac agatggcaat ggacgaccgc    4620
aggcgacagg aaatgaatag ggcttgtcgc gggaaacgtg gatga                   4665
```

<210> SEQ ID NO 38
<211> LENGTH: 1554
<212> TYPE: PRT
<213> ORGANISM: Navicula WT0229
<220> FEATURE:
<221> NAME/KEY: misc_feature
<223> OTHER INFORMATION: translation product 4244509

<400> SEQUENCE: 38

```
Met Gln Thr His Pro Gln Gln Pro Gly Ser Gly Gly Ala Ser Phe Pro
1               5                   10                  15

Gln Pro Pro Thr Gln Gln Gln Gln Gln Gln Ile Phe Pro His Gln
            20                  25                  30

Gly Leu Asn Gly Gly Trp Gln Ser Asp Lys Asp Tyr Glu Asp Arg Arg
        35                  40                  45

Lys Met Ile Ala Lys Ile Val His Leu Leu Gln Gln Arg Lys Pro Asn
    50                  55                  60

Ala Pro Gln Glu Trp Leu Lys Lys Leu Pro Gln Met Ala Lys Arg Leu
65                  70                  75                  80

Glu Glu Ser Leu Tyr Arg Ser Ala Lys Ser Phe Asn Glu Tyr Asn Asp
                85                  90                  95

Ala Asn Thr Leu Lys His Arg Leu Gln Gln Leu Ala Val Asn Ile Gly
            100                 105                 110

Met Lys Thr Lys Lys Leu Gln Gln Gln Ala Met Met Gln Gln Gln
        115                 120                 125

Lys Met Gln Gln Gln Gln Gln Gln Ser Gln Pro Gly Ile Asn
    130                 135                 140

Gln Phe Ser Arg Ser Thr Met Pro Ala Gln Ala Gln Gln Glu Gln Pro
145                 150                 155                 160

Leu Val Lys Pro Gln Ala Gln Pro Ile Pro Leu Ser Ala Pro Gln
                165                 170                 175

Gly Thr Asn Gly Gln Gln Gln Gln Arg Ile Val Asn Met Ala Glu
            180                 185                 190

Ile Asn Pro Met Met Ser Ser Gln Thr Thr Thr Pro Ser Gln Pro Gln
        195                 200                 205

Pro Pro Val Pro Ala Pro Ala Pro Leu Gln Gln Ile Gln Tyr Gly
    210                 215                 220

Gln Pro Gly Ser Ala Pro Val Pro Ser Ala Pro Ala Ala Leu Ser
225                 230                 235                 240

Gly Ala Pro Gly Pro Asn Leu Ser Ala Ala Ser Asn Gly Gly Arg
                245                 250                 255

Gln Ile Ala Asn Arg Gln Gln Val Leu Arg His Gln Gln Arg Leu
            260                 265                 270

Leu Leu Leu Arg His Ala Ala Lys Cys Gln Tyr Asp Asp Gly Arg Cys
        275                 280                 285

Pro Val Thr Pro His Cys Ala Gly Met Lys Arg Leu Trp Lys His Ile
    290                 295                 300

Ala Glu Cys Lys Asn Gln Lys Cys Leu Val Pro His Cys Val Ser Ser
305                 310                 315                 320

Arg Tyr Val Leu Ser His Tyr His Arg Cys Lys Asp Val Arg Cys Pro
                325                 330                 335

Val Cys Gly Pro Val Arg Glu Ala Ile His Arg Ser His Glu Lys Gln
            340                 345                 350

Lys His Met Gln Ala Leu Lys Gln Arg His Gln Gln Ala Val Gln Gln
```

```
                355                 360                 365
Asn Gln Thr Gln Glu Gly Ala Gln Gln Pro Ala Ala Leu Ala Pro
370                 375                 380

Thr Gly Ala Ala Ser Val His Pro Thr Gln Pro Leu Ser Ala Glu Pro
385                 390                 395                 400

Pro Asn Lys Lys Gln Arg Thr Ala Gly Val Leu Thr Ala Pro Ser Phe
            405                 410                 415

Gln Val Gln Gln Arg Pro Leu Gln His Pro Gly Ala Arg Pro Val Ala
            420                 425                 430

Pro Gly Gln Thr Gln Ser Gly Tyr Ser Leu Ser Gln Gln Gln Ser Ala
            435                 440                 445

Gln Gln Ala Gly Pro Gln Leu Ser His His Gln Ala Gly Gln Gln Gln
            450                 455                 460

Gly Ser Arg Pro Val Val Ala Ser Thr Pro Gly Leu Ala Phe Ser Asn
465                 470                 475                 480

Gly Gln Val Ile Thr Pro Lys Tyr Ser Gly Pro Lys Pro Gln Glu Asp
            485                 490                 495

His Thr Leu Ile Asn Cys Phe Ser Val Glu Gln Ile Glu Ser His Ile
            500                 505                 510

Glu Ser Leu Asn Asn Gly Leu Gln Leu Pro Pro Ala Lys Leu Lys Ala
            515                 520                 525

Lys Cys Leu Asp Val Leu Arg Leu Leu Gln Ser His Gln His Ala Trp
530                 535                 540

Val Phe Asn Thr Pro Val Asp Pro Val Glu Leu Gly Leu Pro Asp Tyr
545                 550                 555                 560

Phe Glu Val Ile Lys Thr Pro Met Asp Leu Gly Thr Ile Arg Lys Lys
            565                 570                 575

Leu Glu Asn Gly Val Tyr Gln Lys Ile Glu Glu Phe Glu Gly His Val
            580                 585                 590

Leu Leu Thr Phe Glu Asn Ala Met Leu Tyr Asn Pro Glu Gly Ser Val
            595                 600                 605

Val Tyr Asn Met Ala Lys Glu Met Lys Glu Lys Phe Val Arg Asp Tyr
610                 615                 620

Ala Lys Leu Ile Glu Ile Leu Asn Glu Glu Asp Val Lys Arg Lys
625                 630                 635                 640

Asn Gly Glu Ala Cys Leu Leu Cys Gly Cys Glu Lys Leu Leu Phe Glu
            645                 650                 655

Pro Pro Val Phe Tyr Cys Asn Gly Met Asn Cys Pro Ser Lys Arg Ile
            660                 665                 670

Arg Arg Asn Ser His Tyr Tyr Val Gly Gly Asn Asn Gln Tyr His Trp
            675                 680                 685

Cys His Gln Cys Tyr Gln Asp Leu Arg Asp Asn Ser Thr Ile Asp Leu
            690                 695                 700

Gly Asp Ile Gln Val Lys Lys Glu Ser Leu Thr Lys Lys Asn Asp
705                 710                 715                 720

Glu Val His Glu Glu Ser Trp Val Gln Cys Asp Arg Cys Glu Arg Trp
            725                 730                 735

Val His Gln Ile Cys Ala Leu Phe Asn Thr Arg Gln Asn Lys Asp Gln
            740                 745                 750

Arg Ser Glu Tyr Ala Cys Pro Arg Cys Thr Ile Glu Glu Arg Met Lys
            755                 760                 765

Arg Gly Asn Leu Glu Ala Ile Ser Ser Pro Met Ala Glu Asp Leu
770                 775                 780
```

```
Pro Arg Thr Lys Met Ser Glu Tyr Leu Glu Ser His Val Arg Gln Lys
785                 790                 795                 800

Val Asp Glu Phe Val Glu Lys Lys Ser Lys Ala Val Ser Ile Ala Glu
            805                 810                 815

Asn Ile Pro Phe Glu Ala Lys Lys Lys Ile Gln Met Gly Gly Glu
                820                 825                 830

Ile Thr Ile Arg Gln Val Thr Ser Met Asp Arg Lys Leu Glu Val Arg
            835                 840                 845

Glu Arg Met Lys Arg Arg Tyr Ala Phe Lys Asn Tyr Pro Glu Glu Phe
850                 855                 860

Thr Phe Arg Cys Lys Cys Phe Val Val Phe Gln Asn Leu Asp Gly Val
865                 870                 875                 880

Asp Val Val Leu Phe Gly Leu Tyr Val Tyr Glu His Asp Glu Lys Asn
                885                 890                 895

Pro Leu Pro Asn Ser Arg Thr Val Tyr Val Ser Tyr Leu Asp Ser Val
                900                 905                 910

His Tyr Met Arg Pro Arg Gln Met Arg Thr Phe Ile Tyr His Glu Ile
            915                 920                 925

Leu Ile Ser Tyr Leu Asp Tyr Val Arg Arg Gly Phe Ser Thr Ala
930                 935                 940

His Ile Trp Ala Cys Pro Pro Leu Lys Gly Asp Asp Tyr Ile Leu Tyr
945                 950                 955                 960

Ala Lys Pro Glu Asp Gln Lys Thr Pro Arg Asp Asp Arg Leu Lys Gln
                965                 970                 975

Trp Tyr Ile Asp Met Leu Val Glu Ser Gln Arg Gly Ile Val Gly
                980                 985                 990

Lys Leu Thr Asn Met Tyr Asp Leu Tyr Phe Ser Asn Pro Lys Asn Asp
                995                 1000                1005

Ala Thr Val Val Pro Tyr Met Asp Gly Asp Tyr Phe Pro Ala Glu
    1010                1015                1020

Ala Glu Asn Ile Ile Lys Asp Ile Glu Glu Gly Lys Thr Gly Lys
    1025                1030                1035

Lys Ser Ser Ser Gln Gly Lys Lys Lys Glu Lys Ala Lys Gln Lys
    1040                1045                1050

Lys Lys Ser Gly Ser Ser Arg Gly Gly Thr Arg Ser Thr Gly Leu
    1055                1060                1065

Asp Glu Asp Ala Leu Lys Ala Ser Gly Ile Leu Pro Pro Gly Ala
    1070                1075                1080

Asp Gln Lys Ser Leu Glu Glu Gly Gly Arg Asp Phe Val Met Ala
    1085                1090                1095

Lys Leu Gly Glu Thr Ile Gln Pro Met Lys Glu Ser Phe Ile Val
    1100                1105                1110

Ala Tyr Leu Ala Trp Ser Gly Ala Lys Asp Glu Asp Met Gln Val
    1115                1120                1125

Pro Lys Glu Ile Glu Glu Tyr Arg Asn Glu His Gly Ile Thr Trp
    1130                1135                1140

Lys Ile Asn Glu Glu Ala Ser Ser Glu Lys Gly Asp Lys Glu Asn
    1145                1150                1155

Pro Lys Pro Thr Glu Ser Ile Glu Met Glu Thr Thr Pro Thr Glu
    1160                1165                1170

Val Ser Thr Ser Val Asn Ala Thr Ala Gly Val Ala Glu Asn Lys
    1175                1180                1185
```

Asp Pro Glu Lys Gln Thr Gly Asn Asp Gly Asp Glu Lys Asn Ala
1190                1195                1200

Thr Met Ser Met Asp Thr Gly Ala Ser Ser Leu Glu Pro Lys Ser
1205                1210                1215

Asp Asp Ala Cys Asp Asp Ser Ser Lys Ala Lys Thr Ser Ala Asp
1220                1225                1230

Asn Met Glu Ser Asp Pro Glu Ile Lys Val Glu Ser Gln Thr Arg
1235                1240                1245

Ser Gln Leu Asp Thr Gln Val Glu Gln Ser Ser Asp Ser Ala Asn
1250                1255                1260

Ala Ser Gln Pro Asn Ala Val Asn Met Ser Ile Arg Glu Gly Lys
1265                1270                1275

Phe Ala Ala Met Ala Ala Arg Lys Arg Asp Ile Asp Gly Val Pro
1280                1285                1290

Lys Glu Ser Ser Glu Gly Glu Glu Ser Thr Lys Ala Lys Asn Glu
1295                1300                1305

Pro Ser Lys Thr Val Thr Val Lys Asp Ser Lys Gly Arg Thr Val
1310                1315                1320

Lys Val Leu Asp Asp Asp Glu Glu Leu Asp Cys Glu Phe Leu
1325                1330                1335

Asn Asn Arg Gln Ala Phe Leu Asn Leu Cys Gln Gly Asn His Tyr
1340                1345                1350

Gln Phe Asp Thr Ile Arg Arg Ala Lys His Ser Ser Met Met Val
1355                1360                1365

Leu Trp His Leu His Asn Arg Asp Ala Pro Lys Phe Val Gln Gln
1370                1375                1380

Cys Ala Thr Cys Ser Arg Glu Ile Leu Thr Gly Met Arg Phe His
1385                1390                1395

Cys Pro Thr Cys Ala Asp Phe Asp Gln Cys Gln Asp Cys Val Ser
1400                1405                1410

Asn Ser Lys Ile Pro Arg His Pro His Pro Leu Lys Pro Ile Ala
1415                1420                1425

Val Gly Asn Gly Gln Gln Ser Asp Leu Thr Asp Glu Gln Arg Lys
1430                1435                1440

Glu Arg Gln Arg Ser Ile Gln Leu His Met Thr Leu Leu Gln His
1445                1450                1455

Ala Ala Thr Cys Ser Asn Ala Lys Cys Pro Ser Ala Asn Cys Thr
1460                1465                1470

Lys Met Lys Gly Leu Leu Lys His Gly Ser Gln Cys Gln Ile Lys
1475                1480                1485

Ala Thr Gly Gly Cys Asn Val Cys Lys Arg Ile Trp Ala Leu Leu
1490                1495                1500

Gln Ile His Ala Arg Gln Cys Lys Thr Ser Ser Cys Ala Val Pro
1505                1510                1515

Asn Cys Met Ala Ile Arg Glu Arg Phe Arg Gln Leu Lys Lys Gln
1520                1525                1530

Gln Met Ala Met Asp Asp Arg Arg Gln Glu Met Asn Arg Ala
1535                1540                1545

Cys Arg Gly Lys Arg Gly
1550

<210> SEQ ID NO 39
<211> LENGTH: 4080
<212> TYPE: DNA

<213> ORGANISM: Ectocarpus silicosus
<220> FEATURE:
<221> NAME/KEY: misc_feature
<223> OTHER INFORMATION: encodes polypeptide of SEQ ID NO:40

<400> SEQUENCE: 39

```
atgggggtg ggctcgtcgc aggggcgggg cagagcccgg cgttgatgcg caacgggagc      60
atgtcctcca gcgccggggg ggggatgggt atgggaagcg ttggcatcgg cggcagcatg    120
acggctaccg ctagcggtag cggcggcggt gctgccgctg ccggcggtgg gagcggtggc    180
ggtggcggtg gcggtggcgg tgggggcgc gatggtggga gctccgggcg tggggacag     240
cagcgaagga ggaacgctga gtttactccg aagatcgta aggccgccct ccggcagcag    300
cagcagcggc tgttgctgct gcgacacgcg agcaagtgcc ctgcggaggg ggagcaatgc    360
aaggttacgc cgcactgcca ggcgatgaag cgtttgtgga agcacatcgc cgagtgcaag    420
aaccagcagt gcccggacct caagtgtgcc gtgtgcgctc ccgtgcgcga ggtcattgcc    480
aagtcacacc agcgccagat ggtgactcag gaggcgagga accgagtagc cgggtcgggg    540
cagcccggtg cggggggggt ctccggacag cagcttgttc ccggcagtag tggtcacatg    600
gtggggccca atgggtggc gggtgggtcg ggcggaggca acttctcgaa cccacgcgat    660
ttgacgctgg cgcagaggca gcagcagcag cagcagctgg agacgcagcg gggtttgatc    720
acctcccagc aggcggccca ggcgcgccag cagcagcaaa atcaactcat gtccggacag    780
caggcgcccg ggttgcatca gtcgggatcg attgaccagt ttaataatgc gcacggagga    840
ggcgacaccg gtaggggtgg ggcacgcagc agctctaagt cgtccgcgtc taacgggaag    900
cgatcgtcga gtctgatcgg cgcgccgggc accatcggca ccgcgtcggc aagcggcggc    960
ggtggtggcg cggggagcag cagcaacggc atgatggtgg acccgaatgc cgtcgttccg   1020
gcgaataact cgagggcggc gcggtcggtc gcgcatcagc agggcgcgta ccccgcgggg   1080
tctgcggggc agccggttcg gactgttcag caggctcgag ccacgcccgg caagatgctc   1140
tcccccgagg actgcacttc tctcatcgaa gcgtttacgg aggatcagat cctgaaccac   1200
gtcaagtccc tcgacacggg catgcatgtt agccaggagc gtatccaggc ggcagcgggg   1260
gctgtcctga cgaagctgag ggactctcag ttcggttggg ttttcaacga cccggtggac   1320
ccggtccacc tcaacctgcc ggactacttc gagatcatca cgcacccgat ggacctcggg   1380
actgtggcgc gcaaactggc gaaggagggc gcgggcgggt acctggagca cgaggagttc   1440
gccgcagacg tgcagctggt gttcgacaac gccatgaagt acaacgggcc ggagagcgag   1500
gtgtaccctg tggcgagcg catgaagaag gaattcaaca aggattgggc gctggcgttg   1560
aagcgtatgg aggcggaaga gaacggccgc aaggagaggg gcgagacctg caacctgtgc   1620
ggctactccg ccaagacgtt cgagcccatg acgtactact gcaacgggc tcagtgcaac   1680
gggaagcgca tcgggagggg gcggtacttc taccacgcca cgggctccaa ccagtggcac   1740
tggtgttcca gttgctacaa cgaccttaag gacggggaga tcatcgcgct agccgagacg   1800
gcggtgcgaa aggcggacct gaagaggaag aagaacgacg agcaggcgga ggttggggat   1860
gtggacaacg caagcaagct ctcttggagt ttcacggggg tttgcacctg cgagcgttca   1920
cggcggggta cgagggccgg caacatcgct ccgacggctc acaagttggg cggcaaggac   1980
ctcccgcacg gcccctgag cgcgtacgtg gaggcgcagg tgaagaagcg gctcgatgcg   2040
gcctacgagg cagaggcgaa ggagagaggg gtccccgtgg accaggtgac gaaggcgaat   2100
accctgtaca tccgcgaggt gtcggtgatg gacacggtcc acctcgtcaa gccgggtttc   2160
```

-continued

| | |
|---|---|
| caccggcgtt acggccctgc gggggagtac ccggcagact tcccggtccg aagcaagtgc | 2220 |
| atcgtgctgt tccaggagct ggacggcgtg gacgtgctcc tgttcgggat gtacgtgtac | 2280 |
| gagtacggcc acacgtgccc agcgccgaac cagcgaaggg tgtacatcag ctacctggac | 2340 |
| tcggttcact acttccgccc gaggaactat cgaaccatgg tgtatcacga tcctgatc | 2400 |
| gcctacctgg aggaggtgaa gacaagaggc ttccacacgg cgcacatctg ggcgtgcccc | 2460 |
| cctgccaagg gggacgacta catcctctac tgccaccccc cggagcagca gactcccaag | 2520 |
| gatgaccgcc tgcagcaatg gtacgtcacg atgcttgagg aggcgaaaaa gagggggcatc | 2580 |
| gtggagggat tgaccaacct cttcgacgag tactggtcaa accagaaaac cgcggacgca | 2640 |
| cgccagctgc catacctcga gggggactat tggatagggg aggcggagaa catcatcaag | 2700 |
| gacctcccgg agggcacccc cctgatttgc aagccgaagg tggaggcaaa ggccgatggc | 2760 |
| tccgccgcag cagcgccgcc ggactcggcc ggcggcaccg cggccgcaga cggggcgggg | 2820 |
| gcggcagcag ggagtggcgc agctccagca acggcagggg ctgccggtga cggcgaggct | 2880 |
| ttggtgaagg tcgaggacag cgctgctaag gcggagggtg gtggtggtgg ggatggcgga | 2940 |
| gggcgagggg gggagggtaa cggggcagag gcgaagaagg tggaggggggg gaagggaag | 3000 |
| gaggaggagg agaaggagga gaagtcgccc gggaagaagg gcaagcgaaa ggcgggagac | 3060 |
| ggtgtgaaga agaaggcgaa gaaggcgaga acatccaagt ccggtggcgg aagcaagaag | 3120 |
| cgaggggtta agccggagga agctcccatc gtcggtgacc ccctgatgca caagctggcg | 3180 |
| gcgatagtgt cgccgatgaa gtcctcgttc atcgtggccc acctcagacc gagagagttc | 3240 |
| gttacccaga tgcaggagcg gcgtgcaaag gagaaggcga tcgaagcagc caagaagacg | 3300 |
| gtgtcgacgg cggtgagcga gaagaggaaa ccggaccccg agatggcgaa gctggcggag | 3360 |
| caggccatcg ccaaagacga gacggaggag gggcagtcta gccaggagtg cgaggtgctg | 3420 |
| gacacgagac agaccttcct caacctgtgc caggggaacc actaccagtt cgacatgctc | 3480 |
| agacgaggga agcactcttc gatgatggtg ctgtaccacc tgtgcaaccc ggacgtgccc | 3540 |
| aagttcctgt cgacgtgctc gaactgctac aaggagatcc actcagggga ccggtatcac | 3600 |
| tgtgaggtct gcacggactt cgacctctgc aaggagtgct acaaggcggt gccgcacccc | 3660 |
| caccccctca gcccatccc ggtgcgcccg gcggcgcagc agcagaagca cctcagcccc | 3720 |
| gcgcagcgag aggagcggca gaggcacatc aagctgcaca tgcagctgct ccagcacgct | 3780 |
| tcgacgtgcg aggatcgaaa ctgccagtcc aagaactgct cacggatgaa gaacctcttg | 3840 |
| acgcacgggg cgagctgcac catccgggcc cagggcggct cgggcgtgtg caagcgcatt | 3900 |
| tgggctcttc tgcagattca cgcgaggcag tgcaagaagg atcgatgctc cgtgccgaag | 3960 |
| tgtcggcagc tgcggcagca catgcgcttc ctgcgagagc agcagcaggc catgacgac | 4020 |
| cggcgaaggc aggcgatgaa cgagtggtct cggaacagac aggagggaag cggcagctag | 4080 |

<210> SEQ ID NO 40
<211> LENGTH: 1359
<212> TYPE: PRT
<213> ORGANISM: Ectocarpus silicosus
<220> FEATURE:
<221> NAME/KEY: misc_feature
<223> OTHER INFORMATION: translation product 656007

<400> SEQUENCE: 40

Met Gly Gly Gly Leu Val Ala Gly Ala Gly Gln Ser Pro Ala Leu Met
1               5                   10                  15

Arg Asn Gly Ser Met Ser Ser Ser Ala Gly Gly Gly Met Gly Met Gly

-continued

```
                20                  25                  30
Ser Val Gly Ile Gly Gly Ser Met Thr Ala Thr Ala Ser Gly Ser Gly
            35                  40                  45
Gly Gly Ala Ala Ala Gly Gly Ser Gly Gly Gly Gly Gly
50                  55                  60
Gly Gly Gly Gly Gly Arg Asp Gly Gly Ser Ser Gly Arg Gly Gly Gln
65                  70                  75                  80
Gln Arg Arg Arg Asn Ala Glu Phe Thr Pro Glu Asp Arg Lys Ala Ala
                85                  90                  95
Leu Arg Gln Gln Gln Gln Arg Leu Leu Leu Leu Arg His Ala Ser Lys
            100                 105                 110
Cys Pro Ala Glu Gly Glu Gln Cys Lys Val Thr Pro His Cys Gln Ala
            115                 120                 125
Met Lys Arg Leu Trp Lys His Ile Ala Glu Cys Lys Asn Gln Gln Cys
            130                 135                 140
Pro Asp Leu Lys Cys Ala Val Cys Ala Pro Val Arg Glu Val Ile Ala
145                 150                 155                 160
Lys Ser His Gln Arg Gln Met Val Thr Gln Glu Ala Arg Asn Arg Val
                165                 170                 175
Ala Gly Ser Gly Gln Pro Gly Ala Gly Val Ser Gly Gln Gln Leu
            180                 185                 190
Val Pro Gly Ser Ser Gly His Met Val Gly Pro Asn Gly Val Ala Gly
            195                 200                 205
Gly Ser Gly Gly Gly Asn Phe Ser Asn Pro Arg Asp Leu Thr Leu Ala
            210                 215                 220
Gln Arg Gln Gln Gln Gln Gln Leu Glu Thr Gln Arg Gly Leu Ile
225                 230                 235                 240
Thr Ser Gln Gln Ala Ala Gln Ala Arg Gln Gln Gln Asn Gln Leu
                245                 250                 255
Met Ser Gly Gln Gln Ala Pro Gly Leu His Gln Ser Gly Ser Ile Asp
            260                 265                 270
Gln Phe Asn Asn Ala His Gly Gly Asp Thr Gly Arg Gly Gly Ala
            275                 280                 285
Arg Ser Ser Ser Lys Ser Ser Ala Ser Asn Gly Lys Arg Ser Ser Ser
            290                 295                 300
Leu Ile Gly Ala Pro Gly Thr Ile Gly Thr Ala Ser Ala Ser Gly Gly
305                 310                 315                 320
Gly Gly Gly Ala Gly Ser Ser Ser Asn Gly Met Met Val Asp Pro Asn
                325                 330                 335
Ala Val Val Pro Ala Asn Asn Ser Arg Ala Ala Arg Ser Val Ala His
            340                 345                 350
Gln Gln Gly Ala Tyr Pro Ala Gly Ser Ala Gly Gln Pro Val Arg Thr
            355                 360                 365
Val Gln Gln Ala Arg Ala Thr Pro Gly Lys Met Leu Ser Pro Glu Asp
            370                 375                 380
Cys Thr Ser Leu Ile Glu Ala Phe Thr Glu Asp Gln Ile Leu Asn His
385                 390                 395                 400
Val Lys Ser Leu Asp Thr Gly Met His Val Ser Gln Glu Arg Ile Gln
                405                 410                 415
Ala Ala Ala Gly Ala Val Leu Thr Lys Leu Arg Asp Ser Gln Phe Gly
            420                 425                 430
Trp Val Phe Asn Asp Pro Val Asp Pro Val His Leu Asn Leu Pro Asp
            435                 440                 445
```

```
Tyr Phe Glu Ile Ile Thr His Pro Met Asp Leu Gly Thr Val Ala Arg
    450                 455                 460

Lys Leu Ala Lys Glu Gly Ala Gly Gly Tyr Leu Glu His Glu Glu Phe
465                 470                 475                 480

Ala Ala Asp Val Gln Leu Val Phe Asp Asn Ala Met Lys Tyr Asn Gly
                485                 490                 495

Pro Glu Ser Glu Val Tyr Pro Val Ala Glu Arg Met Lys Lys Glu Phe
            500                 505                 510

Asn Lys Asp Trp Ala Leu Ala Leu Lys Arg Met Glu Ala Glu Glu Asn
        515                 520                 525

Gly Arg Lys Glu Arg Gly Glu Thr Cys Asn Leu Cys Gly Tyr Ser Ala
530                 535                 540

Lys Thr Phe Glu Pro Met Thr Tyr Tyr Cys Asn Gly Ala Gln Cys Asn
545                 550                 555                 560

Gly Lys Arg Ile Gly Arg Gly Arg Tyr Phe Tyr His Ala Thr Gly Ser
                565                 570                 575

Asn Gln Trp His Trp Cys Ser Ser Cys Tyr Asn Asp Leu Lys Asp Gly
                580                 585                 590

Glu Ile Ile Ala Leu Ala Glu Thr Ala Val Arg Lys Ala Asp Leu Lys
            595                 600                 605

Arg Lys Lys Asn Asp Glu Gln Ala Glu Val Gly Asp Val Asp Asn Ala
610                 615                 620

Ser Lys Leu Ser Trp Ser Phe Thr Gly Val Cys Thr Cys Glu Arg Ser
625                 630                 635                 640

Arg Arg Gly Thr Arg Ala Gly Asn Ile Ala Pro Thr Ala His Lys Leu
                645                 650                 655

Gly Gly Lys Asp Leu Pro His Gly Pro Leu Ser Ala Tyr Val Glu Ala
                660                 665                 670

Gln Val Lys Lys Arg Leu Asp Ala Ala Tyr Glu Ala Glu Ala Lys Glu
            675                 680                 685

Arg Gly Val Pro Val Asp Gln Val Thr Lys Ala Asn Thr Leu Tyr Ile
690                 695                 700

Arg Glu Val Ser Val Met Asp Thr Val His Leu Val Lys Pro Gly Phe
705                 710                 715                 720

His Arg Arg Tyr Gly Pro Ala Gly Glu Tyr Pro Ala Asp Phe Pro Val
                725                 730                 735

Arg Ser Lys Cys Ile Val Leu Phe Gln Glu Leu Asp Gly Val Asp Val
                740                 745                 750

Leu Leu Phe Gly Met Tyr Val Tyr Glu Tyr Gly His Thr Cys Pro Ala
            755                 760                 765

Pro Asn Gln Arg Arg Val Tyr Ile Ser Tyr Leu Asp Ser Val His Tyr
770                 775                 780

Phe Arg Pro Arg Asn Tyr Arg Thr Met Val Tyr His Glu Ile Leu Ile
785                 790                 795                 800

Ala Tyr Leu Glu Glu Val Lys Thr Arg Gly Phe His Thr Ala His Ile
                805                 810                 815

Trp Ala Cys Pro Pro Ala Lys Gly Asp Asp Tyr Ile Leu Tyr Cys His
                820                 825                 830

Pro Pro Glu Gln Gln Thr Pro Lys Asp Asp Arg Leu Gln Gln Trp Tyr
            835                 840                 845

Val Thr Met Leu Glu Glu Ala Lys Lys Arg Gly Ile Val Glu Gly Leu
850                 855                 860
```

```
Thr Asn Leu Phe Asp Glu Tyr Trp Ser Asn Pro Glu Thr Ala Asp Ala
865                 870                 875                 880

Arg Gln Leu Pro Tyr Leu Glu Gly Asp Tyr Trp Ile Gly Glu Ala Glu
                885                 890                 895

Asn Ile Ile Lys Asp Leu Pro Glu Gly Thr Pro Leu Ile Cys Lys Pro
            900                 905                 910

Lys Val Glu Ala Lys Ala Asp Gly Ser Ala Ala Ala Pro Pro Asp
        915                 920                 925

Ser Ala Gly Gly Thr Ala Ala Asp Gly Ala Gly Ala Ala Ala Gly
    930                 935                 940

Ser Gly Ala Ala Pro Ala Thr Ala Gly Ala Ala Gly Asp Gly Glu Ala
945                 950                 955                 960

Leu Val Lys Val Glu Asp Ser Ala Ala Lys Ala Glu Gly Gly Gly
            965                 970                 975

Gly Asp Gly Gly Gly Arg Gly Gly Glu Gly Asn Gly Ala Glu Ala Lys
                980                 985                 990

Lys Val Glu Gly Gly Glu Gly Lys Glu Glu Glu Glu Lys Glu Glu Lys
            995                 1000                1005

Ser Pro Gly Lys Lys Gly Lys Arg Lys Ala Gly Asp Gly Val Lys
    1010                1015                1020

Lys Lys Ala Lys Lys Ala Arg Thr Ser Lys Ser Gly Gly Gly Ser
    1025                1030                1035

Lys Lys Arg Gly Val Lys Pro Glu Ala Pro Ile Val Gly Asp
    1040                1045                1050

Pro Leu Met His Lys Leu Ala Ala Ile Val Ser Pro Met Lys Ser
    1055                1060                1065

Ser Phe Ile Val Ala His Leu Arg Pro Arg Glu Phe Val Thr Gln
    1070                1075                1080

Met Gln Glu Arg Arg Ala Lys Glu Lys Ala Ile Glu Ala Ala Lys
    1085                1090                1095

Lys Thr Val Ser Thr Ala Val Ser Glu Lys Arg Lys Pro Asp Pro
    1100                1105                1110

Glu Met Ala Lys Leu Ala Glu Gln Ala Ile Ala Lys Asp Glu Thr
    1115                1120                1125

Glu Glu Gly Gln Ser Ser Gln Glu Cys Glu Val Leu Asp Thr Arg
    1130                1135                1140

Gln Thr Phe Leu Asn Leu Cys Gln Gly Asn His Tyr Gln Phe Asp
    1145                1150                1155

Met Leu Arg Arg Gly Lys His Ser Ser Met Met Val Leu Tyr His
    1160                1165                1170

Leu Cys Asn Pro Asp Val Pro Lys Phe Leu Ser Thr Cys Ser Asn
    1175                1180                1185

Cys Tyr Lys Glu Ile His Ser Gly Asp Arg Tyr His Cys Glu Val
    1190                1195                1200

Cys Thr Asp Phe Asp Leu Cys Lys Glu Cys Tyr Lys Ala Val Pro
    1205                1210                1215

His Pro His Pro Leu Lys Pro Ile Pro Val Arg Pro Ala Ala Gln
    1220                1225                1230

Gln Gln Lys His Leu Ser Pro Ala Gln Arg Glu Glu Arg Gln Arg
    1235                1240                1245

His Ile Lys Leu His Met Gln Leu Leu Gln His Ala Ser Thr Cys
    1250                1255                1260

Glu Asp Arg Asn Cys Gln Ser Lys Asn Cys Ser Arg Met Lys Asn
```

| | | | | | | | | | | |
|---|---|---|---|---|---|---|---|---|---|---|
| | | 1265 | | | 1270 | | | 1275 | | |
| Leu | Leu | Thr | His | Gly | Ala | Ser | Cys | Thr | Ile | Arg | Ala | Gln | Gly | Gly |
| | | 1280 | | | | 1285 | | | | 1290 | | | | |
| Cys | Gly | Val | Cys | Lys | Arg | Ile | Trp | Ala | Leu | Leu | Gln | Ile | His | Ala |
| | | 1295 | | | | 1300 | | | | 1305 | | | | |
| Arg | Gln | Cys | Lys | Lys | Asp | Arg | Cys | Ser | Val | Pro | Lys | Cys | Arg | Gln |
| | | 1310 | | | | 1315 | | | | 1320 | | | | |
| Leu | Arg | Gln | His | Met | Arg | Phe | Leu | Arg | Glu | Gln | Gln | Gln | Ala | Met |
| | | 1325 | | | | 1330 | | | | 1335 | | | | |
| Asp | Asp | Arg | Arg | Arg | Gln | Ala | Met | Asn | Glu | Trp | Ser | Arg | Asn | Arg |
| | | 1340 | | | | 1345 | | | | 1350 | | | | |
| Gln | Glu | Gly | Ser | Gly | Ser | | | | | | | | | |
| | | 1355 | | | | | | | | | | | | |

```
<210> SEQ ID NO 41
<211> LENGTH: 2622
<212> TYPE: DNA
<213> ORGANISM: Aureococcus anophagefferens
<220> FEATURE:
<221> NAME/KEY: misc_feature
<223> OTHER INFORMATION: Encodes polypeptide of SEQ ID NO:42

<400> SEQUENCE: 41
atgcaacctg tcgatccggt cgaactcaac ttgccggact acttcgatat aatcaagaat      60
ccaatggatc tagggtcaat taaaaaacgc atggaaaata actgctacaa gtccatatct     120
gaatttgggt ctgacgtacg gctcacgttc gacaatgcaa tctcgtataa cggagatggc     180
tcggatgttt gcaaagttgc acgtgaaatg aaagctgttt ttgagaagtt gtatcatgcc     240
atgatcacaa gtattgaagc cgaggaagag catcgcaagt caaatggcga tgtgtgcgtg     300
ctctgtggtt gcgaaaagtt gcttttttgaa cccacggtct actactgcaa tggctcctgc     360
aatggacaac gaatccggag gaattcgtat tattacactg gagggcgaaa tcagtatcac     420
tggtgtcaac aatgttttaa tgaattacgc gaaaaggaac cactcgagtt tgcggattgc     480
accctgtgga gaaagaatt gcagaagaag aaaaatgatg agatgcacga agagccttgg     540
gttgaatgct cgcaatgcaa ccgatgggtg caccaaatct gcgccttatt caatggccgc     600
atgaacaaag gaaccactat ctatcactgc ccattttgtt ttatggcaag acgcggcgcc     660
aaagagccac atgcgaagcc acttggcgcc aaagagatcc gccacaccaa aatgtcacgt     720
ttcctcgaag atcgagtgat caagtcgcta gatgatgcat atgcacttag gtcttcaaat     780
ggggtccccc atttgacagc atctgctgtg tatgtgcgtc agttatctaa cattgagaaa     840
gcgcatcagg tgaaacctag aatacttcag cgttatgcag atcagaaata tccacgcgag     900
tttccagttc gatcaaaatg catcctcctc tttcaagaaa tggatggtgt tgatgtcatt     960
ctatttggaa tgtacttgta cgaatatggc cataactgcc cccaaccaaa tcaacgacgc    1020
gtctatgtca gctatcttga ttcagtctac tactttcgac cgcggcaata cagaacgctt    1080
gtctatcatg agatgctcat tgcttatcta gcccacacga aggagcgcgg tttccacacc    1140
gcgcatattt gggcatgccc cccctgcaag ggcgatgatt acattttctt ttgtcaccca    1200
gaggaccaga aaactcccaa ggatgatcgt cttcgctcat ggtacataac cctactagaa    1260
aaagcgaagg aagagggtat tgtcactcac atcacgaatc tctgggacga acatttccag    1320
gcagactacg atgtgaatca tattcccttat tttgagggtg attattggcc cggtgaggct    1380
gaaaacgtgg tcaaggctct tgaagacgag gccaatgagc gaaacgaatc taaatctcgt    1440
```

-continued

```
aaagcaggga gtgctaccaa atcaaaagca aaaatgaaag ggcgaacgca gcgcggcctt    1500
cgatcagatg gctccataga ggaggaaaat gggcaggatg cacttgtcgc acgaatgggc    1560
aaaattctag aaccaatgaa agacgccttc atcgtagcat acttgcagcc acgtgacttt    1620
gctcatgtca tggaaggacg atatgaaaga gagcagaaac ggttgttggg cgatgatgtt    1680
ccaaaatcca acgcgggaag tccagccggc caagtcctta atagcgaggt gtctgcggag    1740
tgctcatcac caccatcaga tacagtggga gctccagtga tatcaacgaa cattgccgag    1800
cccacggttc gattggatgt cactcatccc gtgtcaaata atgaagataa tcaggccccg    1860
actgaaccaa ccgctgacgt caacgcaaaa cctagccacg gtaaagcctt cgacgaaaca    1920
gaagataccg acgaaatcat tgaatctgag ttttatgata cgcgacagca atttctgaat    1980
ctgtgtcaag gaatcatta tcaattcgat gatctacggc gggccaaaca tacctcaatg    2040
atgtcgctat atcacatgca caatccagat gtaccaaaat ttcttgtaac gtgctcaaat    2100
tgcaatgttg acataaattc tggctactgc tatacctcag aaaaagatac tgagtttcat    2160
ctttgtcagg actgctatca aaagatgcac aaggttttcg ctgacaaatt tccttttcga    2220
aggtctgttg ttggaagtga ttcccaggcc cagctcaccg aagagcaacg tcgtgaccgc    2280
catcgctcca tacaattgca tatgcagcta cttcagcacg cttctggctg ccgaaaccaa    2340
caatgccctt cagcgaactg caacaaaatg aagaatctgt tgaagcacgg agcgacttgc    2400
gtgacacgtg tacagggcgg ctgcgctatt tgccgccgta tttgggcact gttgcagatt    2460
catgcgcgtc aatgtcgccg tgatgcgtgt atggtaccta agtgcaggca gctcaaggaa    2520
cagttgaggg ctcttgccca acaacaagcc caaatggatg aacgtcgccg agcagcaatg    2580
aacgctgctt atcgcaggga gggctccaaa gcggccgtat aa                      2622
```

<210> SEQ ID NO 42
<211> LENGTH: 873
<212> TYPE: PRT
<213> ORGANISM: Aureococcus anophagefferens
<220> FEATURE:
<221> NAME/KEY: misc_feature
<223> OTHER INFORMATION: Translation product 378924

<400> SEQUENCE: 42

```
Met Gln Pro Val Asp Pro Val Glu Leu Asn Leu Pro Asp Tyr Phe Asp
1               5                   10                  15

Ile Ile Lys Asn Pro Met Asp Leu Gly Ser Ile Lys Lys Arg Met Glu
            20                  25                  30

Asn Asn Cys Tyr Lys Ser Ile Ser Glu Phe Gly Ser Asp Val Arg Leu
        35                  40                  45

Thr Phe Asp Asn Ala Ile Ser Tyr Asn Gly Asp Gly Ser Asp Val Cys
    50                  55                  60

Lys Val Ala Arg Glu Met Lys Ala Val Phe Glu Lys Leu Tyr His Ala
65                  70                  75                  80

Met Ile Thr Ser Ile Glu Ala Glu Glu His Arg Lys Ser Asn Gly
                85                  90                  95

Asp Val Cys Val Leu Cys Gly Cys Glu Lys Leu Leu Phe Glu Pro Thr
            100                 105                 110

Val Tyr Tyr Cys Asn Gly Ser Cys Asn Gly Gln Arg Ile Arg Arg Asn
        115                 120                 125

Ser Tyr Tyr Tyr Thr Gly Gly Arg Asn Gln Tyr His Trp Cys Gln Gln
    130                 135                 140

Cys Phe Asn Glu Leu Arg Glu Lys Glu Pro Leu Glu Phe Ala Asp Cys
```

```
                145                 150                 155                 160
Thr Leu Trp Lys Lys Glu Leu Gln Lys Lys Asn Asp Glu Met His
                165                 170                 175
Glu Glu Pro Trp Val Glu Cys Ser Gln Cys Asn Arg Trp Val His Gln
                180                 185                 190
Ile Cys Ala Leu Phe Asn Gly Arg Met Asn Lys Gly Thr Thr Ile Tyr
                195                 200                 205
His Cys Pro Phe Cys Phe Met Ala Arg Arg Gly Ala Lys Glu Pro His
    210                 215                 220
Ala Lys Pro Leu Gly Ala Lys Glu Ile Arg His Thr Lys Met Ser Arg
225                 230                 235                 240
Phe Leu Glu Asp Arg Val Ile Lys Ser Leu Asp Asp Ala Tyr Ala Leu
                245                 250                 255
Arg Ser Ser Asn Gly Val Pro His Leu Thr Ala Ser Ala Val Tyr Val
                260                 265                 270
Arg Gln Leu Ser Asn Ile Glu Lys Ala His Gln Val Lys Pro Arg Ile
                275                 280                 285
Leu Gln Arg Tyr Ala Asp Gln Lys Tyr Pro Arg Glu Phe Pro Val Arg
                290                 295                 300
Ser Lys Cys Ile Leu Leu Phe Gln Glu Met Asp Gly Val Asp Val Ile
305                 310                 315                 320
Leu Phe Gly Met Tyr Leu Tyr Glu Tyr Gly His Asn Cys Pro Gln Pro
                325                 330                 335
Asn Gln Arg Arg Val Tyr Val Ser Tyr Leu Asp Ser Val Tyr Tyr Phe
                340                 345                 350
Arg Pro Arg Gln Tyr Arg Thr Leu Val Tyr His Glu Met Leu Ile Ala
                355                 360                 365
Tyr Leu Ala His Thr Lys Glu Arg Gly Phe His Thr Ala His Ile Trp
    370                 375                 380
Ala Cys Pro Pro Cys Lys Gly Asp Asp Tyr Ile Phe Phe Cys His Pro
385                 390                 395                 400
Glu Asp Gln Lys Thr Pro Lys Asp Asp Arg Leu Arg Ser Trp Tyr Ile
                405                 410                 415
Thr Leu Leu Glu Lys Ala Lys Glu Glu Gly Ile Val Thr His Ile Thr
                420                 425                 430
Asn Leu Trp Asp Glu His Phe Gln Ala Asp Tyr Asp Val Asn His Ile
                435                 440                 445
Pro Tyr Phe Glu Gly Asp Tyr Trp Pro Gly Glu Ala Glu Asn Val Val
    450                 455                 460
Lys Ala Leu Glu Asp Glu Ala Asn Glu Arg Asn Glu Ser Lys Ser Arg
465                 470                 475                 480
Lys Ala Gly Ser Ala Thr Lys Ser Lys Ala Lys Met Lys Gly Arg Thr
                485                 490                 495
Gln Arg Gly Leu Arg Ser Asp Gly Ser Ile Glu Glu Asn Gly Gln
                500                 505                 510
Asp Ala Leu Val Ala Arg Met Gly Lys Ile Leu Glu Pro Met Lys Asp
                515                 520                 525
Ala Phe Ile Val Ala Tyr Leu Gln Pro Arg Asp Phe Ala His Val Met
    530                 535                 540
Glu Gly Arg Tyr Glu Arg Glu Gln Lys Arg Leu Leu Gly Asp Asp Val
545                 550                 555                 560
Pro Lys Ser Asn Ala Gly Ser Pro Ala Gly Gln Val Leu Asn Ser Glu
                565                 570                 575
```

Val Ser Ala Glu Cys Ser Ser Pro Ser Asp Thr Val Gly Ala Pro
            580                 585                 590

Val Ile Ser Thr Asn Ile Ala Glu Pro Thr Val Arg Leu Asp Val Thr
        595                 600                 605

His Pro Val Ser Asn Asn Glu Asp Asn Gln Ala Pro Thr Glu Pro Thr
610                 615                 620

Ala Asp Val Asn Ala Lys Pro Ser His Gly Lys Ala Phe Asp Glu Thr
625                 630                 635                 640

Glu Asp Thr Asp Glu Ile Ile Glu Ser Glu Phe Tyr Asp Thr Arg Gln
                645                 650                 655

Gln Phe Leu Asn Leu Cys Gln Gly Asn His Tyr Gln Phe Asp Asp Leu
            660                 665                 670

Arg Arg Ala Lys His Thr Ser Met Met Ser Leu Tyr His Met His Asn
        675                 680                 685

Pro Asp Val Pro Lys Phe Leu Val Thr Cys Ser Asn Cys Asn Val Asp
690                 695                 700

Ile Asn Ser Gly Tyr Cys Tyr Thr Ser Glu Lys Asp Thr Glu Phe His
705                 710                 715                 720

Leu Cys Gln Asp Cys Tyr Gln Lys Met His Lys Val Phe Ala Asp Lys
                725                 730                 735

Phe Pro Phe Arg Arg Ser Val Val Gly Ser Asp Ser Gln Ala Gln Leu
            740                 745                 750

Thr Glu Glu Gln Arg Arg Asp Arg His Arg Ser Ile Gln Leu His Met
        755                 760                 765

Gln Leu Leu Gln His Ala Ser Gly Cys Arg Asn Gln Gln Cys Pro Ser
770                 775                 780

Ala Asn Cys Asn Lys Met Lys Asn Leu Leu Lys His Gly Ala Thr Cys
785                 790                 795                 800

Val Thr Arg Val Gln Gly Gly Cys Ala Ile Cys Arg Arg Ile Trp Ala
                805                 810                 815

Leu Leu Gln Ile His Ala Arg Gln Cys Arg Arg Asp Ala Cys Met Val
            820                 825                 830

Pro Lys Cys Arg Gln Leu Lys Glu Gln Leu Arg Ala Leu Ala Gln Gln
        835                 840                 845

Gln Ala Gln Met Asp Glu Arg Arg Arg Ala Ala Met Asn Ala Ala Tyr
850                 855                 860

Arg Arg Glu Gly Ser Lys Ala Ala Val
865                 870

<210> SEQ ID NO 43
<211> LENGTH: 5262
<212> TYPE: DNA
<213> ORGANISM: Schizochytrium limacinum
<220> FEATURE:
<221> NAME/KEY: misc_feature
<223> OTHER INFORMATION: Encodes polypeptide of SEQ ID NO:44

<400> SEQUENCE: 43
atgaaacgtt tgtggaagca catttccaag tgtaaagatc ctcgttgtcc tgaacctcat    60
tgtgtatcat ctcgctatgt attgtcacat taccatcgtt gcgagaaaga agaatgccct   120
gtttgtaaac ctgtccgcct catctcagca tcacaacgta gtcaggctct tgctgcccag   180
cgtaagcagc aacaacaatt acagggcctt ggtcagccaa gttccggtgg agctgtacaa   240
ccaggagtgg cagtggcgcc tagttcttct gcatcttcag cagctgcatc acaaactgct   300

```
gtaacatccc cagctgctgc tgctgctgct ccggtagtca caggcgcaac ctccacaccg    360
aagcttgcag ctgcaagtac tgctgtccct cctgttgttt tgcgacgtcc cgatggtagt    420
gttgtcaatg acccggcggt tcttgcaagg tataataacc tctctaggca acaacaacag    480
gccctggcat tgcgtcaaca acaacagagc aaccagttag cattgcaacg tcaacgcgtt    540
ttgcagcagc ggcaacagct gctggcaaaa gaacaacgtg cgcagtttcc aaatgctatc    600
gatccaacta aagctcgcca ctgtaagtct ggcactgggc cttcttttgcc gttcagtatg    660
tctcgtagaa gcgttgaaaa gcacattgaa tctctccgtg ttgaacgatt gcagccaaac    720
cttcgcccac tcttgcgaaa acttattgaa cacaaatcca acaaaggcat ttacaatgcc    780
cctgtggatt ggaaggccat gaatattccg gactatccac gaattatcaa aactccaatg    840
gatcttggca caattcgcaa gcgtcttgat gcttcctatt acacaacccct ggaccaattt    900
aaaaacgaca ttgtgcttac tttcaagaat gcaatgacct ttaaccctcc tgaaaatgag    960
taccatacac gtgctgcaga cttgctcaag gtagcacata aagagtttcc gctgatccta   1020
aacaagattg agcgaaatgg caggcccaaa aaccaagact gtcagctttg tcgtcaatct   1080
gtttgtgaac aatgtccttt atgtgagcgc ggctgcattc cttttccagcc caaactccta   1140
ttttgctcgg gaacctgtgg caaacgtatc cagcccaata gcgtatacta tacgggtgtt   1200
gggtacaact attgctggtg cagtgactgt tatgacaaag ctcgtaccgg tgttctttca   1260
gttaatggcc agtcctataa caagacagt ttgacaaaga aaagaacaa cgaactttac   1320
ggtgagcctt gggtatcatg tgataaatgt gaccgctggg tgcatcagat ttgtgcgctt   1380
ttcaactcac gtaagaacag cctcacatcc tcacaggatt acatttgccc tctctgtctc   1440
atcgaggaat caaaacttgg tgaagcagaa cgagcaaacg agtccaagtc caagtctggt   1500
ggaggcaaga aggcagcagc tgcagcaact gaggaaacta aacccaagcc tgaacaggct   1560
actgtagcga aagatgccaa ggatgaaaag ccaactacag gagacgatgc tacacgtgcg   1620
aagggaaagt acaagcattt tgtccttcct gctggcaagc gggtaccgag tgcaagagag   1680
cttgatcaat ctcgccttgg cgtatttctg gaaaaatggc ttcgtaactg tattactgaa   1740
ttccgcacta gggagatgga gcgcaaacct gacatttctg actatgagct tggacctgat   1800
gcggacaaac tgcatgttcg catcctgtcc aattttgatg aaaagtgcca ggtgaagcct   1860
tttgtgaaac gacttatccc ggagtatcct gatgcttttc cattccgttc acgttgtatt   1920
ttcttgttcc aagaacttaa tggtgttgac gttctcttct ttgcaatgtt tgtccaagaa   1980
tacggatctg agtgccctga accgaaccgt cgcaagattt acatcgctta ccttgattct   2040
gtgtattatt ccaaccccg cagaatgcgt acaaccgtgt atcatgagct tcttctcggg   2100
tatcttgaat acatgcgtcg catgggcatg acatcaacgt acatttgggc atgtcctcct   2160
cctaacaaac gtgatgatta cattatccat tgccatcctg aagatcagcg tgtgcaaaca   2220
cctgaacgtt tacgaaaatg gtatcatgat atgattaagg ttggtgctga tcgaaggatt   2280
tttatgggtt cgtgtgctat gtttgaggag cacttcgaag ttctgctcg tacaaaccag   2340
aagaagagca atctaaatc taaaaagcgc tcgagcaagt ctaagtccaa gtctaagtca   2400
aagagcagca aaaagggaaa gaagagtagt ggtcgaaagg gtacctcaac acgccgcgtg   2460
agcggagcag ctgccgctgc tgctgctgct gctgctgctg ctgctgccga agcaaaagca   2520
gctgccgagg ccgcagaggc agagactgaa gcgaagaacg gggacggcga aacgagaat   2580
aacgaggatg acaataacga tgaggcactt ggacttcttg ctgatgttcc cgatatggac   2640
ggtgatgatg atgaggaaga cgatgatgcg aacaccgaag caaaggcgac acctgaagat   2700
```

```
ggcgttccgc tgagtgaagc agacaaagct aaagccattg ctgaggctgc aggtgttact    2760
tttcttacac cagccaatgg ggttcgtgct ggtgatgatc gcatgcttgc agaagacttg    2820
gaacgccgaa agcttacgaa acttgctgct tccggtaatt tgccttactt tgagggcgat    2880
tactggcctc aagaagccga agaacttgcg aaggagcgtg ctagacaaaa gaagaaggat    2940
gaagatggaa agggtggtcg tagtaagcga aagcgtcgtc gcgctgggga agaagctgaa    3000
gaaaagaccg aagaagctga acctgaggaa aaacctgttg cagaacttgc tgttgagctt    3060
tctgaagagg aggctgtaga ggctcgtgtc caactaatgc agcgacttgc ccaacaactt    3120
gaggtcatga aggatgattt cctggttgtc aaaatggcgc acgagtgctc ccgatgcgga    3180
aagtatctgc ttcggggacg atgggaatgc cgccatcctt catgccttga ggagtttggc    3240
tttaacaaat cttgtccatt cgctctgtgt aatagttgct acattctcga atcgaaacgc    3300
ccaaaggaac aacaacacgg tggaggttgt attgctgatg gtgaagctgg taggccaaaa    3360
tctgtttcag aagaagcgga caaggacgct ggtaaagacc aggaggtgat cgacgtaaac    3420
gttgagttca acgcaagga gcgcgagcgc gaagagaagg atgctagaga aaaggcaaaa    3480
cgcgatgctg agattaaaaa gaagaaggag gccagagaaa aagcaaacgg caaccctgat    3540
cagaagaagg tcaaagtaga ggcttctgca gcagatgcta agaggctac agctggaaac    3600 tcttccgcac catcagcatt aggggatact tctaagagct gggtagcga ggtggcaaac    3660 ttggagatga agaaagagcc tggcgataat acaaaatctg ttagtgcttc cgggtctgta    3720
aaacgcagcg ctccggagag cacttcggta gtcaaaccaa tttcttcatc ttccgtctct    3780
gaaacgaagg tagatccacc agcaaagccg aatggattgt cccgagcaaa agaggtgaat    3840
aacgaagcta agaaggcaga atcgtcgccg gcagctgctg tggaagttga tgagcagagc    3900
cagcaggtag tgaagaagca aaaggtctca gaaacctcgt ccaaggtaat tgaaacctcg    3960
gctaatagtt cttcaaccac tcaggctggg gacaaaacca agtcacaaga cgagaaagga    4020
acaacaaaca aggccgaaga tggtaagaag cactccgatg cggaagacga ggataagaaa    4080
aaggaacttc tcgctgaatg ggagaagcaa agtattgagt gtactcgtgc tcctgttcac    4140
agcccgtctg aagatcatat tcttcactac gtggatgaaa atcttcctgt gcagactcct    4200
gactacgaca agattattaa gaaccatttg cttgaatctc gccacgcttt tctatctctg    4260
tgtacgggga accgttacca gtttgaccag caacgtcgag ccaagcattc aacaatgatg    4320
gttctctatc atcttcacaa cccagatgca ccagctcatc tttacacgtg ctttgagtgt    4380
cacaatgata ttcttacagg aaagcgctac cactgtgatg tctgtaacgg aggtgattac    4440
gatatctgta ttcattgtaa gagacagacg cgccacgatc atactctcac ccctttgtt    4500 gttacccgtg gtgttcaggc agaaacgtca gaatcgcaac ggatgcaacg tgtccaggag    4560
atgcagagag ctcgccaaca ctccctcacg ctattcttgg atgcattggt gcactcttca    4620
cagtgtgacg acctcagtg cacaaaggct ccttgcaaga agatgaagga cttgctcaaa    4680
catcgtatga cttgcgaagt tcgagttcgt ggtggctgcg aaatatgtcg ccgtgtactt    4740
tgccttgtgc aaatgcacgc tcgtaactgt accactgtga actgtcgtgt gccacactgc    4800
gaggacctca aggtccacat caacaaacac aaacagcaaa tgcagctcgc tcgccaaccg    4860
gcgggtgatg ctgctccagg tgcatctgct tcgactgcag ctccggctgc acgttcacag    4920
cagcagccgc agcagcagcc gcagcaactt actcaacagc agttgcaaca tcaacatcaa    4980
ctgcttcaac agcgacaacg ccagctgcag gctcaggctc aagcccttgc ccaagctcag    5040
```

```
gcccgtggtg cgcgtggcaa ccgcgcaccc cgtacagtag gggctgctgc ccaagccatc    5100
actcaagccg acagcaaat ccaagctact gtagtagaag gaagtggagg aacaaaaatc     5160
aagattcgtc caactaattt gaagccttcg aacacaacgg cacctcctgc ttcaggatct    5220
aactcccgtg ccccgcgtgg ccaacggaac gcgcgaagat aa                       5262
```

<210> SEQ ID NO 44
<211> LENGTH: 1753
<212> TYPE: PRT
<213> ORGANISM: Schizochytrium limacinum
<220> FEATURE:
<221> NAME/KEY: misc_feature
<223> OTHER INFORMATION: Translation product 6503

<400> SEQUENCE: 44

```
Met Lys Arg Leu Trp Lys His Ile Ser Lys Cys Lys Asp Pro Arg Cys
1               5                   10                  15

Pro Glu Pro His Cys Val Ser Ser Arg Tyr Val Leu Ser His Tyr His
                20                  25                  30

Arg Cys Glu Lys Glu Glu Cys Pro Val Cys Lys Pro Val Arg Leu Ile
            35                  40                  45

Ser Ala Ser Gln Arg Ser Gln Ala Leu Ala Ala Gln Arg Lys Gln Gln
        50                  55                  60

Gln Gln Leu Gln Gly Leu Gly Gln Pro Ser Ser Gly Gly Ala Val Gln
65                  70                  75                  80

Pro Gly Val Ala Val Ala Pro Ser Ser Ser Ala Ser Ser Ala Ala Ala
                85                  90                  95

Ser Gln Thr Ala Val Thr Ser Pro Ala Ala Ala Ala Ala Pro Val
                100                 105                 110

Val Thr Gly Ala Thr Ser Thr Pro Lys Leu Ala Ala Ala Ser Thr Ala
            115                 120                 125

Val Pro Pro Val Val Leu Arg Arg Pro Asp Gly Ser Val Val Asn Asp
        130                 135                 140

Pro Ala Val Leu Ala Arg Tyr Asn Asn Leu Ser Arg Gln Gln Gln Gln
145                 150                 155                 160

Ala Leu Ala Leu Arg Gln Gln Gln Ser Asn Gln Leu Ala Leu Gln
                165                 170                 175

Arg Gln Arg Val Leu Gln Gln Arg Gln Gln Leu Leu Ala Lys Glu Gln
            180                 185                 190

Arg Ala Gln Phe Pro Asn Ala Ile Asp Pro Thr Lys Ala Arg His Cys
        195                 200                 205

Lys Ser Gly Thr Gly Pro Ser Leu Pro Phe Ser Met Ser Arg Arg Ser
    210                 215                 220

Val Glu Lys His Ile Glu Ser Leu Arg Val Glu Arg Leu Gln Pro Asn
225                 230                 235                 240

Leu Arg Pro Leu Leu Arg Lys Leu Ile Glu His Lys Ser Asn Lys Gly
                245                 250                 255

Ile Tyr Asn Ala Pro Val Asp Trp Lys Ala Met Asn Ile Pro Asp Tyr
            260                 265                 270

Pro Arg Ile Ile Lys Thr Pro Met Asp Leu Gly Thr Ile Arg Lys Arg
        275                 280                 285

Leu Asp Ala Ser Tyr Tyr Thr Thr Leu Asp Gln Phe Lys Asn Asp Ile
    290                 295                 300

Val Leu Thr Phe Lys Asn Ala Met Thr Phe Asn Pro Pro Glu Asn Glu
305                 310                 315                 320
```

```
Tyr His Thr Arg Ala Ala Asp Leu Leu Lys Val Ala His Lys Glu Phe
                325                 330                 335

Pro Leu Ile Leu Asn Lys Ile Glu Arg Asn Gly Arg Pro Lys Asn Gln
            340                 345                 350

Asp Cys Gln Leu Cys Arg Gln Ser Val Cys Glu Gln Cys Pro Leu Cys
        355                 360                 365

Glu Arg Gly Cys Ile Pro Phe Gln Pro Lys Leu Leu Phe Cys Ser Gly
    370                 375                 380

Thr Cys Gly Lys Arg Ile Gln Pro Asn Ser Val Tyr Tyr Thr Gly Val
385                 390                 395                 400

Gly Tyr Asn Tyr Cys Trp Cys Ser Asp Cys Tyr Asp Lys Ala Arg Thr
                405                 410                 415

Gly Val Leu Ser Val Asn Gly Gln Ser Tyr Asn Lys Asp Ser Leu Thr
            420                 425                 430

Lys Lys Lys Asn Asn Glu Leu Tyr Gly Glu Pro Trp Val Ser Cys Asp
        435                 440                 445

Lys Cys Asp Arg Trp Val His Gln Ile Cys Ala Leu Phe Asn Ser Arg
    450                 455                 460

Lys Asn Ser Leu Thr Ser Ser Gln Asp Tyr Ile Cys Pro Leu Cys Leu
465                 470                 475                 480

Ile Glu Glu Ser Lys Leu Gly Glu Ala Glu Arg Ala Asn Glu Ser Lys
                485                 490                 495

Ser Lys Ser Gly Gly Lys Lys Ala Ala Ala Ala Thr Glu Glu
            500                 505                 510

Thr Lys Pro Lys Pro Glu Gln Ala Thr Val Ala Lys Asp Ala Lys Asp
        515                 520                 525

Glu Lys Pro Thr Thr Gly Asp Asp Ala Thr Arg Ala Lys Gly Lys Tyr
    530                 535                 540

Lys His Phe Val Leu Pro Ala Gly Lys Arg Val Pro Ser Ala Arg Glu
545                 550                 555                 560

Leu Asp Gln Ser Arg Leu Gly Val Phe Leu Lys Trp Leu Arg Asn
                565                 570                 575

Cys Ile Thr Glu Phe Arg Thr Arg Glu Met Glu Arg Lys Pro Asp Ile
            580                 585                 590

Ser Asp Tyr Glu Leu Gly Pro Asp Ala Asp Lys Leu His Val Arg Ile
        595                 600                 605

Leu Ser Asn Phe Asp Glu Lys Cys Gln Val Lys Pro Phe Val Lys Arg
    610                 615                 620

Leu Ile Pro Glu Tyr Pro Asp Ala Phe Pro Phe Arg Ser Arg Cys Ile
625                 630                 635                 640

Phe Leu Phe Gln Glu Leu Asn Gly Val Asp Val Leu Phe Phe Ala Met
                645                 650                 655

Phe Val Gln Glu Tyr Gly Ser Glu Cys Pro Glu Pro Asn Arg Arg Lys
            660                 665                 670

Ile Tyr Ile Ala Tyr Leu Asp Ser Val Tyr Phe Gln Pro Arg Arg
        675                 680                 685

Met Arg Thr Thr Val Tyr His Glu Leu Leu Gly Tyr Leu Glu Tyr
    690                 695                 700

Met Arg Arg Met Gly Met Thr Ser Thr Tyr Ile Trp Ala Cys Pro Pro
705                 710                 715                 720

Pro Asn Lys Arg Asp Asp Tyr Ile Ile His Cys His Pro Glu Asp Gln
                725                 730                 735

Arg Val Gln Thr Pro Glu Arg Leu Arg Lys Trp Tyr His Asp Met Ile
```

-continued

```
             740                 745                 750
Lys Val Gly Ala Asp Arg Arg Ile Phe Met Gly Ser Cys Ala Met Phe
             755                 760                 765

Glu Glu His Phe Glu Gly Ser Ala Arg Thr Asn Gln Lys Lys Ser Lys
             770                 775             780

Ser Lys Ser Lys Lys Arg Ser Ser Lys Ser Lys Ser Lys Ser
785                 790                 795                 800

Lys Ser Ser Lys Lys Gly Lys Lys Ser Ser Gly Arg Lys Gly Thr Ser
                 805                 810                 815

Thr Arg Arg Val Ser Gly Ala Ala Ala Ala Ala Ala Ala Ala Ala
             820                 825                 830

Ala Ala Ala Ala Glu Ala Lys Ala Ala Glu Ala Ala Glu Ala Glu
             835                 840                 845

Thr Glu Ala Lys Asn Gly Asp Gly Glu Asn Glu Asn Asn Glu Asp Asp
             850                 855                 860

Asn Asn Asp Glu Ala Leu Gly Leu Leu Ala Asp Val Pro Asp Met Asp
865                 870                 875                 880

Gly Asp Asp Asp Glu Glu Asp Asp Ala Asn Thr Glu Ala Lys Ala
                 885                 890                 895

Thr Pro Glu Asp Gly Val Pro Leu Ser Glu Ala Asp Lys Ala Lys Ala
             900                 905                 910

Ile Ala Glu Ala Ala Gly Val Thr Phe Leu Thr Pro Ala Asn Gly Val
             915                 920                 925

Arg Ala Gly Asp Asp Arg Met Leu Ala Glu Asp Leu Glu Arg Arg Lys
             930                 935                 940

Leu Thr Lys Leu Ala Ala Ser Gly Asn Leu Pro Tyr Phe Glu Gly Asp
945                 950                 955                 960

Tyr Trp Pro Gln Glu Ala Glu Glu Leu Ala Lys Glu Arg Ala Arg Gln
                 965                 970                 975

Lys Lys Lys Asp Glu Asp Gly Lys Gly Gly Arg Ser Lys Arg Lys Arg
             980                 985                 990

Arg Arg Ala Gly Glu Glu Ala Glu Glu Lys Thr Glu Glu Ala Glu Pro
             995                1000                1005

Glu Glu  Lys Pro Val Ala Glu  Leu Ala Val Glu Leu  Ser Glu Glu
     1010                1015                 1020

Glu Ala  Val Glu Ala Arg Val  Gln Leu Met Gln Arg  Leu Ala Gln
     1025                1030                 1035

Gln Leu  Glu Val Met Lys Asp  Phe Leu Val Val  Lys Met Ala
     1040                1045                 1050

His Glu  Cys Ser Arg Cys Gly  Lys Tyr Leu Leu Arg  Gly Arg Trp
     1055                1060                 1065

Glu Cys  Arg His Pro Ser Cys  Leu Glu Glu Phe Gly  Phe Asn Lys
     1070                1075                 1080

Ser Cys  Pro Phe Ala Leu Cys  Asn Ser Cys Tyr Ile  Leu Glu Ser
     1085                1090                 1095

Lys Arg  Pro Lys Glu Gln Gln  His Gly Gly Gly Cys  Ile Ala Asp
     1100                1105                 1110

Gly Glu  Ala Gly Arg Pro Lys  Ser Val Ser Glu Glu  Ala Asp Lys
     1115                1120                 1125

Asp Ala  Gly Lys Asp Gln Glu  Val Ile Asp Val Asn  Val Glu Phe
     1130                1135                 1140

Lys Arg  Lys Glu Arg Glu Arg  Glu Glu Lys Asp Ala  Arg Glu Lys
     1145                1150                 1155
```

-continued

```
Ala Lys Arg Asp Ala Glu Ile Lys Lys Lys Glu Ala Arg Glu
    1160                1165            1170

Lys Ala Asn Gly Asn Pro Asp Gln Lys Lys Val Lys Val Glu Ala
    1175                1180            1185

Ser Ala Ala Asp Ala Lys Glu Ala Thr Ala Gly Asn Ser Ser Ala
    1190                1195            1200

Pro Ser Ala Leu Gly Asp Thr Ser Lys Ser Leu Gly Ser Glu Val
    1205                1210            1215

Ala Asn Leu Glu Met Lys Lys Glu Pro Gly Asp Asn Thr Lys Ser
    1220                1225            1230

Val Ser Ala Ser Gly Ser Val Lys Arg Ser Ala Pro Glu Ser Thr
    1235                1240            1245

Ser Val Val Lys Pro Ile Ser Ser Ser Val Ser Glu Thr Lys
    1250                1255            1260

Val Asp Pro Pro Ala Lys Pro Asn Gly Leu Ser Arg Ala Lys Glu
    1265                1270            1275

Val Asn Asn Glu Ala Lys Lys Ala Glu Ser Ser Pro Ala Ala Ala
    1280                1285            1290

Val Glu Val Asp Glu Gln Ser Gln Gln Val Val Lys Lys Gln Lys
    1295                1300            1305

Val Ser Glu Thr Ser Ser Lys Val Ile Glu Thr Ser Ala Asn Ser
    1310                1315            1320

Ser Ser Thr Thr Gln Ala Gly Asp Lys Thr Lys Ser Gln Asp Glu
    1325                1330            1335

Lys Gly Thr Thr Asn Lys Ala Glu Asp Gly Lys Lys His Ser Asp
    1340                1345            1350

Ala Glu Asp Glu Asp Lys Lys Lys Glu Leu Leu Ala Glu Trp Glu
    1355                1360            1365

Lys Gln Ser Ile Glu Cys Thr Arg Ala Pro Val His Ser Pro Ser
    1370                1375            1380

Glu Asp His Ile Leu His Tyr Val Asp Glu Asn Leu Pro Val Gln
    1385                1390            1395

Thr Pro Asp Tyr Asp Lys Ile Ile Lys Asn His Leu Leu Glu Ser
    1400                1405            1410

Arg His Ala Phe Leu Ser Leu Cys Thr Gly Asn Arg Tyr Gln Phe
    1415                1420            1425

Asp Gln Gln Arg Arg Ala Lys His Ser Thr Met Met Val Leu Tyr
    1430                1435            1440

His Leu His Asn Pro Asp Ala Pro Ala His Leu Tyr Thr Cys Phe
    1445                1450            1455

Glu Cys His Asn Asp Ile Leu Thr Gly Lys Arg Tyr His Cys Asp
    1460                1465            1470

Val Cys Asn Gly Gly Asp Tyr Asp Ile Cys Ile His Cys Lys Arg
    1475                1480            1485

Gln Thr Arg His Asp His Thr Leu Thr Pro Phe Val Val Thr Arg
    1490                1495            1500

Gly Val Gln Ala Glu Thr Ser Glu Ser Gln Arg Met Gln Arg Val
    1505                1510            1515

Gln Glu Met Gln Arg Ala Arg Gln His Ser Leu Thr Leu Phe Leu
    1520                1525            1530

Asp Ala Leu Val His Ser Ser Gln Cys Asp Asp Pro Gln Cys Thr
    1535                1540            1545
```

| | | | | | | | | | | | | | |
|---|---|---|---|---|---|---|---|---|---|---|---|---|---|
| Lys | Ala | Pro | Cys | Lys | Lys | Met | Lys | Asp | Leu | Leu | Lys | His | Arg Met |
| | 1550 | | | | 1555 | | | | 1560 | | | | |
| Thr | Cys | Glu | Val | Arg | Val | Arg | Gly | Gly | Cys | Glu | Ile | Cys | Arg Arg |
| 1565 | | | | | 1570 | | | | | 1575 | | | |
| Val | Leu | Cys | Leu | Val | Gln | Met | His | Ala | Arg | Asn | Cys | Thr | Thr Val |
| 1580 | | | | | 1585 | | | | | 1590 | | | |
| Asn | Cys | Arg | Val | Pro | His | Cys | Glu | Asp | Leu | Lys | Val | His | Ile Asn |
| 1595 | | | | | 1600 | | | | | 1605 | | | |
| Lys | His | Lys | Gln | Gln | Met | Gln | Leu | Ala | Arg | Gln | Pro | Ala | Gly Asp |
| 1610 | | | | | 1615 | | | | | 1620 | | | |
| Ala | Ala | Pro | Gly | Ala | Ser | Ala | Ser | Thr | Ala | Ala | Pro | Ala | Ala Arg |
| 1625 | | | | | 1630 | | | | | 1635 | | | |
| Ser | Gln | Gln | Gln | Pro | Gln | Gln | Gln | Pro | Gln | Gln | Leu | Thr | Gln Gln |
| 1640 | | | | | 1645 | | | | | 1650 | | | |
| Gln | Leu | Gln | His | Gln | His | Gln | Leu | Leu | Gln | Gln | Arg | Gln | Arg Gln |
| 1655 | | | | | 1660 | | | | | 1665 | | | |
| Leu | Gln | Ala | Gln | Ala | Gln | Ala | Leu | Ala | Gln | Ala | Gln | Ala | Arg Gly |
| 1670 | | | | | 1675 | | | | | 1680 | | | |
| Ala | Arg | Gly | Asn | Arg | Ala | Pro | Arg | Thr | Val | Gly | Ala | Ala | Ala Gln |
| 1685 | | | | | 1690 | | | | | 1695 | | | |
| Ala | Ile | Thr | Gln | Ala | Gly | Gln | Gln | Ile | Gln | Ala | Thr | Val | Val Glu |
| 1700 | | | | | 1705 | | | | | 1710 | | | |
| Gly | Ser | Gly | Gly | Thr | Lys | Ile | Lys | Ile | Arg | Pro | Thr | Asn | Leu Lys |
| 1715 | | | | | 1720 | | | | | 1725 | | | |
| Pro | Ser | Asn | Thr | Thr | Ala | Pro | Pro | Ala | Ser | Gly | Ser | Asn | Ser Arg |
| 1730 | | | | | 1735 | | | | | 1740 | | | |
| Ala | Pro | Arg | Gly | Gln | Arg | Asn | Ala | Arg | Arg | | | | |
| 1745 | | | | | 1750 | | | | | | | | |

<210> SEQ ID NO 45
<211> LENGTH: 3057
<212> TYPE: DNA
<213> ORGANISM: Schizochytrium limacinum
<220> FEATURE:
<221> NAME/KEY: misc_feature
<223> OTHER INFORMATION: Encodes polypeptide of SEQ ID NO:26

<400> SEQUENCE: 45

| | | |
|---|---|---|
| atgaaagctt tatggaaaca tattgcaaag tgtaaggata agcagtgtca gttcccccat | 60 |
| tgtgtctctt cgcgctacgt tttgtcacac taccatcgat gcaagaaccc caagtgtgag | 120 |
| gtttgccgtc ccgtgaagga cgctattcag aaacaacaag agagcagcgg aatgcccaat | 180 |
| cgcgggaatc ctcgcccccc tcatccacct acaggtgtgt acagtccgg cggcagtatg | 240 |
| ccaccacact ctgcacatcc gggacatcga cctggtgtga gtggctcctc aatgtacaaa | 300 |
| tcgtcatcgc caccccctcc tccttctgga tcgagtgcgg atgcctccca aagggccctc | 360 |
| attgagaaac ttgagcgaga gcgcaaggct cggaggatg ccgctcgtag caaactctg | 420 |
| aaggtacaac agcttgaaaa acaaatgcag gatttgcaaa gacaagctgc gcagataaaa | 480 |
| ccggctgagt tgcgcaccaa actgactccg ctactgcgga aacagatgga cttgcagttt | 540 |
| gcctacatct tcctcaaacc agtggatccc atcgcaatgg aaattcctga ctactttgat | 600 |
| gtagtcaaga accctatgga tttgactaca atcaagcgtc gcctcgactc cagctggtac | 660 |
| aagaccatga agtcctttgc cagcgacgtt cttttggtat atgataatgc aatcctttat | 720 |
| aaccctgtaa caccagatgg atacggcgtg aatgagacgg cgcgagaata tgcccaaatt | 780 |

-continued

```
ttcattgacg actacaacaa gttactgctc aaattaaagg atgaggagtc gaagaagcga      840
actaatgccg aagcttgtag gctctgcggt gggcgacagt tccttttga gccccagtc       900
tactattgcc attcatgcaa ccaaaagatc cgtcgtgggg ctcactatta tccatctcct     960
gatgggaaga tgtattggtg tgttacatgt tatggcagtc tccgcactcc aattgagttg    1020
gaggatggta ctactgtgga aaagtcttct ttggagaaaa agaagaactc cgatgagtct    1080
gaagaatcat gggttcagtg taaccagtgc aaccggtggt atcaccagat tgtgccatg     1140
ttcaatgggc gcaatgaaga agcaaaacag agtcaatact tctgcccaat gtgtattctt    1200
cggcaccttg acaaggctcg tctggaccgt atccctgacc acattgcaac agcaaaaggc    1260
aaaggtttcc gcgcaaagga cttgccacgt actaagttta gcgacttcat cgaggagcgt    1320
ttagtgggc gaattctgga cgagcgcaaa cgcgaagcaa agaagcagaa tcttctgctc      1380
ggggacatcc ctgtccctgg cgaattaact attcgtgtag tattgaacaa ggaaactgaa    1440
gtgcttcccc gccagaacct cgaacgctta tacaaagatc ctccttacaa ctacccacgc    1500
tcctttccgc accgcgtaaa gtgtgtcctt ctctttcaga atattgatgg tgttgatgtg    1560
ctcatctttg cactctacac gcagacatat gggtcggatt gccctgagcc taatgcccgt    1620
acattgtaca ttgcgtatct tgactctgtg ttttaccttg aacctcggtt cttgcgtaca    1680
ccgatttacc atgagcttct tctcgctact ttcgaatatg aaaagcgccg tggtatcacg    1740
aagtccttta tttgggcttg tccacccatg gctggtgatg actacatcct gtactgtcac    1800
cctcgtgaac agaggactca aaaggttgat atgcttcgat cttggtactg gattctcctc    1860
gagcaagcac gtaaagaaca cattgtctgc tctgttgaca atctcttcga tgcttacttt    1920
cgccgtgttt gcagtccttg tggtgtccct aattttgaag gtgactactg gccaggtgta    1980
acagaacagt atatcacaga tctcgaaaag gagaagggtc gcactgctgc tgccaagaag    2040
tcaaaagcga agtccaagag taagatgcgt actcgtccta atgatcgtaa gggttctcaa    2100
attaaggagg aagcaattga ggaagaggaa gaggaagaag acgaccctct atggcctcct    2160
ccccagcctg caaagtgggt tgagatccca cagcaggatg ctcttacagc aaagattgga    2220
gaatatctga agagtaccaa agaagacttc tttgttgttt actttcacca tatttgtgca    2280
aattgtgcgg ttcgcattga ccagccagat cagctattct ggttgccacg tcgatacaag    2340
gaaggtatgg gaaagaacaa gactgcggca aatggtatgg cgggtgctac atccaattca    2400
gcagcccaag gtaaacctcc tgctgaaagt actgcttcgg atccgctgat ggataatcag    2460
ttctttgaca ctcgtcagca gttccttttct ctttgccaag gtaaccatta ccagtttgat    2520
cagctgcgtc gggctaagca cagcagtatg atggtgttat accatctgca caaccctgac    2580
gagcctggtt tgttactac ttgtaacact tgctcgcaag aaattaagga tgattcctgg     2640
tataagtgta ctgtctgcga ggactttgac tcatgcaata attgccataa aactagaccg    2700
cacccgcacc cgatgaaaat taccgagcag aagcgctcta cagcagaccg caagaagaac    2760
agcagccgtg ctcagaacgt caaattacat atggagcttc tggcccatgc agcgggttgt    2820
actaatgatc cttgcgagca gtacagcaac tgcgcgaaga tgaaggcatt gttgaaccat    2880
ggcaagacat gtaaggttcg cttgcaaggc aagtgtcttg tatgtcgtcg aatctgggtt    2940
cttttacaga ttcatgctcg gaaatgtcgt atcccgatgg gtcgttgccc tgtgcctcgc    3000
tgtgcagata ttcgcactca gatccgtcgc gcgcaggctg ccatgtcaga tcgccgt       3057
```

```
<210> SEQ ID NO 46
<211> LENGTH: 1019
```

<212> TYPE: PRT
<213> ORGANISM: Schizochytrium limacinum
<220> FEATURE:
<221> NAME/KEY: misc_feature
<223> OTHER INFORMATION: Translation product 12739

<400> SEQUENCE: 46

Met Lys Ala Leu Trp Lys His Ile Ala Lys Cys Lys Asp Lys Gln Cys
1               5                   10                  15

Gln Phe Pro His Cys Val Ser Ser Arg Tyr Val Leu Ser His Tyr His
                20                  25                  30

Arg Cys Lys Asn Pro Lys Cys Glu Val Cys Arg Pro Val Lys Asp Ala
            35                  40                  45

Ile Gln Lys Gln Gln Glu Ser Ser Gly Met Pro Asn Arg Gly Asn Pro
    50                  55                  60

Arg Pro Pro His Pro Pro Thr Gly Val Leu Gln Ser Gly Gly Ser Met
65                  70                  75                  80

Pro Pro His Ser Ala His Pro Gly His Arg Pro Gly Val Ser Gly Ser
                85                  90                  95

Ser Met Tyr Lys Ser Ser Pro Pro Pro Pro Ser Gly Ser Ser
                100                 105                 110

Ala Asp Ala Ser Gln Arg Ala Leu Ile Glu Lys Leu Glu Arg Glu Arg
            115                 120                 125

Lys Ala Ala Glu Asp Ala Ala Arg Arg Gln Thr Leu Lys Val Gln Gln
130                 135                 140

Leu Glu Lys Gln Met Gln Asp Leu Gln Arg Gln Ala Ala Gln Ile Lys
145                 150                 155                 160

Pro Ala Glu Leu Arg Thr Lys Leu Thr Pro Leu Leu Arg Lys Gln Met
                165                 170                 175

Asp Leu Gln Phe Ala Tyr Ile Phe Leu Lys Pro Val Asp Pro Ile Ala
            180                 185                 190

Met Glu Ile Pro Asp Tyr Phe Asp Val Val Lys Asn Pro Met Asp Leu
    195                 200                 205

Thr Thr Ile Lys Arg Arg Leu Asp Ser Ser Trp Tyr Lys Thr Met Lys
210                 215                 220

Ser Phe Ala Ser Asp Val Leu Leu Val Tyr Asp Asn Ala Ile Leu Tyr
225                 230                 235                 240

Asn Pro Val Thr Pro Asp Gly Tyr Gly Val Asn Glu Thr Ala Arg Glu
                245                 250                 255

Tyr Ala Gln Ile Phe Ile Asp Asp Tyr Asn Lys Leu Leu Leu Lys Leu
            260                 265                 270

Lys Asp Glu Glu Ser Lys Lys Arg Thr Asn Ala Glu Ala Cys Arg Leu
    275                 280                 285

Cys Gly Gly Arg Gln Phe Leu Phe Glu Pro Pro Val Tyr Tyr Cys His
290                 295                 300

Ser Cys Asn Gln Lys Ile Arg Arg Gly Ala His Tyr Tyr Pro Ser Pro
305                 310                 315                 320

Asp Gly Lys Met Tyr Trp Cys Val Thr Cys Tyr Gly Ser Leu Arg Thr
                325                 330                 335

Pro Ile Glu Leu Glu Asp Gly Thr Thr Val Lys Ser Ser Leu Glu
            340                 345                 350

Lys Lys Lys Asn Ser Asp Glu Ser Glu Glu Ser Trp Val Gln Cys Asn
    355                 360                 365

Gln Cys Asn Arg Trp Tyr His Gln Ile Cys Ala Met Phe Asn Gly Arg
370                 375                 380

```
Asn Glu Glu Ala Lys Gln Ser Gln Tyr Phe Cys Pro Met Cys Ile Leu
385                 390                 395                 400

Arg His Leu Asp Lys Ala Arg Leu Asp Arg Ile Pro Asp His Ile Ala
            405                 410                 415

Thr Ala Lys Gly Lys Gly Phe Arg Ala Lys Asp Leu Pro Arg Thr Lys
            420                 425                 430

Phe Ser Asp Phe Ile Glu Glu Arg Leu Val Gly Arg Ile Leu Asp Glu
            435                 440                 445

Arg Lys Arg Glu Ala Lys Lys Gln Asn Leu Leu Leu Gly Asp Ile Pro
450                 455                 460

Val Pro Gly Glu Leu Thr Ile Arg Val Val Leu Asn Lys Glu Thr Glu
465                 470                 475                 480

Val Leu Pro Arg Gln Asn Leu Glu Arg Leu Tyr Lys Asp Pro Pro Tyr
            485                 490                 495

Asn Tyr Pro Arg Ser Phe Pro His Arg Val Lys Cys Val Leu Leu Phe
            500                 505                 510

Gln Asn Ile Asp Gly Val Asp Val Leu Ile Phe Ala Leu Tyr Thr Gln
            515                 520                 525

Thr Tyr Gly Ser Asp Cys Pro Glu Pro Asn Ala Arg Thr Leu Tyr Ile
530                 535                 540

Ala Tyr Leu Asp Ser Val Phe Tyr Leu Glu Pro Arg Phe Leu Arg Thr
545                 550                 555                 560

Pro Ile Tyr His Glu Leu Leu Ala Thr Phe Glu Tyr Glu Lys Arg
            565                 570                 575

Arg Gly Ile Thr Lys Ser Phe Ile Trp Ala Cys Pro Pro Met Ala Gly
            580                 585                 590

Asp Asp Tyr Ile Leu Tyr Cys His Pro Arg Glu Gln Arg Thr Gln Lys
            595                 600                 605

Val Asp Met Leu Arg Ser Trp Tyr Trp Ile Leu Leu Glu Gln Ala Arg
610                 615                 620

Lys Glu His Ile Val Cys Ser Val Asp Asn Leu Phe Asp Ala Tyr Phe
625                 630                 635                 640

Arg Arg Val Cys Ser Pro Cys Gly Val Pro Asn Phe Glu Gly Asp Tyr
            645                 650                 655

Trp Pro Gly Val Thr Glu Gln Tyr Ile Thr Asp Leu Glu Lys Glu Lys
            660                 665                 670

Gly Arg Thr Ala Ala Lys Lys Ser Lys Ala Lys Ser Lys Ser Lys
            675                 680                 685

Met Arg Thr Arg Pro Asn Asp Arg Lys Gly Ser Gln Ile Lys Glu Glu
            690                 695                 700

Ala Ile Glu Glu Glu Glu Glu Glu Asp Asp Pro Leu Trp Pro Pro
705                 710                 715                 720

Pro Gln Pro Ala Lys Trp Val Glu Ile Pro Gln Gln Asp Ala Leu Thr
            725                 730                 735

Ala Lys Ile Gly Glu Tyr Leu Lys Ser Thr Lys Glu Asp Phe Phe Val
            740                 745                 750

Val Tyr Phe His His Ile Cys Ala Asn Cys Ala Val Arg Ile Asp Gln
            755                 760                 765

Pro Asp Gln Leu Phe Trp Leu Pro Arg Arg Tyr Lys Glu Gly Met Gly
            770                 775                 780

Lys Asn Lys Thr Ala Ala Asn Gly Met Ala Gly Ala Thr Ser Asn Ser
785                 790                 795                 800
```

```
Ala Ala Gln Gly Lys Pro Pro Ala Glu Ser Thr Ala Ser Asp Pro Leu
                805                 810                 815
Met Asp Asn Gln Phe Phe Asp Thr Arg Gln Gln Phe Leu Ser Leu Cys
            820                 825                 830
Gln Gly Asn His Tyr Gln Phe Asp Gln Leu Arg Arg Ala Lys His Ser
        835                 840                 845
Ser Met Met Val Leu Tyr His Leu His Asn Pro Asp Glu Pro Gly Phe
    850                 855                 860
Val Thr Thr Cys Asn Thr Cys Ser Gln Glu Ile Lys Asp Asp Ser Trp
865                 870                 875                 880
Tyr Lys Cys Thr Val Cys Glu Asp Phe Asp Ser Cys Asn Asn Cys His
                885                 890                 895
Lys Thr Arg Pro His Pro His Pro Met Lys Ile Thr Glu Gln Lys Arg
            900                 905                 910
Ser Thr Ala Asp Arg Lys Lys Asn Ser Ser Arg Ala Gln Asn Val Lys
        915                 920                 925
Leu His Met Glu Leu Leu Ala His Ala Ala Gly Cys Thr Asn Asp Pro
    930                 935                 940
Cys Glu Gln Tyr Ser Asn Cys Ala Lys Met Lys Ala Leu Leu Asn His
945                 950                 955                 960
Gly Lys Thr Cys Lys Val Arg Leu Gln Gly Lys Cys Leu Val Cys Arg
                965                 970                 975
Arg Ile Trp Val Leu Leu Gln Ile His Ala Arg Lys Cys Arg Ile Pro
            980                 985                 990
Met Gly Arg Cys Pro Val Pro Arg Cys Ala Asp Ile Arg Thr Gln Ile
        995                 1000                1005
Arg Arg Ala Gln Ala Ala Met  Ser Asp Arg Arg
    1010                    1015

<210> SEQ ID NO 47
<211> LENGTH: 11263
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: vector pSGE-6206

<400> SEQUENCE: 47
gcggccgccg tatggtcgac ggttgctcgg atggggggggg cggggagcga tggagggagg    60
aagatcaggt aaggtctcga cagactagag aagcacgagt gcaggtataa gaaacagcaa   120
aaaaaagtaa tgggcccagg cctggagagg gtatttgtct tgttttttctt tggccaggaa   180 cttgttctcc tttcttcgtt tctaggaccc cgatccccgc tcgcatttct ctcttcctca   240
gccgaagcgc agcggtaaag catccatttt atcccaccga aagggcgctc ccagccttcg   300
tcgagcggaa ccggggttac agtgcctcaa ccctcccaga cgtagccaga gggaagcaac   360
tccctgatgc caaccgctgt gggctgccca tcggaatctt tgacaattgc cttgatcccc   420
gggtgcaagt caagcagcac ctgccgacat cgcccgcacg agacagaat gccgcggttt    480 tcgttcccga tggccactat gcacgtcaga tttccggcag cagccgcagc ggccgttccg   540
aggaccacga gctccgcgca tggccctccg gtgaaatgat atacattcac gccggtaaag   600
atccgaccgt cggacgagag ggctgcactg gccaccgagt agtcctcgct aataggtatg   660
ctgttgatgg tcgcagttgc acgttcgatc agcgtggatt cctcttggga taaaggcttg   720
```

```
gccatcgagc tcggtacccg gggatccatg attgttgtat tatgtaccta tgtttgtgat    780
gagacaataa atatgagaag agaacgttgc ggccactttt ttctccttcc ttcgcgtgct    840
catgttggtg gtttgggagg cagaagatgc atggagcgcc acacattcgg taggacgaaa    900
cagcctcccc cacaaaggga ccatgggtag ctaggatgac gcacaagcga gttcccgctc    960
tcgaagggaa acccaggcat ttccttcctc ttttcaagcc acttgttcac gtgtcaacac   1020
aattttggac taaatgccc ctcggaactc ggcaggcctc cctctgctcc gttgtcctgg    1080
tcgccgagaa cgcgagaccg tgccgcatgc catcgatctg ctcgtctgta ctactaatcg   1140
tgtgcgtgtt cgtgcttgtt tcgcacgaaa ttgtcctcgt tcggccctca caacggtgga   1200
aatcggtgct agaataaagt gaggtggctt atttcaatgg cggccgtcat catgcgggat   1260
caactgaagt acgcgggtt ctcgagattt catcgtgctc gtccagagca ggtgttttgc    1320
ctgcagctct tcatgtttag gggtcatgat ttcatctgat atgccgtaag aaaaccaata   1380
ttcacttctc aattttccat ggaaaggtga aggcctaggt tgtgtgcgag caacgactg    1440 gggagggatc gcaacattct tgctaacctc cctctatct tggccgctgt gaatcggcat    1500
atttaccggg ctgaattgag aaagtgtttt gagggaatta aaaggtggct gtcttgcaag   1560
cttggcttca gtgcctgctt aattcgaacc gatccagctt gtgatgaggc cttcctaagc   1620
ctggtagtca gaagcgacat ggcgctataa atttcgtctc agttggagag tagaaaagca   1680
tgattcgaac acgttttca actgccaaag atatctccat tgtttccttc aatctgtaca    1740
cctgcacggt gcaccagttg gtacggcata ttatggttta ataagcatac atcatatgaa   1800
tacaattcag cttaaattta tcatacaaag atgtaagtgc agcgtgggtc tgtaacgatc   1860
gggcgtaatt taagataatg cgagggaccg ggggaggttt tggaacggaa tgaggaatgg   1920
gtcatggccc ataataataa tatgggtttg gtcgcctcgc acagcaaccg tacgtgcgaa   1980
aaaggaacag atccatttaa taagttgaac gttattcttt cctatgcaat gcgtgtatcg   2040
gaggcgagag caagtcatag gtggctgcgc acaataattg agtctcagct gagcgccgtc   2100
cgcgggtggt gtgagtggtc atcctcctcc cggcctatcg ctcacatcgc ctctcaatgg   2160
tggtggtggg gcctgatatg acctcaatgc cgacccatat taaacccag taaagcattc    2220 accaacgaac gaggggctct tttgtgtgtg ttttgagtat gattttacac ctctttgtgc   2280
atctctctgg tcttccttgg ttcccgtagt tgggcatca tcactcacgc ttccctcgac    2340
cttcgttctt cctttacaac cccgacacag gtcagagttg gagtaatcaa aaaagggtg    2400 cacgaatgag atacattaga ttttgacaga tatcctttta ctggagaggg ttcaagggat   2460
caaatgaaca gcgggcgttg gcaatctagg gagggatcgg aggttggcag cgagcgaaag   2520
cgtgtccatc ctttggctg tcacacctca cgaaccaact gttagcaggc cagcacagat    2580
gacatacgag aatctttatt atatcgtaga ccttatgtgg atgacctttg gtgctgtgtg   2640
tctggcaatg aacctgaagg cttgataggg aggtggctcc cgtaaaccct ttgtcctttc   2700
cacgctgagt ctcccccgca ctgtccttta tacaaattgt tacagtcatc tgcaggcggt   2760
ttttctttgg caggcaaaga tgcccaagaa aaagcggaag gtcggcgact acaaggatga   2820
cgatgacaag ttgagcctg gagagaagcc ctacaaatgc cctgagtgcg aaagagctt    2880 cagccaatct ggagccttga cccggcatca acgaacgcat acacgagaca agaagtactc   2940
catcgggctg gacatcggga cgaactccgt gggatgggcc gtgatcacag acgaatacaa   3000
ggtgccttcc aagaagttca aggtgctggg gaacacggac agacactcca tcaagaagaa   3060
cctcatcggg gccttgctct tcgactccgg agaaaccgcc gaagcaacgc gattgaaaag   3120
```

-continued

```
aaccgccaga agacgataca cacgacggaa gaaccgcatc tgctacctcc aggagatctt    3180
cagcaacgag atggccaagg tggacgactc gttctttcat cgcctggagg agagcttcct    3240
ggtggaggaa gacaagaaac atgagcgcca cccgatcttc gggaacatcg tggacgaagt    3300
ggcctaccac gagaaatacc ccacgatcta ccacttgcgc aagaaactcg tggactccac    3360
ggacaaagcg gacttgcggt tgatctactt ggccttggcc cacatgatca aatttcgggg    3420
ccacttcctg atcgagggcg acttgaatcc cgacaattcc gacgtggaca agctcttcat    3480
ccagctggtg cagacctaca accagctctt cgaggagaac cccatcaatg cctccggagt    3540
ggacgccaaa gccatcttgt ccgcccgatt gtccaaatcc agacgcttgg agaacttgat    3600
cgcacaactt cctggcgaga agaagaacgg cctcttcggc aacttgatcg cgctgtcgct    3660
gggattgacg cctaacttca gtccaacttc gacttggcc gaggacgcca agttgcaact    3720
gtccaaggac acctacgacg acgacctcga caacctgctg gcccaaattg gcgaccaata    3780
cgcggacttg ttttggcgg ccaagaactt gagcgacgcc atcttgttga gcgacatctt    3840
gcgcgtgaat acggagatca ccaaaagcccc tttgtccgcc tctatgatca agcggtacga    3900
cgagcaccac caagacttga ccctgttgaa agccctcgtg cggcaacaat gcccgagaa     3960
gtacaaggag atcttcttcg accagtccaa gaacgggtac gccggctaca tcgacggagg    4020
agcctcccaa gaagagttct acaagttcat caagcccatc ctggagaaga tggacggcac    4080
cgaggagttg ctcgtgaagc tgaaccgcga agacttgttg cgaaaacagc ggacgttcga    4140
caatggcagc atcccccacc aaatccattt gggagagttg cacgccatct tgcgacggca    4200
agaggacttc tacccgttcc tgaaggacaa ccgcgagaaa atcgagaaga tcctgacgtt    4260
cagaatcccc tactacgtgg gacccttggc ccgaggcaat tcccggtttg catggatgac    4320
gcgcaaaagc gaagagacga tcacccctg gaacttcgaa gaagtggtcg acaaaggagc    4380
atccgcacag agcttcatcg agcgaatgac gaacttcgac aagaacctgc caacgagaa     4440
ggtgttgccc aagcattcgc tgctgtacga gtacttcacg gtgtacaacg agctgaccaa    4500
ggtgaagtac gtgaccgagg gcatgcgcaa acccgcgttc ctgtcgggag agcaaaagaa    4560
ggccattgtg gacctgctgt tcaagaccaa ccggaaggtg accgtgaaac agctgaaaga    4620
ggactacttc aagaagatcg agtgcttcga ctccgtggag atctccggcg tggaggaccg    4680
attcaatgcc tccttgggaa cctaccatga cctcctgaag atcatcaagg acaaggactt    4740
cctggacaac gaggagaacg aggacatcct ggaggacatc gtgctgaccc tgaccctgtt    4800
cgaggaccga gagatgatcg aggaacggtt gaaaacgtac gcccacttgt cgacgacaa     4860
ggtgatgaag cagctgaaac gccgccgcta caccggatgg ggacgattga ccgcaaact     4920
gattaatgga attcgcgaca agcaatccgg aaagaccatc ctggacttcc tgaagtccga    4980
cgggttcgcc aaccgcaact tcatgcagct catccacgac gactccttga ccttcaagga    5040
ggacatccag aaggcccaag tgtccggaca aggagactcc ttgcacgagc acatcgccaa    5100
tttggccgga tcccccgcaa tcaaaaaagg catcttgcaa accgtgaaag tggtcgacga    5160
actggtgaag gtgatgggac ggcacaagcc cgagaacatc gtgatcgaaa tggcccgcga    5220
gaaccaaacc acccaaaaag gacagaagaa ctcccgagag cgcatgaagc ggatcgaaga    5280
gggcatcaag gagttgggct cccagatcct gaaggagcat cccgtggaga atacccaatt    5340
gcaaaacgag aagctctacc tctactacct ccagaacggg cggacatgt acgtcgacca     5400
agagctggac atcaaccgcc tctccgacta cgatgtggat catattgtgc cccagagctt    5460
```

```
cctcaaggac gacagcatcg acaacaaggt cctgacgcgc agcgacaaga accggggcaa    5520
gtctgacaat gtgccttccg aagaagtcgt gaagaagatg aagaactact ggcggcagct    5580
gctcaacgcc aagctcatca cccaacggaa gttcgacaac ctgaccaagg ccgagagagg    5640
aggattgtcc gagttggaca aagccggctt cattaaacgc caactcgtgg agacccgcca    5700
gatcacgaag cacgtggccc aaatcttgga ctcccggatg aacacgaaat acgacgagaa    5760
tgacaagctg atccgcgagg tgaaggtgat cacgctgaag tccaagctgg tgagcgactt    5820
ccggaaggac ttccagttct acaaggtgcg ggagatcaac aactaccatc acgcccatga    5880
cgcctacctg aacgccgtgg tcggaaccgc cctgatcaag aaataccca agctggagtc    5940 cgaattcgtg tacggagatt acaaggtcta cgacgtgcgg aagatgatcg cgaagtccga    6000
gcaggagatc ggcaaagcca ccgccaagta cttcttttac tccaacatca tgaacttctt    6060
caagaccgag atcacgctcg ccaacggcga gatccgcaag cgcccctga tcgagaccaa    6120 cggcgagacg ggagagattg tgtgggacaa aggaagagat tttgccacag tgcgcaaggt    6180
gctgtccatg cctcaggtga acatcgtgaa gaagaccgag gtgcaaacag agggttttc    6240 caaagagtcc attttgccta agaggaattc cgacaagctc atcgcccgca agaaggactg    6300
ggaccccaag aagtacgggg gcttcgactc ccccacggtg gcctactccg tgttggtggt    6360
ggccaaagtg gagaagggaa agagcaagaa gctgaaatcc gtgaaggagt gctcggaat    6420 cacgatcatg aacgatcgt cgttcgagaa aaaccccatc gacttcctcg aagccaaagg    6480
gtacaaagag gtgaagaagg acctgatcat caagctgccc aagtactccc tgttcgagct    6540
ggagaacggc cgcaagcgga tgctggcctc cgccggggaa ctgcagaaag gaacgaatt    6600 ggccttgccc tccaaatacg tgaacttcct ctacttggcc tcccattacg aaaagctcaa    6660
aggatcccct gaggacaatg agcagaagca actcttcgtg gaacaacaca agcactacct    6720
ggacgagatc atcgagcaga tcagcgagtt ctccaagcgc gtgatcctcg ccgacgccaa    6780
cctggacaag gtgctctccg cctacaacaa gcaccgcgac aagcctatcc gcgagcaagc    6840
cgagaatatc attcacctgt ttaccctgac gaatttggga gcccctgccg ccttttaaata    6900 cttttgacacc accatcgacc gcaaaagata cacctccacc aaggaagtct tggacgccac    6960
cctcatccac cagtccatca cgggcctcta cgagacgcgc atcgacctct cccaattggg    7020
cggcgactaa agtgatgcgg cctttaggaa acaccacaaa agtaattgac aatctcagga    7080
acgatctgcg tgtttacagc ttcccaaata acaattatac cacgtaccaa aagggttta    7140 atgtatctca caaattcttc taataggtac agcttctcaa attgggtgta tgatgtgaca    7200
cttcgtctca cacacgtcac gataattcag cgtatggctt ccctttcatca cattcacgca    7260 aacttctaca caaccctggg catatttctt gtgttggcaa cactcccgaa atcgattctg    7320
cacacaatgg ttcattcaat gattcaagta cgttttagac ggactaggca gtttaattaa    7380
aaacatctat cctccagatc accagggcca gtgaggccgg cataaaggac ggcaaggaaa    7440
gaaaagaaag aaagaaaagg acacttatag catagtttga agttataagt agtcgcaatc    7500
tgtgtgcagc cgacagatgc ttttttttc cgtttggcag gaggtgtagg gatgtcgaag    7560
accagtccag ctagtatcta tcctacaagt caatcatgct cgacaaaaa tttctcgcac    7620 gaggcctctc gataaacaaa actttaaaag cacacttcat tgtcatgcag agtaataact    7680
cttccgcgtc gatcaattta tcaatctcta tcatttccgc ccctttcctt gcatagcaca    7740
agaaaagcga cccggatgag gataaacatgt cctgcgccag tagtgtggca ttgcctgtct    7800
ctcatttaca cgtactgaaa gcataatgca cgcgcatacc aatattttc gtgtacggag    7860
```

```
atgaagagac gcgacacgta agatcacgag aaggcgagca cggttgccaa tggcagacgc    7920
gctagtctcc attatcgcgt tgttcggtag cttgctgcat gtcttcagtg cactatatc    7980 cactctgcct cgtcttctac acgagggcca catcggtgca agttcgaaaa atcatatctc    8040
aatcttcaga tcctttccag aaacggtgct caggcgggaa agtgaaggtt ttctactcta    8100
gtggctaccc caattctctc cgactgtcgc agacggtcct tcgttgcgca cgcaccgcgc    8160
actacctctg aaattcgaca accgaagttc aattttacat ctaacttctt tcccattctc    8220
tcaccaaaag cctagcttac atgttggaga gcgacgagag cggcctgccc gccatggaga    8280
tcgagtgccg catcaccggc accctgaacg gcgtggagtt cgagctggtg ggcggcggag    8340
agggcacccc cgagcagggc cgcatgacca acaagatgaa gagcaccaaa ggcgccctga    8400
ccttcagccc ctacctgctg agccacgtga tgggctacgg cttctaccac ttcggcacct    8460
accccagcgg ctacgagaac cccttcctgc acgccatcaa caacggcggc tacaccaaca    8520
cccgcatcga gaagtacgag gacggcgcg tgctgcacgt gagcttcagc taccgctacg    8580
aggccggccg cgtgatcggc gacttcaagg tgatgggcac cggcttcccc gaggacagcg    8640
tgatcttcac cgacaagatc atccgcagca acgccaccgt ggagcacctg caccccatgg    8700
gcgataacga tctggatggc agcttcaccc gcaccttcag cctgcgcgac ggcggctact    8760
acagctccgt ggtggacagc cacatgcact tcaagagcgc catccacccc agcatcctgc    8820
agaacggggg ccccatgttc gccttccgcc gcgtggagga ggatcacagc aacaccgagc    8880
tgggcatcgt ggagtaccag cacgccttca gacccccgga tgcagatgcc ggtgaagaat    8940
aagggtggga aggagtcggg gagggtcctg gcagagcggc gtcctcatga tgtgttggag    9000
acctggagag tcgagagctt cctcgtcacc tgattgtcat gtgtgtatag gttaagggggg    9060 cccactcaaa gccataaaga cgaacacaaa cactaatctc aacaaagtct actagcatgc    9120
cgtctgtcca tctttatttc ctggcgcgcc tatgcttgta aaccgttttg tgaaaaaatt    9180
tttaaaataa aaaggggac ctctagggtc cccaattaat tagtaatata atctattaaa    9240
ggtcattcaa aaggtcatcc agacgaaagg gcctcgtgat acgcctattt ttataggtta    9300
atgtcatgat aataatggtt tcttagacgt caggtggcac ttttcgggga aatgtgcgcg    9360
gaacccctat ttgtttattt ttctaaatac attcaaatat gtatccgctc atgagacaat    9420
aaccctgata aatgcttcaa taatattgaa aaaggaagag tatgagtatt caacatttcc    9480
gtgtcgccct tattcccttt tttgcggcat tttgccttcc tgttttgct cacccagaaa    9540 cgctggtgaa agtaaaagat gctgaagatc agttgggtgc acgagtgggt tacatcgaac    9600
tggatctcaa cagcggtaag atccttgaga gttttcgccc cgaagaacgt tttccaatga    9660
tgagcacttt taaagttctg ctatgtggcg cggtattatc ccgtattgac gccgggcaag    9720
agcaactcgg tcgccgcata cactattctc agaatgactt ggttgagtac tcaccagtca    9780
cagaaaagca tcttacggat ggcatgacag taagagaatt atgcagtgct gccataacca    9840
tgagtgataa cactgcggcc aacttacttc tgacaacgat cggaggaccg aaggagctaa    9900 ccgcttttt gcacaacatg gggatcatg taactcgcct tgatcgttgg aaccggagc    9960 tgaatgaagc cataccaaac gacgagcgtg acaccacgat gcctgtagca atggcaacaa    10020
cgttgcgcaa actattaact ggcgaactac ttactctagc ttcccggcaa caattaatag    10080
actggatgga ggcggataaa gttgcaggac cacttctgcg ctcggccctt ccggctggct    10140
ggtttattgc tgataaatct ggagccggtg agcgtgggtc tcgcggtatc attgcagcac    10200
```

```
tggggccaga tggtaagccc tcccgtatcg tagttatcta cacgacgggg agtcaggcaa    10260
ctatggatga acgaaataga cagatcgctg ataggtgc ctcactgatt aagcattggt      10320
aactgtcaga ccaagtttac tcatatatac tttagattga tttaaaactt catttttaat    10380
ttaaaaggat ctaggtgaag atccttttg ataatctcat gaccaaaatc ccttaacgtg     10440
agttttcgtt ccactgagcg tcagaccccg tagaaaagat caaaggatct tcttgagatc    10500 cttttttct gcgcgtaatc tgctgcttgc aaacaaaaaa accaccgcta ccagcggtgg     10560
tttgtttgcc ggatcaagag ctaccaactc tttttccgaa ggtaactggc ttcagcagag    10620
cgcagatacc aaatactgtc cttctagtgt agccgtagtt aggccaccac ttcaagaact    10680
ctgtagcacc gcctacatac ctcgctctgc taatcctgtt accagtggct gctgccagtg    10740
gcgataagtc gtgtcttacc gggttggact caagacgata gttaccggat aaggcgcagc    10800
ggtcgggctg aacggggggt tcgtgcacac agcccagctt ggagcgaacg acctacaccg    10860
aactgagata cctacagcgt gagctatgag aaagcgccac gcttcccgaa gggagaaagg    10920
cggacaggta tccggtaagc ggcagggtcg aacaggaga gcgcacgagg gagcttccag     10980
ggggaaacgc ctggtatctt tatagtcctg tcgggtttcg ccacctctga cttgagcgtc    11040
gatttttgtg atgctcgtca gggggggcgga gcctatggaa aaacgccagc aacgcggcct    11100
ttttacggtt cctggccttt tgctggcctt ttgctcacat gttctttcct gcgttatccc    11160
ctgattctgt ggataaccgt attaccgcct ttgagtgagc tgataccgct cgccgcagcc    11220
gaacgaccga gcgcagcgag tcagtgagcg aggaagcgga aga                      11263

<210> SEQ ID NO 48
<211> LENGTH: 4101
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Cas9 gene from Streptococcus pyogenes codon
      optimized for Nannochloropsis

<400> SEQUENCE: 48
gacaagaagt actccatcgg gctggacatc gggacgaact ccgtgggatg ggccgtgatc      60
acagacgaat acaaggtgcc ttccaagaag ttcaaggtgc tggggaacac ggacagacac     120
tccatcaaga agaacctcat cggggccttg ctcttcgact ccggagaaac cgccgaagca     180
acgcgattga aagaaccgc cagaagacga tacacacgac ggaagaaccg catctgctac      240
ctccaggaga tcttcagcaa cgagatggcc aaggtggacg actcgttctt tcatcgcctg    300
gaggagagct tcctggtgga ggaagacaag aaacatgagc gccacccgat cttcgggaac    360
atcgtggacg aagtggccta ccacgagaaa taccccacga tctaccactt gcgcaagaaa    420
ctcgtggact ccacggacaa agcggacttg cggttgatct acttggcctt ggcccacatg    480
atcaaatttc ggggccactt cctgatcgag ggcgacttga tcccgacaa ttccgacgtg    540 gacaagctct tcatccagct ggtgcagacc tacaaccagc tcttcgagga aaccccatc     600 aatgcctccg gagtggacgc caaagccatc ttgtccgccc gattgtccaa atccagacgc    660
ttggagaact tgatcgcaca acttcctggc gagaagaaga acggcctctt cggcaacttg    720
atcgcgctgt cgctgggatt gacgcctaac ttcaagtcca acttcgactt ggccgaggac    780
gccaagttgc aactgtccaa ggacacctac gacgacgacc tcgacaacct gctgccccaa    840
attggcgacc aatacgcgga cttgttttg gcggccaaga acttgagcga cgccatcttg    900
```

-continued

```
ttgagcgaca tcttgcgcgt gaatacggag atcaccaaag ccccttttgtc cgcctctatg   960
atcaagcggt acgacgagca ccaccaagac ttgaccctgt tgaaagccct cgtgcggcaa  1020
caattgcccg agaagtacaa ggagatcttc ttcgaccagt ccaagaacgg gtacgccggc  1080
tacatcgacg gaggagcctc ccaagaagag ttctacaagt tcatcaagcc catcctggag  1140
aagatggacg gcaccgagga gttgctcgtg aagctgaacc gcgaagactt gttgcgaaaa  1200
cagcggacgt tcgacaatgg cagcatcccc caccaaatcc atttgggaga gttgcacgcc  1260
atcttgcgac ggcaagagga cttctacccg ttcctgaagg acaaccgcga gaaaatcgag  1320
aagatcctga cgttcagaat cccctactac gtgggaccct tggcccgagg caattcccgg  1380
tttgcatgga tgacgcgcaa aagcgaagag acgatcaccc cctggaactt cgaagaagtg  1440
gtcgacaaag gagcatccgc acagagcttc atcgagcgaa tgacgaactt cgacaagaac  1500
ctgcccaacg agaaggtgtt gcccaagcat tcgctgctgt acgagtactt cacggtgtac  1560
aacgagctga ccaaggtgaa gtacgtgacc gagggcatgc gcaaacccgc gttcctgtcg  1620
ggagagcaaa agaaggccat tgtggacctg ctgttcaaga ccaaccggaa ggtgaccgtg  1680
aaacagctga agaggactac cttcaagaag atcgagtgct tcgactccgt ggagatctcc  1740
ggcgtggagg accgattcaa tgcctccttg ggaacctacc atgacctcct gaagatcatc  1800
aaggacaagg acttcctgga caacgaggag aacgaggaca tcctggagga catcgtgctg  1860
accctgaccc tgttcgagga ccgagagatg atcgaggaac ggttgaaaac gtacgcccac  1920
ttgttcgacg acaaggtgat gaagcagctg aaacgccgcc gctacaccgg atggggacga  1980
ttgagccgca aactgattaa tggaattcgc gacaagcaat ccggaaagac catcctggac  2040
ttcctgaagt ccgacgggtt cgccaaccgc aacttcatgc agctcatcca cgacgactcc  2100
ttgaccttca aggaggacat ccagaaggcc caagtgtccg acaaggagac tccttgcac  2160
gagcacatcg ccaatttggc cggatccccc gcaatcaaaa aaggcatctt gcaaaccgtg  2220
aaagtggtcg acgaactggt gaaggtgatg ggacggcaca gcccgagaa catcgtgatc  2280
gaaatggccc gcgagaacca aaccacccaa aaaggacaga gaactcccg agagcgcatg  2340
aagcggatcg aagagggcat caaggagttg gctcccaga tcctgaagga gcatcccgtg  2400
gagaataccc aattgcaaaa cgagaagctc tacctctact acctccagaa cgggcgggac  2460
atgtacgtcg accaagagct ggacatcaac cgcctctccg actacgatgt ggatcatatt  2520
gtgccccaga gcttcctcaa ggacgacagc atcgacaaca aggtcctgac gcgcagcgac  2580
aagaaccggg gcaagtctga caatgtgcct tccgaagaag tcgtgaagaa gatgaagaac  2640
tactggcggc agctgctcaa cgccaagctc atcacccaac ggaagttcga caacctgacc  2700
aaggccgaga gaggaggatt gtccgagttg acaaagccg gcttcattaa cgccaactc  2760
gtggagaccc gccagatcac gaagcacgtg gcccaaatct ggactcccg gatgaacacg  2820
aaatacgacg agaatgacaa gctgatccgc gaggtgaagg tgatcacgct gaagtccaag  2880
ctggtgagcg acttccggaa ggacttccag ttctacaagg tgcgggagat caacaactac  2940
catcacgccc atgacgccta cctgaacgcc gtggtcggaa ccgccctgat caagaaatac  3000
cccaagctgg agtccgaatt cgtgtacgga gattacaagg tctacgacgt gcggaagatg  3060
atcgcgaagt ccgagcagga gatcggcaaa gccaccgcca agtacttctt ttactccaac  3120
atcatgaact tcttcaagac cgagatcacg ctcgccaacg gcgagatccg caagcgcccc  3180
ctgatcgaga ccaacggcga gacgggagag attgtgtggg acaaaggaag agattttgcc  3240
```

```
acagtgcgca aggtgctgtc catgcctcag gtgaacatcg tgaagaagac cgaggtgcaa    3300
acaggagggt tttccaaaga gtccattttg cctaagagga attccgacaa gctcatcgcc    3360
cgcaagaagg actgggaccc caagaagtac gggggcttcg actcccccac ggtggcctac    3420
tccgtgttgg tggtggccaa agtggagaaa gggaagagca agaagctgaa atccgtgaag    3480
gagttgctcg gaatcacgat catggaacga tcgtcgttcg agaaaaaccc catcgacttc    3540
ctcgaagcca agggtacaa agaggtgaag aaggacctga tcatcaagct gcccaagtac    3600
tccctgttcg agctggagaa cggccgcaag cggatgctgg cctccgccgg ggaactgcag    3660
aaagggaacg aattggcctt gccctccaaa tacgtgaact tcctctactt ggcctcccat    3720
tacgaaaagc tcaaaggatc ccctgaggac aatgagcaga agcaactctt cgtggaacaa    3780
cacaagcact acctggacga gatcatcgag cagatcagcg agttctccaa gcgcgtgatc    3840
ctcgccgacg ccaacctgga caaggtgctc tccgcctaca caagcaccg cgacaagcct    3900 atccgcgagc aagccgagaa tatcattcac ctgtttaccc tgacgaattt gggagcccct    3960
gccgccttta aatactttga caccaccatc gaccgcaaaa gatacacctc caccaaggaa    4020
gtcttggacg ccaccctcat ccaccagtcc atcacgggcc tctacgagac gcgcatcgac    4080
ctctcccaat gggcggcga c                                                4101

<210> SEQ ID NO 49
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes FLAG tag

<400> SEQUENCE: 49
gactacaagg atgacgatga caag                                             24

<210> SEQ ID NO 50
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes Nuclear Localization Sequence

<400> SEQUENCE: 50
cccaagaaaa agcggaaggt cggc                                             24

<210> SEQ ID NO 51
<211> LENGTH: 147
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes peptide linker

<400> SEQUENCE: 51
atgcccaaga aaagcggaa ggtcggcgac tacaaggatg acgatgacaa gttggagcct      60
ggagagaagc cctacaaatg ccctgagtgc ggaaagagct tcagccaatc tggagccttg     120
acccggcatc aacgaacgca tacacga                                         147
```

<210> SEQ ID NO 52
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: RPL24 promoter

<400> SEQUENCE: 52

```
aataagcata catcatatga atacaattca gcttaaattt atcatacaaa gatgtaagtg      60
cagcgtgggt ctgtaacgat cgggcgtaat ttaagataat gcgagggacc gggggaggtt     120
ttggaacgga atgaggaatg ggtcatggcc cataataata atatgggttt ggtcgcctcg     180
cacagcaacc gtacgtgcga aaaggaaca gatccattta ataagttgaa cgttattctt      240
tcctatgcaa tgcgtgtatc ggaggcgaga gcaagtcata ggtggctgcg cacaataatt     300
gagtctcagc tgagcgccgt ccgcgggtgg tgtgagtggt catcctcctc ccggcctatc     360
gctcacatcg cctctcaatg gtggtggtgg ggcctgatat gacctcaatg ccgacccata    420
ttaaaaccca gtaaagcatt caccaacgaa cgaggggctc ttttgtgtgt gttttgagta    480
tgattttaca cctctttgtg catctctctg gtcttccttg gttcccgtag tttgggcatc    540
atcactcacg cttccctcga ccttcgttct tcctttacaa ccccgacaca ggtcagagtt    600
ggagtaatca aaaaggggt gcacgaatga gatacattag attttgacag atatcctttt    660
actggagagg gttcaaggga tcaaatgaac agcgggcgtt ggcaatctag ggagggatcg    720
gaggttggca gcgagcgaaa gcgtgtccat ccttttggct gtcacacctc acgaaccaac    780
tgttagcagg ccagcacaga tgacatacga gaatctttat tatatcgtag accttatgtg   840
gatgaccttt ggtgctgtgt gtctggcaat gaacctgaag gcttgatagg gaggtggctc    900
ccgtaaaccc tttgtccttt ccacgctgag tctcccccgc actgtccttt atacaaattg    960
ttacagtcat ctgcaggcgg tttttctttg gcaggcaaag                         1000
```

<210> SEQ ID NO 53
<211> LENGTH: 317
<212> TYPE: DNA
<213> ORGANISM: Nannochloropsis gaditana
<220> FEATURE:
<221> NAME/KEY: misc_feature
<223> OTHER INFORMATION: bidirectional terminator 2

<400> SEQUENCE: 53

```
agtgatgcgg cctttaggaa acaccacaaa agtaattgac aatctcagga acgatctgcg      60
tgtttacagc ttcccaaata acaattatac cacgtaccaa aaggggttta atgtatctca    120
caaattcttc taataggtac agcttctcaa attgggtgta tgatgtgaca cttcgtctca    180
cacacgtcac gataattcag cgtatggctt cccttcatca cattcacgca aacttctaca    240
caaccctggg catatttctt gtgttggcaa cactcccgaa atcgattctg cacacaatgg    300
ttcattcaat gattcaa                                                  317
```

<210> SEQ ID NO 54
<211> LENGTH: 399
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: blast gene from Aspergillus terreus codon
     optimized for Nannochloropsis gaditana

<400> SEQUENCE: 54

```
atggccaagc ctttatccca agaggaatcc acgctgatcg aacgtgcaac tgcgaccatc    60
aacagcatac ctattagcga ggactactcg gtggccagtg cagccctctc gtccgacggt   120
cggatcttta ccggcgtgaa tgtatatcat ttcaccggag ggccatgcgc ggagctcgtg   180
gtcctcggaa cggccgctgc ggctgctgcc ggaaatctga cgtgcatagt ggccatcggg   240
aacgaaaacc gcggcattct gtctccgtgc gggcgatgtc ggcaggtgct gcttgacttg   300
cacccgggga tcaaggcaat tgtcaaagat tccgatgggc agcccacagc ggttggcatc   360
agggagttgc ttccctctgg ctacgtctgg gagggttga                          399
```

<210> SEQ ID NO 55
<211> LENGTH: 999
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: TCTP promoter

<400> SEQUENCE: 55

```
cgtgcaggtg tacagattga aggaaacaat ggagatatct ttggcagttg aaaaccgtgt    60
tcgaatcatg cttttctact ctccaactga gacgaaattt atagcgccat gtcgcttctg   120
actaccaggc ttaggaaggc ctcatcacaa gctggatcgg ttcgaattaa gcaggcactg   180
aagccaagct tgcaagacag ccacctttta attccctcaa aacactttct caattcagcc   240
cggtaaatat gccgattcac agcggccaag atagagggga ggttagcaag aatgttgcga   300
tccctcccca gtcgttgcct cgcacacaac ctaggccttc acctttccat ggaaaattga   360
gaagtgaata ttggtttctc tacggcatat cagatgaaat catgacccct aaacatgaag   420
agctgcaggc aaaacacctg ctctggacga gcacgatgaa atctcgagaa cccgccgtac   480
ttcagttgat cccgcatgat gacggccgcc attgaaataa gccacctcac tttattctag   540
caccgatttc caccgttgtg agggccgaac gaggacaatt tcgtgcgaaa caagcacgaa   600
cacgcacacg attagtagta cagacgagca gatcgatggc atgcggcacg gtctcgcgtt   660
ctcggcgacc aggacaacgg agcagaggga ggcctgccga gttccgaggg gcattttagt   720
ccaaaattgt gttgacacgt gaacaagtgg cttgaaaaga ggaaggaaat gcctgggttt   780
cccttcgaga gcgggaactc gcttgtgcgt catcctagct acccatggtc cctttgtggg   840
ggaggctgtt tcgtcctacc gaatgtgtgg cgctccatgc atcttctgcc tcccaaacca   900
ccaacatgag cacgcgaagg aaggagaaaa aagtggccgc aacgttctct tctcatattt   960
attgtctcat cacaaacata ggtacataat acaacaatc                          999
```

<210> SEQ ID NO 56
<211> LENGTH: 318
<212> TYPE: DNA
<213> ORGANISM: Nannochloropsis gaditana
<220> FEATURE:
<221> NAME/KEY: misc_feature
<223> OTHER INFORMATION: EIF3 terminator

<400> SEQUENCE: 56

```
ggcactgtaa ccccggttcc gctcgacgaa ggctgggagc gcccttcgg tgggataaaa    60
tggatgcttt accgctgcgc ttcggctgag gaagagagaa atgcgagcgg ggatcgggt   120
```

| | |
|---|---:|
| cctagaaacg aagaaaggag aacaagttcc tggccaaaga aaaacaagac aaataccctc | 180 |
| tccaggcctg ggcccattac tttttttgc tgtttcttat acctgcactc gtgcttctct | 240 |
| agtctgtcga gaccttacct gatcttcctc cctccatcgc tccccgcccc ccccatccga | 300 |
| gcaaccgtcg accatacg | 318 |

```
<210> SEQ ID NO 57
<211> LENGTH: 702
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: TurboGFP gene codon optimized for
      Nannochloropsis gaditana

<400> SEQUENCE: 57
```

| | |
|---|---:|
| atgttggaga gcgacgagag cggcctgccc gccatggaga tcgagtgccg catcaccggc | 60 |
| accctgaacg gcgtggagtt cgagctggtg ggcggcggag agggcacccc cgagcagggc | 120 |
| cgcatgacca acaagatgaa gagcaccaaa ggcgccctga ccttcagccc ctacctgctg | 180 |
| agccacgtga tgggctacgg cttctaccac ttcggcacct accccagcgg ctacgagaac | 240 |
| cccttcctgc acgccatcaa caacggcggc tacaccaaca cccgcatcga agtacgag | 300 |
| gacggcggcg tgctgcacgt gagcttcagc taccgctacg aggccggccg cgtgatcggc | 360 |
| gacttcaagg tgatgggcac cggcttcccc gaggacagcg tgatcttcac cgacaagatc | 420 |
| atccgcagca cgccaccgt ggagcacctg caccccatgg gcgataacga tctggatggc | 480 |
| agcttcaccc gcaccttcag cctgcgcgac ggcggctact acagctccgt ggtggacagc | 540 |
| cacatgcact tcaagagcgc catccacccc agcatcctgc agaacggggg ccccatgttc | 600 |
| gccttccgcc gcgtggagga ggatcacagc aacaccgagc tgggcatcgt ggagtaccag | 660 |
| cacgccttca gacccccgga tgcagatgcc ggtgaagaat aa | 702 |

```
<210> SEQ ID NO 58
<211> LENGTH: 822
<212> TYPE: DNA
<213> ORGANISM: Nannochloropsis gaditana
<220> FEATURE:
<221> NAME/KEY: misc_feature
<223> OTHER INFORMATION: 4A-III promoter

<400> SEQUENCE: 58
```

| | |
|---|---:|
| ggcataaagg acggcaagga aagaaaagaa agaaagaaaa ggacacttat agcatagttt | 60 |
| gaagttataa gtagtcgcaa tctgtgtgca gccgacagat gctttttttt tccgtttggc | 120 |
| aggaggtgta gggatgtcga agaccagtcc agctagtatc tatcctacaa gtcaatcatg | 180 |
| ctgcgacaaa aatttctcgc acgaggcctc tcgataaaca aaactttaaa agcacacttc | 240 |
| attgtcatgc agagtaataa ctcttccgcg tcgatcaatt tatcaatctc tatcatttcc | 300 |
| gccccttcc ttgcatagag caagaaaagc gacccggatg aggataacat gtcctgcgcc | 360 |
| agtagtgtgg cattgcctgt ctctcattta cacgtactga agcataatg cacgcgcata | 420 |
| ccaatatttt tcgtgtacgg agatgaagag acgcgacacg taagatcacg agaaggcgag | 480 |
| cacggttgcc aatggcagac gcgctagtct ccattatcgc gttgttcggt agcttgctgc | 540 |
| atgtcttcag tggcactata tccactctgc ctcgtcttct acacgagggc cacatcggtg | 600 |
| caagttcgaa aaatcatatc tcaatcttca gatccttttc agaaacggtg ctcaggcggg | 660 |

| | |
|---|---|
| aaagtgaagg ttttctactc tagtggctac cccaattctc tccgactgtc gcagacggtc | 720 |
| cttcgttgcg cacgcaccgc gcactacctc tgaaattcga caaccgaagt tcaattttac | 780 |
| atctaacttc tttcccattc tctcaccaaa agcctagctt ac | 822 |

<210> SEQ ID NO 59
<211> LENGTH: 200
<212> TYPE: DNA
<213> ORGANISM: Nannochloropsis gaditana
<220> FEATURE:
<221> NAME/KEY: misc_feature
<223> OTHER INFORMATION: bidirectional terminator 5

<400> SEQUENCE: 59

| | |
|---|---|
| gggtgggaag gagtcgggga gggtcctggc agagcggcgt cctcatgatg tgttggagac | 60 |
| ctggagagtc gagagcttcc tcgtcacctg attgtcatgt gtgtataggt taaggggggcc | 120 |
| cactcaaagc cataaagacg aacacaaaca ctaatctcaa caaagtctac tagcatgccg | 180 |
| tctgtccatc tttatttcct | 200 |

<210> SEQ ID NO 60
<211> LENGTH: 101
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Guide RNA for Bromo-1091 gene knockout

<400> SEQUENCE: 60

| | |
|---|---|
| uguggcagac gccgacgggu uuuagagcua gaaauagcaa guuaaaauaa ggcuaguccg | 60 |
| uuaucaacuu gaaaaagugg caccgagucg gugcuuuuuu u | 101 |

<210> SEQ ID NO 61
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Bromo-1091 gene target sequence used in
    chimeric guide RNA for knockout (SEQ ID NO:60)

<400> SEQUENCE: 61

| | |
|---|---|
| tgtggcagac gccgacgg | 18 |

<210> SEQ ID NO 62
<211> LENGTH: 1029
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Hygromycin resistance gene

<400> SEQUENCE: 62

| | |
|---|---|
| atggggaaga aaccggaact gaccgctacg tccgtggaga aattccttat tgagaagttc | 60 |
| gactctgtct ccgacttgat gcaactgagc gagggagagg agagtagggc gttctcgttt | 120 |
| gacgtagggg gtcggggata cgtgttgagg gttaatagtt gtgcggacgg gttctacaag | 180 |
| gatcggtatg tctaccgtca tttcgcctcc gccgctctcc ccataccaga ggtactggac | 240 |
| attggggagt ttagcgaatc tctcacgtac tgcatctcgc gccgagccca gggagtgacg | 300 |

```
ttgcaagatc tgcccgaaac tgaattgcct gccgttttgc aacccgtggc cgaggccatg      360
gacgcgatcg ctgccgcaga tctgtctcag acgtccggct ttggaccttt tgggccccag      420
ggcatcgggc agtacacgac ctggcgagac ttcatctgcg ccattgccga tcctcacgtc      480
tatcattggc agacagtcat ggatgacacc gtgtctgcat ccgtggccca agcactggac      540
gaactcatgt tgtgggccga ggattgccct gaggtcaggc acctggtgca cgcggatttc      600
ggcagcaata acgtacttac agacaatggt cggattactg ctgtcatcga ctggtccgaa      660
gcgatgtttg gtgatagcca atacgaagtg gcgaacatat tcttctggcg tccctggttg      720
gcgtgcatgg agcagcagac acgctacttt gaacggaggc acccggagct ggccggctcc      780
ccacgactcc gcgcctatat gttgcgtatc ggactcgatc agctttacca gtctctcgtc      840
gacggcaact tcgacgacgc cgcgtgggcg cagggccgct cgacgcgat agtccgcagc       900 ggggctggga cggtgggtcg gacccaaatc gcacgccggt cggctgcggt gtggacagac      960
ggctgtgttg aggtgcttgc ggactcgggc aaccgtaggc cgagcacccg accgcgtgca     1020
aaggagtga                                                             1029

<210> SEQ ID NO 63
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: EIF3 promoter

<400> SEQUENCE: 63
tcataatcaa agatgagcca gccacgaagc taccggagaa ttctgtaaga aaatgttta       60 aagttgaaaa tgctaacagt gaagtgatat cctttttaa tggagtgttg aggtgaagtc      120
tagcatcgta ggggaaaaca ggattctgtg tcttccattc tactccttga taaagcgaag     180
aaatccgaca aaaccaaaga gattgttcaa gtttaagatt tgtaagcgta caactatgaa     240
cttcttctct ttgtaggcct gagtggtcgt atgcatacga ttcatgaagt gaatcagtat     300
cgctggattt tgcttaggag taaagcacaa ctaagaaaat atgctgcctg gcaggcatcc     360
tgagacatga ggcaagcgac gtagcaattg aatcctaatt taagccaggg catctgtatg     420
actctgttag ttaattgatg aaccaatgag ctttaaaaaa aaatcgttgc gcgtaatgta     480
gttttaattc tccgccttga ggtgcggggc catttcggac aaggttcttt ggacggagat     540
ggcagcatgt gtcccttctc caaattggtc cgtgtggtag ttgagatgct gccttaaaat     600
tctgctcggt catcctgcct tcgcattcac tcctttcgag ctgtcgggtt cctcacgagg     660 cctcgggag cggattgcgc agaaaggcga cccggagaca cagagaccat acaccgacta      720
aattgcactg gacgatacgg catggcgacg acgatggcca agcattgcta cgtgattatt     780
cgccttgtca ttcagggaga aatgatgaca tgtgtgggac ggtctttaca tgggaagagg     840
gcatgaaaat aacatggcct ggcgggatgg agcgtcacac ctgtgtatgc gttcgatcca     900
caagcaactc accatttgcg tcggggcctg tctccaatct gctttaggct acttttctct     960
aatttagcct attctataca gacagagaca cacagggatc                          1000

<210> SEQ ID NO 64
<211> LENGTH: 27
<212> TYPE: DNA
<213> ORGANISM: Artificial Sequence
<220> FEATURE:
<223> OTHER INFORMATION: Synthetic
<220> FEATURE:
```

<221> NAME/KEY: misc_feature
<223> OTHER INFORMATION: 5'ID sequence

<400> SEQUENCE: 64
tccacagccc gaacccatga gagagaa                                              27

<210> SEQ ID NO 65
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3'ID sequence

<400> SEQUENCE: 65
gcccgaatcg agttgatggc ccgcaaa                                              27

<210> SEQ ID NO 66
<211> LENGTH: 2400
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Donor Fragment with HygR cassette

<400> SEQUENCE: 66
tccacagccc gaacccatga gagagaatca taatcaaaga tgagccagcc acgaagctac           60
cggagaattc tgtaagaaaa atgtttaaag ttgaaaatgc taacagtgaa gtgatatcct          120
tttttaatgg agtgttgagg tgaagtctag catcgtaggg gaaaacagga ttctgtgtct          180
tccattctac tccttgataa agcgaagaaa tccgacaaaa ccaaagagat tgttcaagtt          240
taagatttgt aagcgtacaa ctatgaactt cttctctttg taggcctgag tggtcgtatg          300
catacgattc atgaagtgaa tcagtatcgc tggattttgc ttaggagtaa agcacaacta          360
agaaaatatg ctgcctggca ggcatcctga gacatgaggc aagcgacgta gcaattgaat          420
cctaatttaa gccagggcat ctgtatgact ctgttagtta attgatgaac caatgagctt          480
taaaaaaaaa tcgttgcgcg taatgtagtt ttaattctcc gccttgaggt gcggggccat          540
ttcggacaag gttctttgga cggagatggc agcatgtgtc ccttctccaa attggtccgt          600
gtggtagttg agatgctgcc ttaaaattct gctcggtcat cctgccttcg cattcactcc          660
tttcgagctg tcgggttcct cacgaggcct ccggagcgg attgcgcaga aaggcgaccc           720
ggagacacag agaccataca ccgactaaat tgcactggac gatacggcat ggcgacgacg          780
atggccaagc attgctacgt gattattcgc cttgtcattc aggagaaat gatgacatgt           840 gtgggacggt ctttacatgg aagagggca tgaaataac atggcctggc gggatggagc            900
gtcacacctg tgtatgcgtt cgatccacaa gcaactcacc atttgcgtcg ggcctgtct           960 ccaatctgct ttaggctact tttctctaat ttagcctatt ctatacagac agagacacac         1020
agggatcatg gggaagaaac cggaactgac cgctacgtcc gtggagaaat tccttattga         1080
gaagttcgac tctgtctccg acttgatgca actgagcgag ggagaggaga gtaggcgtt          1140 ctcgtttgac gtaggggggtc gggatacgt gttgagggtt aatagttgtg cggacgggtt        1200
ctacaaggat cggtatgtct accgtcattt cgcctccgcc gctctcccca taccagaggt         1260
actggacatt ggggagttta gcgaatctct cacgtactgc atctcgcgcc gagcccaggg         1320

```
agtgacgttg caagatctgc ccgaaactga attgcctgcc gttttgcaac ccgtggccga    1380
ggccatggac gcgatcgctg ccgcagatct gtctcagacg tccggctttg acccttttgg    1440
gccccagggc atcgggcagt acacgacctg gcgagacttc atctgcgcca ttgccgatcc    1500
tcacgtctat cattggcaga cagtcatgga tgacaccgtg tctgcatccg tggcccaagc    1560
actggacgaa ctcatgttgt gggccgagga ttgccctgag gtcaggcacc tggtgcacgc    1620
ggatttcggc agcaataacg tacttacaga caatggtcgg attactgctg tcatcgactg    1680
gtccgaagcg atgtttggtg atagccaata cgaagtggcg aacatattct tctggcgtcc    1740
ctggttggcg tgcatggagc agcagacacg ctactttgaa cggaggcacc cggagctggc    1800 cggctccccca cgactccgcg cctatatgtt gcgtatcgga ctcgatcagc tttaccagtc    1860
tctcgtcgac ggcaacttcg acgacgccgc gtgggcgcag ggccgctgcg acgcgatagt    1920
ccgcagcggg gctgggacgg tgggtcggac ccaaatcgca cgccggtcgg ctgcggtgtg    1980
gacagacggc tgtgttgagg tgcttgcgga ctcgggcaac cgtaggccga gcacccgacc    2040
gcgtgcaaag gagtgattga atcattgaat gaaccattgt gtgcagaatc gatttcggga    2100
gtgttgccaa cacaagaaat atgcccaggg ttgtgtagaa gtttgcgtga atgtgatgaa    2160
gggaagccat acgctgaatt atcgtgacgt gtgtgagacg aagtgtcaca tcatacaccc    2220
aatttgagaa gctgtaccta ttagaagaat ttgtgagata cattaaaccc cttttggtac    2280
gtggtataat tgttatttgg gaagctgtaa acacgcagat cgttcctgag attgtcaatt    2340
acttttgtgg tgtttcctaa aggccgcatc actgcccgaa tcgagttgat ggcccgcaaa    2400
```

<210> SEQ ID NO 67
<211> LENGTH: 101
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: BASH-1 Bromo-1091 gene Guide RNA
<400> SEQUENCE: 67

```
uguggcagac gccgacgggu uuuagagcua gaaauagcaa guuaaaauaa ggcuaguccg    60
uuaucaacuu gaaaaagugg caccgagucg gugcuuuuuu u                        101
```

<210> SEQ ID NO 68
<211> LENGTH: 17
<212> TYPE: DNA
<213> ORGANISM: Nannochloropsis gaditana
<220> FEATURE:
<221> NAME/KEY: misc_feature
<223> OTHER INFORMATION: Bromo-1091 gene target sequence used in guide
      RNA for BASH-1 knockdown (SEQ ID NO:67)

<400> SEQUENCE: 68

```
actgaaaggg cagagtg                                                   17
```

<210> SEQ ID NO 69
<211> LENGTH: 101
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: BASH-4 Bromo-1091 Guide RNA
<400> SEQUENCE: 69
uguggcagac gccgacgggu uuuagagcua gaaauagcaa guuaaaauaa ggcuaguccg    60
uuaucaacuu gaaaaagugg caccgagucg gugcuuuuuu u                      101

<210> SEQ ID NO 70
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Bromo-1091 gene target sequence used in guide
      RNA for BASH-4 knockdown (SEQ IDNO:69)

<400> SEQUENCE: 70
tgtggacgct agtacagg                                                18

<210> SEQ ID NO 71
<211> LENGTH: 101
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: BASH-5 Guide RNA

<400> SEQUENCE: 71
uguggcagac gccgacgggu uuuagagcua gaaauagcaa guuaaaauaa ggcuaguccg    60
uuaucaacuu gaaaaagugg caccgagucg gugcuuuuuu u                      101

<210> SEQ ID NO 72
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bromo-1091 gene target sequence used in guide
      RNA for BASH-5 knockdown (SEQ ID NO:71)

<400> SEQUENCE: 72
aaaagcgccg tctcggaa                                                18

<210> SEQ ID NO 73
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward primer, Bromo-1091 gene 5' end

<400> SEQUENCE: 73
attgctagcc gtgctttcaa c                                            21

<210> SEQ ID NO 74
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, Bromo-1091 gene 5' end

<400> SEQUENCE: 74
gtcggtttgg agaccctaga                                              20

```
<210> SEQ ID NO 75
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward primer for RT PCR, Bromo-1091 gene

<400> SEQUENCE: 75
gaataggcgg tcagaatgta gg                                              22

<210> SEQ ID NO 76
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse primer for RT PCR, Bromo-1091 gene

<400> SEQUENCE: 76
atattttgtg ggcgttgctg                                                 20

<210> SEQ ID NO 77
<211> LENGTH: 19
<212> TYPE: DNA
<213> ORGANISM: Nannochloropsis gaditana
<220> FEATURE:
<221> NAME/KEY: misc_feature
<223> OTHER INFORMATION: Forward primer, housekeeping gene 1T5001704

<400> SEQUENCE: 77
gaggaagcgg aagaggatg                                                  19

<210> SEQ ID NO 78
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Reverse primer, housekeeping gene 1T5001704

<400> SEQUENCE: 78
tcaagtacca gttccacacg                                                 20
```

ALGAL MUTANTS WITH INCREASED LIPID PRODUCTIVITY

CROSS-REFERENCE TO RELATED APPLICATIONS

This application claims benefit of priority under 35 U.S.C. § 119(e) of U.S. Ser. No. 62/249,834 filed Nov. 2, 2015, the entire contents of which is incorporated herein by reference in its entirety.

INCORPORATION OF SEQUENCE LISTING

The material in the accompanying sequence listing is hereby incorporated by reference into this application. The accompanying sequence listing text file, name SGII1980_1_Sequence_Listing.txt, was created on Nov. 1, 2016, and is 425 kb. The file can be assessed using Microsoft Word on a computer that uses Windows OS.

BACKGROUND OF THE INVENTION

The invention relates to mutant microorganisms, such as algae and heterokonts, having increased lipid productivity and methods of their use in producing lipids.

Many microorganisms such as algae, labyrinthulomycetes ("chytrids"), and oleaginous yeast induce lipid biosynthesis in response to nutrient stress, such as nitrogen starvation. Under conditions of nitrogen depletion, such microorganisms redirect compound biosynthesis from protein to storage lipids, typically triacylglyceride lipids ("TAG"). Because nitrogen depletion simultaneously decreases cell growth, optimal lipid biosynthesis is limited to a relatively short window before the cells become too metabolically impaired to maintain high levels of production.

Various attempts to improve lipid productivity by increasing lipid biosynthesis during nutrient replete growth have focused on manipulating genes encoding enzymes for nitrogen assimilation or lipid metabolism as well as genes encoding polypeptides involved in lipid storage. For example, US2014/0162330 discloses a *Phaeodactylum tricornutum* strain in which the nitrate reductase (NR) gene has been attenuated by RNAi-based knockdown; Trentacoste et al. ((2013) *Proc. Natl. Acad. Sci. USA* 110: 19748-19753) disclose diatoms transformed with an RNAi construct targeting the Thaps3_264297 gene predicted to be involved in lipid catabolism; and WO2011127118 discloses transformation of *Chlamydomonas* with genes encoding oleosins (lipid storage protein) as well as with genes encoding diacylglycerol transferase (DGAT) genes. Although in each case increased lipid production was asserted based on microscopy or staining with lipophilic dyes, no quantitation of lipid production by the manipulated cells was provided, nor was the relationship between biomass and lipid productivities over time determined.

Daboussi et al. 2014 (*Nature Comm.* 5:3881) report that disruption of the UGPase gene in *Phaeodactylum triconornutum*, which is believed to provide precursors to laminarin (a storage carbohydrate) synthesis, results in increased lipid accumulation. However, no biochemical data was shown to indicate that laminarin content was affected (or even present) and lipid and biomass productivities were not reported. Similarly, several groups have reported increases in lipid accumulation in *Chlamydomonas* starchless mutants (Wang et al. 2009 *Eukaryotic Cell* 8:1856-1868; Li et al. 2010 *Metab Eng.* 12:387-391) however, successive reports that actually measured lipid productivity concluded that these strains were impaired in growth when grown in phototrophic conditions (Siaut et al. 2011 *BMC Biotechnol.* 11:7; Davey et al. 2014 *Eukaryot Cell* 13:392-400). These reports concluded that the highest lipid productivities (measured as TAG per liter per day) were actually achieved by the wild-type parental strain.

WO 2011/097261 and US20120322157 report that a gene denoted "SN03" encoding an arrestin protein has a role in increasing lipid production under nutrient replete conditions when overexpressed in *Chlamydomonas*. However, overexpression of the SN03 gene was observed to result in the appearance of unidentified polar lipids, which were not quantified, and did not result in an increase in triglycerides (TAG). Another polypeptide identified as potentially regulating stress-induced lipid biosynthesis has been described by Boyle et al. ((2012) *J. Biol. Chem.* 287:15811-15825). Knockout of the NRR1 gene in *Chlamydomonas* encoding a "SQUAMOUSA" domain polypeptide resulted in a reduction of lipid biosynthesis with respect to wild type cells under nitrogen depletion; however, no mutants were obtained demonstrating increased lipid production. US 2010/0255550 suggests the overexpression of putative transcription factors (TF1, TF2, TF3, TF4, and TF5) in algal cells to increase lipid production, but no such strains are disclosed.

WO 2015/130832 and Ngan et al. (*Nature Plants*, 1:1507, 2015) report that overexpression of the PSR1 gene, a regulator of the phosphate starvation response, leads to cellular lipid accumulation in *Chlamydomonas*. Cells engineered to overexpress PSR1 are disclosed as having the large round phenotype of cells induced to produce lipid via nutrient starvation. Transformed cells were also observed to have higher amounts of cellular lipid with respect to control cells as visualized by electron microscopy and measured by staining with lipophilic fluorophores. However, increased lipid production by cultures on a volumetric basis was not demonstrated, nor was culture propagation, biomass accumulation, or overexpression of the PSR1 gene determined from the cultures in which lipid accumulation was observed. Conversely, growth rate of the PSR1-transformed cultures was demonstrated under conditions that were nonselective for the expression of the gene, and neither PSR1 gene expression level nor lipid production was assessed during the growth assay period.

Copending and commonly-owned U.S. Utility application Ser. No. 15/210,845 filed Jul. 14, 2016, entitled "Microorganisms Having Increased Lipid Productivity" discloses algal mutants having attenuated expression of a lipid regulator gene "ZnCys-2845" referred to herein as "LION1" mutants and their use in lipid production.

SUMMARY OF THE DISCLOSURE

Disclosed herein are mutant microorganisms that produce more lipid than a control microorganism (such as a wild type microorganisms from which the mutants are derived) while producing biomass at levels that are at least 45% of the level of biomass produced by the control microorganism cultured under the same conditions, which are conditions under which the control microorganism produces biomass, for example, nitrogen replete or nutrient replete conditions with respect to the control microorganism. In various embodiments, a mutant microorganism as provided herein can produce at least 20% more lipid than a control microorganism while experiencing a decrease of no more than 20%, no more than 15%, no more than 10%, no more than 5%, or no more than 3% in biomass accumulation with respect to the control microorganism. For example, a mutant microorganism can produce at least 20%, at least 25%, at least 30%, at least 35%, at least 40%, at least 45%, or at least 50% more lipid than a control microorganism while producting at least 80%, at least 85%, at least 90%, at least 95%, at least 100%, or approximately 100% of the biomass produced by the control microorganism cultured under the same conditions as the mutant microorganism, which are conditions in which the control microorganism produces biomass. The control microorganism can be, in some examples, a wild type microorganism, for example, a wild type microorganism from which the mutant microorganism is directly or indirectly derived. The mutant microorganisms may be generated, for example, by classical mutagenesis or by genetic engineering techniques, and can have a mutation in or attenuated expression of a gene encoding a polypeptide having a TAZ zinc finger domain and/or a Bromo domain, and/or a gene encoding a polypeptide having at least 50%, 55%, 60%, 65%, 70%, 75%, 80%, 85%, 90%, or 95% to any of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46.

Provided herein, in a first aspect, is a mutant microorganism that produces at least 20% more lipid than is produced by a control microorganism while producing not less than 45% of the biomass produced by the control microorganism cultured under the same conditions, in which the culture conditions support production of biomass by the control microorganism. For example, a mutant microorganism as provided herein can produce at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 105%, at least 110%, or at least 115% more lipid than is produced by a control microorganism while producing at least 45%, at least 50%, at least 55%, at least 60%, at least 65%, at least 70%, at least 75%, at least 80%, at least 85%, at least 90%, at least 95%, or at least 100% of the amount of biomass produced by the control microorganism, when the control microorganism is cultured under the same conditions as the mutant microorganism, which are conditions in which the control microorganism accumulates biomass. In some examples, a mutant microorganism as provided herein produces at least 20% more lipid, for example, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 105%, at least 110%, or at least 115% more lipid than is produced by a control microorganism while producing not less than 45% of the biomass produced by the control microorganism cultured under the same conditions, in which the culture conditions are nitrogen replete, and are preferably nutrient replete, with respect to the control microorganism and the culture conditions support production of biomass by both the control microorganism and the mutant microorganism. The lipid can be fatty acid methyl ester-derivatizable lipid, i.e., "FAME lipid" or "FAME". Biomass accumulation can be, for example, dry weight, ash free dry weight (AFDW), or total organic carbon (TOC) accumulation. The control microorganism can be, in some examples, a wild type microorganism, for example, a wild type microorganism from which the mutant microorganism is directly or indirectly derived.

The increased productivity can be increased average daily productivity, where the amount produced is averaged over multiple days. The mutant microorganism can produce, in some embodiments, at least 45%, at least about 50%, at least 55%, at least 60%, at least 65%, at least 70%, at least 75%, at least 80%, at least 85%, at least 90%, at least 95%, or at least about 100% of the amount of biomass produced by a control microorganism and at least about 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, or at least 120% more lipid than is produced by a control microorganism cultured under the same conditions over a culture period of at least three, at least five, at least seven, at least eight, at least ten, at least twelve, at least fourteen, at least fifteen, at least twenty, at least twenty-five, at least thirty, at least sixty, or at least ninety days, where the control microorganism and the mutant microorganism both produce biomass during the culture period. For example, the mutant can produce an average daily amount of lipid that is at least 25% greater than the average daily amount of a control microorganism while producing an average daily amount of biomass that is at least 45% of the daily amount produced by the control cell, for a period of from three to ninety days, such as from five to sixty days, from five to thirty days, or from five to fourteen days. In various embodiments a mutant microorganism as provided herein produces at least 70%, at least 75%, at least 80%, at least 85%, at least 90%, or at least 95% of the biomass and at least 25%, at least 30%, at least 35%, at least 40%, at least 45%, at least 50%, or at least 55% of the amount of lipid produced by a control microorganism for at least three, at least five, at least seven, at least eight, at least ten, at least twelve, at least fourteen, at least twenty, at least thirty, at least sixty, or at least ninety days, where the mutant and control microorganisms are cultured under the same conditions in which both the control microorganism and the mutant microorganism accumulate biomass. For example, the culture conditions can be nitrogen-replete with respect to the control microorganism and are in various examples nutrient-replete with respect to the control microorganism. In some embodiments in which a mutant microorganism as provided herein produces at least 45% of the biomass and at least 20% more lipid than a control microorganism (e.g., a wild type microorganism), the culture medium includes nitrate as substantially the sole nitrogen source for growth and propagation of the mutant and control microorganisms.

For example, a mutant microorganism as provided herein can produce more FAME-derivatizable lipids ("FAME lipids" or "FAME"), for example, at least 20% more FAME lipids, than a control microorganism while producing not less than 45% of the biomass produced by the control microorganism, when the mutant microorganism and control microorganism are cultured under the same culture conditions under which the control microorganism produces biomass. For example, the FAME productivity of a mutant as provided herein, which can be, for example, the average daily FAME productivity of a mutant as provided herein, can be at least 25%, at least 30%, at least 35%, at least 40%, at least 45%, at least 50%, or at least 55% greater than that of a control or wild type microorganism while the average daily biomass (e.g., AFDW or TOC) productivity can be at least 45%, at least about 50%, at least about 55%, at least about 60%, at least about 65%, at least about 70%, at least about 80%, at least about 85%, at least about 90%, at least about 95%, or at least about 100% of the average daily biomass productivity of the control or wild type microorganism over a culture period of at least three days, at least five days, at least seven days, at least ten days, at least twelve days, at least fifteen days, at least twenty days, at least thirty days, or at least sixty days during which both the mutant microorganism and the control microorganism are producing biomass. In particular embodiments, a mutant microorganism as provided herein can produce at least 25% more FAME lipids than a control or wild type microorganism while producing at least 45% as much biomass as the control microorganism over a culture period of at least ten days, where the where the daily amount of FAME produced by the mutant is not lower than the daily amount of FAME produced by the control or wild type microorganism on any day during the at least ten day culture period, during which both the mutant and control microorganism accumulate biomass.

In some examples, the culture conditions under which the mutant produces more lipid than a control or wild type microorganism can be culture conditions in which the concentration of ammonium in the culture medium is less than about 2.5 mM, for example, the concentration of ammonium in the culture medium can be about 2 mM or less than about 2 mM, less than about 1.5 mM, less than about 1 mM, or less than or equal to about 0.5 mM. In some examples the culture medium can include no added ammonium or includes substantially no ammonium. In some examples, the culture medium can include no added source of reduced nitrogen for the microorganism, e.g., no added ammonium, urea, or amino acids that can support growth and/or propagation of the culture. The culture medium can in some examples include a nitrogen source such as nitrate. For example, nitrate can be present at a concentration at greater than about 1 mM, or of at least about 2 mM, at least about 2.5 mM, at least about 3 mM, at least about 4 mM, or at least about 5 mM. In some examples the culture medium includes nitrate as substantially the sole nitrogen source for growth and/or propagation of the culture. For example, in some embodiments a mutant microorganism as disclosed herein can produce more lipid than a control microorganism while producing biomass at levels that are at least 45% of the level of biomass produced by the control microorganism when cultured under nutrient replete conditions in which nitrate is substantially the sole source of nitrogen for growth and propagation of the culture. The culture medium can be, in various embodiments, nutrient replete with respect to a wild type microorganism of the species from which the mutant microorganism is derived.

A mutant microorganism as provided herein can produce more lipid, for example more FAME lipids, than a control or wild type microorganism while producing at least 45%, at least 50%, at least 55%, at least 60%, at least 65%, at least 70%, at least 75%, at least 80%, at least 85%, at least 90%, or at least 95% the amount of biomass produced by a control or wild type microorganism in any of batch, continuous, or semi-continuous culture conditions. In some embodiments, the mutant microorganism is a mutant photosynthetic microorganism, such as an alga, and the culture is exposed to light for at least a portion of the culture period. In some examples the culture conditions under which the mutant photosynthetic microorganism produces at least 20% more lipid while producing at least 45% as much biomass as a control photosynthetic microorganism are photoautotrophic conditions, for example, conditions in which inorganic carbon is substantially the sole source of carbon available to the microorganism. In some examples, the mutant microorganism is a mutant photosynthetic microorganism, such as an alga, and the mutant demonstrates increased productivity under photoautotrophic conditions that include a diel cycle, where the light period can be between about two hours and about twenty-two hours, for example, between about four hours and about twenty hours per twenty-four hour cycle, such as between about six and about sixteen hours, between about eight and about eighteen hours, or between about twelve and about sixteen hours, per twenty-four hour diel cycle.

In some embodiments, a mutant microorganism as provided herein can produce at least 20% more lipid while producing at least 75% of the amount of biomass produced by a wild type or control microorganism during a culture period of at least three, at least four, at least five, at least six, at least seven, at least eight, at least nine, at least ten, at least eleven, at least twelve, or at least thirteen days of culturing, for example, at least five, at least ten, at least fifteen, at least twenty, or at least thirty days where the mutant and control microorganism are cultured under the same conditions in which both the control and mutant microorganism cultures produce biomass. For example, the average daily FAME productivity of a mutant as provided herein can be at least 30%, at least 35%, at least 40%, at least 45%, at least 50%, or at least 55% more than that of a wild type or control microorganism under conditions in which both the control and mutant microorganism cultures produce biomass and the average daily biomass productivity (e.g., TOC productivity) of the mutant is at least 75%, at least 80%, at least 85%, at least 90%, or at least 95% of the daily biomass productivity (e.g., TOC productivity) of a control microorganism, for example, under conditions in which the mutant has substantially the same biomass productivity as a control microorganism. In some examples, a mutant microorganism can produce at least 30% more, at least 35% more, at least 40% more, at least 45% more, or at least 50% more FAME lipids than a wild type or control microorganism while producing at least about 90% or at least about 95% of the biomass produced by a wild type microorganism cultured under identical conditions, which are nutrient replete with respect to the wild type microorganism. In other examples a mutant microorganism can produce at least 50% more FAME lipids than a wild type or control microorganism while producing approximately as much biomass as is produced by a wild type microorganism cultured under identical conditions under which the wild type or control microorganism produces biomass (e.g., within 5% of the amount of biomass produced by the control microorganism). In various examples, the average daily FAME productivity for at least three, at least four, at least five, at least six, at least seven, at least eight, at least nine, at least ten, at least eleven, at least twelve, or at least thirteen days of culturing, for example, at least five, at least ten, at least fifteen, at least twenty, or at least thirty days of culturing can be at least 50% greater than the average daily FAME productivity of a wild type or control microorganism while the mutant microorganism exhibits approximately as much biomass productivity as a wild type microorganism (e.g., within about 5% of the amount of biomass productivity of the control microorganism) cultured under identical conditions, which are conditions in which the wild type or control microorganism produces biomass.

A mutant microorganism such as any provided herein that produces at least 25% more lipid than is produced by a control microorganism while producing not less than 45% or not less than about 50% of the biomass produced by the control microorganism when the mutant microorganism and control microorganism are cultured under the same culture conditions can have FAME lipids (FAME)/total organic carbon (TOC) ratios at least 25% higher than the FAME/TOC ratio of a wild type microorganism. The FAME/TOC ratio of a mutant microorganism as provided herein can be, for example, at least 30% higher, at least 40% higher, at least 50% higher, at least 60% higher, or at least 70% higher than the FAME/TOC ratio of a control microorganism cultured under identical conditions under which both the control microorganism and the mutant microorganism produce biomass. The FAME/TOC ratio of a mutant microorganism as provided herein can be, for example, at least 25% higher, at least 30% higher, at least 35% higher, at least 40% higher, at least 45% higher, at least 50% higher, at least 55% higher, at least 60% higher, at least 65% higher, or at least 70% higher than the FAME/TOC ratio of a control microorganism cultured under identical conditions under which both the control microorganism and the mutant microorganism produce biomass, and which are nutrient replete with respect to the wild type microorganism.

A mutant microorganism as provided herein having greater lipid productivity that a control microorganism while producing at least 45% of the biomass of the control microorganism can have attenuated expression of a gene encoding a protein whose attenuated expression affects the expression of other genes, e.g., at least ten, at least twenty, at least thirty, at least forty, at least fifty, at least sixty, at least seventy, at least eighty, at least ninety, or at least 100 additional genes. For example, a mutant as provided herein can have at least ten genes that are upregulated with respect to a wild type microorganism and at least ten genes that are downregulated with respect to a wild type microorganism under conditions in which the mutant phenotype (e.g., greater lipid production) is expressed. A mutant as provided herein can have at least twenty, at least thirty, at least forty, at least fifty, at least sixty, at least seventy, at least eighty, at least ninety, or at least 100 genes that are upregulated with respect to a wild type microorganism and at least twenty, at least thirty, at least forty, at least fifty, at least sixty, at least seventy, at least eighty, at least ninety, or at least 100 genes that are downregulated with respect to a wild type microorganism under conditions in which the mutant phenotype (e.g., greater lipid production with respect to the wild type microorganism) is expressed.

In various examples, mutants as disclosed herein that produces at least 20% more lipid than a control microorganism while producing at least 45% as much biomass as the control microorganism can have attenuated expression of a gene encoding a polypeptide that has a TAZ Zinc Finger domain, e.g., has an amino acid sequence encoding a TAZ Zinc Finger domain characterized as conserved domain c102660 or SMART domain smart00551 or a TAZ Zinc Finger domain belonging to pfam PF02135. In some embodiments, a mutant microorganism as provided herein can have attenuated expression of a gene encoding a polypeptide that includes an amino acid sequence having at least 50%, at least 55%, at least 60%, at least 65%, at least 70%, at least 75%, at least 80%, at least 85%, at least 90%, or at least 95% identity to SEQ ID NO:9. Alternatively or in addition, a mutant microorganism such as any disclosed herein that produces at least 20% more lipid than a control microorganism while producing at least 45% as much biomass as the control microorganism can have attenuated expression of a gene encoding a polypeptide that has a Bromo domain, e.g., can have an amino acid sequence encoding a Bromo domain characterized as conserved domain cd05506 or SMART domain smart00297 or a Bromo domain belonging to pfam PF00439. In some examples, the Bromo domain can include an amino acid sequence having at least 50%, at least 55%, at least 60%, at least 65%, at least 70%, at least 75%, at least 80%, at least 85%, at least 90%, or at least 95% identity to SEQ ID NO:10.

Thus, provided herein in various embodiments are mutant microorganisms having attenuated expression of a gene encoding a polypeptide having a TAZ Zinc Finger domain, in which the mutant microorganism produces at least 20% more lipid and at least 45% as much biomass, and in various embodiments produces at least 90% as much biomass as is produced by a control microorganism that does not have attenuated expression of the gene encoding a polypeptide having a TAZ Zinc Finger domain. For example, a mutant microorganism as provided herein having attenuated expression of a polypeptide having a TAZ Zinc Finger domain can produce at least 30%, at least 35%, at least 40%, at least 45%, at least 50%, or at least 55% more lipid (e.g., FAME) than is produced by a wild type or control microorganism under culture conditions in which both the control and mutant microorganism cultures produce biomass, and the mutant produces at least 45%, at least 50%, at least 60%, at least 70%, at least 80%, at least 90%, or at least 95% of the biomass produced by a control microorganism when the mutant microorganism and control microorganism are cultured under identical conditions under which the control microorganism experiences an increase in TOC. The polypeptide that includes a TAZ Zinc Finger domain in some embodiments can further include a Bromo domain.

Also provided herein is a mutant microorganism having attenuated expression of a gene encoding a polypeptide having a Bromo domain, in which the mutant microorganism produces at least 20% more lipid and at least 45% as much biomass and in various examples at least 90% biomass, as a control microorganism that does not have attenuated expression of the gene encoding a polypeptide having a Bromo domain. For example, a mutant microorganism as provided herein having attenuated expression of a polypeptide having a Bromo domain can produce at least 30%, at least 35%, at least 40%, at least 45%, at least 50%, or at least 55% more lipid (e.g., FAME) than is produced by a wild type or control microorganism under conditions in which both the control and mutant microorganism cultures produce biomass, and the mutant produces at least 45%, at least 50%, at least 60%, at least 70%, at least 80%, at least 90%, or at least 95% of the biomass produced by a control microorganism when the mutant microorganism and control microorganism are cultured under identical conditions under which the control microorganism culture experiences an increase in TOC. The polypeptide that includes a Bromo domain in some embodiments can further include a TAZ Zinc Finger domain.

Alternatively or in addition, a mutant microorganism as provided herein that produces at least 20% more lipid and at least 45% as much biomass as a control microorganism can have attenuated expression of a gene encoding a polypeptide including an amino acid sequence with at least 50%, at least 55%, at least 60%, at least 65%, at least 70%, at least 75%, at least 80%, at least 85%, at least 90%, or at least 95% identity to any of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46. The encoded polypeptide can have at least one TAZ Zinc Finger domain and/or can have at least one Bromo domain. In exemplary embodiments a mutant microorganism as provided herein can have attenuated expression of a gene encoding a polypeptide that includes an amino acid sequence having at least 50%, at least 55%, at least 60%, at least 65%, at least 70%, at least 75%, at least 80%, at least 85%, at least 90%, or at least 95% identity to any of SEQ ID NO:2, SEQ ID NO:4, SEQ ID NO:6, SEQ ID NO:8, SEQ ID NO:12.

An attenuated gene encoding a polypeptide having a TAZ Zinc Finger domain and/or a Bromo domain, or that has 50%, at least 55%, at least 60%, at least 65%, at least 70%, at least 75%, at least 80%, at least 85%, at least 90%, or at least 95% identity to any of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46 can be a gene that has an insertion, deletion, and/or one or more base changes with respect to the wild type gene. The insertion, deletion, or one or more base changes can be in a coding region, intron, 3' untranslated region, or 5' untranslated region of the gene, or can be upstream of the 5' untranslated region of the gene, e.g., in the promoter region of a gene. Alternatively or in addition, a mutant microorganism as provided herein can include an antisense molecule or construct, an RNAi molecule or construct, a guide RNA (gRNA) as part of a CRISPRi system or a construct for expressing a guide RNA, a ribozyme, or construct for producing a ribozyme that targets the gene encoding the polypeptide having a TAZ Zinc Finger domain and/or a Bromo domain or having at least 50% identity to any of the recited sequences, wherein the presence or expression of the construct results in reduced expression of the gene.

A mutant microorganism as provided herein can be any eukaryotic microorganism, and in some examples is a heterokont or alga. For example, the mutant microorganism can be a *Labyrinthulomycte* species, such as, for example, a species of *Labryinthula, Labryinthuloides, Thraustochytrium, Schizochytrium, Aplanochytrium, Aurantiochytrium, Oblongichytrium, Japonochytrium, Diplophrys*, or *Ulkenia*. Alternatively a mutant microorganism can be an algal species such as for example, a species belonging to any of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phwodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox* In some examples, the mutant alga is a heterokont alga, and may belong to the diatoms (bacillariophytes), *eustigmatophytes*, xanthophytes, phaeophytes, chrysophytes, or raphidophytes. In some examples, the mutant alga is a diatom and belongs to a genus such as but not limited to *Amphiprora, Amphora, Chaetoceros, Cyclotella, Fragilaria, Fragilaropsis, Hantzschia, Navicula, Nitzschia, Phæodactylum, Phæodactylum, Skeletonema*, and *Thalassiosira*. In some examples, the mutant alga is a Eustigmatophyte and belongs to a genus selected from the group consisting of *Chloridella, Chlorobptrys, Ellipsoidion, Eustigmatos, Goniochloris, Monodopsis, Monodus, Nannochloropsis, Pseudocharaciopsis, Pseudostaruastrum, Pseudotetraedriella*, and *Vischeria*. In some examples, the mutant alga cell is a *Nannochloropsis* species.

A further aspect is a method of producing lipid, comprising culturing a mutant microorganism as provided herein and isolating lipid from the microorganism, the culture medium, or both. The culture medium can be nutrient replete with respect to a control (e.g. wild type) microorganism. In some embodiments of the method the mutant microorganism can be cultured in a medium that comprises less than about 5 mM ammonium, for example, less than about 2.5 mM ammonium, less than or equal to about 1.5 mM ammonium, less than or equal to about 2 mM ammonium, less than or equal to about 1.5 mM ammonium, less than or equal to about 1 mM ammonium, or less than or equal to about 0.5 mM. The culture medium can include, for example, from about 0 to about 5 mM ammonium, from about 0 to about 4 mM ammonium, from about 0 to about 3 mM ammonium, from about 0 to about 2.5 mM ammonium, from about 0.1 to about 2.5 mM ammonium, from about 0.5 to about 2.5 mM ammonium, from about 0 to about 2 mM ammonium, from about 0.1 to about 2 mM ammonium, from about 0.2 to about 2 mM ammonium, from about 0.5 to about 1.5 mM ammonium, from about 0.1 to about 1.5 mM ammonium, from about 0.2 to about 1.5 mM ammonium, from about 0.5 to about 1.5 mM ammonium, from about 1 mM to about 1.5 mM ammonium, from about 0.1 to about 1.5 mM ammonium, or from about 0.2 to about 1 mM ammonium. The microorganism can be cultured in a medium that includes nitrate, which in some examples may be substantially the sole nitrogen source in the culture medium or may be present in addition to ammonium that may be present at a concentration of less than 5 mM, less than 2.5 mM, less than 2 mM, less than 1.5 mM, or less than 1 mM. In some examples the mutant microorganism is a mutant alga and the microorganism is exposed to light during at least a portion of the culturing period. In some examples the mutant microorganism is a mutant alga and the microorganism is cultured under photoautotrophic conditions e.g., conditions in which inorganic carbon is substantially the sole carbon source in the culture medium. The method can further include extracting lipid from the microorganism, the culture medium, or both.

Yet another aspect of the disclosure is a nucleic acid molecule comprising a nucleic acid sequence encoding a polypeptide including an amino acid sequence having at least 50%, at least 55%, at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46. For example, the nucleic acid molecule can have at least 30%, at least 35%, at least 40%, at least 45%, at least 50%, at least 55%, at least 60%, at least 65%, at least 70%, or at least 75%, at least 80%, at least 85%, at least 90%, or at least 95% identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45.

The encoded polypeptide encoded by a nucleic acid molecule as provided herein can include an amino acid sequence encoding a TAZ Zinc Finger domain and/or can include an amino acid sequence encoding a Bromo domain. The nucleic acid molecule in various examples can be or comprise a cDNA and/or can lack one or more introns present in the naturally-occurring gene, or, alternatively or in addition, the nucleic acid molecule can include one or more introns not present in the naturally-occurring gene. The nucleic acid molecule in various examples can have a sequence that is not 100% identical to a naturally-occurring gene. The nucleic acid molecule in various examples can comprise a heterologous promoter operably linked to the sequence encoding a polypeptide that includes an amino acid sequence having at least 30%, at least 35%, at least 40%, at least 45%, at least 50%, at least 55%, at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46 and/or can comprise a vector that includes a sequence encoding a polypeptide that includes an amino acid sequence having at least 50%, at least 55%, at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46. For example, the nucleic acid molecule can be a cDNA, expression cassette, or vector comprising a nucleic acid sequence having at least 50%, at least 55%, at least 60%, at least 65%, at least 70%, or at least 75%, at least 80%, at least 85%, at least 90%, or at least 95% identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45.

A further aspect is a construct designed for attenuating expression of a gene encoding a polypeptide containing a TAZ Zinc Finger domain and/or a Bromo domain. The construct can be or comprise, in various examples, a sequence encoding a guide RNA of a CRISPR system, an RNAi construct, an antisense construct, a ribozyme construct, or a construct for homologous recombination, e.g., a construct having one or more nucleotide sequences having homology to a naturally-occurring TAZ Zinc Finger domain-encoding and/or Bromo domain-encoding gene as disclosed herein and/or sequences adjacent thereto in the native genome from which the gene is derived. For example, the construct can include at least a portion of a gene that encodes a polypeptide having a TAZ Zinc Finger domain and/or Bromo domain or a sequence homologous to at least a portion of an gene that encodes a polypeptide that includes an amino acid sequence having at least 50%, at least 55%, at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46, including a nucleic acid sequence complementary to the coding strand of a gene or portion thereof. Alternatively or in addition, the construct can include a sequence having at least 30%, at least 35%, at least 40%, at least 45%, at least 50%, at least 55%, at least 60%, least 65%, at least 70%, at least 75%, at least 80%, at least 85% at least 90%, or at least 95% identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45, or a portion thereof, including a sequence complementary to the coding strand of any of SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45, a sequence having at least least 30%, at least 35%, at least 40%, at least 45%, at least 50%, at least 55%, at least 60%, least 65%, at least 70%, at least 75%, at least 80%, at least 85% at least 90%, or at least 95% identity to any thereof or to a portion of any thereof.

Also included is a guide RNA targeting a gene encoding a polypeptide having at least 50%, at least 55%, at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46 or guide RNA targeting a gene having at least 30%, at least 35%, at least 40%, at least 45%, at least 50%, at least 55%, at least 60%, least 65%, at least 70%, at least 75%, at least 80%, at least 85% at least 90%, or at least 95% identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45, or a portion thereof. In particular embodiments the invention provides a guide RNA that includes a sequence corresponding to the target sequence of any of SEQ ID NO:61, SEQ ID NO:68, SEQ ID NO:70, and SEQ ID NO:72, and in exemplary embodiments may be a chimeric guide such as any of SEQ ID NO:60, SEQ ID NO:67, SEQ ID NO:69, and SEQ ID NO:71.

These and other objects and features of the invention will become more fully apparent when the following detailed description of the invention is read in conjunction with the accompanying drawings.

BRIEF DESCRIPTION OF THE DRAWINGS

FIGS. 2A-2C are an alignment of the four Bromo-1091 isoforms encoded by four Bromo-1091 transcripts of the *N. gaditana* Bromo-1091 gene. FIG. 2A) provides the N-terminal portions of the polypeptides; FIG. 2B) provides the invariant central portion of the polypeptides; and C) provides the C terminal regions of the polypeptides.

FIG. 4A) is a graph depicting FAME productivity of wild-type and Bromo-1091 knockout *N. gaditana* cells cultured in batch mode in nitrate-only medium as determined from samples taken on odd days (3, 5, and 7) of the culture; FIG. 4B) is a graph depicting TOC values for days 3-7 of the batch productivity assay. FIG. 4C) is a graph depicting FAME/TOC ratios calculated from samples taken on odd days of the culture. Error bars in graphs represent the standard deviation of the three independent cultures (biological replicates). Symbols used in graphs: asterisks represent wild type WT-3730 pre-cultured in nitrate-plus-ammonium medium PM124, black diamonds represent knockout mutant GE-8563 pre-cultured in nitrate-plus-ammonium medium PM124, X's represent wild type WT-3730 pre-cultured in nitrate-only medium PM074, and black circles represent knockout mutant GE-8563 pre-cultured in nitrate-only medium PM074.

FIG. 5A) shows daily FAME productivity over seven days of the assay; FIG. 5B) shows daily TOC productivity over the same seven days of the assay; and FIG. 5C) provides the FAME/TOC ratios for the same seven days of the assay. Error bars in graphs represent the standard deviation of the three independent cultures (biological replicates). Symbols used in graphs: circles represent wild type WT-3730 and Xs represent knockout mutant GE-8563.

FIGS. 8A-8F provides tables and graphs depicting productivities of the *N. gaditana* wild type strain and Bromo-1091 knockdown strains in a semi-continuous assay in which the culture medium used for daily dilution includes nitrate as the sole nitrogen source. FIG. 8A) is a table of average FAME productivity from three cultures of each Bromo-1091 knockdown strain as well as wild type strain WT-3730 on each day of the ten day semi-continuous assay, standard deviations for the three culture averages are in parentheses; FIG. 8B) is a graph showing average daily FAME productivities (mg/L culture) over the ten days of the assay; FIG. 8C) is a table of average TOC productivity from three cultures of each Bromo-1091 knockdown strain as well as wild type strain WT-3730 on each day of the ten day semi-continuous assay, standard deviations for the three culture averages are in parentheses; FIG. 8D) is a graph showing the daily TOC productivities of the cultures in g/m²/day over ten days of the assay; FIG. 8E) is a table providing the FAME/TOC ratios for each day of the assay; and FIG. 8F) is a graph providing the daily FAME/TOC ratios of the cultures over ten days of the assay. Symbols used in graphs: circles represent wild type WT-3730; triangles represent "BASH-1" knockdown mutant GE-13127; Xs represent "BASH-4" knockdown mutant GE-13130; and diamonds represent "BASH-5" knockdown mutant GE-13132. Error bars in graphs represent the standard deviation of the three independent cultures (biological replicates).

FIG. 11A) depicts relative transcript abundance in the presence of ammonium. Left to right: Bromo 1091 knockdown strain GE-13032 sample 1, Bromo 1091 knockdown strain GE-13032 sample 2, ZnCys-2845 knockout strain GE-8564 sample 1, ZnCys-2845 knockout strain GE-8564 sample 2, Cas9 parental strain sample 1, and Cas9 parental strain sample 2; FIG. 11B) depicts relative transcript abundance in the presence of nitrate. Left to right: Bromo 1091 knockdown strain GE-13032 sample 1, Bromo 1091 knockdown strain GE-13032 sample 2, ZnCys-2845 knockout strain GE-8564 sample 1, ZnCys-2845 knockout strain GE-8564 sample 2, NR knockout strain sample 1, NR knockout sample 2, Cas9 parental strain sample 1, and Cas9 parental strain sample 2.

DETAILED DESCRIPTION

Definitions

Figure 1A:
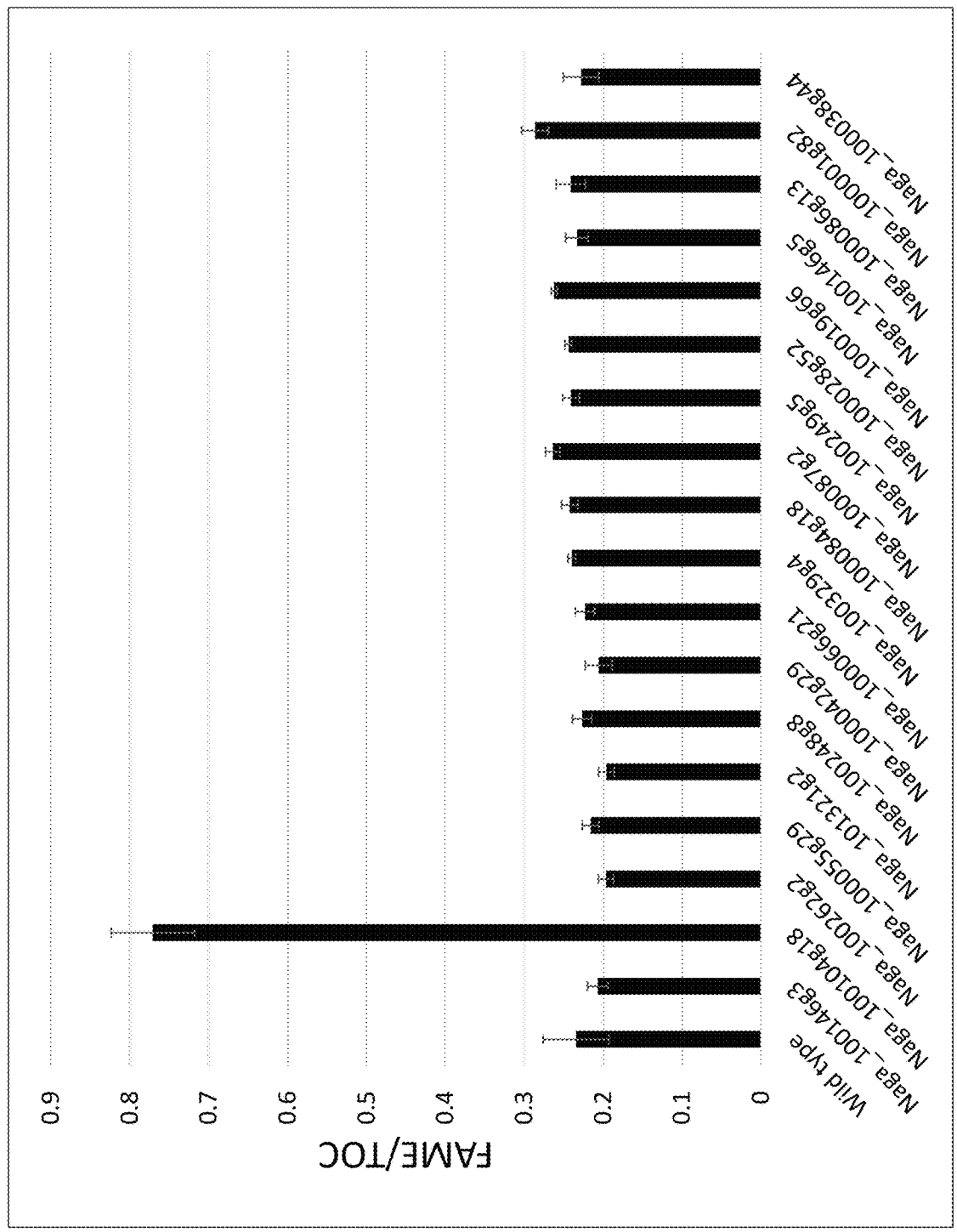
FIG. 1A is a graph showing the FAME/TOC ratio of wild type *Nannochloropsis gaditana* strain WT-3730 grown in batch assay on nitrate-containing culture medium alongside the FAME to TOC rations of eighteen mutant strains, each of which knocked out (has a gene disrupting insertion) in a transcription factor gene whose genome locus is provided under each column along the x axis of the graph. Of the eighteen strains assayed, only the strain knocked out in the gene identified as the Naga_100104 g18 has a higher FAME/TOC ratio than wild type.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All ranges provided within the application are inclusive of the values of the upper and lower ends of the range unless specifically indicated otherwise.

All publications, patents and other references mentioned herein are incorporated by reference in their entireties for all purposes as if each individual publication or patent application were specifically and individually indicated to be incorporated by reference.

The term "and/or" as used in a phrase such as "A and/or B" herein is intended to include "A and B", "A or B", "A", and "B".

"About" means either within 10% of the stated value, or within 5% of the stated value, or in some cases within 2.5% of the stated value, or, "about" can mean rounded to the nearest significant digit.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, "gene" may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids and other modified nucleic acids or nucleic acid analogs (e.g., Efimov and Chakhmakhcheva (2005) Methods Mol Biol. 288: 147-163)) or modified or non-naturally-occurring nucleobases. The nucleic acid molecules can be double-stranded or single-stranded; a single stranded nucleic acid molecule that comprises a gene or a portion thereof can be a coding (sense) strand or a non-coding (antisense) strand.

A nucleic acid molecule may be "derived from" an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source, which may be, for example, a species of organism. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other gene synthesis or molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 65%, at least 70%, at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be substantially free of chemicals beyond buffer or solvent, for example "Substantially free" is not intended to mean that other components beyond the novel nucleic acid molecules are undetectable.

The terms "naturally-occurring" and "wild type" refer to a form found in nature. For example, a naturally occurring or wild type nucleic acid molecule, nucleotide sequence or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, truncation, frameshifting, or insertional mutation) that does not encode a complete functional open reading frame or that has decreased expression due to alteration or disruption of gene regulatory sequences. An attenuated gene may also be a gene targeted by a construct that reduces expression of the gene, such as, for example, an antisense RNA, microRNA, RNAi molecule, or ribozyme. Attenuated gene expression can be gene expression that is eliminated, for example, reduced to an amount that is insignificant or undetectable. Attenuated gene expression can also be gene expression that results in an RNA or protein that is not fully functional or nonfunctional, for example, attenuated gene expression can be gene expression that results in a truncated RNA and/or polypeptide.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene or nucleic acid molecule may be derived from a different species (and so "heterologous"), or from the same species (and so "homologous"), relative to the cell being transformed. An "endogenous" nucleic acid molecule, gene or protein is a native nucleic acid molecule, gene, or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. Thus, a "non-native" nucleic acid molecule is a nucleic molecule that is not naturally present in the host cell, for example, the non-native nucleic acid molecule is exogenous to the host cell or microorganism into which it is introduced, and may be heterologous with respect to the host cell or microorganism. Additionally, a nucleic acid sequence or amino acid sequence that has been removed from a cell, subjected to laboratory manipulation, and introduced or reintroduced into a host cell such that it differs in sequence or location in the genome with respect to its position in a non-manipulated organism (i.e., is juxtaposed with or operably linked to sequences it is not juxtaposed with or operably linked to in a non-transformed organism) is considered "non-native". Non-native genes also include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering regardless of whether the amino acid varies from that of a wild-type protein.

When applied to organisms, the term recombinant, engineered, or genetically engineered refers to organisms that have been manipulated by introduction of a heterologous or exogenous recombinant nucleic acid sequence into the organism (e.g., a non-native nucleic acid sequence), and includes gene knockouts, targeted mutations, gene replacement, and promoter replacement, deletion, disruption, or insertion, as well as introduction of transgenes or synthetic genes or nucleic acid sequences into the organism. That is, recombinant, engineered, or genetically engineered refers to organisms that have been altered by human intervention. Recombinant or genetically engineered organisms can also be organisms into which constructs for gene "knockdown" have been introduced. Such constructs include, but are not limited to, RNAi, microRNA, shRNA, siRNA, antisense, and ribozyme constructs. Also included are organisms whose genomes have been altered by the activity of meganucleases, zinc finger nucleases, TALENs, or cas/CRISPR systems. An exogenous or recombinant nucleic acid molecule can be integrated into the recombinant/genetically engineered organism's genome or in other instances may not be integrated into the host genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bidirectional (initiate transcription in either direction). A promoter may be a constitutive promoter, a repressible promoter, or an inducible promoter. A promoter region can include, in addition to the gene-proximal promoter where RNA polymerase binds to initiate transcription, additional sequences upstream of the gene that can be within 1 kb, 2 kb, 3 kb, 4 kb, 5 kb or more of the transcriptional start site of a gene, where the additional sequences can influence the rate of transcription of the downstream gene and optionally the responsiveness of the promoter to developmental, environmental, or biochemical (e.g., metabolic) conditions.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

Gene and protein Accession numbers, commonly provided in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics. Gene loci identifiers refer to the published genome described in Corteggiani Carpinelli et al. (2014) *Mol Plant* 7:323-335 and available online at nannochloropsis.org.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. For polypeptide sequences, N-terminal or C-terminal insertions or deletions shall not be construed as affecting homology, and internal deletions and/or insertions into the polypeptide sequence of less than about 65, less than about 60, less than about 50, less than about 40, less than about 30, less than about 20, or less than about 10 amino acid residues shall not be construed as affecting homology of compared amino acid (protein) sequences. For nucleic acid sequences, 5' end or 3' end insertions or deletions shall not be construed as affecting homology, and internal deletions and/or insertions into the polypeptide sequence of less than about 200, less than about 180, less than about 150, less than about 120, less than about 100, less than about 90, less than about 80, less than about 70, less than about 60, less than about 50, less than aobut 40, or less than about 30 nucleotides shall not be construed as affecting homology of compared nucleic acid sequences. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present invention, included are sequence identities of at least 40%, at least 45%, at least 50%, at least 55%, of at least 70%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" [of a gene product] includes an increase in the amount of polypeptide expression, in the level of the enzymatic activity of a polypeptide, or a combination of both, as compared to the native production or enzymatic activity of the polypeptide.

Some aspects of the present invention include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site directed homologous recombination or targeted integration or mutation using a cas/CRISPR system to knockout a particular gene of interest. In still other embodiments, targeted insertion into or mutation of a gene regulatory region using a cas/CRISPR system, RNAi, or antisense DNA (asDNA) constructs may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified", "genetically engineered" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

As used herein, "mutant" refers to an organism that has a mutation in a gene that is the result of classical mutagenesis, for example, using gamma irradiation, UV, or chemical mutagens. "Mutant" as used herein also refers to a recombinant cell that has altered structure or expression of a gene as a result of genetic engineering that many include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild type polypeptide, and/or dominant negative polypeptides); gene attenuation via RNAi, antisense RNA, or ribozymes, or the like; and genome engineering using meganucleases, TALENs, and/or CRISPR technologies, and the like. A mutant is therefore not a naturally-occurring organism. A mutant organism of interest will typically have a phenotype different than that of the corresponding wild type or progenitor strain that lacks the mutation, where the phenotype can be assessed by growth assays, product analysis, photosynthetic properties, biochemical assays, etc. When referring to a gene "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region, e.g., within 2 kb of the transcriptional start site or within 3 kb or the translational start site. For example, a mutant having attenuated expression of a gene as disclosed herein can have a mutation, which can be one or more nucleobase changes and/or one or more nucleobase deletions and/or one or more nucleobase insertions, into the region of a gene 5' of the transcriptional start site, such as, in non-limiting examples, within 2 kb, within 1.5 kb, within 1 kb, or within 0.5 kb of the known or putative transcriptional start site, or within 3 kb, within 2.5 kb, within 2 kb, within 1.5 kb, within 1 kb, or within 0.5 kb of the translational start site. As nonlimiting examples, a mutant gene can be a gene that has a mutation, insertion, or deletion within the promoter region that can either increase or decrease expression of the gene; can be a gene that has a deletion that results in production of a nonfunctional protein, truncated protein, dominant negative protein, or no protein; can be a gene that has one or more point mutations leading to a change in the amino acid of the encoded protein or results in aberrant splicing of the gene transcript, etc.

Conserved domains of polypeptides include those identified in the "cd" (conserved domain) database, the COG database, the SMART database, the PRK database, the TIGRFAM database, or others known the art. The National Center for Biotechnology Information website (ncbi.nlm.nih.gov/Structure/cdd/wrpsb.cgi) sponsored by the U.S. National Institutes of Health includes a conserved domain database (CDD) which it describes as "a protein annotation resource that consists of a collection of well-annotated multiple sequence alignment models for ancient domains and full-length proteins. These are available as position-specific score matrices (PSSMs) for fast identification of conserved domains in protein sequences via RPS-BLAST. CDD content includes NCBI-curated domains, which use 3D-structure information to explicitly define domain boundaries and provide insights into sequence/structure/function relationships, as well as domain models imported from a number of external source databases (Pfam, SMART, COG, PRK, TIGRFAM)." Sequences can be searched for conserved domains at the cdd database of NCBI (ncbi.nlm.nih.gov/Structure/cdd/wrpsb.cgi). See, Marchler-Bauer et al. (2015) *Nucleic Acids Res.* 43(D) 222-226.

The term "Pfam" refers to a large collection of protein domains and protein families maintained by the Pfam Consortium and available at several sponsored world wide web sites, including: pfam.sanger.ac.uk/ (Welcome Trust, Sanger Institute); pfam.sbc.su.se (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr. The latest release of Pfam is Pfam 30.0 (June 2016) based on the UniProt protein database release 2012_06. Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) *Nucleic Acids Research* 26, 263-266; Bateman (2004) *Nucleic Acids Research* 32, Database Issue, D138-D141; Finn (2006) *Nucleic Acids Research* Database Issue 34, D247-251; Finn (2010) *Nucleic Acids Research* Database Issue 38, D211-222). By accessing the Pfam database, for example, using any of the above-reference websites, protein sequences can be queried against the HMMs using HMMER homology search software (e.g., HMMER2, HMMER3, or a higher version, hmmer.janelia.org/). Significant matches that identify a queried protein as being in a pfam family (or as having a particular Pfam domain) are those in which the bit score is greater than or equal to the gathering threshold for the Pfam domain Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be double stranded or single stranded and can be, for example, the complement of the mRNA sequence. In preferred examples, a cDNA does not include one or more intron sequences that occur in the naturally-occurring gene that the cDNA corresponds to (i.e., the gene as it occurs in the genome of an organism). For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences or compiled from the sequences multiple partial cDNAs.

Reference to properties that are "substantially the same" or "substantially identical" without further explanation of the intended meaning, is intended to mean the properties are within 10%, and preferably within 5%, and may be within 2.5%, of the reference value. Where the intended meaning of "substantially" in a particular context is not set forth, the term is used to include minor and irrelevant deviations that are not material to the characteristics considered important in the context of the subject matter of the invention.

A "control cell" or "control microorganism" is either a wild type cell or microorganism from which the mutant microorganism (genetically engineered or mutagenized microorganism) is directly or indirectly derived, or is a cell or microorganism that is substantially identical to the mutant cell or microorganism referred to (i.e., of the same genus and species, preferably of the same strain) with the exception that the control cell or microorganism does not have the mutation resulting in increased lipid production that the subject microroganism has. For example, where the mutant microorganism has attenuated expression of a gene encoding a polypeptide that includes a TAZ zinc finger domain and/or a Bromo domain or a gene encoding a polypeptide having at least 50%, at least 55%, at least 60%, at least 65%, at least 70%, at least 75%, at least 80%, at least 85%, at least 90%, or at least 95% identity to any of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46, a control cell can be substantially identical to the mutant microorganism with the exception that the control microorganism does not have attenuated expression of a gene encoding a polypeptide that includes a TAZ zinc finger domain and/or a Bromo domain or a gene encoding a polypeptide having at least 50%, at least 55%, at least 60%, at least 65%, at least 70%, at least 75%, at least 80%, at least 85%, at least 90%, or at least 95% identity to any of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46.

"The same conditions" or "the same culture conditions", as used herein, means substantially the same conditions, that is, any differences between the referenced conditions that may be present are minor and not relevant to the function or properties of the microorganism that are material to the invention, including lipid production or biomass production.

As used herein "lipid" or "lipids" refers to fats, waxes, fatty acids, fatty acid derivatives such as fatty alcohols, wax esters, alkanes, and alkenes, sterols, monoglycerides, diglycerides, triglycerides, phospholipids, sphingolipids, saccharolipids, and glycerolipids. "FAME lipids" or "FAME" refers to lipids having acyl moieties that can be derivatized to fatty acid methyl esters, such as, for example, monoacylglycerides, diacylglycerides, triacylglycerides, wax esters, and membrane lipids such as phospholipids, galactolipids, etc. Lipid productivity can be assessed as FAME productivity in milligrams per liter (mg/L) and for algae, may be reported as grams per meter$^2$ per day (g/m$^2$/day). In the semi-continuous assays provided herein, mg/L values are converted to g/m2/day by taking into account the area of incident irradiance (the SCPA flask rack aperture of 1½"×33/8", or 0.003145 m$^2$) and the volume of the culture (550 ml). To obtain productivity values in g/m$^2$/day, mg/L values are multiplied by the daily dilution rate (30%) and a conversion factor of 0.175. Where lipid or subcategories thereof (for example, TAG or FAME) are referred to as a percentage, the percentage is a weight percent unless indicated otherwise.

"Biomass" refers to cellular mass, whether of living or dead cells, and can be assessed, for example, as aspirated pellet weight, but is more preferably dry weight (e.g., lyophilate of a culture sample or pelleted cells), ash-free dry weight (AFDW), or total organic carbon (TOC), using methods known in the art. Biomass increases during the growth of a culture under growth permissive conditions and may be referred to as "biomass accumulation" in batch cultures, for example. In continuous or semi-continuous cultures that undergo steady or regular dilution, biomass that is produced that would otherwise accumulate in the culture is removed during culture dilution. Thus, daily biomass productivity (increases in biomass) by these cultures can also be referred to as "biomass accumulation". Biomass productivity can be assessed as TOC productivity in milligrams per liter (mg/L) and for algae, may be reported as grams per meter$^2$ per day (g/m$^2$/day). In the semi-continuous assays provided herein, mg/L values are converted to g/m2/day by taking into account the area of incident irradiance (the SCPA flask rack aperture of 1½"×33/8", or 0.003145 m$^2$) and the volume of the culture (550 ml). To obtain productivity values in g/m$^2$/day, mg/L values are multiplied by the daily dilution rate (30%) and a conversion factor of 0.175. Where biomass is expressed as a percentage, the percentage is a weight percent unless indicated otherwise.

In the context of the invention, a "nitrogen source" is a source of nitrogen that can be taken up and metabolized by the subject microorganism and incorporated into biomolecules for growth and propagation. For example, compounds including nitrogen that cannot be taken up and/or metabolized by the microorganism for growth (e.g., nitrogen-containing biological buffers such as Hepes, Tris, etc.) are not considered nitrogen sources in the context of the invention.

"Reduced nitrogen", as used herein, is nitrogen in the chemical form of ammonium, ammonia, urea, or an amino acid (e.g., an amino acid that can be taken up and metabolized by the microorganism being cultured to provide a source of nitrogen for incorporation into biomolecules, thereby supporting growth). Examples of amino acids that may be nitrogen sources can include, without limitation, glutamate, glutamine, histidine, proline, lysine, arginine, asparagine, alanine, and glycine. "Non-reduced nitrogen" in the context of a nitrogen source that can be present in a culture medium for microorganisms refers to nitrate or nitrite that must be reduced prior to assimilation into organic compounds by the microorganism.

"The sole source of nitrogen [in the culture medium]" is used interchangeably with "substantially the sole source of nitrogen" and indicates that no other nitrogen source that can be metabolized by the microorganism (i.e., the nitrogen source provides nitrogen that can be taken up by the microorganism and incorporated by the microorganism into biomolecules such as proteins and nucleic acids) is intentionally added to the culture medium, or that no other nitrogen source is present in an amount sufficient to significantly increase the growth of the microorganisms or cells cultured in the referenced medium. Throughout this application, for brevity, the terms "nitrate-only" is used to characterize culture media in which nitrate is the only source of nitrogen that is available to the microorganisms for supporting growth.

Similarly, "the sole source of carbon [in the culture medium]" is used interchangeably with "substantially the sole source of carbon" and indicates that no other carbon source that can be metabolized by the microorganism (i.e., used for energy or for as a carbon source for the production of biomolecules) is present in an amount sufficient to increase the productivity, growth, or propagation of the microorganisms or cells cultured in the referenced medium or that can become incorporated into biomolecules such as lipids produced by the microorganisms or cells at a percentage of greater than 5% of the carbon incorporated into the biomolecule.

"Nitrogen replete" conditions refer to media conditions in which no further growth or propagation benefit is conferred by adding additional nitrogen (in a form that can be used by the microorganism) to the medium. Similarly, "nutrient replete" conditions refer to media conditions in which no nutrient is limiting to growth or propagation, that is, when a medium is nutrient replete, adding additional nutrient(s) to the medium does not result in an improved growth or propagation rate. In the context of "nutrient replete", "nutrients" includes, as nonlimiting examples, phosphate, sulfur, iron, and optionally silica, but excludes carbon sources such as sugars or organic acids that may be used by the organism as an energy source.

Disclosed herein are methods for manipulating, assaying, culturing, and analyzing microorganisms. The invention set forth herein also makes use of standard methods, techniques, and reagents for cell culture, transformation of microorganisms, genetic engineering, and biochemical analysis that are known in the art. Although methods and materials similar or equivalent to those described herein can be used in practice or testing of the present invention, suitable methods and materials are described below. The materials, methods, and examples are illustrative only and are not intended to be limiting. Other features and advantages of the invention will be apparent from the detailed description and from the claims.

All references cited herein are incorporated by reference in their entireties. All headings are for the convenience of the reader and do not limit the invention in any way. References to aspects or embodiments of the invention do not necessarily indicate that the described aspects may not be combined with other described aspects of the invention or features of other aspects of the invention.

Mutant Microorganisms Having Increased Lipid Productivity

The invention provides mutant microorganisms (for example, microorganisms obtained by classical mutagenesis or genetic engineering) having at least 20% higher lipid productivity with respect to a control microorganism while producing at least 45% of the biomass produced by the control microorganism when both the mutant microorganism and control microorganism are cultured under substantially identical conditions in which the control microorganism culture produces biomass, for example, under culture conditions in which both the mutant and control microorganism are producing biomass. The culture conditions under which a mutant microorganism as provided herein produces at least 20% more lipid and at least 45% as much biomass as a control microorganism can be nitrogen replete, and can be nutrient replete, with respect to the control microorganism. In some embodiments the control microorganism is a wild type microorganism of the same species from which the mutant is directly or indirectly derived, and the culture conditions under which a mutant microorganism as provided herein produces at least 20% more lipid and at least 45% as much biomass as a wild type microorganism are nitrogen replete, and can be nutrient replete, with respect to the wild type microorganism.

A mutant microorganism as provided herein can demonstrate greater lipid productivity than a control microorganism and at least 45% of the biomass productivity (e.g., average daily biomass productivity) of the control microorganism over a culture period of at least three days, for example, over a culture period of at least four, at least five, at least six, at least seven, at least eight, at least nine, at least ten, at least eleven, at least twelve, at least thirteen, at least fourteen, at least fifteen, at least twenty, at least thirty, or at least sixty days when the mutant microorganism and the control microorganism are cultured under substantially identical conditions that support growth and propagation of the control microorganism, i.e., under conditions in which the control microorganism culture produces biomass. In some examples the culture period in which a mutant microorganism as provided herein produces at least 45% of the biomass and produces at least 20% more lipid with respect to a control microorganism can be less than 180 days, less than 120 days, or less than 90 days, where the mutant can have a higher average daily lipid productivity over the time period. For example, a mutant microorganism as provided herein can produce at least 45% of the biomass and at least 20% more lipid than a control microorganism during a culture period of from three to 90 days, from three to 60 days, from three to thirty days, or from three to fifteen days. For example, a mutant microorganism as provided herein can produce at least 45% of the biomass and at least 20% more lipid than a control microorganism during a culture period ranging from five to 90 days, from five to 60 days, from five to thirty days, or from five to fifteen days, or from seven to 90 days, from seven to 60 days, from seven to thirty days, from seven to twenty days, or from seven to at least fifteen days.

Productivity can be volumetric productivity, for example, the productivity of a culture can be expressed as weight per milliliter or liter of culture, and can be a daily productivity (e.g., mg/liter/day or g/liter/day), for example, an average daily productivity over multiple days of the culture (for example, at least three, four, five, six, seven, eight, nine, ten, eleven, twelve, thirteen, fourteen fifteen, or more days), or can be a total amount produced per unit volume for a defined period of time in culture. Productivity is preferably measured multiple times during the culture period, for example, at least twice or at least three times, and may be assessed every day, every other day, every third day, etc.

Biomass productivity can be assessed, for example, by measuring total organic carbon (TOC) or by other methods, such as measuring dry weight, ash-free dry weight (AFDW). Methods for measuring TOC are known in the art (e.g., U.S. Pat. No. 8,835,149) and are provided herein. Methods of measuring AFDW are also well-known and can be found, for example, in U.S. Pat. No. 8,940,508, incorporated herein by reference in its entirety.

Methods of measuring the amount of lipid produced by microorganisms are also well-known in the art and provided in the examples herein. For example, total extractable lipid can be determined according to Folch et al. (1957) *J. Biol. Chem.* 226: 497-509; Bligh & Dyer (1959) *Can. J. Biochem. Physiol.* 37: 911-917; or Matyash et al. (2008) *J. Lipid Res.*

49:1137-1146, for example, and the percentage of biomass present as lipid can also be assessed using Fourier transform infrared spectroscopy (FT-IR) (Pistorius et al. (2008) *Biotechnol & Bioengin*. 103:123-129). Additional references for gravimetric analysis of FAME and TAGs are provided in U.S. Pat. No. 8,207,363 and WO 2011127118 for example, each incorporated herein by reference in its entirety.

A mutant as provided herein can produce, in various embodiments, at least 20%, at least 25%, at least 30%, at least 35%, at least 40%, at least 45%, at least 50%, at least 55%, at least 60%, at least 65%, at least 70%, at least 80%, at least 90%, or at least 100% more lipid with respect to a control microorganism under culture conditions in which both the mutant and control microorganism are producing biomass and the mutant produces at least 45%, at least 50%, at least 55%, at least 60%, at least 65%, at least 70%, at least 75%, at least 80%, at least 85%, at least 90%, at least 95%, at least 100%, at least 105%, at least 110%, or at least 115% of the biomass produced by a wild type microorganism per day averaged over at least three, at least five, at least seven, at least nine, at least ten, at least twelve, at least thirteen, or at least fourteen days. In some embodiments, a mutant microorganism as provided herein produces higher amounts of lipid with respect to a control microorganism and at least 45% of the biomass but less than 150%, less than 200%, less than 250%, or less than 300% of the biomass produced by the control microorganism. In some embodiments, a mutant microorganism as provided herein produces at least 45% of the biomass with respect to a control microorganism and at least 20% more lipid but not more than 100%, not more than 150%, not more than 200% more lipid than is produced by the control microorganism.

In various examples, a mutant microorganism as provided herein produces an average of at least 25% more FAME lipids per day, for example, at least 30%, at least 35%, at least 40%, at least 45%, at least 50%, at least 55%, at least 60%, at least 65%, at least 70%, at least 80%, at least 90%, or at least 100% more lipid per day with respect to a control microorganism while producing not less than an average of about 50% of the biomass produced by the control microorganism per day, and can produce at least 50%, at least 55%, at least 60%, at least 65%, at least 70%, at least 75%, at least 80%, at least 85%, at least 90%, at least 95%, at least 100%, at least 105%, at least 110%, or at least 115% of the biomass produced by a wild type microorganism per day, when the mutant microorganism and control microorganism are cultured under the same culture conditions under which the culture of the control microorganism produces biomass, where the culture conditions are nitrogen-replete, and are preferably nutrient replete culture conditions with respect to the control microorganism, over a period of at least three days, at least four days, at least five days, at least seven days, at least ten days, at least twelve days, or at least fourteen days. The culture conditions can include culturing in a culture medium that includes less than about 3 mM, less than about 2.5 mM, less than about 2 mM, or less than about 1.5 mM of a reduced nitrogen source such as ammonium. Alternatively or in addition, the culture conditions can include culturing in a culture medium that includes nitrate as substantially the sole source of nitrogen. The control microorganism in some examples is a wild type microorganism, e.g., a wild type microorganism from which the mutant microorganism is directly or indirectly derived.

In some embodiments, a mutant microorganism as disclosed herein can be an algal or heterokont cell that produces at least 25% more FAME while producing at least 45% of the amount of TOC as a control microorganism in a culture medium that includes less than about 5 mM, less than about 4.5 mM, less than about 4 mM, less than about 3.5 mM, less than about 3 mM, about 2.5 mM ammonium or less, about 2.0 mM ammonium or less, about 1.5 mM ammonium or less, about 1.0 mM ammonium or less, about 0.5 mM ammonium or less, or substantially no ammonium, and includes, for example, at least 1.0 mM, at least 2.0 mM, at least 3.0 mM, at least 4.0 mM, at least 5.0 mM, at least 6.0 mM, at least 7.0 mM, at least 8.0 mM, or at least 10.0 mM nitrate. For example, the ammonium concentration may be at a concentration ranging from about 0 to about 5 mM, from about 0 to about 4.0 mM, from about 0 to about 3 mM, from about 0 to about 2.5 mM, from about 0 to about 2.0 mM, from about 0 to about 1.5 mM, from about 0 to about 1.0 mM, or from about 0 to about 0.5 mM. The ammonium concentration may be at a concentration ranging from about 0.2 to about 3 mM, 0.2 to about 2.5 mM, from about 0.2 to about 2.0 mM, from about 0.2 to about 1.5 mM, about 0.2 to about 1 mM, or from about 0.3 to about 2.5 mM, or from about 0.3 to about 1 mM, from about 0.3 to about 1.5 mM, or from about 0.3 to about 2 mM. In further examples, the ammonium concentration may be at a concentration ranging from about 0.5 mM to about 2.5 mM, from about 0.4 to about 2 mM, or from about 0.4 to about 1.5 mM.

Alternatively or in addition, a mutant as provided herein can produce at least 45% of the biomass produced by a control cell and at least 25% more lipid than the control cell over the same time period in a culture that includes nitrate, for example, at least about 1 mM, at least about 1.5 mM, at least about 2 mM, at least about 2.5 mM, at least about 3 mM, at least about 3.5 mM, at least about 4 mM, at least about 4.5 mM, or at least about 5 mM nitrate and in some examples can further optionally include less than about 5 mM ammonium, such as less than about 2.5 mM, ammonium, less than about 2 mM, ammonium, less than about 1 mM ammonium, or less than about 0.5 mM ammonium.

The mutant microorganism can be, in some embodiments, a photosynthetic microorganism and can produce more lipid and at least 45% of the lipid of a control or wild type cell under photoautotrophic conditions, which may be under a diel cycle. The light period of the diel cycle may be of any length and can be, for example, from about four hours to about twenty-two hours, and can be, for example, from about six hours to about twenty hours, e.g., from about eight hours to about eighteen hours per twenty four hour cycle. The microorganism can be exposed to natural or artificial light or a combination thereof. The available light can vary in intensity throughout the light period.

Mutant microorganisms provided herein can have greater partitioning of carbon to lipid with respect to a control microorganism cultured under identical conditions in which both the control microorganism and the mutant microorganism are producing biomass. A mutant having increased partitioning of carbon to lipid with respect to a control microorganism can have increased partitioning of carbon to total extractable lipid, to total neutral lipids, to triglycerides, and/or to FAME-derivatizable lipids. For example, a mutant microorganism as provided herein can have a ratio of the amount of FAME-derivatizable lipids ("FAME") produced to biomass (TOC or ash-free dry weight (AFDW), for example) produced that is at least 25% higher than that of a control microorganism. Lipid and biomass production and/or production can be assessed, for example, by gravimetric analysis as known in the art and demonstrated in the examples herein. For example, a mutant microorganism as provided herein can have a ratio of FAME to TOC that is at least 25%, at least 30%, at least 35%, at least 40%, at least 45%, at least 50%, at least 55%, at least 60%, at least 65%, at least 70%, or at least 75% higher than the FAME/TOC ratio of a control microorganism when both the mutant microorganism and the control microorganism are cultured under conditions in which both the culture of the mutant microorganism and the culture of the control microorganism produce biomass. In some embodiments, the FAME/TOC ratio of a mutant microorganism as provided herein can be increased with respect to the FAME/TOC ratio of a control microorganism cultured under identical conditions by less than about 200% or less than about 150%.

In various examples a mutant microorganism as provided herein can have a ratio of the amount of FAME produced to TOC produced that is at least 25%, at least 30%, at least 35%, at least 40%, at least 45%, at least 50%, at least 55%, at least 60%, at least 65%, at least 70%, or at least 75% higher than the FAME/TOC ratio of a control microorganism when both the mutant microorganism and the control microorganism are cultured under conditions in which the control culture produces biomass (e.g., TOC) and the mutant culture produces at least 45%, at least 50%, at least 60%, at least 70%, at least 80%, at least 90%, or at least 95% of the amount of biomass that is produced by the control culture. In various examples, the FAME/TOC ratio of a mutant as provided herein can be at least 0.27, at least 0.30, at least 0.35, at least 0.40, at least 0.45, at least 0.50, or at least 0.55 when cultured under conditions in which the mutant microorganism culture produces at least 45%, at least 50%, at least 60%, at least 65%, at least 70%, at least 75%, at least 80%, at least 85, at least 90%, or at least 95% as much biomass (e.g., TOC) as a control microorganism culture, under conditions where both the control and mutant cultures produce biomass. In various examples, the FAME/TOC ratio of a mutant as provided herein can be at least 0.27, at least 0.30, at least 0.35, at least 0.40, at least 0.45, at least 0.50, or at least 0.55 when cultured under conditions in which the mutant culture produces at least about 50%, at least 60%, at least 65%, at least 70%, at least 75%, at least 80%, at least 85, at least 90%, at least 95%, or at least 100% as much biomass (e.g., TOC) as a control microorganism produces when both the mutant and the control microorganism are cultured under conditions that are nitrogen replete, for example, nutrient replete, with respect to the control microorganism.

In some examples, a mutant microorganism as provided herein can produce at least 50% more FAME while producing at least 80%, at least 85%, or at least 90% of the TOC produced by a control cell (such as a wild type cell) when cultured under conditions in which both the control and mutant microorganism produce biomass, and the FAME/TOC ratio of the mutant microorganism is at least 25%, at least 30%, at least 35%, at least 40%, at least 45%, at least 50%, at least 55%, at least 60%, at least 65%, at least 70%, or at least 75% higher than the FAME/TOC ratio of a control microorganism. The FAME/TOC ratio of the mutant microorganism can be, for example, at least 0.30, at least 0.35, at least 0.40, at least 0.45, or at least 0.50. The culture conditions can include, for example, a culture medium that includes less than 2.5 mM, less than 2 mM, less than 1.5 mM, less than 1.0 mM, or less than 0.5 mM ammonium and in some examples can include at least 2 mM, at least 4 mM, or at least 6 mM nitrate. The culture conditions can in some examples include substantially no ammonium, and in some examples can include substantially no reduced nitrogen as a nitrogen source. The culture in some examples includes nitrate as a nitrogen source, which can optionally be substantially the sole nitrogen source in the culture medium.

The properties of a mutant as provided herein having increased lipid production are compared to the same properties of a control microorganism that may be a wild type organism of the same species as the mutant, preferably the progenitor strain of the lipid-overproducing mutant. Alternatively, a control microorganism can be a microorganism that is substantially identical to the mutant microorganism with the exception that the control microorganism does not have the mutation that leads to higher lipid productivity. For example, a control microorganism can be a genetically engineered microorganism or classically mutated organism that has been further mutated or engineered to generate a mutant having increased lipid productivity and/or increased lipid partitioning as disclosed herein.

In some examples, a control microorganism can be a microorganism that is substantially identical to the mutant microorganism, with the exception that the control microorganism does not have a mutation in a gene that regulates lipid induction (i.e., the gene whose mutation results in increased lipid production under conditions in which the mutant microorganism has at least about half the biomass productivity of the progenitor strain). The properties of a lipid-overproducing mutant having a disrupted, attenuated, or otherwise directly or indirectly genetically manipulated gene (resulting in altered structure or expression of the lipid induction regulator gene) are also be compared with the same properties of a control cell that does not have a disrupted, attenuated, or otherwise directly or indirectly genetically manipulated lipid induction regulator gene resulting in altered structure or expression of the lipid induction regulator gene (regardless of whether the cell is "wild type"). For example, a control cell may be a recombinant cell that includes one or more non-native genes or a cell mutated in a gene other than the lipid induction regulator gene whose effects are being assessed, etc.

Heterokont species considered for use in the invention include, but are not limited to, Bacillariophytes (diatoms), *Eustigmatophytes*, Labrinthulids, and Thraustochytrids, such as, for example, species of *Labryinthula, Labryinthuloides, Thraustochytrium, Schizochytrium, Aplanochytrium, Aurantiochytrium, Oblongichytrium, Japonochytrium, Diplophrys,* or *Ulkenia*.

Mutant microorganisms having the properties disclosed herein, such as mutant microorganisms having attenuated expression of a gene that regulates lipid biosynthesis, such as the Bromo-1091 gene of *N. gaditana* and orthologs thereof can be, in various examples, of any eukaryotic microalgal strain such as, for example, any species of any of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phwodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus,*

*Tetrachlorella, Tetraselmis, Thalassiosira, Tribonema, Vaucheria, Viridiella, Vischeria,* and *Volvox*. Non-limiting examples of particularly suitable species include, for instance, diatoms such as, for example, a species of any of the genera *Amphora, Chaetoceros, Cyclotella, Fragilaria, Fragilaropsis, Hantzschia, Monodus, Navicula, Nitzschia, Phæodactylum,* or *Thalassiosira,* or *Eustigmatophytes,* e.g., *Eustigmatos, Nannochloropsis, Pseudostaurastrum,* or *Vischeria*.

The mutants can be spontaneous mutants, classically-derived mutants, or engineered mutants having attenuated expression of a regulator gene, for example, a gene whose expression affects the the expression of many other genes such as a gene encoding a transcription factor or a transcriptional activator. For example, a mutant microorganism as disclosed herein that produces at least 25% more lipid and at least 45% as much biomass as a control microorganism under conditions in which both the control microorganism and the mutant microorganism are accumulating biomass (e.g., under conditions that are nutrient replete with respect to the control microorganism, which can be a wild type microorganism) can have attenuated expression of a gene encoding a polypeptide that has a TAZ Zinc Finger domain, e.g., has an amino acid sequence encoding a TAZ Zinc Finger domain characterized as belonging to conserved domain family cd15614 or SMART domain 00551 or a TAZ Zinc Finger domain belonging to pfam PF02135. TAZ zinc finger (Transcription Adaptor putative Zinc finger) domains are zinc binding domains found in the transcriptional co-activators CREB-binding protein (CBP) and P300. Transcriptional coactivators are proteins that are recruited to DNA-binding transcription factors through their activation domains and increase transcription. CBP and P300 are histone acetyltransferases (EC) that catalyse the reversible acetylation of all four histones in nucleosomes, acting to regulate transcription via chromatin remodelling (De Guzman et al. (2004) *J. Biol. Chem.* 279:3042-3049). Such domains can be identified in a polypeptide encoded by a gene as provided herein with an e value of less than about 0.01, less than about 0.001, or less than about $10^{-6}$, for example. In some embodiments, a mutant microorganism as provided herein can have attenuated expression of a gene encoding a polypeptide that recruits to pfam PF02135 with a bit score of greater than 20.0 (the gathering cutoff of PF02135) and an e valure of less than than 0.01, less than about 0.001, or less than about $10^{-6}$, for example. In some embodiments, a mutant microorganism as provided herein can have attenuated expression of a gene encoding a polypeptide that has an amino acid sequence having at least 50%, at least 55%, at least 60%, at least 65%, at least 70%, at least 75%, at least 80%, at least 85%, at least 90%, or at least 95% identity to SEQ ID NO:9.

Alternatively or in addition, a mutant microorganism such as any disclosed herein that produces at least 20% more lipid than a control microorganism while producing at least 45% as much biomass as the control microorganism can have attenuated expression of a gene encoding a polypeptide that has a Bromo domain, e.g., can have an amino acid sequence encoding a Bromo domain characterized as conserved domain cd05506, SMART domain 00297, COG domain 5076, or a Bromo domain belonging to pfam PF00439. A bromodomain is an approximately 110 amino acid protein domain found on some chromatin associated proteins. The bromodomain recognizes acetylatedlysine residues, such as those on the N-terminal tails of histones. Changes in histone acetylation has been found to accompany chromatin remodelling that occurs with changes in transcriptional activity (Dhalluin et al. *Nature* 399:491-496). In some embodiments, a mutant microorganism as provided herein can have attenuated expression of a gene encoding a polypeptide that recruits to pfam PF00439 with a bit score of greater than 21.0 (the gathering cutoff of PF00439) and an e value of less than 0.01, less than about 0.001, or less than about $10^{-6}$, for example. In some embodiments, a mutant microorganism as provided herein can have attenuated expression of a gene encoding a polypeptide that has an amino acid sequence having at least 50%, at least 55%, at least 60%, at least 65%, at least 70%, at least 75%, at least 80%, at least 85%, at least 90%, or at least 95% identity to SEQ ID NO:10.

For example, a mutant microorganism as provided herein that produces at least 20% more lipid than a control microorganism while producing at least 45% as much biomass as the control microorganism can have attenuated expression of a gene encoding a polypeptide that includes a TAZ Zinc Finger domain and/or includes a Bromo domain. In some embodiments the mutant microorganism has attenuated expression of a gene encoding a polypeptide having a TAZ domain characterized as pfam PF02135 with a bit score of greater than 20.0 and an e value of less than 0.01, and a Bromo domain characterized as pfam PF00439 with a bit score of greater than 21.0 and an e value of less than 0.01. Alternatively or in addition, a mutant microorgnaism can include an amino acid sequence having at least 50%, at least 55%, at least 60%, at least 65%, at least 70%, at least 75%, at least 80%, at least 85%, at least 90%, or at least 95% identity to SEQ ID NO:9 and/or an amino acid sequence having at least 50%, at least 55%, at least 60%, at least 65%, at least 70%, at least 75%, at least 80%, at least 85%, at least 90%, or at least 95% identity to SEQ ID NO:10.

Alternatively or in addition, in various embodiments, a mutant microorganism as disclosed herein that produces at least 25% more lipid and at least 45% as much biomass as a control microorganism under conditions in which both the control microorganism and the mutant microorganism are accumulating biomass (e.g., under conditions that are nutrient replete with respect to the control microorganism, which can be a wild type microorganism) can have attenuated expression of a gene encoding a polypeptide that has at least 50%, at least 55%, at least 60%, at least 65%, at least 70%, at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46 and/or has a coding region having at least 50%, at least 55%, at least 60%, at least 65%, at least 70%, at least 75%, at least 80%, at least 85%, at least 90%, or at least 95% identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45.

The mutant microorganism having attenuated expression of a gene that regulates lipid production can be a "knockout" mutant, for example, in which the reading frame of the polypeptide is disrupted such that the functional protein is not produced. For example, the gene can include an insertion, deletion, or mutation in the reading frame that results in no functional protein being made. In various examples, a knockout mutation can be generated by insertion of a sequence, often but not necessarily including a selectable marker gene, into the gene, for example, into the coding region of the gene. Such an insertion can be by use is a cas/CRISPR system that inegrates a donor fragment into a targeted locus, or can be by homologous recombination, for example Such an insertion can disrupt an open reading frame and/or splicing signals, or generate nonfunctional fusion proteins or truncated proteins. In other examples, the mutant microorganism can be a "knockdown" mutant in which expression of the gene is reduced but not eliminated, for example, reduced from 5% or less to 95% or more, for example, from 5% to 95% or 10% to 90%, with respect to expression levels of a wild type cell. Knockdowns can be mutants in which a mutation, insertion, or deletion occurs in a non-coding region of the gene, for example, the 5' or 3' region of a gene, or can be effected by expressing constructs in the cells that reduce expression of the targeted gene, such as RNAi, ribozyme, or antisense constructs. In addition to CRISPR systems, homologous recombination can be used to generate insertion mutants (either knockdown or knockout).

A mutant microorganism as provided herein can be designed by targeting an endogenous gene of a microorganism of interest that encodes a polypeptide that includes a TAZ Zinc Finger domain as disclosed herein and/or a Bromo domain as disclosed herein. Such genes can be identified in a microorgnaism of interest using bioinformatics methods, molecular biology techniques and combinations thereof. For example, a gene encoding a polypeptide that includes a TAZ Zinc Finger domain and/or a Bromo domain can be identified using Southern hybridization, screening of cDNA libraries by hybridization, or PCR, for example, using degenerate probes and/or primers. Genome sequences available in public or proprietary databases can be searched by any of a number of programs that perform sequence matching (e.g., blast programs such as blastp, blastn, and tblastn (protein sequence queried against translated nucleotide sequence)) or analyze domain structures of encoded amino acid sequences. For example, hmmer.org provides software for analyzing structural and functional domains encoded by genes that can be used to scan genome sequences, including, for example, hmmsearch and hmmscan. Such searches can be done online. Programs such as MUSCLE and hmmalign can also be used to search for orthologs of proteins such as the proteins disclosed herein (e.g., TAZ Zinc Finger domain-containing polypeptides) by constructing phylogenetic trees to determine relationships among proteins. Gene targeting can make use of sequences identified in the genome of the microorganism of interest. It is not necessary to resolve the complete structure of a gene to target the gene for attenuation. For example, using methods disclosed herein, including, without limitation, cas/CRISPR genome editing, RNAi constructs, antisense constructs, homologous recombination constructs, and ribozyme constructs, only a portion of a gene sequence can be employed in gene attenuation constructs and techniques.

Gene Attenuation

A mutant microorganism as provided herein having attenuated expression of a gene that regulates lipid biosynthesis is a mutant generated by human intervention, for example, by classical mutagenesis or genetic engineering. For example, a mutant microorganism as provided herein can be a mutant generated by any feasible mutagenesis method, including but not limited to UV irradiation, gamma irradiation, or chemical mutagenesis, and screening for mutants having increased lipid production, for example by staining with lipophilic dyes such as Nile Red or BODIPY (e.g., Cabanelas et al. (2015) *Bioresource Technology* 184: 47-52). Methods for generating mutants of microbial strains are well-known.

A mutant as provided herein that produces at least 25% more lipid while producing at least 50% of the biomass as the progenitor cell can also be a genetically engineered mutant, for example, a mutant in which a regulatory gene such as Bromo-1091 or an ortholog thereof (e.g., a gene encoding a polypeptide having at least 55%, at least 60%, at least 65%, at least 70%, at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46) has been targeted by homologous recombination for knockout or gene replacement (for example with mutated form of the gene that may encode a polypeptide having reduced activity with respect to the wild type polypeptide). For example, a microbial strain of interest may be engineered by site directed homologous recombination to insert a sequence into a genomic locus and thereby alter a gene and/or its expression, or to insert a promoter into a genetic locus of the host microorganism to affect the expression of a particular gene or set of genes at the locus.

For example, gene knockout or replacement by homologous recombination can be by transformation of a nucleic acid (e.g., DNA) fragment that includes a sequence homologous to the region of the genome to be altered, where the homologous sequence is interrupted by a foreign sequence, typically a selectable marker gene that allows selection for the integrated construct. The genome-homologous flanking sequences on either side of the foreign sequence or mutated gene sequence can be for example, at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides in length. A gene knockout or gene "knock in" construct in which a foreign sequence is flanked by target gene sequences, can be provided in a vector that can optionally be linearized, for example, outside of the region that is to undergo homologous recombination, or can be provided as a linear fragment that is not in the context of a vector, for example, the knock-out or knock-in construct can be an isolated or synthesized fragment, including but not limited to a PCR product. In some instances, a split marker system can be used to generate gene knock-outs by homologous recombination, where two DNA fragments can be introduced that can regenerate a selectable marker and disrupt the gene locus of interest via three crossover events (Jeong et al. (2007) *FEMS Microbiol Lett* 273: 157-163).

In one aspect the invention provides genetically modified organisms, e.g. microorganisms having one or more genetic modifications for attenuating expression of a lipid regulator gene such as a gene encoding a polypeptide having at least 55% identity to any of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46, or a gene having a coding region with at least 55% identity to any of SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45. As used herein "attenuating expression of a lipid regulator gene" means reducing or eliminating expression of the gene in any manner that reduces production of the fully functional protein. Means for attenuating a lipid regulator gene include, for example, homologous recombination constructs; CRISPR systems, including guide RNAs, Cas9 or other cas enzymes, and optionally, donor fragments for insertion into the targeted site; RNAi constructs, including shRNAs, antisense RNA constructs; ribozyme constructs; TALENS, Zinc Finger nucleases; and meganucleases.

For example, a recombinant microorganism engineered to have attenuated expression of a lipid regulator gene can have a disrupted lipid regulator gene that includes as least one insertion, mutation, or deletion that reduces or abolishes expression of the gene such that a fully functional lipid regulator gene is not produced or is produced in lower amounts than is produced by a control microorganism that does not include a disrupted lipid regulator gene.

The mutation (change, deletion, and/or insertion of one or more nucleotides) can be in the coding region of the gene or can be in an intron, 3' UTR, 5' UTR, or promoter region, e.g., within 2 kb of the transcriptional start site or within 3 kb or the translational start site. For example, a mutant having attenuated expression of a gene as disclosed herein can have a mutation, which can be one or more nucleobase changes and/or one or more nucleobase deletions and/or one or more nucleobase insertions, into the region of a gene 5' of the transcriptional start site, such as, in non-limiting examples, within 2 kb, within 1.5 kb, within 1 kb, or within 0.5 kb of the known or putative transcriptional start site, or within 3 kb, within 2.5 kb, within 2 kb, within 1.5 kb, within 1 kb, or within 0.5 kb of the translational start site. As nonlimiting examples, a mutant gene can be a gene that has a mutation, insertion, or deletion within the promoter region that can either increase or decrease expression of the gene; can be a gene that has a deletion that results in production of a nonfunctional protein, truncated protein, dominant negative protein, or no protein; can be a gene that has one or more point mutations leading to a change in the amino acid of the encoded protein or results in aberrant splicing of the gene transcript, etc.

The disrupted lipid regulator gene can be disrupted by, for example, an insertion or gene replacement mediated by homologous recombination and/or by the activity of a meganuclease, zinc finger nuclease (Perez-Pinera et al. (2012) Curr. Opin. Chem. Biol. 16: 268-277), TALEN (WO 2014/207043; WO 2014/076571), or a cas protein (e.g., a Cas9 protein) of a CRISPR system.

CRISPR systems, reviewed recently by Hsu et al. (Cell 157:1262-1278, 2014) include, in addition to the cas nuclease polypeptide or complex, a targeting RNA, often denoted "crRNA", that interacts with the genome target site by complementarity with a target site sequence, a trans-activating ("tracr") RNA that complexes with the cas polypeptide and also includes a region that binds (by complementarity) the targeting crRNA.

The invention contemplates the use of two RNA molecules (a "crRNA" and a "tracrRNA") that can be co-transformed into a host strain (or expressed in a host strain) that expresses or is transfected with a cas protein for genome editing, or the use of a single guide RNA that includes a sequence complementary to a target sequence as well as a sequence that interacts with a cas protein. That is, in some strategies a CRISPR system as used herein can comprise two separate RNA molecules (RNA polynucleotides: a "tracrRNA" and a "targeter-RNA" or "crRNA", see below) and referred to herein as a "double-molecule DNA-targeting RNA" or a "two-molecule DNA-targeting RNA." Alternatively, as illustrated in the examples, the DNA-targeting RNA can also include the trans-activating sequence for interaction with the cas protein (in addition to the target-homologous ("cr") sequences), that is, the DNA-targeting RNA can be a single RNA molecule (single RNA polynucleotide) and is referred to herein as a "chimeric guide RNA," a "single-guide RNA," or an "sgRNA." The terms "DNA-targeting RNA" and "gRNA" are inclusive, referring both to double-molecule DNA-targeting RNAs and to single-molecule DNA-targeting RNAs (i.e., sgRNAs). Both single-molecule guide RNAs and two RNA systems have been described in detail in the literature and for example, in U.S. Patent Application Publication No. US 2014/0068797, incorporated by reference herein in its entirety.

Any cas protein can be used in the methods herein, e.g., Cas1, Cas1B, Cas2, Cas3, Cas4, Cas5, Cas6, Cas7, Cas8, Cas9 (also known as Csn1 and Csx12), Cas10, Cbf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Cpf1, Csb1, Csb2, Csb3, Csx17, Csx14, Csx10, Csx16, CsaX, Csx3, Csx1, Csx15, Csf1, Csf2, Csf3, Csf4, C2c2, C2c3, and homologs thereof, or modified versions thereof. The cas protein can be a Cas9 protein, such as a Cas9 protein of *Staphylococcus pyogenes, S. thermophilus, S. pneumonia, S. aureus*, or *Neisseria meningitidis*, as non-limiting examples. Also considered are the Cas9 proteins provided as SEQ ID NOs:1-256 and 795-1346 in U.S. Patent Application Publication No. US 2014/0068797, incorporated herein by reference in its entirety, and chimeric Cas9 proteins that may combine domains from more than one Cas9 protein, as well variants and mutants of identified Cas9 proteins.

Cas nuclease activity cleaves target DNA to produce double strand breaks. These breaks are then repaired by the cell in one of two ways: non-homologous end joining or homology-directed repair. In non-homologous end joining (NHEJ), the double-strand breaks are repaired by direct ligation of the break ends to one another. In this case, no new nucleic acid material is inserted into the site, although some nucleic acid material may be lost, resulting in a deletion, or altered, often resulting in mutation. In homology-directed repair, a donor polynucleotide (sometimes referred to as a "donor DNA" or "editing DNA") which may have homology to the cleaved target DNA sequence is used as a template for repair of the cleaved target DNA sequence, resulting in the transfer of genetic information from the donor polynucleotide to the target DNA. As such, new nucleic acid material may be inserted/copied into the site. The modifications of the target DNA due to NHEJ and/or homology-directed repair (for example using a donor DNA molecule) can lead to, for example, gene correction, gene replacement, gene tagging, transgene insertion, nucleotide deletion, gene disruption, gene mutation, etc.

In some instances, cleavage of DNA by a site-directed modifying polypeptide (e.g., a cas nuclease, zinc finger nuclease, meganuclease, or TALEN) may be used to delete nucleic acid material from a target DNA sequence by cleaving the target DNA sequence and allowing the cell to repair the sequence in the absence of an exogenously provided donor polynucleotide. Such NHEJ events can result in mutations ("mis-repair") at the site of rejoining of the cleaved ends that can resulting in gene disruption.

Alternatively, if a DNA-targeting RNA is co-administered to cells that express a cas nuclease along with a donor DNA, the subject methods may be used to add, i.e. insert or replace, nucleic acid material to a target DNA sequence (e.g. "knock out" by insertional mutagenesis, or "knock in" a nucleic acid that encodes a protein (e.g., a selectable marker and/or any protein of interest), an siRNA, a miRNA, etc., to modify a nucleic acid sequence (e.g., introduce a mutation), and the like.

A donor DNA can in particular embodiments include a gene regulatory sequence (e.g., a promoter) that can, using CRISPR targeting, be inserted upstream of the coding regions of the gene and upstream of the presumed proximal promoter region of the gene, for example, at least 50 bp, at least 100 bp, at least 120 bp, at least 150 bp, at least 200 bp, at least 250 bp, at least 300 bp, at least 350 bp, at least 400 bp, at least 450 bp, or at least 500 bp upstream of the initiating ATG of the coding region of the lipid regulator gene. The donor DNA can include a sequence, such as for example a selectable marker or any convenient sequence, that may be interfere with the native promoter. The additional sequence inserted upstream of the initiating ATG of the lipid regulator open reading frame (e.g., in the 5'UTR or upstream of the transcriptional start site of the lipid regulator gene) can decrease or even eliminate expression of the endogenous lipid regulator gene. Alternatively or in addition, the native lipid regulator gene can have its endogenous promoter wholly or partially replaced by a weaker or differently regulated promoter, or a non-promoter sequence.

In some examples, a nucleic acid molecule introduced into a host cell for generating a high efficiency genome editing cell line encodes a Cas9 enzyme that is mutated to with respect to the corresponding wild-type enzyme such that the mutated Cas9 enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (an enzyme that cleaves a single strand). Other examples of mutations that render Cas9 a nickase include, without limitation, H840A, N854A, and N863A. In some embodiments, a Cas9 nickase may be used in combination with guide sequence(s), e.g., two guide sequences, which target respectively sense and antisense strands of the DNA target. This combination allows both strands to be nicked and used to induce NHEJ. Two nickase targets (within close proximity but targeting different strands of the DNA) can be used to inducing mutagenic NHEJ. Such targeting of a locus using enzymes that cleave opposite strains at staggered positions can also reduce nontarget cleavage, as both strands must be accurately and specifically cleaved to achieve genome mutation.

In additional examples, a mutant Cas9 enzyme that is impaired in its ability to cleave DNA can be expressed in the cell, where one or more guide RNAs that target a sequence upstream of the transcriptional or translational start site of the targeted gene are also introduced. In this case, the cas enzyme may bind the target sequence and block transcription of the targeted gene (Qi et al. (2013) *Cell* 152:1173-1183). This CRISPR interference of gene expression can be referred to as RNAi and is also described in detail in Larson et al. (2013) *Nat. Protoc.* 8: 2180-2196.

In some cases, a cas polypeptide such as a Cas9 polypeptide is a fusion polypeptide, comprising, e.g.: i) a Cas9 polypeptide (which can optionally be variant Cas9 polypeptide as described above); and b) a covalently linked heterologous polypeptide (also referred to as a "fusion partner").

A heterologous nucleic acid sequence may be linked to another nucleic acid sequence (e.g., by genetic engineering) to generate a chimeric nucleotide sequence encoding a chimeric polypeptide. In some embodiments, a Cas9 fusion polypeptide is generated by fusing a Cas9 polypeptide with a heterologous sequence that provides for subcellular localization (i.e., the heterologous sequence is a subcellular localization sequence, e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a hemagglutinin (HA) tag; a FLAG tag; a Myc tag; and the like).

Host cells can be genetically engineered (e.g. transduced or transformed or transfected) with, for example, a vector construct that can be, for example, a vector for homologous recombination that includes nucleic acid sequences homologous to a portion of a lipid regulator gene locus of the host cell or to regions adjacent thereto, or can be an expression vector for the expression of any or a combination of: a cas protein (e.g., a Cas9 protein), a CRISPR chimeric guide RNA, a crRNA, and/or a tracrRNA, an RNAi construct (e.g., a shRNA), an antisense RNA, or a ribozyme. The vector can be, for example, in the form of a plasmid, a viral particle, a phage, etc. A vector for expression of a polypeptide or RNA for genome editing can also be designed for integration into the host, e.g., by homologous recombination. A vector containing a polynucleotide sequence as described herein, e.g., sequences having homology to host lipid regulator gene sequences (including sequences that are upstream and downstream of the lipid regulator-encoding sequences), as well as, optionally, a selectable marker or reporter gene, can be employed to transform an appropriate host to cause attenuation of a lipid regulator gene.

The recombinant microorganism in some examples can have reduced but not abolished expression of the lipid regulator gene, and the recombinant microorganism can have an increase in lipid production of from about 25% to about 200% or more, for example. A genetically modified microorganism as provided herein can in some examples include a nucleic acid construct for attenuating the expression of a lipid regulator gene, such as, for example, a gene encoding a polypeptide having at least 55%, at least 60%, at least 65%, at least 70%, at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46. For example, a host microorganism can include a construct for expressing an RNAi molecule, ribozyme, or antisense molecule that reduces expression of a lipid regulator gene encoding a polypeptide having at least 55% identity to any of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46. In some examples, a recombinant microorganism as provided herein can include at least one introduced (exogenous or non-native) construct for reducing expression of a lipid regulator gene.

In some examples, engineered strains can be selected for expression of a lipid regulator gene that is decreased with respect to a control cell that does not include a genetic modification for attenuating lipid regulator gene expression, but not eliminated, using methods known in the art, such as, for example, RNA-Seq or reverse transcription-PCR (RT-PCR).

A genetically engineered strain as provided herein can be engineered to include a construct for attenuating gene expression by reducing the amount, stability, or translatability of mRNA of a gene encoding a lipid regulator. For example, a microorganism such as an algal or heterokont strain can be transformed with an antisense RNA, RNAi, or ribozyme construct targeting an mRNA of a lipid regulator gene using methods known in the art. For example, an antisense RNA construct that includes all or a portion of the transcribed region of a gene can be introduced into a microorganism to decrease gene expression (Shroda et al. (1999) *The Plant Cell* 11:1165-78; Ngiam et al. (2000) *Appl. Environ. Microbiol.* 66: 775-782; Ohnuma et al. (2009) *Protoplasma* 236: 107-112; Lavaud et al. (2012) *PLoS One* 7:e36806). Alternatively or in addition, an RNAi construct (for example, a construct encoding a short hairpin RNA) targeting a gene having a TAZ zinc finger domain and/or a Bromo domain can be introduced into a microorganism such as an alga or heterokont for reducing expression of the lipid regulator gene (see, for example, Cerruti et al. (2011) *Eukaryotic Cell* (2011) 10: 1164-1172; Shroda et al. (2006) *Curr. Genet.* 49:69-84).

Ribozymes are RNA-protein complexes that cleave nucleic acids in a site-specific fashion. Ribozymes have specific catalytic domains that possess endonuclease activity. For example, U.S. Pat. No. 5,354,855 (incorporated herein by reference) reports that certain ribozymes can act as endonucleases with a sequence specificity greater than that of known ribonucleases and approaching that of the DNA restriction enzymes. Catalytic RNA constructs (ribozymes) can be designed to base pair with an mRNA encoding a gene as provided herein to cleave the mRNA target. In some examples, ribozyme sequences can be integrated within an antisense RNA construct to mediate cleavage of the target. Various types of ribozymes can be considered, their design and use is known in the art and described, for example, in Haseloff et al. (1988) *Nature* 334:585-591.

Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A, C or U) (Thompson et al., (1995) *Nucl Acids Res* 23:2250-68). The frequency of this dinucleotide occurring in any given RNA is statistically 3 out of 16. Therefore, for a given target messenger RNA of 1,000 bases, 187 dinucleotide cleavage sites are statistically possible.

The general design and optimization of ribozyme directed RNA cleavage activity has been discussed in detail (Haseloff and Gerlach (1988) *Nature* 334:585-591; Symons (1992) *Ann Rev Biochem* 61: 641-71; Chowrira et al. (1994) *J Biol Chem* 269:25856-64; Thompson et al. (1995) supra), all incorporated by reference in their entireties. Designing and testing ribozymes for efficient cleavage of a target RNA is a process well known to those skilled in the art. Examples of scientific methods for designing and testing ribozymes are described by Chowrira et al., (1994) supra and Lieber and Strauss (1995) *Mol Cell Biol.* 15: 540-51, each incorporated by reference. The identification of operative and preferred sequences for use in down regulating a given gene is a matter of preparing and testing a given sequence, and is a routinely practiced "screening" method known to those of skill in the art.

The use of RNAi constructs is described in literature cited above as well as in US2005/0166289 and WO 2013/016267 (both of which are incorporated herein by reference), for example A double stranded RNA with homology to the target gene is delivered to the cell or produced in the cell by expression of an RNAi construct, for example, an RNAi short hairpin (sh) construct. The construct can include a sequence that is identical to the target gene, or at least 70%, 80%, 90%, 95%, or between 95% and 100% identical to a sequence of the target gene. The construct can have at least 20, at least 30, at least 40, at least 50, at least 100, at least 200, at least 300, at least 400, at least 500, at least 600, at least 700, at least 800, at least 900, or at least 1 kb of sequence homologous to the target gene. Expression vectors can be engineered using promoters selected for continuous or inducible expression of an RNAi construct, such as a construct that produces an shRNA.

A nucleic acid construct for gene attenuation, e.g., a ribozyme, RNAi, or antisense construct can include at least fifteen, at least twenty, at least thirty, at least forty, at least fifty, or at least sixty nucleotides having at least 80% identity, such as at least 85%, at least 90%, at least 95%, or at least 99% or complementarity to at least a portion of the sequence of an endogenous lipid regulator gene of the microorganism to be engineered. A nucleic acid construct for gene attenuation, e.g., a ribozyme, RNAi, or antisense construct can include at least fifteen, at least twenty, at least thirty, at least forty, at least fifty, or at least sixty nucleotides having at least 80%, such as at least 95% or about 100%, identity or complementarity to the sequence of a naturally-occurring gene, such as a gene having encoding a polypeptide having at least 50%, at least 55%, at least 60%, at least 65%, at least 70%, at least 75%, at least 80% or at least 85%, at least 90%, or at least 95% sequence identity to an endogenous lipid regulator gene. For example, a nucleic acid construct for gene attenuation, e.g., a ribozyme, RNAi, or antisense construct can include at least fifteen, at least twenty, at least thirty, at least forty, at least fifty, or at least sixty nucleotides having at least 80% identity or complementarity to the sequence of a naturally-occurring lipid regulator gene, such as any provided herein. The nucleotide sequence can be, for example, from about 30 nucleotides to about 3 kilobases or greater, for example, from 30-50 nucleotides in length, from 50 to 100 nucleotides in length, from 100 to 500 nucleotides in length, from 500 nucleotides to 1 kb in length, from 1 kb to 2 kb in length, or from 2 to 5 kb. For example, an antisense sequence can be from about 100 nucleotides to about 1 kb in length. For example, a nucleic acid construct for gene attenuation, e.g., a ribozyme, RNAi, or antisense construct can include at least fifteen, at least twenty, at least thirty, at least forty, at least fifty, at least sixty, or at least 100 nucleotides having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity or complementarity to an endogenous lipid regulator gene or a portion thereof.

Promoters used in antisense, RNAi, or ribozyme constructs can be any that are functional in the host organism and that are suitable for the levels of expression required for reducing expression of the target gene to a desired amount. Promoters functional in algae and heterokonts are known in the art and disclosed herein. The construct can be transformed into algae using any feasible method, include any disclosed herein. A recombinant organism or microorganism transformed with a nucleic acid molecule for attenuating lipid regulator gene expression, such as but not limited to an antisense, RNAi, or ribozyme construct, can have the properties of a lipid regulator mutant as described herein, including, for example, reduced chlorophyll, increased photosynthetic efficiency, and increased productivity in culture, with respect to a host organism or microorganism that does not include the exogenous nucleic acid molecule that results in attenuated gene expression.

Nucleic Acid Molecules and Constructs

Also provided herein are nucleic acid molecules encoding polypeptides that include amino acid sequences having at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46. Alternatively or in addition, a nucleic acid molecule as provided herein can include a sequence having at least 50%, at least 55%, at least 60%, at least 65%, at least 70%, at least 75%, at least 80%, at least 85%, at least 90%, or at least 95% identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45. The polypeptide having at least 60% identity to an amino acid sequence selected from the group consisting of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, and SEQ ID NO:46, and/or encoded by a nucleotide sequence having at least 50%, at least 55%, at least 60%, at least 65%, at least 70%, at least 75%, at least 80%, at least 85%, at least 90%, or at least 95% identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, and SEQ ID NO:45 can include an amino acid sequence encoding a TAZ zinc finger domain, e g, a domain belonging to pfam PF02135. For example, the polypeptide encoded by the nucleic acid molecule can include a TAZ zinc finger domain having an amino acid sequence with at least 60%, at least 65%, at least 70%, or at least 75%, at least 80%, at least 85%, at least 90%, or at least 95% identity to SEQ ID NO:9. Alternatively or in addition, a polypeptide encoded by a nucleic acid molecule as provided herein can optionally further include a Bromo domain, e.g., a domain belonging to pfam PF00439. For example a polypeptide encoded by a nucleic acid molecule as provided herein can include a Bromo domain having at least 60%, at least 65%, at least 70%, or at least 75%, at least 80%, at least 85%, at least 90%, or at least 95% identity to SEQ ID NO:10.

The nucleic acid molecule in various examples can be or comprise a cDNA that lacks one or more introns present in the naturally-occurring gene, or, alternatively, can include one or more introns not present in the naturally-occurring gene. The nucleic acid molecule in various examples can have a sequence that is not 100% identical to a naturally-occurring gene. For example, the nucleic acid molecule can include a mutation with respect to a naturally-occurring gene that reduces the activity of the encoded polypeptide or reduces expression of the mRNA or protein encoded by the gene.

The nucleic acid molecule in various examples can comprise a heterologous promoter operably linked to the sequence encoding a polypeptide that includes an amino acid sequence having at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46 and/or having at least 50%, at least 55%, at least 60%, at least 65%, at least 70%, at least 75%, at least 80%, at least 85%, at least 90%, or at least 95% identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45. Alternatively or in addition, a nucleic acid molecule can comprise a vector that includes a sequence encoding a polypeptide that includes an amino acid sequence having at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46 and/or has at least 50%, at least 55%, at least 60%, at least 65%, at least 70%, at least 75%, at least 80%, at least 85%, at least 90%, or at least 95% identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45.

A further aspect of the invention is a construct designed for attenuating expression of a gene encoding a TAZ zinc finger domain and/or a Bromo domain. The construct can be or comprise, in various examples, a sequence encoding a guide RNA of a CRISPR system, an RNAi construct, an antisense construct, a ribozyme construct, or a construct for homologous recombination, e.g., a construct having one or more nucleotide sequences having homology to a naturally-occurring TAZ zinc finger and/or Bromo domain-encoding gene as disclosed herein and/or sequences adjacent thereto in the native genome from which the gene is derived. For example, the construct can include at least a portion of a gene encoding a polypeptide having a TAZ zinc finger domain and/or a Bromo domain, e.g., a sequence homologous to at least a portion of an gene that encodes a polypeptide that includes an amino acid sequence having at least 60%, at least 65%, at least 70%, or at least 75%, at least 80%, at least 85%, at least 90%, or at least 95% identity to SEQ ID NO:9 or SEQ ID NO:10.

The construct for gene attenuation can include, for example, at least a portion of the coding region, intron, 5'UTR, promoter region, or 3' UTR of a gene encoding a polypeptide having a TAZ zinc finger domain and/or a Bromo domain or a polypeptide having at least 60% identity to any of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46, or at least a portion of a gene having at least 50% identity to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45, in either sense or antisense orientation.

In further examples a construct can be designed for the in vitro or in vivo expression of a guide RNA (e.g., of a CRISPR system) designed to target a gene having a sequence having at least 50%, at least 55%, at least 60%, at least 65%, at least 70%, or at least 75%, at least 80%, at least 85%, at least 90%, or at least 95% identity to at least a portion of SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45, or coding a polypeptide having a TAZ Zinc Finger domain and/or a Bromo domain or a polypeptide having at least 60% identity to any of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46, and/or can include a sequence homologous to a portion of a gene encoding a polypeptide having a TAZ Zinc Finger domain and/or a Bromo domain, including, for example, an intron, a 5'UTR, a promoter region, and/or a 3' UTR.

In yet further examples, a construct for attenuating expression of a gene encoding a TAZ Zinc Finger domain and/or a Bromo domain-containing polypeptide can be a guide RNA or antisense oligonucleotide, where the sequence having homology to a transcribed region of a gene encoding a polypeptide having a TAZ Zinc Finger domain and/or a Bromo domain in antisense orientation.

Nucleic acid constructs for attenuating expression of a TAZ Zinc Finger domain and/or a Bromo domain-encoding gene or a gene encoding a polypeptide having at least 60% identity to any of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46 can include, for example at least 17, at least 18, at least 19, at least 20, at least 21, at least 22, at least 23, at least 24, or at least 25 nucleotides of sequence of a naturally occurring TAZ Zinc Finger domain and/or a Bromo domain-encoding gene or a gene encoding a polypeptide having at least 60% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46 and/or a gene having at least 50% identity to a portion of any of SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45.

In one example, provided herein is a nucleic acid molecule having at least 50%, at least 55%, at least 60%, at least 65%, at least 70%, or at least 75%, at least 80%, at least 85%, at least 90%, or at least 95% identity to at least a portion of SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45, where the nucleic acid molecule encodes a guide RNA of a CRISPR system. The nucleic acid molecule can include, for example at least 17, at least 18, at least 19, at least 20, at least 21, at least 22, at least 23, at least 24, or at least 25 nucleotides of sequence of a naturally occurring TAZ Zinc Finger domain and/or a Bromo domain gene, such as but not limited to SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45.

In addition, provided herein are antisense, ribozyme, or RNAi constructs that include at least a portion of a gene having encoding a TAZ zinc finger domain and/or a Bromo domain or a polypeptide having at least 60% identity to any of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46 and/or a gene having at least 50% identity to a portion of any of SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45, in which a promoter, such as a heterologous promoter, is operably linked to the TAZ zinc finger domain and/or a Bromo domain gene sequence and the TAZ zinc finger domain and/or a Bromo domain gene sequence is in antisense orientation.

Further, provided herein are constructs for homologous recombination that include at least one sequence from a TAZ zinc finger domain and/or a Bromo domain-encoding gene locus of the genome of an alga juxtaposed with a heterologous nucleic acid sequence that can be, in nonlimiting examples, a selectable marker or detectable marker gene. In some examples a construct for homologous recombination includes two nucleic acid sequences from a TAZ zinc finger domain and/or Bromo domain-encoding gene locus of the genome of an alga where the two sequences flank a heterologous sequence for insertion into the TAZ zinc finger domain and/or Bromo domain gene locus.

One skilled in the art will appreciate that a number of transformation methods can be used for genetic transformation of microorganisms and, therefore, can be deployed for the methods of the present invention. "Stable transformation" is intended to mean that the nucleic acid construct introduced into an organism integrates into the genome of the organism or is part of a stable episomal construct and is capable of being inherited by the progeny thereof. "Transient transformation" is intended to mean that a polynucleotide is introduced into the organism and does not integrate into the genome or otherwise become established and stably inherited by successive generations.

Genetic transformation can result in stable insertion and/or expression of transgenes, constructs from either the nucleus or the plastid, and in some cases can result in transient expression of transgenes. The transformation methods can also be used for the introduction of guide RNAs or editing DNAs. Genetic transformation of microalgae has been reported successful for more than 30 different strains of microalgae, which belong to at least ~22 species of green, red, and brown algae, diatoms, euglenids, and dianoflagellates (see, e.g., Radakovits et al., *Eukaryotic Cell,* 2010; and Gong et al., *J. Ind. Microbiol. Biotechnol.,* 2011). Non-limiting examples of such useful transformation methods include agitation of cells in the presence of glass beads or silicon carbide whiskers as reported by, for example, Dunahay, *Biotechniques,* 15(3):452-460, 1993; Kindle, *Proc. Natl. Acad. Sci. U.S.A.,* 1990; Michael and Miller, *Plant J.,* 13, 427-435, 1998. Electroporation techniques have been successfully used for genetic transformation of several microalgal species including *Nannochloropsis* sp. (see, e.g., Chen et al., *J. Phycol.,* 44:768-76, 2008), *Chlorella* sp. (see, e.g., Chen et al., *Curr. Genet.,* 39:365-370, 2001; Chow and Tung, *Plant Cell Rep.* Vol. 18, No. 9, 778-780, 1999), *Chlamydomonas* (Shimogawara et al., *Genetics,* 148: 1821-1828, 1998), *Dunaliella* (Sun et al., *Mol. Biotechnol.,* 30(3): 185-192, 2005). Micro-projectile bombardment, also referred to as microparticle bombardment, gene gun transformation, or biolistic bombardment, has been used successfully for several algal species including, for example, diatoms species such as *Phaeodactylum* (Apt et al., *Mol. Gen. Genet.,* 252:572-579, 1996), *Cyclotella* and *Navicula* (Dunahay et al., *J. Phycol.,* 31:1004-1012, 1995), *Cylindrotheca* (Fischer et al., *J. Phycol.,* 35:113-120, 1999), and *Chaetoceros* sp. (Miyagawa-Yamaguchi et al., *Phycol. Res.* 59: 113-119, 2011), as well as green algal species such as *Chlorella* (El-Sheekh, *Biologia Plantarum,* Vol. 42, No. 2: 209-216, 1999), and *Volvox* species (Jakobiak et al., *Protist,* 155:381-93, 2004). Additionally, *Agrobacterium*-mediated gene transfer techniques can also be useful for genetic transformation of microalgae, as has been reported by, for example, Kumar, *Plant Sci.,* 166(3):731-738, 2004, and Cheney et al., *J. Phycol.,* Vol. 37, Suppl. 11, 2001.

A transformation vector or construct as described herein will typically comprise a marker gene that confers a selectable or scorable phenotype on target host cells, e.g., algal cells or may be co-transformed with a construct that includes a marker. A number of selectable markers have been successfully developed for efficient isolation of genetic transformants of algae. Common selectable markers include antibiotic resistance, fluorescent markers, and biochemical markers. Several different antibiotic resistance genes have been used successfully for selection of microalgal transformants, including blastocidin, bleomycin (see, for example, Apt et al., 1996, supra; Fischer et al., 1999, supra; Fuhrmann et al., *Plant J.,* 19, 353-61, 1999, Lumbreras et al., *Plant J.,* 14(4):441-447, 1998; Zaslayskaia et al., *J. Phycol.,* 36:379-386, 2000), spectinomycin (Cerutti et al., *Genetics,* 145: 97-110, 1997; Doetsch et al., *Curr. Genet.,* 39, 49-60, 2001; Fargo, *Mol. Cell. Biol.,* 19:6980-90, 1999), streptomycin (Berthold et al., *Protist,* 153:401-412, 2002), paromomycin (Jakobiak et al., *Protist,* supra.; Sizova et al., *Gene,* 277: 221-229, 2001), nourseothricin (Zaslayskaia et al., 2000, supra), G418 (Dunahay et al., 1995, supra; Poulsen and Kroger, *FEBS Lett.,* 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin (e.g., ZEOCIN™ pheomycin D1) resistance (Stevens, *Mol. Gen. Genet.* 251:23-30, 1996), and paromomycin and neomycin resistance (Sizova et al., 2001, supra). Other fluorescent or chromogenic markers that have been used include luciferase (Falciatore et al., *J. Mar. Biotechnol.,* 1: 239-251, 1999; Fuhrmann et al., *Plant Mol. Biol.,* 2004; Jarvis and Brown, *Curr. Genet.,* 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.,* 1:165-169, 1994), β-galactosidase (Gan et al., *J. Appl. Phycol.,* 15:345-349, 2003; Jiang et al., *Plant Cell Rep.,* 21:1211-1216, 2003; Qin et al., *High Technol. Lett.,* 13:87-89, 2003), and green fluorescent protein (GFP) (Cheney et al., 2001, supra; Ender et al., *Plant Cell,* 2002, Franklin et al., *Plant J.,* 2002; 56, 148, 210).

One skilled in the art will readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.,* 18:778-780, 1999; Jarvis and Brown, *Curr. Genet.,* 317-321, 1991; Lohuis and Miller, *Plant J.,* 13:427-435, 1998). The SV40 promoter from simian virus has also reported to be active in several algae (Gan et al., *J. Appl. Phycol.,* 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.,* 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.,* 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., *Mar. Biotechnol.*, 1:239-251, 1999; Zaslayskaia et al., *J. Phycol.* 36:379-386, 2000) or the vcp gene encoding a eustigmatophyte violaxanthin-chlorophyll a/b binding protein (see U.S. Pat. No. 8,318,482, incorporated by reference herein). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272:3413-3423, 2005), thus gene expression can be switched off or on when microalgal cells are grown in the presence of ammonium/nitrate. Additional algal promoters that can find use in the constructs and transformation systems provided herein include those disclosed in U.S. Pat. No. 8,883,993; U.S. Patent Appl. Pub. No. US 2013/0023035; U.S. Patent Application Pub. No. US 2013/0323780; and U.S. Patent Application Pub. No. US 2014/0363892, all incorporated herein by reference in their entireties.

Host cells can be either untransformed cells or cells that are already transfected with at least one nucleic acid molecule. For example, an algal host cell that is engineered to have attenuated expression of a lipid regulator gene can further include one or more genes that may confer any desirable trait, such as, but not limited to, increased production of biomolecules of interest, such as one or more proteins, pigments, alcohols, or lipids.

Methods of Producing Lipids

Also provided herein are methods of producing lipid by culturing a mutant microorganism as provided herein that has increased lipid productivity with respect to a control cell while producing at least 45% of the biomass produced by a control cell under the same culture conditions. The methods include culturing a mutant microorganism as provided herein in a suitable medium to produce lipid and recovering biomass or at least one lipid from the culture. The microorganism can in some examples be an alga, and the culture can be a photoautotrophic culture. Culturing can be in batch, semi-continuous, or continuous mode.

The mutant microorganism in some examples can be cultured in a medium that comprises less than about 5 mM ammonium, for example, less than about 2.5 mM ammonium, less than about 2 mM ammonium, less than about 1.5 mM ammonium, less than or equal to about 1 mM ammonium, or less than or equal to about 0.5 mM. The culture medium can include, for example, from about 0 to about 2.5 mM ammonium, from about 0.1 to about 2.5 mM ammonium, from about 0.5 to about 2.5 mM ammonium, from about 0 to about 1.5 mM ammonium, from about 0.1 to about 1 mM ammonium, or from about 0.2 to about 1 mM ammonium. The microorganism can be cultured in a medium that includes nitrate, which in some examples may be substantially the sole nitrogen source in the culture medium or may be present in addition to less than 5 mM ammonium, less than 2.5 mM ammonium, less than 1.0 mM ammonium, or less than or equal to about 0.5 mM ammonium. Alternatively or in addition, the culture medium can comprises urea, which in some examples can be substantially the sole source of nitrogen in the culture medium.

The lipid producing microorganisms may be cultured in any suitable vessel(s), including flasks or bioreactors. In some examples, the mutant microorganism is an alga and is exposed to light for at least a portion of the culture period, in which the algae may be exposed to artificial or natural light (or natural light supplemented with artificial light). The culture comprising mutant algae that are deregulated in their response to low light may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc. Alternatively, an algal mutant can be cultured in continuous light.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. A microorganism as provided herein may be cultured for at least five, at least six, at least seven at least eight, at least nine, at least ten, at least eleven at least twelve, at least thirteen, at least fourteen, or at least fifteen days, or at least one, two three, four, five, six, seven, eight, nine, or ten weeks, or longer. The culturing can be in a culture medium that is nutrient replete with respect to a control alga.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown mixotrophically, using both light and a reduced carbon source. Alternatively, the microorganism or host cell can be cultured phototrophically. When growing phototrophically, the algal strain can advantageously use light as an energy source. An inorganic carbon source, such as $CO_2$ or bicarbonate can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture.

Microorganisms and host cells that can be useful in accordance with the methods of the present invention can be found in various locations and environments throughout the world. The particular growth medium for optimal propagation and generation of lipid and/or other products can vary and may be optimized to promote growth, propagation, or production of a product such as a lipid, protein, pigment, antioxidant, etc. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (www.sbs.utexas.edu/utex/media.aspx); Culture Collection of Algae and Protozoa (www.ccap.ac.uk); and Katedra Botaniky (botany.natur.cuni.cz/algo/caup-media.html).

The culture methods can optionally include inducing expression of one or more genes and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the microorganisms having increased lipid productivity can be cultured in a photobioreactor equipped with an artificial light source, and/or having one or more walls that is transparent enough to light, including sunlight, to enable, facilitate, and/or maintain acceptable microorganism growth and proliferation. For production of fatty acid products or triglycerides, photosynthetic microorganisms or host cells can additionally or alternately be cultured in shake flasks, test tubes, vials, microtiter dishes, petri dishes, or the like, or combinations thereof.

Additionally or alternately, mutant or recombinant photosynthetic microorganisms or host cells may be grown in ponds, canals, sea-based growth containers, trenches, raceways, channels, or the like, or combinations thereof. In such systems, the temperature may be unregulated, or various heating or cooling method or devices may be employed As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose with respect to the growth, proliferation, and/or survival of the microorganisms.

The mutant microorganisms can optionally include one or more non-native genes encoding a polypeptide for the production of a product, such as but not limited to a lipid.

The methods include culturing a mutant microorganism as provided herein, such as a mutant microorganism as provided herein that has increased lipid productivity with respect to a control cell while producing at least 50% of the biomass produced by a control cell under the same culture conditions to produce biomass or lipid. Lipids can be recovered from culture by recovery means known to those of ordinary skill in the art, such as by whole culture extraction, for example, using organic solvents or by first isolating biomass from which lipids are extracted (see, for example, Hussein et al. *Appl. Biochem. Biotechnol.* 175:3048-3057; Grima et al. (2003) *Biotechnol. Advances* 20:491-515). In some cases, recovery of fatty acid products can be enhanced by homogenization of the cells (Gunerken et al. (2015) *Biotechnol. Advances* 33:243-260). For example, lipids such as fatty acids, fatty acid derivatives, and/or triglycerides can be isolated from algae by extraction of the algae with a solvent at elevated temperature and/or pressure, as described in the co-pending, commonly-assigned U.S. patent publication No. US 2013/0225846 entitled "Solvent Extraction of Products from Algae", filed on Feb. 29, 2012, which is incorporated herein by reference in its entirety.

Biomass can be harvested, for example, by centrifugation or filtering. The biomass may be dried and/or frozen. Further products may be isolated from biomass, such as, for example, various lipids or one or more proteins. Also included in the invention is an algal biomass comprising biomass of lipid regulator mutant, such as any disclosed herein, such as but not limited to a lipid regulator mutant that includes a mutation in a gene encoding a polypeptide having at least 50%, at least 55%, at least 60%, at least 65%, at least 70%, at least 75%, at least 80%, at least 85%, at least 90%, or at least 95% identity to a polypeptide comprising an amino acid sequence selected from the group consisting of SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, and SEQ ID NO:46.

Alternatively or in addition to any of the forgoing embodiments, the invention provides the following embodiments:

Embodiment 1 is a mutant microorganism that produces at least 25% more lipid and at least 45% more biomass than is produced by a control microorganism cultured under substantially identical conditions under which the control microorganism and the mutant microorganism produce biomass, optionally wherein any one or more of the following are fulfilled:

(a) the control microorganism is a wild type microorganism;

(b) the mutant microorganism produces at least 45%, at least 50%, at least 55%, at least 60%, at least 65%, at least 70%, at least 75%, at least 80%, at least 85%, at least 90%, at least 95%, at least 100%, at least 105%, at least 110%, at least 120%, or at least 150% as much biomass as the control microorganism, which can be assessed as average biomass (e.g., TOC) productivity per day, during a culture period of at least three, at least four, at least five, at least six, at least seven, at least eight, at least nine, at least ten, at least eleven, at least twelve, at least thirteen days, at least fourteen, at least fifteen, at least twenty, at least thirty, or at least sixty days;

(c) the mutant microorganism produces at least 25%, at least 30%, at least 55%, at least 40%, at least 45%, at least 50%, at least 55%, at least 60%, at least 70%, at least 75%, at least 80%, at least 85%, at least 90%, at least 95%, at least 100%, at least 110%, at least 115%, at least 120%, or at least 150% more lipid, which can be assessed as average lipid (e.g., FAME) productivity per day, than is produced by a control microorganism during a culture period of at least at least three, at least four, at least five, at least six, at least seven, at least eight, at least nine, at least ten, at least eleven, at least twelve, at least thirteen days, at least fourteen, at least fifteen, at least twenty, at least thirty, or at least sixty days;

(d) the culture medium comprises less than about 5 mM, less than about 4 mM, less than about 3 mM, less than 2.5 mM ammonium, less than or equal to about 2 mM ammonium, less than or equal to about 1.5 mM ammonium, less than or equal to about 1 mM ammonium, or less than or equal to about 0.5 mM ammonium;

(e) the culture medium includes nitrate, optionally wherein nitrate is substantially the sole nitrogen source in the culture medium; and/or (f) the microorganism is a heterokont or alga.

Embodiment 2 is a mutant microorganism according to embodiment 1 in which the mutant has attenuated expression of a gene encoding a polypeptide that:

(a) includes a TAZ zinc finger domain and/or a Bromo domain; and/or (b) has at least 50%, at least 55%, at least 60%, at least 65%, at least 70%, at least 75%, at least 80%, at least 85%, at least 90%, at least 95%, at least 96%, at least 97%, at least 98%, or at least 99% to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46.

Embodiment 3 is a mutant microorganism according to embodiment 1 or embodiment 2, wherein the mutant a classically-derived mutant or an engineered mutant, optionally wherein the mutant is an engineered mutant that:

(a) has a disrupted gene encoding a regulator of lipid biosynthesis, wherein the gene is disrupted in a coding region or in a noncoding region;

(b) is deleted in all or a portion of a gene encoding a regulator of lipid biosynthesis;

(c) includes an antisense construct, an RNAi construct, a guide RNA construct, or a ribozyme construct that targets a gene encoding a regulator of lipid biosynthesis;

(d) includes an insertion into a gene encoding a regulator of lipid biosynthesis, optionally wherein the insertion is generated by CRISPR/cas genome editing, further optionally wherein the insertion is in the non-coding portion of the gene, such as, for example, the 5' UTR, the promoter region, the 3' UTR, or an intron of the gene; and/or (e) includes a mutation in a gene encoding a regulator of lipid biosynthesis optionally generated by CRISPR/cas genome editing, optionally wherein the mutation is in the non-coding portion of the gene, further optionally wherein the mutation is in the 5' UTR, the promoter region, the 3' UTR, or an intron of the gene.

Embodiment 4 is a mutant microorganism according to any of embodiments 1-3, wherein:

(a) the mutant produces at least 50% more FAME (e.g., average productivity per day) while producing at least 85% or at least 90% of the TOC produced by a control cell, e.g., TOC productivity on a per day basis, when cultured under conditions in which both the control and mutant microorganism produce biomass; and/or (b) wherein the FAME/TOC ratio of the mutant microorganism is at least 30%, at least 35%, at least 40%, at least 45%, or at least 50% higher than the FAME/TOC of the control microorganism while producing at least 85% or at least 90% of the TOC produced by a control cell (such as a wild type cell) when cultured under conditions in which both the control and mutant microorganism produce biomass; and/or (c) the FAME/TOC ratio of the mutant microorganism is at least 0.30, at least 0.35 at least 0.40, at least 0.5, or between about 0.3 and about 0.8 when cultured under conditions in which both the control and mutant microorganism produce biomass and/or (d) wherein the FAME/TOC ratio is maintained between about 0.3 and about 0.7 for a culture period of at least five, at least six, at least seven, at least eight, at least nine, at least ten, at least eleven, at least twelve, or at least thirteen days during which the mutant microorganism produces at least 50%, at least 60%, at least 70%, or at least 75%, at least 80% or at least 85% of the biomass produced by a control microorganism cultured under the same conditions in which the control microorganism accumulates biomass.

Embodiment 6 is a mutant microorganism according to any of embodiments 1-3, wherein:

(a) the mutant produces at least 25%, at least 30%, at least 35%, at least 40%, at least 45%, or at least 50% more FAME (e.g., on an average per day basis) while producing at least 90%, at least 95%, at least 100% of the TOC produced (e.g., on an average per day basis) by a control microorganism (such as a wild type cell) when cultured under conditions in which both wild type and mutant microorganism are producing biomass; and/or (b) the FAME/TOC ratio of the mutant microorganism is at least 25%, at least 30%, at least 35%, at least 40%, at least 45%, or at least 50% greater than the FAME/TOC ratio of a control microorganism when cultured under conditions in which both wild type and mutant microorganism are producing biomass; and/or (c) the FAME/TOC ratio of the mutant microorganism is at least 0.30, at least 0.35, at least 0.40, at least 0.45, or at least 0.50 and the mutant microorganism produces at least 80%, at least 85%, at least 90%, or at least 95% of the TOC produced by a control microorganism when cultured under conditions in which the wild type accumulates biomass.

Embodiment 7 is a mutant microorganism according to any of embodiments 1-6, wherein:

(a) the culture conditions under which the mutant microorganism produces more lipid is batch, semi-continuous, or continuous culture; and/or (b) the daily lipid productivity of the mutant is greater than the daily lipid productivity of the control microorganism throughout the culture period, e.g., every day throughout a culture period of at least three, at least four, at least five, at least six, at least seven, at least eight, at least nine, at least ten, at least eleven, at least twelve, at least thirteen days, at least fourteen, at least fifteen, at least twenty, at least thirty, or at least sixty days.

Embodiment 8 is a mutant microorganism according to any of embodiments 1-7 in which the mutant microorganism comprises a mutation in a non-coding region of a gene that reduces expression of the gene, optionally wherein the mutation is an insertion.

Embodiment 9 is a mutant microorganism according to any of embodiments 1-7 in which the mutant microorganism comprises a construct that reduces expression of a gene, wherein the construct encodes an RNAi, a guide RNA, an antisense transcript, or a ribozyme.

Embodiment 10 is a mutant microorganism according to any of embodiments 1-9, wherein the mutant microorganism is a *labyrinthulomycte* species, optionally wherein the mutant microorganism is a species belonging to any of the genera *Labryinthula, Labryinthuloides, Thraustochytrium, Schizochytrium, Aplanochytrium, Auranthiochytrium, Oblongichytrium, Japonochytrium, Diplophrys,* or *Ulkenia*; or wherein the mutant microorganism is an algal species, optionally a species belonging to any of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*.

Embodiment 11 is biomass comprising any of the mutant microorganisms of any of embodiments 1-10.

Embodiment 12 is a nucleic acid molecule comprising a sequence encoding a polypeptide having at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46, wherein any one or more of the following are satisfied:

(a) the polypeptide includes an amino acid sequence encoding a TAZ Zinc Finger domain, optionally wherein the TAZ Zinc Finger domain has at least 60%, at least 65%, at least 70%, or at least 75%, at least 80%, at least 85%, at least 90%, or at least 95% identity to SEQ ID NO:9;

(b) the polypeptide includes an amino acid sequence encoding a Bromo domain, optionally wherein the Bromo domain has at least 60%, at least 65%, at least 70%, or at least 75%, at least 80%, at least 85%, at least 90%, or at least 95% identity to SEQ ID NO:10;

(c) the nucleic acid molecule in various examples comprises a cDNA that lacks one or more introns present in the naturally-occurring gene or is a gene construct that includes one or more introns not present in the naturally-occurring gene;

(d) the nucleic acid molecule in various examples can have a sequence that is not 100% identical to a naturally-occurring gene;

(e) the nucleic acid molecule has at least 50%, at least 55%, at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, or a portion of any thereof;

(f) the nucleic acid molecule comprises a heterologous promoter operably linked to the sequence; and/or (g) the nucleic acid molecule comprises a vector.

Embodiment 13 is a nucleic acid molecule construct for attenuating expression of a gene encoding a polypeptide according to having at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46, wherein the nucleic acid molecule construct comprises:

a sequence encoding a guide RNA of a CRISPR system, an RNAi construct, an antisense construct, a ribozyme construct, or a construct for homologous recombination;

further optionally wherein the nucleic acid molecule construct comprises one or more nucleotide sequences having homology to a naturally-occurring TAZ Zinc Finger domain-encoding gene as disclosed herein and/or sequences adjacent thereto in the native genome from which the gene is derived.

Embodiment 14 is method of engineering a cell for increased lipid production comprising attenuating expression of a gene encoding a polypeptide having at least 60%, at least 65%, at least 70%, or at least 75%, at least 80%, at least 85%, at least 90%, or at least 95% identity to SEQ ID NO:2, SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46, optionally a gene having a coding sequence with at least 50%, at least 55%, at least 60%, at least 65%, at least 70%, or at least 75%, at least 80%, at least 85%, at least 90%, or at least 95% identity to any of SEQ ID NO:1, SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, or SEQ ID NO:45, into a microorganism to produce a mutant microorganism having higher lipid productivity than the progenitor microorganism, optionally wherein attenuating expression of the gene comprises introducing a nucleic acid molecule according to embodiment 13 into the microorganism.

Embodiment 15 is method for producing lipid comprising culturing a mutant according to any of embodiments 1-10 to produce lipid, optionally wherein any one or more of the following are satisfied:

(a) the culture medium includes nitrate;

(b) the culture medium includes less than 5 mM, less than 4 mM, less than 3 mM, less than 2.5 mM ammonium, less than or equal to about 2 mM ammonium, less than or equal to about 1.5 mM ammonium, less than or equal to about 1 mM ammonium, or less than or equal to about 0.5 mM ammonium;

(c) the culture is a batch, semi-continuous, or continuous culture;

(d) the culture period is at least 5, 7, 8, 9, 10, 11, 12, 13 day, at least 15, 20, 30, 40, 50, or 60 days;

(e) the mutant is an algal mutant and the culture is photoautotrophic;

(f) the mutant produces at least 25% more lipid, preferably FAME lipid, and at least 45% of the biomass of a control microorganism during the culture period;

(g) the mutant produces more lipid, preferably FAME lipid, on each day of the culture period; and/or (h) the mutant accumulates biomass on each day of the culture period.

Embodiment 16 is method for producing lipid comprising culturing a microorganism under conditions in which the FAME/TOC ratio is maintained at between about 0.3 and about 0.8 throughout the culture period, optionally wherein any one or more of the following are satisfied:

(a) the culture medium includes nitrate;
(b) the culture medium includes less than 5 mM, less than 4 mM, less than 3 mM, less than 2.5 mM ammonium, less than 2 mM ammonium, less than or equal to about 1.5 mM ammonium, less than or equal to about 1 mM ammonium, or less than or equal to about 0.5 mM ammonium;
(c) the culture is a batch, semi-continuous, or continuous culture;
(d) the culture period is at least 5, 7, 8, 9, 10, 11, 12, 13 day, at least 15, 20, 30, 40, 50, or 60 days;
(e) the microorganism is an algal microorganism and the culture is photoautotrophic;
(f) the microorganism accumulates biomass on each day of the culture period; and/or
(g) the microorganism is a mutant microorganism according to any of embodiments 1-10.

EXAMPLES

Media Used in Examples

PM066 medium (Example 1) includes 10 mM nitrate as the sole nitrogen source. PM066 medium included 10 mM nitrate ($NO_3$) and 0.417 mM phosphate ($PO_4$) along with trace metals and vitamins in Instant Ocean salts. PM066 media was made by adding 5.71 ml of a 1.75 M $NaNO_3$ stock solution (148.7 g/L), and 5.41 ml of a 77 mM $K_2HPO_4.3H_2O$ stock solution (17.57 g/L) to 981 mls of Instant Ocean salts solution (35 g/L) along with 4 ml of Chelated Metals Stock Solution and ml of 4 ml Vitamin Stock Solution. Chelated Metals Stock Solution was prepared by adding to 400 mls of water 2.18 g $Na_2EDTA.2H_2O$; 1.575 g $FeCl3.6H_2O$; 500 µl of 39.2 mM stock solution (0.98 g/100 ml) $CuSO_4.5H_2O$; 500 µl of 77.5 mM stock solution (2.23 g/100 ml) $ZnSO_4.7H_2O$; 500 µl of 42.0 mM stock solution (1.00 g/100 ml) $CoCl_2.6H2O$; 500 µl of 910.0 mM stock solution (18.0/100 ml) MnCl2.4H2O; 500 µl of 26.0 mM stock solution (0.63 g/100 ml) $Na_2MoO_4.2H_2O$; bringing up to 500 ml final volume, and filter sterilizing. Vitamin Stock Solution was prepared by adding to 400 mls of water 0.05 g Thiamine HCl; 500 µl of 0.37 mM stock solution (0.05 g/100 ml) of cyanocobalamin; and 2.5 ml of 0.41 mM stock solution (0.01 g/100 ml) of biotin, bringing up to a final volume of 500 mls, and filter sterilizing.

PM067 medium included no nitrogen source (no nitrate or ammonium), and 0.417 mM phosphate ($PO_4$) along with trace metals and vitamins in Instant Ocean salts. PM067 media was made by adding 5.41 ml of a 77 mM $K_2HPO_4.3H_2O$ stock solution (17.57 g/L) to 987 mls of Instant Ocean salts solution (35 g/L) along with 4 ml of Chelated Metals Stock Solution and ml of 4 ml Vitamin Stock Solution. Chelated Metals Stock Solution was prepared by adding to 400 mls of water 2.18 g $Na_2EDTA.2H_2O$; 1.575 g $FeCl3.6H_2O$; 500 µl of 39.2 mM stock solution (0.98 g/100 ml) $CuSO_4.5H_2O$; 500 µl of 77.5 mM stock solution (2.23 g/100 ml) $ZnSO_4.7H_2O$; 500 µl of 42.0 mM stock solution (1.00 g/100 ml) $CoCl_2.6H2O$; 500 µl of 910.0 mM stock solution (18.0/100 ml) $MnCl_2.4H_2O$; 500 µl of 26.0 mM stock solution (0.63 g/100 ml) $Na_2MoO_4.2H_2O$; bringing up to 500 ml final volume, and filter sterilizing. Vitamin Stock Solution was prepared by adding to 400 mls of water 0.05 g Thiamine HCl; 500 µl of 0.37 mM stock solution (0.05 g/100 ml) of cyanocobalamin; and 2.5 ml of 0.41 mM stock solution (0.01 g/100 ml) of biotin, bringing up to a final volume of 500 mls, and filter sterilizing.

PM074 is a nitrogen replete ("nitrate-only") medium that is 10×F/2 made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (35 g/L) (Aquatic Eco Systems, Apopka, Fla.). Proline A and Proline B together include 8.8 mM $NaNO_3$, 0.361 mM $NaH_2PO_4.H_2O$, 10×F/2 Trace metals, and 10×F/2 Vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60).

PM123 medium is PM074 medium supplemented with additional Proline B so that the concentration of nitrate was increased from approximately 8.8 mM to approximately 15 mM. This is also a "nitrate only" medium.

PM124 medium is PM074 supplemented with 5 mM Ammonium and 10 mM HEPES pH 8.0. It is made by adding 10 mls of 1 M HEPES pH 8 and 5 mls of $NH_4Cl$ to the PM074 recipe (final volume of 1 L). Additional media with controlled ammonium levels was made by adjusting the ammonium concentration of PM074 and adding additional Hepes buffer.

PM066, PM074, PM123, and PM124 media are nitrogen replete and nutrient replete with respect to wild type *Nannochloropsis*.

Example 1. Identification of a Polypeptide Downregulated During Nitrogen Starvation To identify genes that influence lipid biosynthesis, a comparative transcriptomics experiment was performed in which the RNA transcript levels of genes of *Nannochloropsis gaditana* cells under nitrogen starvation, under which *Nannochloropsis* induces storage lipid biosynthesis, were compared with the levels of RNA transcripts of the same strain of *Nannochloropsis gaditana* grown under identical conditions except that the amount of nitrogen in the growth medium was not limiting.

Wild type *N. gaditana* (WT-3730) cells were grown in nutrient replete medium under a 16 hour light (120 µE)/8 hour dark cycle to light limitation and at the beginning of the photoperiod were spun down and resuspended in either nitrogen replete medium PM074 or culture medium lacking a nitrogen source ("nitrogen deplete" medium PM067). RNA was isolated from each sample three hours after resuspension in nitrogen replete or nitrogen depete medium. RNA was isolated by spinning down 10 mLs of each algal cell culture (4000×g for 5 minutes) and decanting the supernatant. The pellets were resuspended in 1.8 mL Buffer A (5 mL TLE Grinding Buffer, 5 mL phenol, 1 mL 1-bromo-3-chloropropane and 20 mercaptoethanol, where TLE Grinding Buffer includes 9 mL of 1M Tris pH 8, 5 mL of 10% SDS, 0.6 mL of 7.5 M LiCl, and 0.45 M EDTA in a final volume of 50 mL) and transferred to 2 mL microcentrifuge tubes containing approximately 0.5 mL of 200 µm zirconium beads. The tubes were vortexed vigorously for 5 min at 4° C. and then centrifuged for 2 min at 11.8×g. The aqueous layers were then removed and pipetted into new 2 mL tubes, to which 1 mL 25:24:1 phenol extraction buffer (25 mL phenol pH 8 or 5.1; 24 mL 1-bromo-3-chloropropane, and 1 mL isoamyl alcohol) was added. The tubes were shaken vigorously and centrifuged for 2 min at 11.8×g. After centrifugation, the aqueous layer was removed and pipetted into new 2 mL centrifuge tubes, to which 1 ml 1-bromo-3-chloropropane was added. The tubes were shaken and again centrifuged for 2 min at 11.8×g. The aqueous layer was removed to a new tube and 0.356 volumes of 7.5 M LiCl were added. The tubes were inverted 10-12 times and stored at −20° C. overnight. The next day, samples were allowed to come to room temperature without mixing and were centrifuged at 16,000×g for 30 minutes. The supernatants were removed and the pellets were washed with 1 mL of ice cold 80% ethanol. The tubes were centrifuged for 30 min at 16,000×g and allowed to air dry after the supernatants had been removed. Finally, the RNA pellets were resuspended in 50 µl ultrapure water. The RNA quality was assessed by on-chip gel electrophoresis using an Agilent 2100 Bioanalyzer and RNA6000 LabChip according to manufacturer instructions.

Next-generation sequencing libraries were prepared from the isolated RNA utilizing the TruSeq Stranded mRNA Sample Prep Kit (Illumina, San Diego, Calif.) following manufacturer instructions. The TruSeq libraries were sequenced using sequencing-by-synthesis (Illumina MiSeq) to generate 100 bp paired-end reads using the mRNA-Seq procedure (described in Mortazavi et al. (2008) *Nature Methods* 5:621-628). Mappable reads were aligned to the *N. gaditana* reference genome sequence using TopHat (tophat.cbcb.umd.edu/). Expression levels were computed for every annotated gene using the Cuffdiff component of the Cufflinks software (cufflinks.cbcb.umd.edu). Differential expression analysis was performed using the R package edgeR (McCarthy et al. (2012) *Nucl. Acids Res.* 40:doi:10/1093/nar/gks042)). Expression levels in units of fragments per kilobase per million (FPKM) were reported for every gene in each sample using standard parameters. FPKM is a measure of relative transcriptional levels that normalizes for differences in transcript length.

From this analysis a list was compiled of differentially expressed genes under nitrogen-replete and nitrogen-deplete conditions. The list of differentially expressed genes was compared with a bioinformatically curated list of putative *Nannochloropsis* transcription factors previously generated in-house by mining the *Nannochloropsis* genome for proteins containing DNA binding domains and other conserved pfam domains typical of characterized transcription factors using the Plant Transcription Factor Database as a reference (Perez-Rodriguez et al. (2010) *Nucl. Acids Res.* 38:D822-D827; Jin et al. (2013) *Nucl. Acids Res.* 42: D1182-D1187).

Figure 1B:
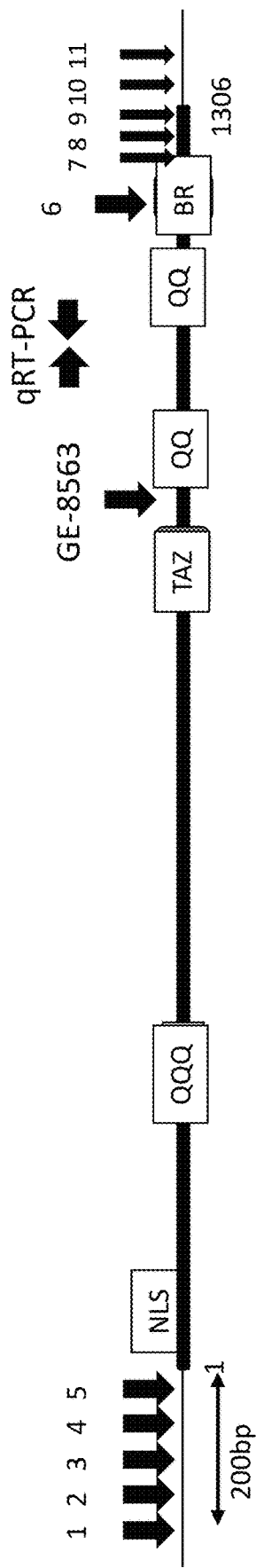
FIG. 1B is a schematic depiction of the *N. gaditana* Bromo-1091 gene. Boxes denote the positions of the TAZ Zn finger domain (TAZ) and the Bromo domain (BR). The approximate location of the putative nuclear localization signal is also shown (NLS), as well as three glutamine-rich regions, denoted by the letter "Q". Arrows 1-5 point to positions upstream of the coding region that were targeted by CRISPR guide sequences. The arrow labeled GE-8563 demonstrates the region of the gene just downstream of the TAZ Zn finger domain where the Hygromycin resistance marker was inserted using CRISPR/Cas9 to generated knockout strain GE-8563. Primer sites for qRT-PCR to determine transcript levels of knockdowns are also denoted. The figure is not to scale.
Figure 3:
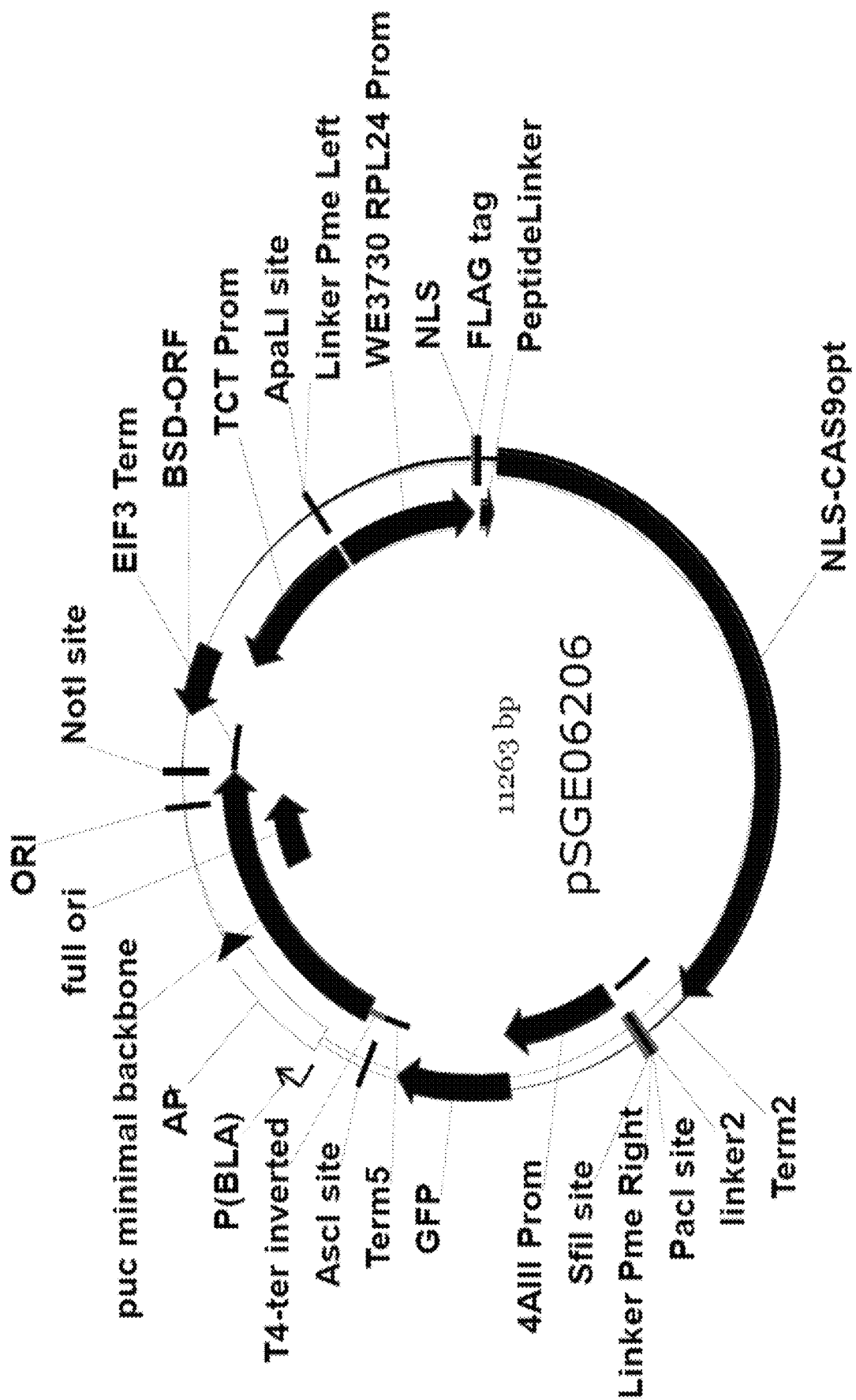
FIG. 3 is a schematic map of vector pSGE-6206 used to introduce Cas9 into the *N. gaditana* wild type strain WT-3730 to generate the Cas9 Editor line.

As disclosed in commonly-owned, copending U.S. patent application Ser. No. 15/210,845, the ZnCys-2845 gene was identified as a transcription factor gene differentially regulated at the outset of nitrogen deprivation (FIG. 1A). A second gene that was not identified as a transcription factor was also identified as differentially expressed between the N-replete and N-deplete samples. This gene (cDNA sequence provided as SEQ ID NO:1) encoding a polypeptide (SEQ ID NO:2) encoded a polypeptide having domains found in transcriptional co-regulators. The polypeptide was observed to have a TAZ Zinc Finger domain (Pfam PF02135), a protein-protein interaction domain found in transcriptional regulators (see, for example, Guzman et al. (2004) *J. Biol. Chem.* 279: 3042-3049) and a Bromo domain (pfam PF00439) (SEQ ID NO:10), a domain known to bind acetylated histones, and was named "Bromo-1091". A diagram of the polypeptide of SEQ ID NO:2 is provided in FIG. 1B.

Figure 2B:
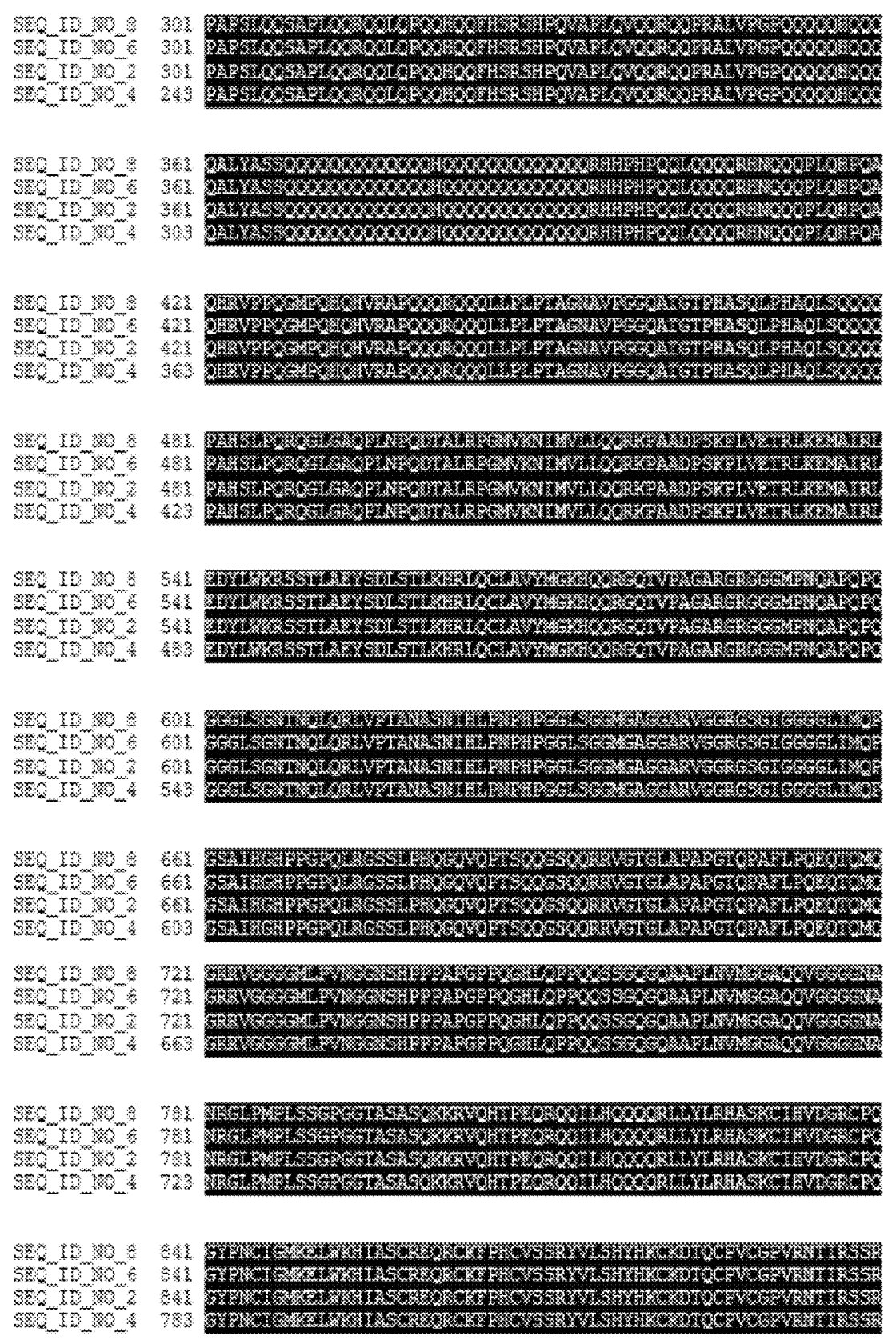

Example 2. Bioinformatic Analysis of the Bromo-1091 Protein: Domains and Orthologs In addition to the transcript encoding SEQ ID NO:2, three additional transcripts were identified by RNA Seq and 3' RACE (rapid amplification of cDNA ends; Frohman, et al. (1988). *Proc. of the Natl Acad Sci. USA* 85: 8998-9002) that originate from the Bromo-1091 gene and extensively overlap with SEQ ID NO:1. RACE was performed using the MARATHON® cDNA amplification kit (Clontech, Mountain/View, Calif.) to obtain cDNAs from RNA isolated using the NUCLEO TRAP® mRNA mini RNA isolation kit (Clontech). The nucleotide sequences of these transcripts are provided as SEQ ID NO:3, SEQ ID NO:5, and SEQ ID NO:7, encoding the polypeptides of SEQ ID NO:4, SEQ ID NO:6, and SEQ ID NO:8, respectively. An alignment of the sequences of the polypeptide variants encoded by the four cDNAs is provided as FIG. 2A-C. Each of the polypeptides encoded by transcripts of the Bromo-1091 gene includes the same "TAZ" zinc finger domain (PF002135), amino acids 827-892 of SEQ ID NO:2 and amino acids 769-834 of SEQ ID NO:4 (SEQ ID NO:9). SEQ ID NO:2 and SEQ ID NO:4 also include the same "Bromo" domain (pfam PF00439), amino acids 1223 to 1264 of SEQ ID NO:2 and 1165-1206 of SEQ ID NO:4 (SEQ ID NO:10), that were identified as conserved domains in the polypeptide encoded by the Bromo-1091 cDNA SEQ ID NO:2. For simplicity, we refer herein to all four polypeptides as the "Bromo-1091 protein" or "Bromo-1091 polypeptide", where the different isoforms (isoforms a, b, c, and d), which appear to result from alternative splicing (referred to as Bromo-1091 transcripts a, b, c, and d), differ primarily in the carboxy terminus (e.g., the terminal 25-35 amino acids of the polypeptides of SEQ ID NOs:2, 4, 6, and 8). SEQ ID NO:4 also lacks a stretch of amino acids present in the other isoforms extending from amino acid 226 to amino acid 289 of SEQ ID NO:2.

Co-pending and commonly-owned U.S. patent application Ser. No. 15/210,845, filed Jul. 14, 2016, discloses a regulator gene "ZnCys-2845" whose mutation results in the ability of the mutant strain to induce lipid synthesis in the presence of a nitrogen source such as nitrate even while continuing to propagate and accumulate biomass. The "Bromo-1091" gene newly disclosed herein that includes a TAZ Zinc Finger domain and a bromo domain is the second gene discovered whose mutation results in the ability of the mutant strain to induce lipid synthesis while continuing to propagate and accumulate biomass in the presence of a nitrogen source such as nitrate. The ZnCys-2845 gene and orthologs thereof in other species may be referred to herein as LION1 ("Lipid Induced On Nitrate 1") genes and the Bromo-1091 gene and orthologs thereof are referred to herein as "LION2" ("Lipid Induced On Nitrate 2") genes.

Several potential orthologs of Bromo-1091 were identified by bioinformatics. In particular, several genes were identified in stramenopiles (heterokonts) that had both a TAZ zinc finger domain and a bromo domain, including a partial sequence of an ortholog in *Nannochloropsis oceanica* (SEQ ID NO:11, encoding amino acid sequence SEQ ID NO:12), in which the amino acid sequence (SEQ ID NO:12), which does not appear to be the complete polypeptide, demonstrates 84% identity to a portion of SEQ ID NO:2, and includes a TAZ Zinc Finger domain that has 95% identity to the TAZ Zinc Finger domain of the *Nannochloropsis gaditana* Bromo-1091 ("LION2") polypeptide (SEQ ID NO:9). Other putative orthologs that include both a bromo domain and a TAZ zinc finger domain include polypeptides from diatoms, e.g., *Phaeodactylum, Thalassiosira, Navicula,*

Fragilariopsis, and Cyclotella, as well as Aureococcus, Ectocarpus, and the labyrinthulomycete Schizochytrium (see Table 1).

TABLE 1

Putative Bromo-1091 Orthologs of N. gaditana Bromo-1091 in Heterokonts

| Species | Nucleotide sequence (cDNA) | Amino acid sequence (polypeptide) | TAZ domain(s) amino acids | Bromo domain amino acids |
|---|---|---|---|---|
| Nannochloropsis oceanica | SEQ ID NO: 11 | SEQ ID NO: 12 | 65-127 | |
| Cyclotella sp. | SEQ ID NO: 13 | SEQ ID NO: 14 | 221-284; 1338-1399 | 631-715 |
| Cyclotella sp. | SEQ ID NO: 15 | SEQ ID NO: 16 | 1438-1515 | 470-564 |
| Cyclotella sp. | SEQ ID NO: 17 | SEQ ID NO: 18 | 704-765; 476-357 | 911-1007 |
| Fragilariopsis cylindrus | SEQ ID NO: 19 | SEQ ID NO: 20 | 350-411; 1328-1387 | 549-644 |
| Fragilariopsis cylindrus | SEQ ID NO: 21 | SEQ ID NO: 22 | 1-42 | 183-273 |
| Thalassiosira pseudonana | SEQ ID NO: 23 | SEQ ID NO: 24 | 761-822 | 51-146 |
| Thalassiosira pseudonana | SEQ ID NO: 25 | SEQ ID NO: 26 | 648-709; 441-502 | 833-929 |
| Phaeodactylum tricornutum | SEQ ID NO: 27 | SEQ ID NO: 28 | 862-925; 2323-2384 | 1251-1341 |
| Phaeodactylum tricornutum | SEQ ID NO: 29 | SEQ ID NO: 30 | 339-400; 1494-1571 | 582-670 |
| Phaeodactylum tricornutum | SEQ ID NO: 31 | SEQ ID NO: 32 | 1-42; 957-1016 | 179-271 |
| Navicula sp. | SEQ ID NO: 33 | SEQ ID NO: 34 | 242-302; 460-521; 1438-1497 | 671-762 |
| Navicula sp. | SEQ ID NO: 35 | SEQ ID NO: 36 | 357-420; 2136-2197 | 764-860 |
| Navicula sp. | SEQ ID NO: 37 | SEQ ID NO: 38 | 277-338; 1444-1521 | 530-520 |
| Ectocarpus silicosus | SEQ ID NO: 39 | SEQ ID NO: 40 | 1244-1322 | 420-516 |
| Aureococcus anophagefferens | SEQ ID NO: 41 | SEQ ID NO: 42 | 758-836 | 2-78 |
| Schizochytrium limacinum | SEQ ID NO: 43 | SEQ ID NO: 44 | 1-42; 1533-1600 | 244-330 |
| Schizochytrium limacinum | SEQ ID NO: 45 | SEQ ID NO: 46 | 1-42; 936-998 | 171-261 |

Example 3. Knockout of the Bromo-1091 Locus in Nannochloropsis

In order to determine whether there was any relationship between the Bromo-1091 polypeptide and lipid induction, the Bromo-1091 gene was knocked out using CRISPR technology as described in commonly owned co-pending U.S. patent application Ser. No. 14/986,492 and corresponding PCT application publication no. WO2016/109840, filed Dec. 31, 2015. As described in U.S. Ser. No. 14/986,492, a highly efficient Nannochloropsis Cas9 Editor line, N. gaditana strain pSGIE-6791, expressing a gene encoding the Streptococcus pyogenes Cas9 nuclease was used as a host for transformation with a chimeric guide RNA and donor DNA for insertional knockout.

To produce the high efficiency Nannochloropsis Cas9 Editor line, a Nannochloropsis strain was engineered and isolated that exhibited expression of the introduced Cas9 genes in close to 100% of the cell population of a growing culture. The vector pSGE-6206 (SEQ ID NO:47), used to transform wild type N. gaditana strain pSGIE-6791, included the following three elements: 1) a Cas9 expression cassette which contained a Cas9 gene from Streptococcus pyogenes codon optimized for Nannochloropsis gaditana (SEQ ID NO:48) that included sequences encoding an N-terminal FLAG tag (SEQ ID NO:49), nuclear localization signal (SEQ ID NO:50), and peptide linker (SEQ ID NO:51), driven by the N. gaditana RPL24 promoter (SEQ ID NO:52) and terminated by N. gaditana bidirectional terminator 2 (SEQ ID NO:53); 2) a selectable marker expression cassette, which contained the blast gene from Aspergillus terreus codon optimized for N. gaditana (SEQ ID NO:54), driven by the N. gaditana TCTP promoter (SEQ ID NO:55) and followed by the EIF3 terminator (SEQ ID NO:56); and 3) a GFP reporter expression cassette, which contained the TurboGFP gene (Evrogen, Moscow, Russia) codon optimized for Nannochloropsis gaditana (SEQ ID NO:57), driven by the N. gaditana 4A-III promoter (SEQ ID NO:58) and followed by the N. gaditana bidirectional terminator 5 (SEQ ID NO:59).

The transformation mixture was plated onto PM074 agar medium containing 100 mg/L of blasticidin. Resulting colonies were patched onto selection media for analysis and archiving. A small bit of biomass was taken from the patches and completely resuspended in 300 μl of 1× Instant Ocean solution. Care was taken to not add too much biomass so that a light green resuspension was obtained. This liquid was directly analyzed by flow cytometry using a BD Accuri C6 flow cytometer, using a 488 nm laser and 530/10 nm filter to measure GFP fluorescence per cell. 10,000-30,000 events were recorded for each sample using the slow fluidics setting. The resulting histograms were overlaid with histograms of wild type cells (i.e., cells not expressing a fluorescent protein) run separately. Only strains with full penetrance expression in culture were carried forward; this meant that the flow cytometry histogram showed a single peak or bell-shaped curve in which the peak was fully shifted higher than the wild type auto fluorescence peak when plotted on a log scale. These strains were designated as "fully penetrant" Cas9 expressing strains, in that the expression of the GFP gene was found throughout the cells of a culture of the strain. That is, while at any given point in time the amount (and therefore fluorescence) of GFP might vary somewhat cell-to-cell, resulting in a bell-shaped curve, there was no subpopulation of cells exhibiting a distinct distribution of GFP expression. Thus, a fully penetrant strain was one in which there was a single peak (or bell-shaped curve having a peak) where the peak was separate from and at a higher fluorescence value than the background peak of non-expressing cells (e.g., cells not transformed with a GFP expression construct). Because the GFP gene was physically associated with the Cas9 gene, it was postulated that the Cas9 gene was also likely expressed throughout the cells of a culture of the strain in fully penetrant GFP strains.

Fully penetrant Cas9 strains demonstrating a single clearly shifted fluorescence peak with respect to nontransformed cells were subsequently tested by western blotting with an anti-FLAG antibody for evidence of Cas9 expression. A strain having a single fluorescence peak that was shifted to a fluorescence level higher than that demonstrated by wild-type cells and also demonstrating Cas9 protein expression by Western, designated strain GE-6791, was selected as a fully penetrant Cas9 strain resulting from transformation with pSGE-6202 for use in mutant generation by genome editing as described herein.

For targeting of the Bromo-1091 gene for disruption, a DNA molecule that included the sequence of a chimeric guide (SEQ ID NO:60) that included an 18 bp sequence (SEQ ID NO:61) corresponding to a sequence within the Bromo-1091 gene was synthesized (SGI-DNA, La Jolla, Calif.) downstream of a T7 promoter sequence. The construct was used in in vitro transcription reactions using the MEGAshortscript™ T7 Kit (Life Technologies # AM1354M) according to the manufacturer's instructions. The resulting RNA was purified using Zymo-Spin™ V-E columns (Zymo Research # C1024-25) according to manufacturer's protocol.

The donor fragment for insertion into the targeted Bromo-1091 locus included a selectable marker cassette that included the hygromycin resistance gene (HygR, SEQ ID NO:62) downstream of the N. gaditana EIF3 promoter (SEQ ID NO:63) and followed by N. gaditana bidirectional terminator 2 (SEQ ID NO:53), with the entire promoter-Hygromycin resistance gene terminator sequence flanked by 27 base pair identification sequences on the 5' (SEQ ID NO:64) and 3' (SEQ ID NO:65) ends to yield the DNA fragment referred to as the "Hyg Resistance Cassette" (SEQ ID NO:66).

For targeted knockout of the Bromo-1091 locus, SGIE-6791 was transformed by electroporation using 5 µg of purified chimeric guide RNA targeting the Bromo-1091 gene (SEQ ID NO:60) and 1 µg of the selectable donor DNA (Hyg Resistance Cassette; SEQ ID NO:66). Following electroporation, cells were plated on agar media containing hygromycin to select for transformants that incorporated the hygromycin resistance cassette. Transformants were screened by colony PCR for insertion of the donor fragment into the Bromo-1091 gene.

For colony PCR screening, a small amount of cells from a colony to be screened was suspended into 100 µl of 5% Chelex 100 Resin (BioRad)/TE solution and the suspension was boiled for boiled 10 minutes at 99° C., after which the tubes were briefly spun. One microliter of the lysate supernatant was added to a PCR reaction mix, in which the PCR mixture and reactions were set up and performed according to the QIAGEN Fast Cycling PCR Master Mix Protocol from the manufacturer (Handbook available at qiagen.com). Based on the PCR-based colony screening, one knockout strain, GE-8563, was selected for further analysis.

Example 4. Bromo-1091 Knockout Mutant in Batch Productivity Assay

To determine the effect of knocking out the Bromo-1091 gene on growth and lipid production, Bromo-1091 knockout strain GE-8563 and the wild type N. gaditana progenitor strain WT-3730 were grown in a batch productivity assay, in which cells were cultured for one week in 75 cm$^2$ rectangular tissue culture flasks containing 175 ml of culture medium PM123 that included 15 mM nitrate as the sole nitrogen source, i.e., the culture medium the starter culture was diluted into for productivity assays had no source of reduced nitrogen. Three flasks each of WT-3730 and GE-8563 were inoculated to an initial OD730 of 0.5 from starter cultures. Starter cultures of Bromo knockout strain GE-8563 used PM124 medium, which included 5 mM ammonium in addition to approximately 8.8 mM nitrate. Wild type WT-3730 starter cultures used PM074 nitrate-only medium. Typical dilutions of starter culture into the assay culture medium were from 15-35 mls of starter culture brought up to 175 mls total using PM123 (nitrate only) medium. Thus the initial concentration of ammonium in the batch assays ranged from approximately 0.4 mM to approximately 1 mM. Air that included 1% $CO_2$ was bubbled into the cultures by tubing connected to the cap of each flask and the lights, which were directed at the flasks from one narrow side (i.e., the light was introduced from the side along the narrowest width dimension of the culture flask), were programmed to simulate the intensities experienced on a spring day in Southern California, peaking at an intensity of approximately 1200 µE at "solar noon". The diel cycle was 16 h light/8 h dark. The temperature was held at approximately 25° C. by positioning the culture flasks in a water bath. Cultures were inoculated on day 0 and samples (5 mls) were removed on days 3, 5, and 7 for assessing cell density, fatty acid methyl esters (FAME), and total organic carbon (TOC).

FAME analysis was performed on 2 mL samples that were dried using a GeneVac HT-4X. To the dried pellets the following was added: 500 µL of 500 mM KOH in methanol, 200 µL of tetrahydrofuran containing 0.05% butylated hydroxyl toluene, 40 µL of a 2 mg/ml C11:0 free fatty acid/C13:0 triglyceride/C23:0 fatty acid methyl ester internal standard mix and 500 µL of glass beads (425-600 µm diameter). The vials were capped with open top PTFE septa-lined caps and placed in an SPEX GenoGrinder at 1.65 krpm for 7.5 minutes. The samples were then heated at 80° C. for five minutes and allowed to cool. For derivatization, 500 µL of 10% boron trifluoride in methanol was added to the samples prior to heating at 80° C. for 30 minutes. The tubes were allowed to cool prior to adding 2 mL of heptane and 500 µL of 5 M NaCl. The samples were then vortexed for five minutes at 2 krpm and finally centrifuged for three minutes at 1 krpm. The heptane layer was sampled using a Gerstel MPS Autosampler. Quantitation used the 80 µg of C23:0 FAME internal standard.

Total organic carbon (TOC) was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of $r^2 > 0.999$.

The results of the FAME and TOC analyses of the strains cultured in batch mode in medium that included nitrate as the sole nitrogen source are provided in Tables 2-4.

TABLE 2

FAME (µg/ml) produced by wild type and Bromo-1091 knockout cells

| DAY | WT | s.d. | Bromo-KO | s.d. | Difference | % Increase (Bromo v. wt) |
|---|---|---|---|---|---|---|
| 3 | 105.03 | 9.71 | 139.66 | 5.56 | 34.63 | 32.97 |
| 5 | 140.01 | 13.48 | 167.71 | 4.58 | 27.70 | 19.78 |
| 7 | 198.49 | 2.035 | 199.08 | 20.60 | 0.58 | 0.29 |

TABLE 3

Biomass (TOC) (µg/ml) produced by wild type and Bromo-1091 knockout cells.

| DAY | WT | s.d. | Bromo-KO | s.d. | Difference | % Difference (Bromo v. wt) |
|---|---|---|---|---|---|---|
| 3 | 375.6 | 10.18 | 307.4 | 21.64 | -68.2 | -18.16 |
| 4 | 474.6 | 8.34 | 372.45 | 1.06 | -102.15 | -21.52 |
| 5 | 534.45 | 43.20 | 410.4 | 9.62 | -124.05 | -23.21 |
| 6 | 644.8 | 48.65 | 487.45 | 5.73 | -157.35 | -24.4 |
| 7 | 804.35 | 36.13 | 582.7 | 14.71 | -221.65 | -27.56 |

TABLE 4

FAME/TOC ratios of Bromo-1091 knockout mutant and wild type stains.

| DAY | WT | s.d. | Bromo-KO | s.d. | Difference (Bromo v. wt) | % Increase (Bromo v. wt) |
|---|---|---|---|---|---|---|
| 3 | 0.28 | 0.018 | 0.45 | 0.014 | 0.17 | 60.71 |
| 5 | 0.26 | 0.004 | 0.41 | 0.002 | 0.15 | 57.69 |
| 7 | 0.25 | 0.009 | 0.34 | 0.027 | 0.09 | 36.0 |

Table 2 shows that by Day 3 of the assay, the Bromo-1091 knockout mutant had produced approximately 33% more FAME lipids than wild type cells. The increase in lipid production with respect to wild type cells declined over the course of the assay, however, such that by day 5 of the assay, the mutant strain had produced just 20% more FAME/ml than was produced by wild type. By day 7 the Bromo-1091 knockout cultures had essentially the same amount of FAME/ml as the wild type cultures.

Table 3 shows that at every stage of the batch assay, the Bromo-1091 knockout mutant cultures had less biomass than the wild type cultures, and the Bromo-1091 knockout mutant cultures were falling further behind the wild type cultures in biomass accumulation as the assay progressed.

Table 4 shows that the wild type had typical non-induced FAME/TOC ratios of approximately 0.25 during the assay (the slightly higher value of 0.28 on day 3 may have been due to a stress response resulting from dilution into the assay flask, which results in a period of light stress the cells may have still been recovering from by day 3). The Brom-1091 knockout mutant however was induced for lipid on day 3 as evidenced by an elevated FAME/TOC ratio of 0.45, even though the Bromo-1091 knockout mutant continued to accumulate biomass throughout the assay, for example, the Bromo-1091 knockout mutant accumulated biomass to a level that throughout the assay was only about 20-25% less, e.g., 18-27.5% less, than the amount of biomass accumulated by wild type cells.

The Bromo-1091 mutant and wild type strain WT-3730 were cultured each in the same batch assay, except that the culture medium for the batch assay was PM124, which included both nitrate (8.8 mM) and ammonium (5 mM) as nitrogen sources. Samples were removed as described and analyzed for FAME and TOC as provided above. The results of the FAME and TOC analyses are provided in Tables 5-7.

TABLE 5

FAME (µg/ml) produced by wild type and Bromo-1091 knockout cells pre-cultured in and batch cultured in nitrate plus ammonium medium.

| DAY | WT | s.d. | Bromo-KO | s.d. | Difference (Bromo v. wt) | % Difference (Bromo v. wt) |
|---|---|---|---|---|---|---|
| 3 | 93.03 | 6.94 | 69.74 | 3.65 | -23.29 | -25.03 |
| 4 | 120.14 | 8.43 | 101.93 | 1.44 | -18.21 | -15.16 |
| 5 | 121.31 | 0.79 | 117.93 | 3.37 | -3.37 | -2.8 |
| 6 | 169.70 | 6.07 | 165.57 | 4.24 | -4.13 | -2.43 |
| 7 | 198.11 | 7.95 | 210.79 | 4.74 | 12.68 | +6.4 |

TABLE 6

Biomass (TOC) (µg/ml) produced by wild type and Bromo-1091 knockout cells batch cultured in nitrate plus ammonium medium.

| DAY | WT | s.d. | Bromo-KO | s.d. | Difference | % Difference (Bromo v. wt) |
|---|---|---|---|---|---|---|
| 3 | 321.5 | 35.07 | 186.1 | 13.86 | 135.4 | -42.12 |
| 4 | 392.3 | 16.69 | 298.3 | 10.47 | 94 | -23.96 |
| 5 | 464 | 4.38 | 399.75 | 12.80 | 64.25 | -13.85 |
| 6 | 556.45 | 20.15 | 504.1 | 7.50 | 52.35 | -9.41 |
| 7 | 679.95 | 6.01 | 635.35 | 38.82 | 44.6 | -6.56 |

TABLE 7

FAME/TOC ratios of Bromo-1091 knockout mutant and wild type stains in Batch Assay with nitrate plus ammonium medium.

| DAY | WT | s.d. | Bromo-KO | s.d. | Difference (Bromo v. wt) | % Difference (Bromo v. wt) |
|---|---|---|---|---|---|---|
| 3 | 0.29 | 0.0100 | 0.38 | 0.0476 | 0.11 | 37.93 |
| 4 | 0.31 | 0.0085 | 0.34 | 0.0072 | 0.03 | 9.68 |
| 5 | 0.26 | 0.0008 | 0.30 | 0.0010 | 0.04 | 15.38 |
| 6 | 0.31 | 0.02196 | 0.33 | 0.0035 | 0.02 | 6.45 |
| 7 | 0.29 | 0.0091 | 0.33 | 0.0128 | 0.04 | 13.79 |

Figure 4A:
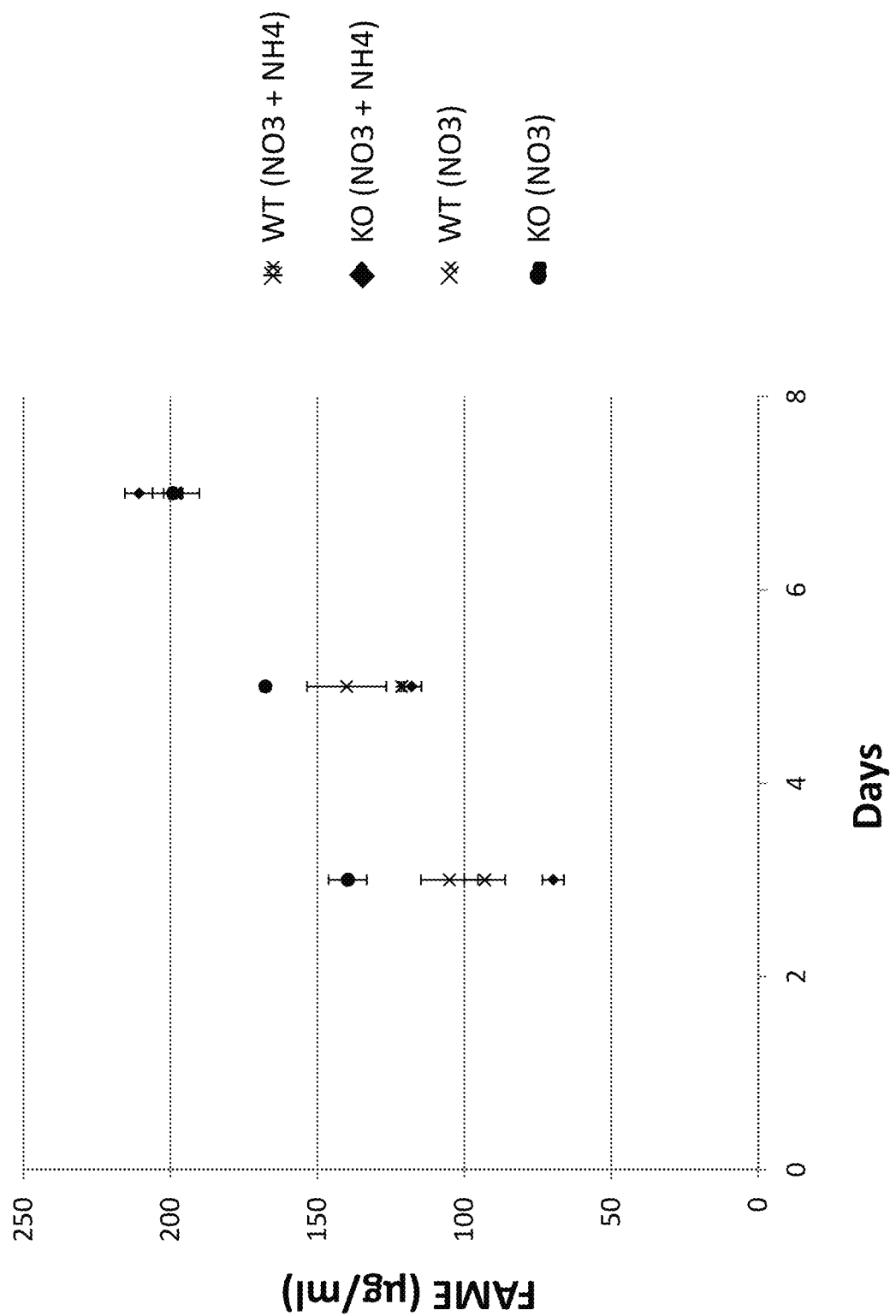
FIGS. 4A-4C are graphs depicting FAME/TOC values.

The results of FAME analysis provided in Table 2 and Table 5 are depicted in FIG. 4A, in which it can be seen that the Bromo-1091 knockout cultures, when grown on nitrate as the sole nitrogen source (but not when the culture medium included ammonium), had increased FAME with respect to wild type at the outset of the culture (on day 3) but actually produced less FAME per day with respect to wild type on days 3-7, such that the amount of FAME in the cultures was highly similar by day 7. The lower FAME productivity could be attributed to a slower overall growth rate, as evidenced in FIG. 4B, which provides a graph of biomass accumulation during the assay. Table 6 shows that biomass accumulation by the Bromo-1091 knockout mutant grown in the presence of ammonium and nitrate tracked FAME accumulation of the same culture (Table 5), with both being similar to wild type by day 5 of the assay. The FAME/TOC ratio of the Bromo-1091 knockout mutant was elevated approximately 60% with respect to wild type (non-induced) cells when both the mutant and wild type were cultured in nitrate only medium (Table 4). A much smaller increase (38%) in the FAME/TOC ratio was observed on day 3 of the Bromo-1091 knockout mutant cultures that included ammonium in the culture medium; however this increase with respect to wild type cells lessened considerably over the next 4 days to only 10-15% greater than the wild type FAME/TOC ratios. Thus, as evidenced by the FAME/TOC ratios over the course of the batch assay (FIG. 4C) the Bromo-1091 knockout mutant was induced for lipid biosynthesis on nitrate-only medium, but not when ammonium was present in the culture medium.

Example 5. Growth and Lipid Biosynthesis of the Bromo-1091 Knockout Mutant in Semi-Continuous Culture Bromo-1091 Cas9 knockout strain GE-8563 was also assayed in the semi-continuous productivity assay. In the continuous productivity assay PM074 (nitrate only) medium in a 225 cm$^2$ flask was inoculated with *Nannochloropsis* seed culture so that the initial 550 ml (inoculated final volume) culture had an initial $OD_{730}$ of 0.15. A typical dilution used approximately 150 mls of starter culture in PM124 medium (containing 5 mM ammonium) which was brought up to 550 mls using PM074 medium, such that the starting concentration of ammonium in the semi-continuous assay was less than 1.5 mM. Daily dilutions with PM074 medium further reduced the ammonium concentration as the assay progressed. Three cultures were initiated per strain. The flasks included stir bars and had stoppers having tubing connected with syringe filters for delivering $CO_2$ enriched air (1% $CO_2$, flow rate, 100 ml per min) that was bubbled through the cultures. The flasks were set on stir plates set to 450 rpm. The flasks were aligned with the width (narrowest dimension) against an LED light bank that was programmed with a light/dark cycle and light profile that increased until "solar noon" and then declined to the end of the light period. The "depth" dimension of the flasks, extending back from the light source, was 13.7 cm. Taking into account the positioning of the flasks the farthest distance of the cells in the flasks from the surface of the light source was approximately 15.5 cm. The light profile was designed to mimic a spring day in Southern California: 16 h light: 8 h dark, with the light peaking at approximately 2000 µE. The culture were diluted daily at the middle (peak) of the light period by removing 30% (150 ml) of the culture volume and replacing it with fresh PM074 media diluted (66 ml di $H_2O$ to 1 L PM074 medium) to adjust for the increase in salinity due to evaporation occurring in the cultures. Samples for FAME and TOC analysis were taken from the culture removed for the dilution. Continuous assays were typically run for 7-14 days. Tables 8-10 show the results of FAME and TOC analysis of knockout and wild type cultures run in the semi-continuous assay. Averages of three cultures are provided with the standard deviation of each value in parentheses.

TABLE 8

Daily production of FAME (µg/ml) by wild type and Bromo-1091 knockout cells in semi-continuous culture with daily dilution in nitrate-only medium.

| DAY | 1 | 2 | 3 | 4 | 5 | 6 | 7 |
|---|---|---|---|---|---|---|---|
| WT | 46.89 | 44.91 | 45.40 | 43.89 | 46.15 | 47.92 | 50.40 |
|  | (1.24) | (0.43) | (1.35) | (0.91) | (0.93) | (1.10) | (1.78) |
| Bromo-KO | 68.20 | 63.56 | 60.64 | 59.34 | 60.86 | 63.53 | 62.18 |
|  | (2.24) | (1.17) | (2.80) | (2.74) | (2.24) | (2.14) | (3.02) |
| % Increase (Bromo v. WT) | 45.45 | 41.53 | 33.57 | 35.20 | 31.87 | 32.58 | 23.37 |

TABLE 9

Daily production of TOC (µg/ml) by wild type and Bromo-1091 knockout cells in semi-continuous culture with daily dilution in nitrate-only medium.

| DAY | 1 | 2 | 3 | 4 | 5 | 6 | 7 |
|---|---|---|---|---|---|---|---|
| WT | 184.07 | 173.07 | 179.23 | 165.4 | 162.9 | 162.6 | 179.23 |
|  | (3.99) | (2.18) | (11.47) | (6.82) | (4.59) | (7.37) | (14.35) |
| Bromo -KO | 192.63 | 182.37 | 189.4 | 183.2 | 171.7 | 170.1 | 190.03 |
|  | (5.25) | (3.95) | (13.78) | (10.11) | (8.73) | (5.98) | (11.06) |
| Difference | 8.56 | 9.3 | 10.17 | 17.8 | 8.8 | 7.5 | 10.8 |
| % Difference (Bromo v. WT) | 4.65 | 5.37 | 5.67 | 10.76 | 5.40 | 4.61 | 6.03 |

TABLE 10

Daily FAME/TOC ratios of wild type and Bromo-1091 knockout cells in semi-continuous culture with daily dilution in nitrate-only medium.

| DAY | 1 | 2 | 3 | 4 | 5 | 6 | 7 |
|---|---|---|---|---|---|---|---|
| WT | 0.21 | 0.21 | 0.21 | 0.21 | 0.23 | 0.23 | 0.23 |
|  | (0.003) | (0.004) | (0.005) | (0.006) | (0.002) | (0.006) | (0.007) |
| Bromo -KO | 0.29 | 0.28 | 0.26 | 0.26 | 0.29 | 0.30 | 0.27 |
|  | (0.003) | (0.001) | (0.004) | (0.001) | (0.005) | (0.003) | (0.014) |

Figure 5A:
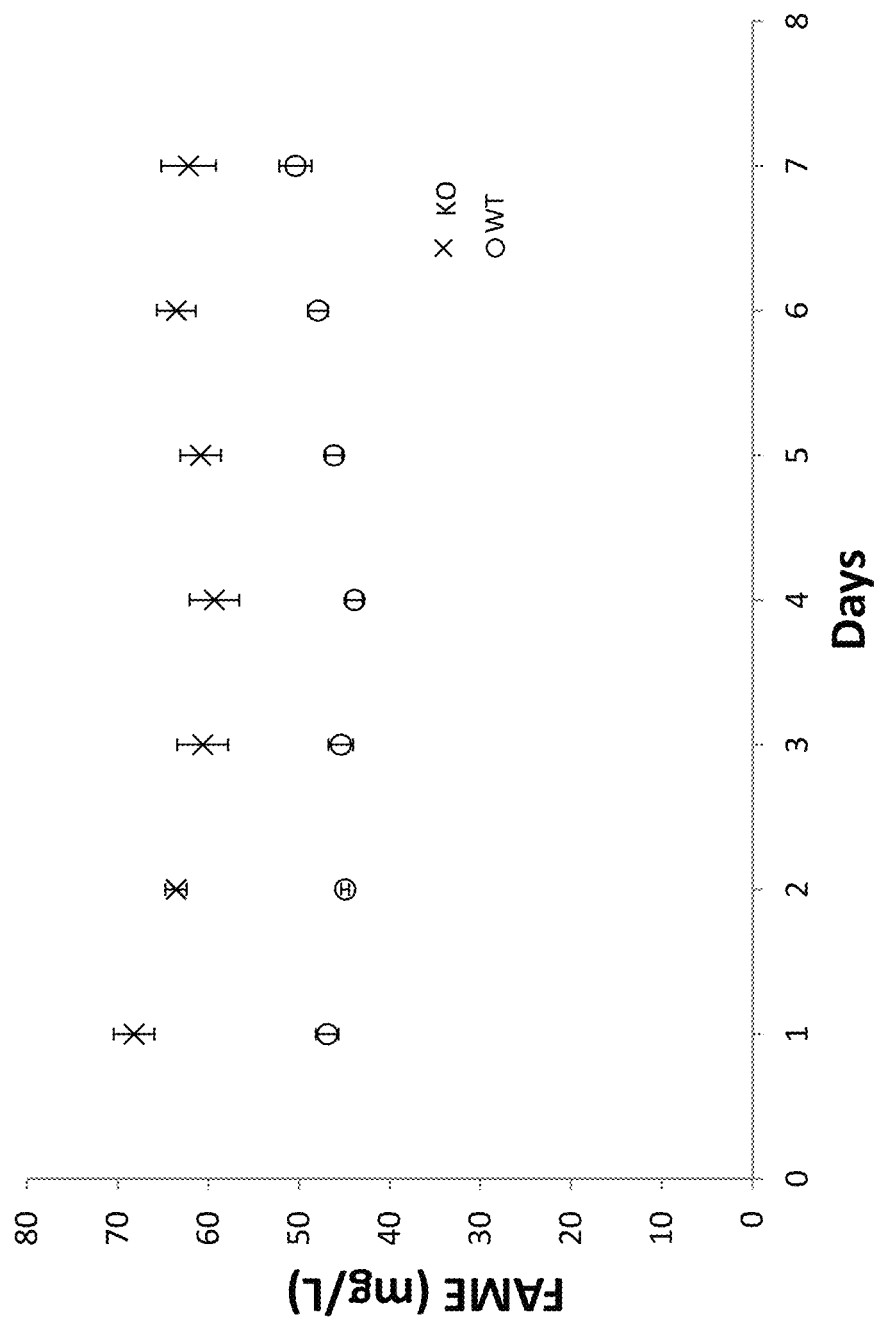
FIGS. 5A-5C provide graphs depicting productivities of the *N. gaditana* wild type strain and the GE-8563 Bromo-1091 knockout strain in a semi-continuous assay in which the culture medium includes nitrate as the sole nitrogen source.
Figure 5B:
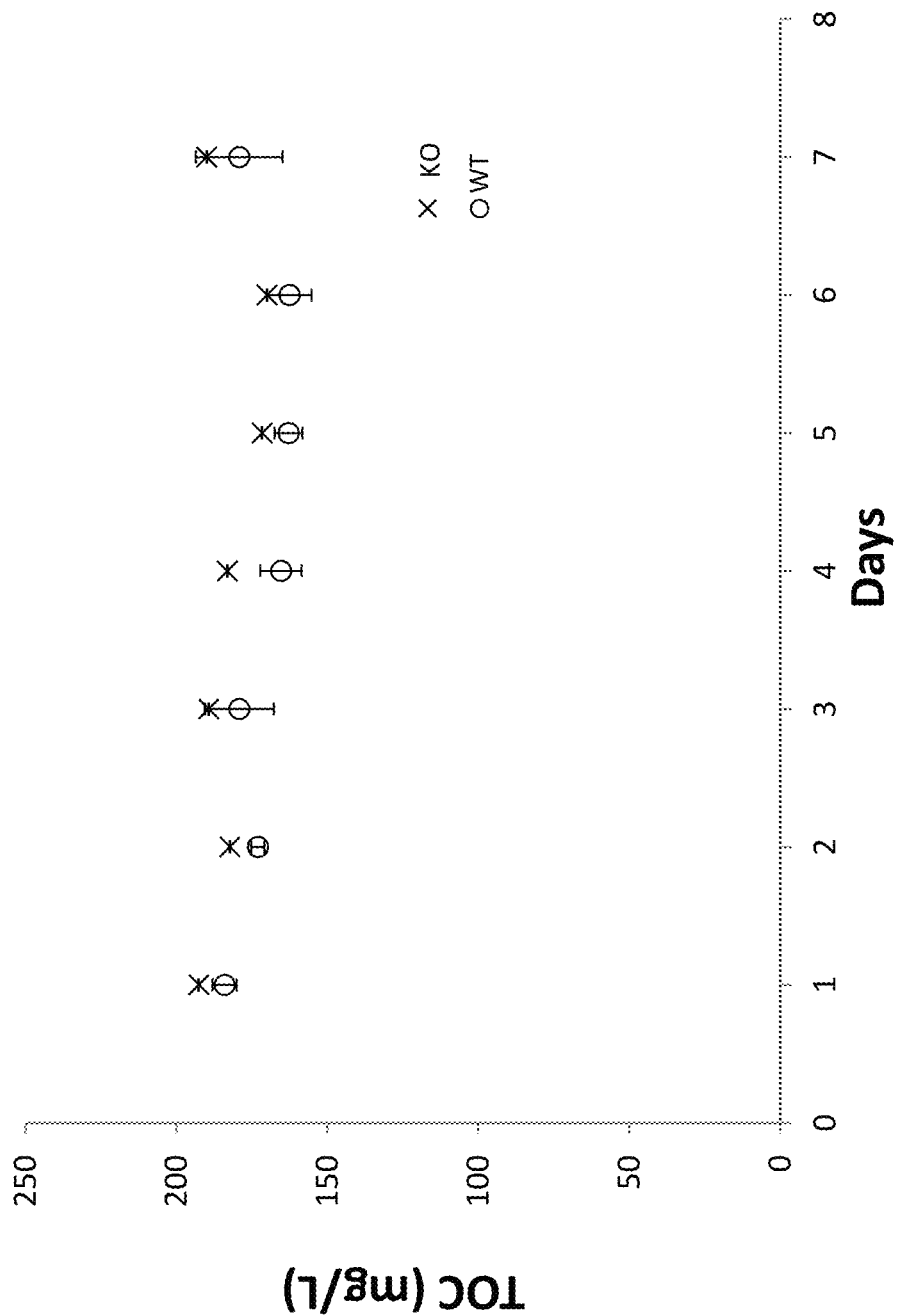
Figure 5C:
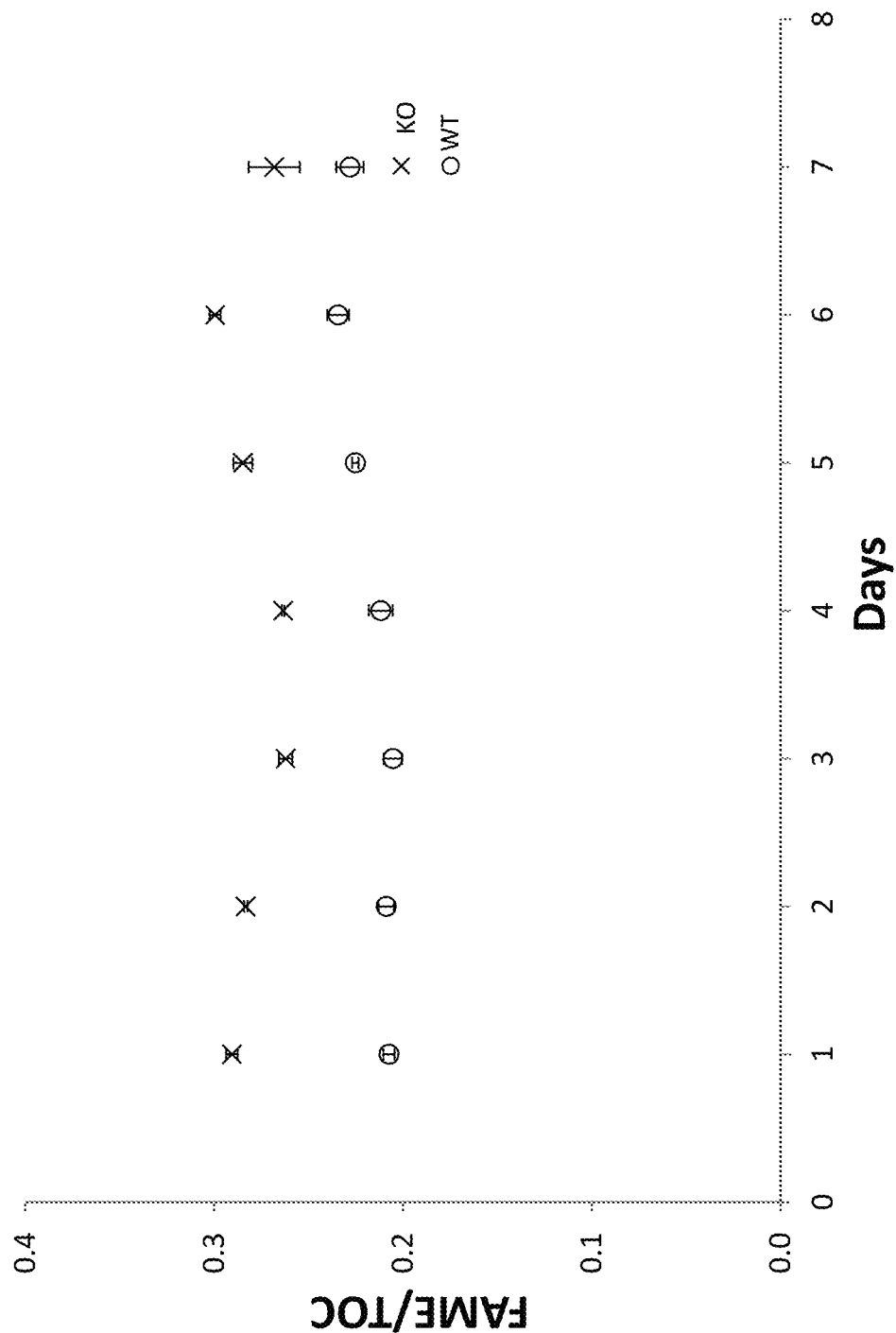

In the semi-continuous assay, performed with nitrate-only culture medium, the Bromo-1091 knockout mutant demonstrated a higher FAME productivity with respect to the wild type strain, with daily productivities ranging from about 20% to about 50% more than the FAME productivities of the wild type cells (Table 8 and FIG. 5A). Biomass (TOC) accumulation by the Bromo-1091 knockout mutant was, however, surprisingly in line with wild type cells (Table 9 and FIG. 5B). The increased partitioning of carbon to lipids was clear from the FAME/TOC ratio of the Bromo-1091 knockout mutant over the course of the assay (Table 10 and FIG. 5C) which showed that the mutant had a FAME/TOC ratio of from about 0.26 to about 0.30 over the course of the assay, whereas the FAME/TOC ratio of the wild type assayed under identical culture conditions varied between about 0.21 to 0.23.

Example 6. Cas9 Bromo-1091 Knockdown Constructs

Figure 6A:
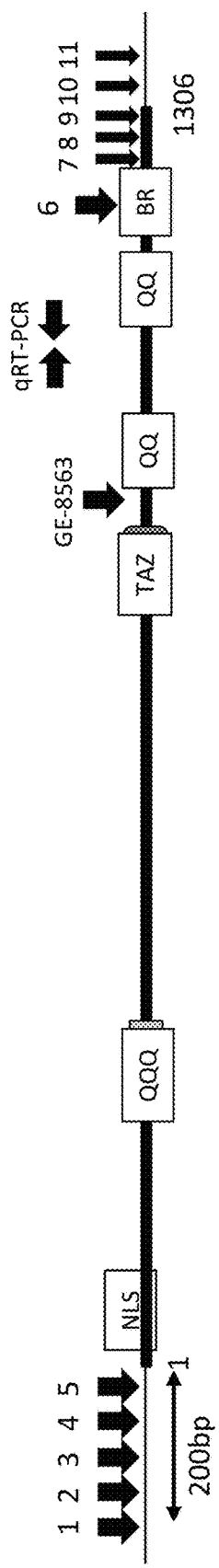
FIG. 6A) is a schematic depiction of the Bromo-1091 gene with the positions of the nuclear localization signal (NLS), TAZ Zn finger domain (TAZ) and Bromo domain (BR) shown as boxes, and arrows depicting the sites of CRISPR-targeted mutations, FIG. 6B) shows the relative transcript levels of the corresponding CRISPR-targeted mutants (position of primers used for transcript assessment shown in FIG. 6A), where "BASH-1" is strain GE-13027, "BASH-4" is GE-13030, and "BASH-5" is GE-13032, and the Bromo-1091 knockout strain is GE-8563. Normalized expression levels are relative to the average wild type level which was set to 1.0.

To test the productivity of additional mutant alleles that might have decreased but not eliminated expression of a Bromo-1091 gene, multiple insertions into the promoter region of the gene were generated using Cas9 (FIG. 6A, see arrows labeled 1-5) using the methods provided in Example 3 and guide RNAs targeting the 5' promoter of the gene as provided in Table 11.

TABLE 11

Guide RNA Sequences used to generate promoter insertions in Bromo-1091 Gene

| Strain | Guide RNA Sequence | N18 portion of guide (crRNA homologous to genomic sequence) |
|---|---|---|
| GE-13027 Bromo BASH-1 | SEQ ID NO: 67 | ACTGAAAGGGCAGAGTG (SEQ ID NO: 68) |
| GE-13030 Bromo BASH-4 | SEQ ID NO: 69 | TGTGGACGCTAGTACAGG (SEQ ID NO: 70) |
| GE-13032 Bromo BASH-5 | SEQ ID NO: 71 | AAAAGCGCCGTCTCGGAA (SEQ ID NO: 72) |

Chimeric guide DNA constructs were synthesized and purified as described in Example 3. Each chimeric guide RNA was individually transformed into *Nannochloropsis* Editor strain GE-6791 along with the donor fragment that included a Hyg resistance ("HygR") cassette (SEQ ID NO:67) as described in Example 3. Hygromycin resistant colonies were selected and screened by colony PCR as described using primers adjacent to the targeted region of the Bromo-1091 gene (Primers Br-promoter-FP (ATTGCTAGCCGTGCTTTCAAC; SEQ ID NO:73) and Br-promoter-RP (GTCGGTTTGGAGACCCTAGA; SEQ ID NO:74) to confirm donor fragment insertion into the 5' region of the Bromo-1091 gene.

Quantitative reverse transcription-PCR (qRT-PCR) was performed on RNA isolated from these "basher" lines to determine whether expression of the Bromo-1091 gene was in fact reduced in these lines. The Bromo-1091 Bash knockdown strains were grown under standard nitrogen replete conditions (PM074 (nitrate-only) medium) and harvested during early stationary phase, and total RNA was isolated from the cells\ using methods provided in Example 1, above. RNA was converted to cDNA BioRad's iScript™ Reverse Transcription Supermix reaction mixture kit for reverse transcription according to the manufacturer's protocol. For PCR, Ssofast™ EvaGreen® Supermix PCR reaction mixture (Bio-Rad, Hercules, Calif.) was used along with gene-specific primers. The PCR reaction was carried out on C1000 Thermal Cycler coupled with a CFX Real-time System (BioRad). Primer and cDNA concentrations were according to the manufacturer's recommendation. Primers for amplifying a sequence of the Bromo-1091 transcript were SEQ ID NO:75 and SEQ ID NO:76 (Table 12).

Transcript levels for each sample were normalized against a housekeeping gene with consistent expression levels under different culture conditions (gene 1T5001704) using primers 1704-F (SEQ ID NO:77) and 1704-R (SEQ ID NO:78) and relative expression levels were calculated using the ddCT method using CFX Manager software from BioRad.

TABLE 12

Primers used for qRT/PCR

| Gene | Primer | Sequence |
|---|---|---|
| Bromo-1091 | JLC-1091-RT-F | GAATAGGCGGTTCAGAATGTAGG (SEQ ID NO: 75) |
| Bromo-1091 | JLC-1091-RT-R | ATATTTTGTGGGCGTTGCTG (SEQ ID NO: 76) |
| Housekeeping gene T5001704 | JLC-RT-1704-F | GAGGAAGCGGAAGAGGATG (SEQ ID NO: 77) |
| Housekeeping gene T5001704 | JLC-RT-1704-R | TCAAGTACCAGTTCCACACG (SEQ ID NO: 78) |

Figure 6B:
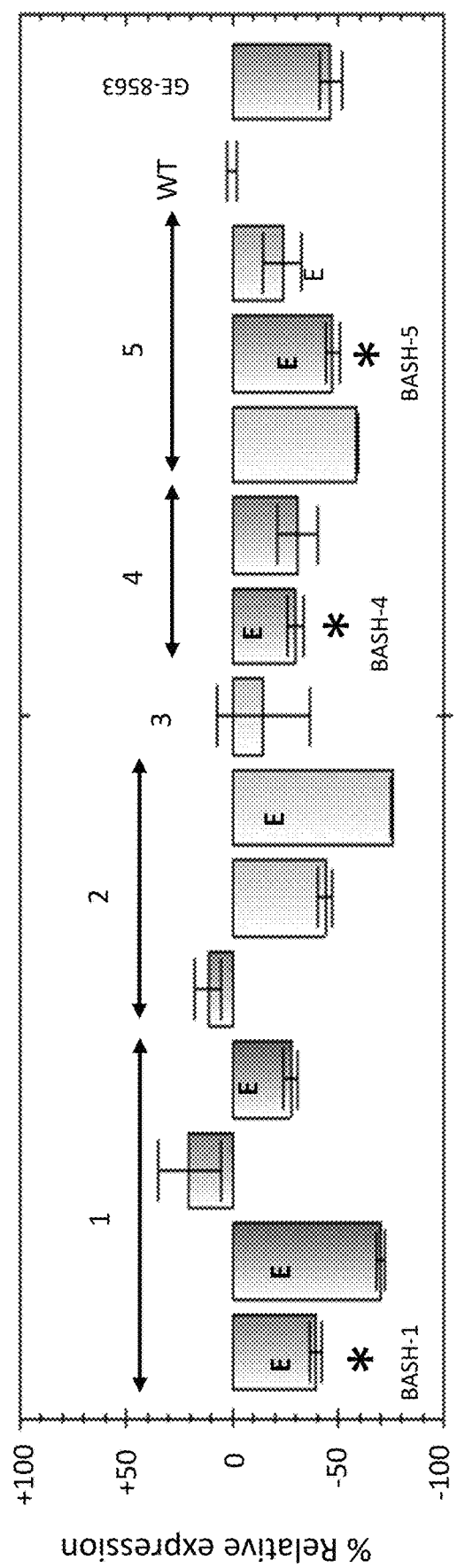

FIG. 6B shows that several of the strains had reduced levels of Bromo-1091 transcript. Of these, strains GE-13027 (Bromo-1091 BASH-1), GE-13030 (Bromo BASH-4), and GE- GE-13032 (Bromo-1091 BASH-5), targeting the 5' end of the Bromo-1091 gene, expressed the Bromo-1091 gene at about 35%, 20%, and 50% of the wild type level of the gene, respectively.

Example 7. Knockdown Constructs in Batch Assay

The Bromo-1091 knockdown "basher" strains GE-13027, GE-13030, and GE-13032 that demonstrated attenuated expression of the Bromo-1091 gene (see FIGS. 6A and 6B) were tested in the batch productivity assay described in Example 4 by scaling up the cultures in culture medium PM124 (which includes both $NH_4$ and $NO_3$ as nitrogen sources) and by carrying out the assay in PM123 culture medium that includes nitrate as the sole nitrogen source. In addition, the wild type *N. gaditana* strain WT-3730 and the Bromo-1091 knockout mutant GE-8563 were tested in the same assay.

FAME and TOC were analyzed as provided in Example 4. The results of these analyses are provided in Tables 13-16, with the values provided being the average of three cultures, and the standard deviations provided in parentheses.

the assay, but by day 7 of the assay was slightly behind wild type in lipid production. Table 14 shows that GE-13027, GE-13030, and GE-13032 did not decrease their biomass production as much as did knockout strain GE-8563 over the course of the assay. In fact, by day 7 of the assay, GE-13027 and GE-13030 were producing within 5% of the amount of biomass produced by wild type cells in the same assay, and strain GE-13032 produced only about 7% less biomass than wild type strain WT-3730. The amount of biomass produced by the knockdown strains was significantly greater than the biomass produced by knockout strain GE-8563 on each day of the assay, in other words, the knockdown strains had only a slight deficit in biomass production with respect to the wild

TABLE 13

FAME productivity of Bromo-1091 Knockdown Strains Compared to Wild Type in Batch Assay with $NO_3$-only Culture Medium (mg/L culture)

| DAY | WT | BASH-1 (GE-13027) | % incr | BASH-4 (GE-13030) | % incr | BASH-5 (GE-13032) | % incr | Bromo-1091 KO (GE-8563) | % diff |
|---|---|---|---|---|---|---|---|---|---|
| 3 | 106.56 (3.89) | 153.39 (4.23) | 43.95 | 127.13 (0.09) | 19.30 | 162.19 (1.12) | 52.21 | 139.66 (5.56) | 31.06 |
| 5 | 154.22 (4.72) | 208.36 (12.21) | 35.11 | 185.68 (2.83) | 20.40 | 225.23 (6.14) | 46.04 | 167.71 (4.58) | 8.75 |
| 7 | 210.97 (15.43) | 264.03 (5.65) | 25.15 | 248.60 (0.53) | 17.84 | 290.4 (16.58) | 37.65 | 199.08 (20.60) | −5.64 |

TABLE 14

TOC productivity of Bromo-1091 Knockdown Strains Compared to Wild Type in Batch Assay with $NO_3$-only Culture Medium (mg/L culture)

| DAY | WT | BASH-1 (GE-13027) | % diff | BASH-4 (GE-13030) | % diff | BASH-5 (GE-13032) | % diff | Bromo-1091 KO (GE-8563) | % diff |
|---|---|---|---|---|---|---|---|---|---|
| 3 | 455.45 (13.93) | 502.4 (5.09) | 10.31 | 441.75 (12.23) | −3.0 | 461.7 (1.70) | 1.37 | 292.1 | −35.87 |
| 5 | 678.75 (22.98) | 663.55 (22.98) | −2.24 | 651.3 (6.93) | −4.0 | 646.8 (10.32) | −4.7 | 417.2 | −38.53 |
| 7 | 811.75 (52.54) | 772.5 (18.67) | −4.84 | 773.6 (0.99) | −4.7 | 756.6 (8.06) | −6.8 | 593.1 | −26.94 |

TABLE 15

FAME/TOC ratios of Bromo-1091 Knockdown Strains Compared to Wild Type in Batch Assay with $NO_3$-only Culture Medium

| DAY | | BASH-1 (GE-13027) | % incr | BASH-4 (GE-13030) | % incr | BASH-5 (GE-13032) | % incr | Bromo-1091 KO (GE-8563) | % incr |
|---|---|---|---|---|---|---|---|---|---|
| 3 | 0.23 (0.0014) | 0.31 (0.0115) | 34.78 | 0.29 (0.0082) | 26.09 | 0.35 (0.0011) | 52.17 | 0.46 (0.0139) | 100 |
| 5 | 0.23 (0.0007) | 0.31 (0.0075) | 34.78 | 0.29 (0.0013) | 26.09 | 0.35 (0.0039) | 52.17 | 0.41 (0.0016) | 78.26 |
| 7 | 0.26 (0.0022) | 0.34 (0.001) | 30.77 | 0.32 (0.0003) | 23.08 | 0.38 (0.0178) | 46.15 | 0.34 (0.0267) | 30.77 |

Table 13 shows that all of the gene attenuation knockdown strains that had reduced expression of the Bromo-1091 gene, GE-13027, GE-13030, and GE-13032, produced more lipid than the wild type strain as measured on days 3, 5, and 7 of the assay. These knockdown strains were more consistent lipid producers than knockout strain GE-8563, which produced at least 30% more lipid than wild type by day 3 of the assay, but by day 7 of the assay was slightly behind wild type strain, as compared with an about 25%-40% reduction in biomass production by the knockout strain GE-8563 in relation to the wild type biomass production level over the course of the assay. Table 15 provides the FAME/TOC ratios of the mutant and wild type cultures on days 3, 5, and 7 of the batch assay. With respect to the wild type strain, knockout strain GE-8563 on day 3 had a FAME/TOC ratio that was double that of the wild type (i.e., 100% higher) but this ratio decreased over the course of the assay to about 30% greater than the wild type FAME/TOC ratio. The knockdown strains began with more modest increases in the FAME/TOC ratio than was seen for GE-8563, but the increase over wild type was more consistent over the course of the assay, ranging from 30-35% for GE-13027, from 23-26% for GE13030, and from 45-53% for GE-13032.

Figure 4B:
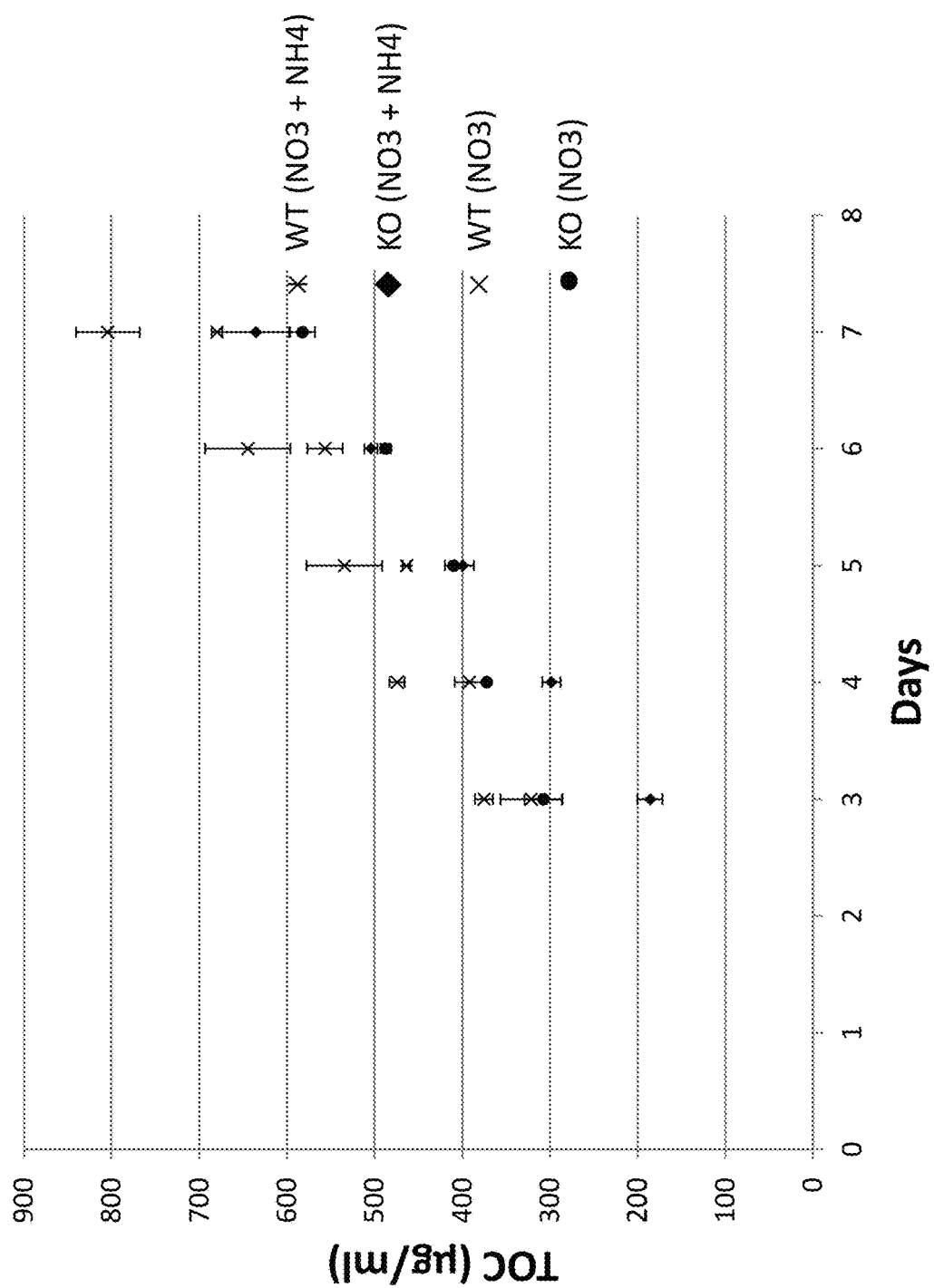
Figure 7A:
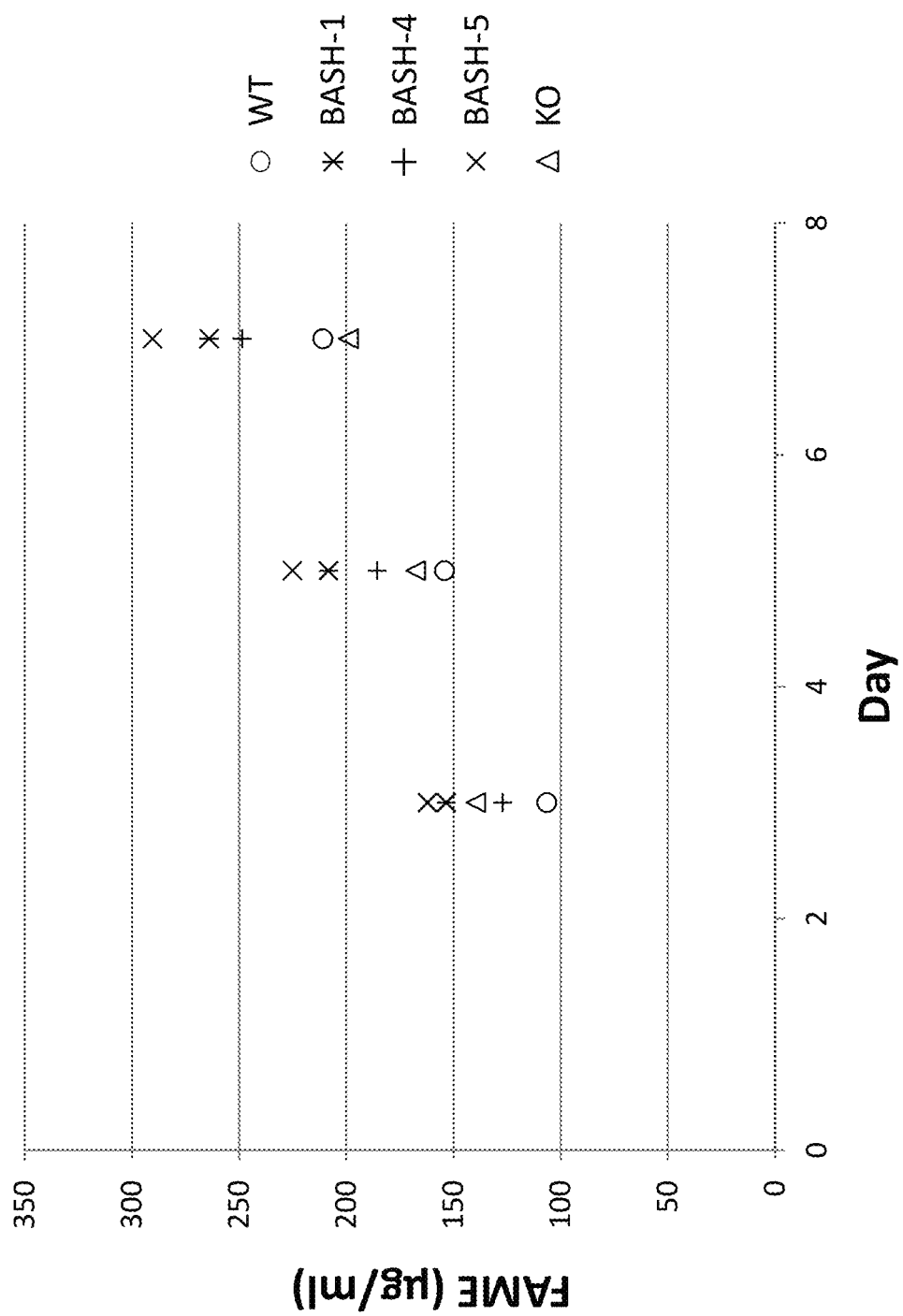
FIG. 7A) is a graph depicting FAME productivity of wild-type and Bromo-1091 knockdown *N. gaditana* cells cultured in batch mode in nitrate-only medium.
Figure 7B:
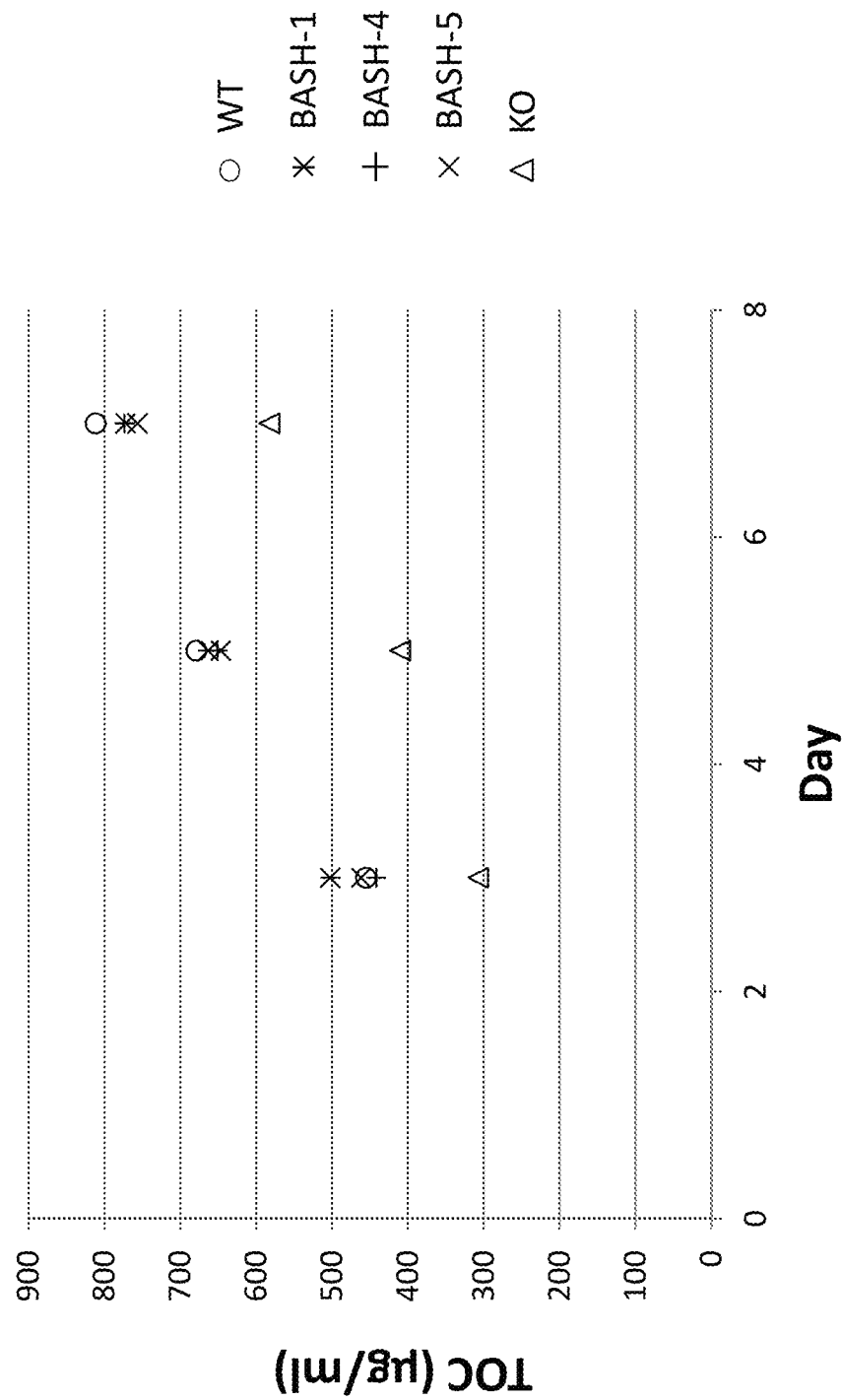
FIG. 7B) is a graph depicting TOC values for the odd days of the batch screen in nitrate-only medium (days 3, 5, and 7)
Figure 7C:
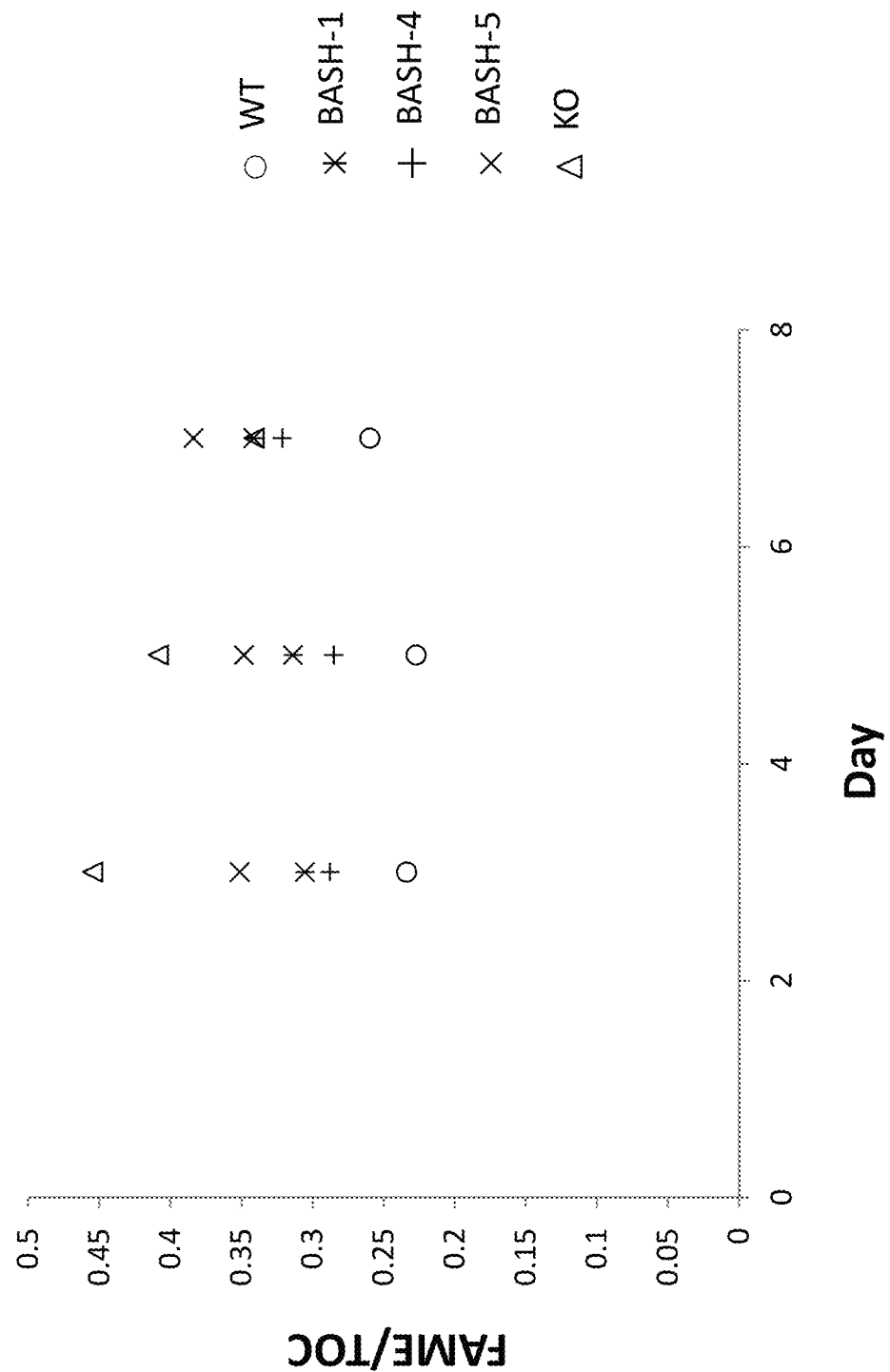
FIG. 7C) is a graph providing FAME/TOC ratios of the cultures calculated on days 3, 5, and 7. Symbols used in graphs: open circles represent wild type WT-3730, an asterisk represents "BASH-1" knockdown mutant GE-13027; a plus sign represents "BASH-4" knockdown mutant GE-13130; and X's represent "BASH-5" knockdown mutant GE-13132; open triangles represent Bromo-1091 knockout mutant GE-8563.

The results are depicted graphically in FIGS. 7A-C. FIG. 7A shows that all Bromo-1091 gene knockdown attenuation mutants (GE-13027 (bisected X), GE-13030 (plus sign), and GE-13032 (X)), produced FAME in amounts greater than wild type (circles) when cultured with nitrate as the sole nitrogen source, with the increase in lipid production being greatest at the end of the assay. This is in contrast to the knockout mutant (GE-8563, triangles) cultured in nitrate-only medium, in which an increase in FAME with respect to wild type on day 3 disappeared by the end of the assay (day 7). Thus, in overall FAME production, the Bromo-1091 knockdown mutants were a significant improvement over the knockout mutant. FIG. 7B provides even more surprising results—unlike the knockdown strain (triangles), in batch culture with nitrate as the sole nitrogen source the knockdown mutants (GE-13027 (bisected X), GE-13030 (plus sign), and GE-13032 (X)) were close to wild type levels of biomass production throughout the culture assay. The knockdown mutant (triangles), however, as also seen in FIG. 4B, had consistently significantly reduced TOC accumulation when compared with the wild type strain (circles).

Figure 4C:
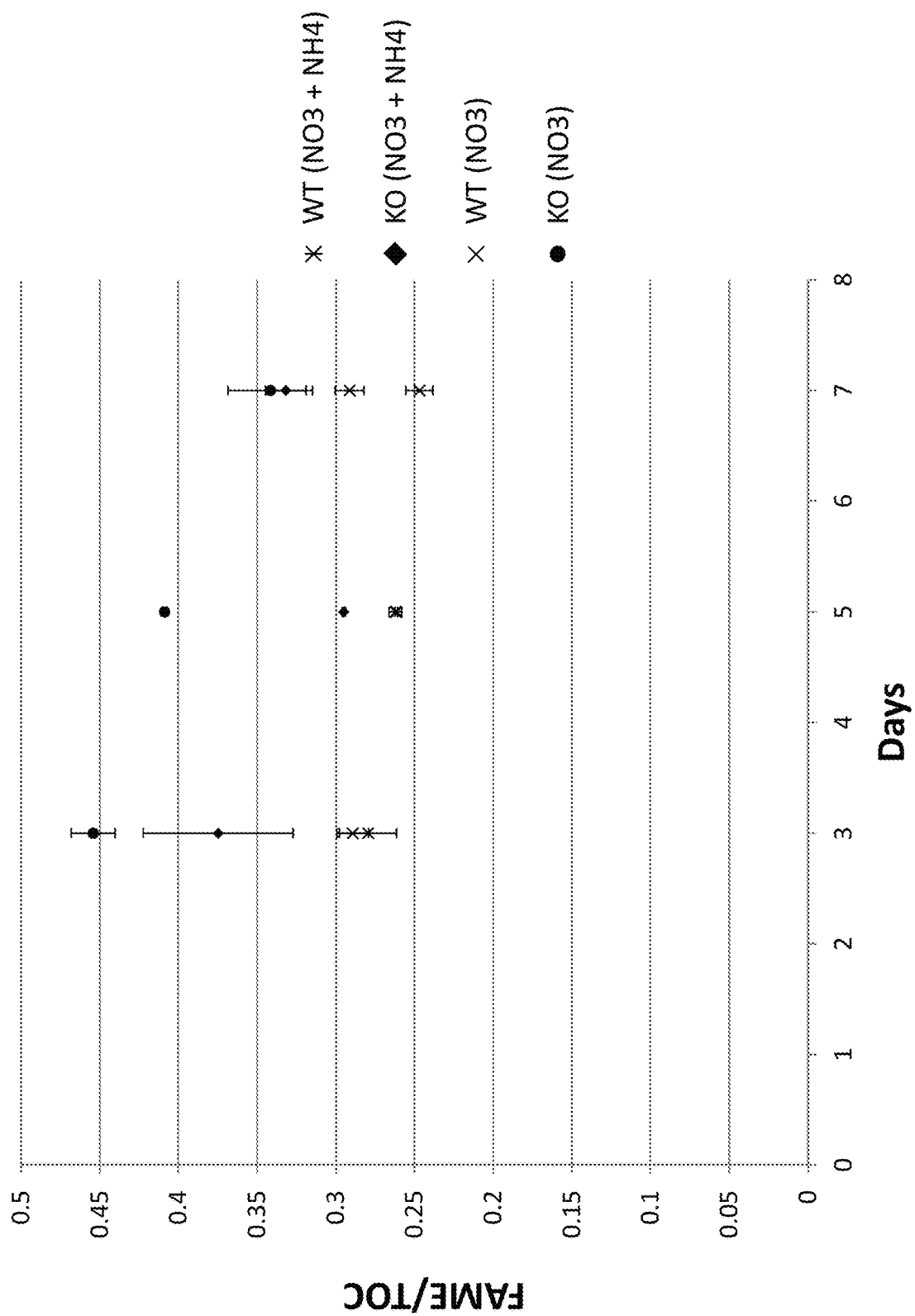

FIG. 7C shows the increased FAME/TOC ratio of the knockout strain with respect to the wild type strain when both strains are batch-cultured in nitrate-only medium (as also seen in FIG. 4C). The Figure also shows that FAME/TOC ratios of the knockdown mutants are enhanced with respect to the wild type strain and for the most part intermediate between wild type and knockout strain ratios.

Example 8. Bromo-1091 Knockdown Mutants in the Semi-Continuous Productivity Assay Bromo-1091 attenuation (BASH) strains GE-13127, GE-13130, and GE-13132 were then assayed in the semi-continuous productivity assay described in Example 5, in which the assay medium, PM074, included nitrate as the sole nitrogen source and the knockdown strains were pre-cultured in PM124 medium that included 5 mM ammonium in addition to 8.8 mM nitrate.

The starter cultures were used to inoculate 225 cm$^2$ rectangular tissue culture flasks, each of which contained a final total volume of 550 ml of culture after inoculation. The cultures were inoculated so that each 550 ml culture had an initial $OD_{730}$ of 0.9. A typical inoculum volume was approximately 200 ml of scale-up culture that was added to approximately 350 ml of assay culture medium, which was PM074 (nitrate-only medium). Cultures were diluted daily at mid-day, when the light intensity was at its peak, by removing 30% of the volume (165 mls) and replacing it with the same volume of the assay medium (PM074) plus an additional 10 ml of deionized water to make up for evaporation (included in the make-up medium). Thus, assay cultures inoculated from scale-up cultures that included 5 mM ammonium in the culture medium (PM124 medium) started out with a significant amount of ammonium (e.g., less than 2 mM ammonium) that was progressively diluted out further during the course of the assay. After the cultures reached equilibrium (the growth rate of the cultures equaled the dilution rate of 30% as determined by cell counts and optical density) the semi-continuous assays were run for 10 days. Daily lipid and biomass productivities were only calculated for cultures that had reached steady state (where the increase in growth was equal to the dilution factor for the assay). Three cultures were run for each strain.

Figure 8B:
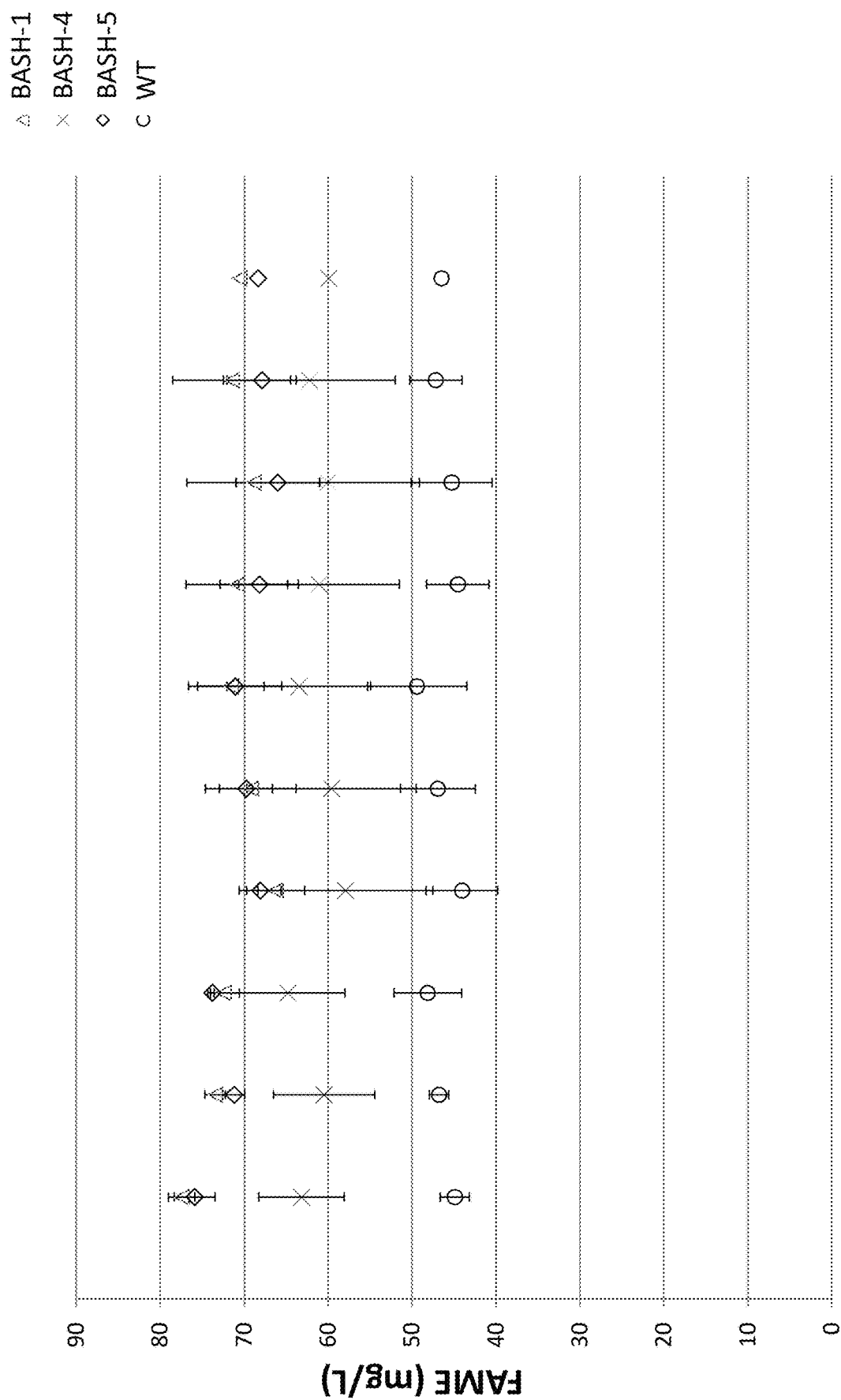

The results of the assay are provided in FIGS. 8A-F. The table provided in FIG. 8A shows the daily FAME productivities of the semi-continuous cultures over a ten day period in which they were diluted by 30% each day, with each value being the average of three cultures (standard deviations are provided in parentheses). Each of the Bromo-1091 knockdown mutants has significantly higher FAME productivity than the wild type strain, with GE-13127 and GE-13132 each demonstrating at least 50% greater FAME productivity than wild type over the course of the ten day assay in which nitrate was the sole nitrogen source for the cells. The graph in FIG. 8B shows clearly the largely consistent production of FAME by the knockdown mutants at levels considerably higher than wild type.

Figure 8D:
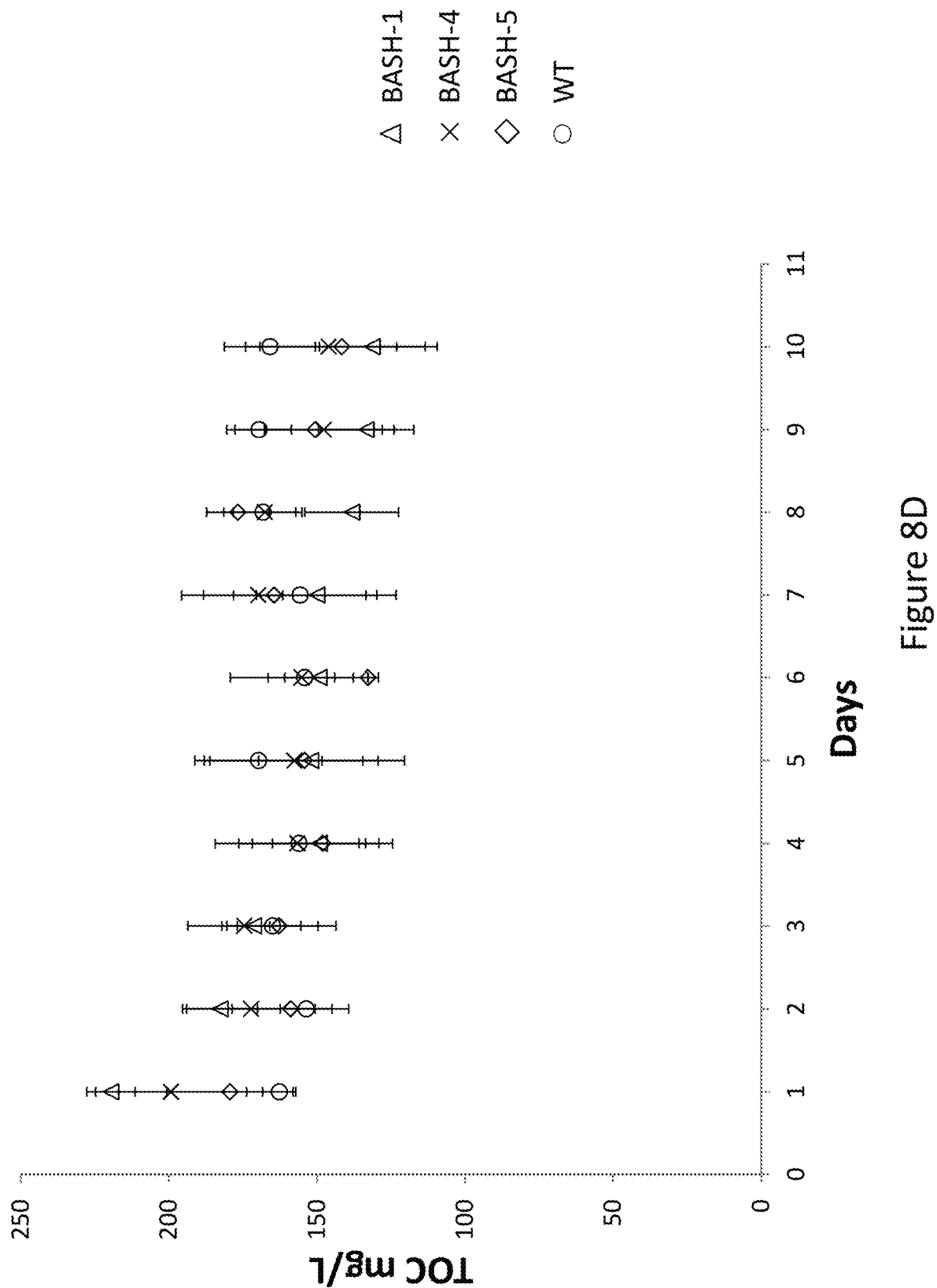

FIG. 8C provides the daily biomass productivity, measured as TOC of the semi-continuous cultures of the same assay depicted in FIGS. 8A and 8B, with each value being the average of three cultures (standard deviations are provided in parentheses). Astonishingly, although the mutants produced more lipid than wild type cells every day of the assay (FIGS. 8A and 8B), they did not produce significantly less biomass (measured as TOC). Thus, unlike classical lipid induction that occurs when cells are starved for nitrogen, the cultures experience no loss of biomass as compared to wild type cells while producing much more lipid than wild type. FIG. 8D shows this clearly: while the cultures show minor variations in biomass production from day to day, on average the wild type (circles) does not significantly outperform the Bromo-1091 attenuation mutants.

Figure 8F:
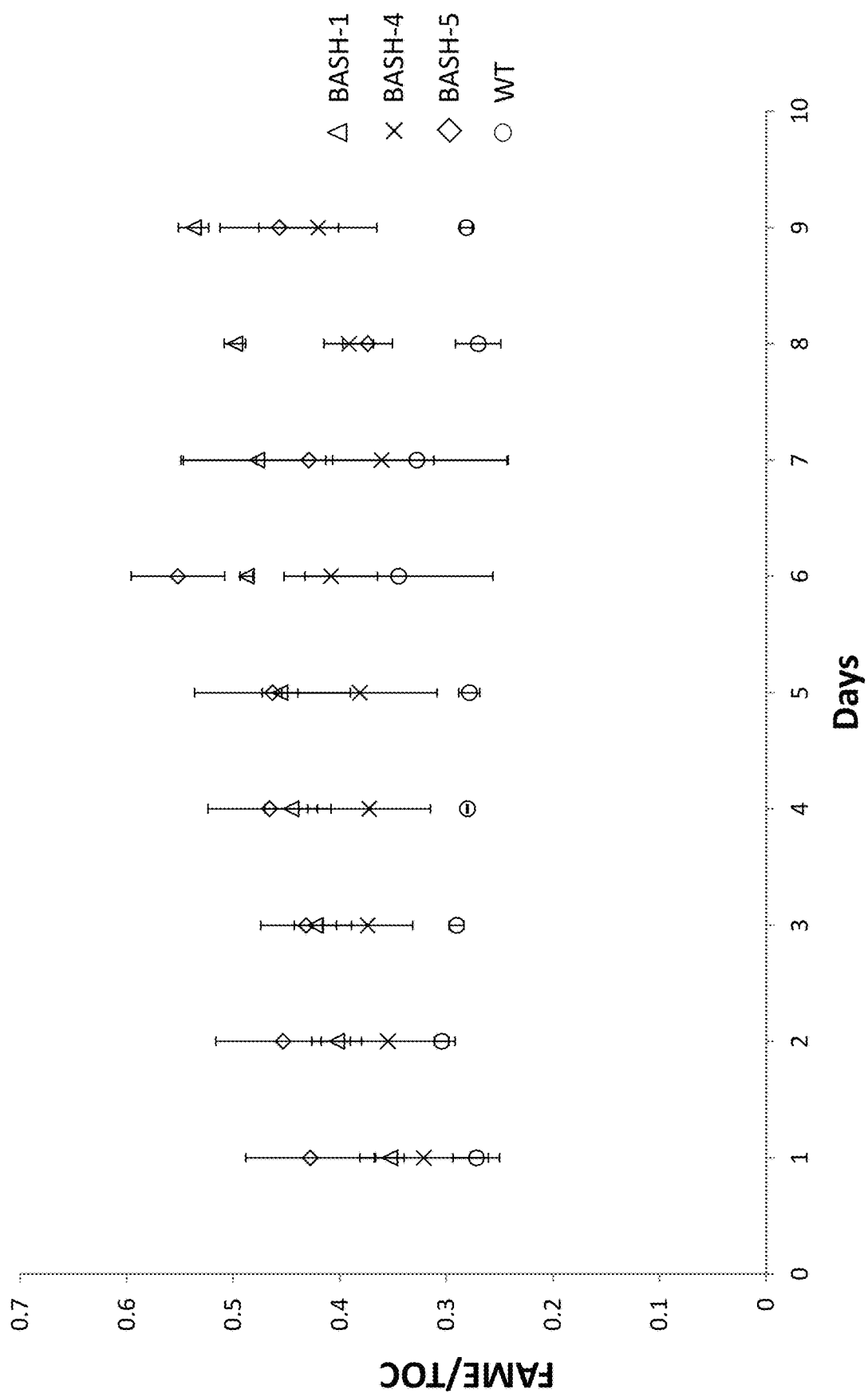

FIG. 8E provides the daily FAME/TOC ratios of the cultures. Over the course of the entire culture period, the wild type cultures had an average FAME/TOC ratio of 0.29, whereas the cultures of strains having attenuated expression of the Bromo-1091 gene had average FAME/TOC ratios of 0.39 (strain GE-13030), 0.42 (strain GE-13032), and 0.50 (strain GE-13127) over the culture period. Strain GE-13030 had an average FAME/TOC value that was 33% higher than that of wild type cultures, strain GE-13132 had an average FAME/TOC value that was 43% higher than that of wild type cultures, and strain GE-13027 had an average FAME/TOC value that was 72% higher than that of wild type cultures, over the course of the ten day assay. The graph in FIG. 8F shows clearly the largely consistent FAME/TOC ratio of the knockdown mutants at ratios considerably higher than wild type.

Example 9. Proximate Analysis of Bromo-1091 Knockdown Mutants

To determine the overall biomass composition of the Bromo-1091 attenuation mutants, quantitative analysis of samples from cultures of Example 8 was performed to determine the lipid, protein, and carbohydrate content of the cells in semi-continuous culture.

FAME lipids were analyzed as described in Example 4 for strains cultured in the semi-continuous assay of Example 8, with the results provided in FIG. 8A.

To determine protein content, isolated biomass samples were hydrolyzed and the amino acids were derivatized to propoxycarbonyl propyl esters (AAPE's), analyzed via GC/MS, and quantitated against an internal standard, as detailed below.

0.5 ml aliquots of wild type *N. gaditana* (WT-3730) and Bromo-1091 attenuation (BASH) strains GE-13127 ("Bromo Bash-1") and GE-13132 ("Bromo Bash-5") from the cultures of Example 8 (taken from the same dilution samples that were used to determine FAME content) were centrifuged and the pellets were washed twice with phosphate buffered saline (PBS). The cells were finally resuspended to a final volume of 0.5 ml (the starting volume) and transferred to a 4 ml glass vial. To the culture sample, 800 µl of 6M HCl with TGA was added (400 µl of thioglycolic acid (TGA) was added to 19.6 ml of 6M HCl just before use). Ten µl of beta mercaptoethanol was then added to the vial, followed by 200 µl of 20 mM norvaline, used as an internal standard. Each vial was blanketed with N2 for 10 seconds, after which the vials were vortexed for 1 min at 2500 rpm to homogenize the samples. The vials were then placed in a 110° C. oven for 22 hours.

At the end of the hydrolysis incubation, the vials were vortexed for 10 min at 2500 rpm, and then centrifuged up to 1000 rpm after which the centrifuge was stopped. A 50 aliquot was removed from each vial and dried by placing in an acid safe EZ-2 Genevac which was run on the HCl method for at least 3 hours prior to derivatization.

For derivativization, 250 µl of milli-Q H$_2$O was added to the dried acid hydrolysates, followed by 10 µl of antioxidant mix and then 120 µl of 0.5M NaOH. The antioxidant mix was made by adding 0.25 ml of n-propanol, 50 µl of thiodiglycol, and a few granules of phenol to 2.20 ml of Milli-Q H$_2$O, and vortexing. 80 µl of the catalyst, a 4:1 mix of pyridine and n-propanol was then added, and the vial was capped and vortexed at 2500 rpm for 1 min After a 1 min incubation, the vial was again vortexed at 2500 rpm for 1 min 500 µl of a 4:1 mixture of isooctane and chloroform was then added to the vial which was again capped and vortexed at 2500 rpm for 1 min. The rack of sample vials was then covered with another sample rack and shaken 20 times to ensure emulsion of the samples. The samples were then centrifuged until the centrifuge reached 1000 rpm and then the centrifuge was stopped. 200 µl of the organic layer was removed into a new GC vial with a glass insert and analyzed by GC/MS.

The samples were analyzed by GC/MS using a ZB-AAA 10×0.25 mm ID Amino Acid Analysis GC column and quantitated using the internal norvaline standard. The needle Wash 1 solvent was acetone and the needle Wash 2 solvent was isooctane/chloroform (80/20) with a program of 110° C., hold 0 min, 30° C./min to 320° C., hold 0.5 min, using a 4 µl injection at 15:1 split, 250° C. at 1.1 ml/min with a 300° C. transfer line.

The GC-MS data was multiplied by 0.0005 L to obtain µmol values, and multiplied by the molecular weight of the amino acid. The value was divided by 5 to correct for the volume to obtain µg/ml of each amino acid. Asparagine is converted to aspartic acid during acid hydrolysis, thus asparagine plus aspartic acid are determined as aspartic acid in these methods. Tryptophan is not measured by these methods but does not make up a significant fraction of the amino acids in *Nannochloropsis* proteins.

For total carbohydrate quantitation, biomass was hydrolyzed for one hour in 6N hydrochloric acid to convert polysaccharides to monosaccharides. The resulting monosaccharides were converted to trimethylsilyl ethers using MSTFA N-methyl-N-trinethylsilyltrifluoroacetamide with 1% trimethylchlorosilane, and the ethers were resolved and quantitated using GC-MS analysis. In this analysis, we are able to quantitate arabinose, rhamnose, xylose, mannose, galactose, mannitol, and glucose, which encompass the majority of the sugars present in *Nannochloropsis* sp.

For acid hydrolysis of culture samples, 500 µl of Milli-Q H$_2$O was added to 500 µl culture samples in 4 ml vials, or, where the culture sample was more concentrated (higher TOC), 800 µl of Milli-Q H$_2$O was added to 200 µl of culture sample. 20 µl of 2.5 mg/ml ribitol and U-$^{13}$C-glucose as an internal standard was added to the 1 ml diluted culture samples in 4 ml vials. 1 ml of concentrated HCl was then added to each of the vials, the vials were capped and placed in a 105° C. dry bath for 1 hour. The samples were then allowed to cool to room temperature, and 100 µl was transferred to a glass insert inside a 1.5 ml microcentrifuge tube.

For derivatization, the microfuge tubes that included glass inserts containing the samples were place in an acid safe EZ-2 Genevac which was run on the HCl method for at least 3 hours. After drying, 100 µl of the derivatization reagent, which consisted of 800 µl of dry pyridine added to 1 ml of freshly opened MFSTA-1% TMCS, was added to each sample. The samples were incubated for 1 hour at 40° C. while mixing at 1000 rpm in an Eppendorf Thermomixer. Following incubation, the samples were directly analyzed by GC/MS.

The samples were analyzed by GC/MS using a DB5-MS 30 m×250 µm×25 µm GC column and quantitated using the internal U-$^{13}$C-glucose standard. The needle wash solvent was pyridine with a program of 1 min equilibration, 170° C. for 8 min, 10° C./min to 210° C. for 0 min, then 50° C./min to 325° C. for 2 min (total run time 16.3 min).

Figure 9:
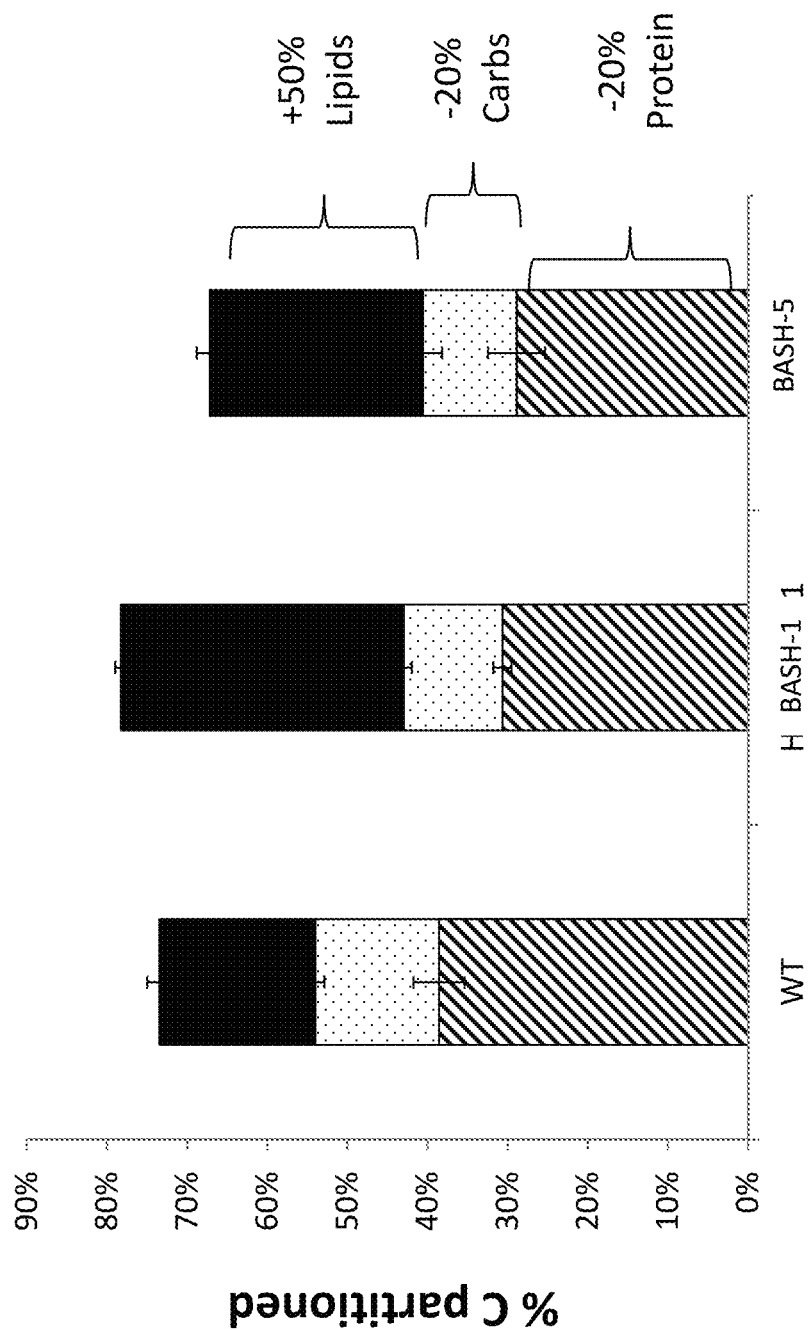
FIG. 9 is a bar graph of the biomolecular composition of Bromo knockdown mutants as compared to wild type cells.

FIG. 9 shows the results of this analysis on the wild type *N. gaditana* strain as well as the Bromo-1091 gene attenuation knockdown mutants GE-13127 and GE-13132. As expected from the elevated FAME/TOC ratios of the "basher" mutants with respect to wild type (see, for example, Table 15 and FIG. 9E), the knockdown mutants had an increased percentage of their total organic carbon as lipid with respect to wild type. Interestingly, the mutants, which as demonstrated in Example 8 had essentially the same total organic carbon accumulation as wild type in the semi-continuous assay, were reduced by about the same extent in protein and carbohydrate content, demonstrating an approximately 20% reduction in both protein and carbohydrate with respect to wild type levels.

Example 10. Chlorophyll Content of Bromo-1091 Knockdown Mutants

Interestingly, Bromo-1091 gene attenuation mutant cultures were noticeably paler than corresponding wild type cultures. Chlorophyll a content (chlorophyll a is the only chlorophyll present in *Nannochloropsis*) of the GE-13127 and GE-13132 mutants was determined along with that of wild type cells cultured under the same conditions (the semi-continuous productivity cultures of Example 8) by extracting cells with DMSO/acetone, and analyzing the extraction supernatants by spectrophotometry.

Briefly, 200-250 µl aliquots of culture were pipetted into 2.0 ml microfuge tubes and pelleted using a table top microcentrifuge at 12,000 rpm for 3 minutes. The supernatants were immediately aspirated off of the pellets, and each pellet was resuspended in 1 ml of 1:1 DMSO:acetone. Samples were then vortexed for 2-5 min, and the cell debris was pelleted using the table top microcentrifuge at 12,000 rpm for 3 min at room temperature. The resulting pellets were white.

Cuvettes containing 1 ml 1:1 DMSO:acetone were blanked at 663 nm and 720 nm and the supernatants of the DMSO:acetone extracted cells were read (using at least 750 of sample supernatant).

To calculated the chlorophyll a present in each sample, the absorption at 720 nm was subtracted from the absorption at 663 nm. The absorption value was multiplied by the dilution factor (e.g., 5 for a 200 µl aliquot of cell culture) and extinction coefficient of 20.15 to determine the ug/ml concentration of chlorophyll a or by 18.01 to determine the µmol/ml concentration.

Figure 10:
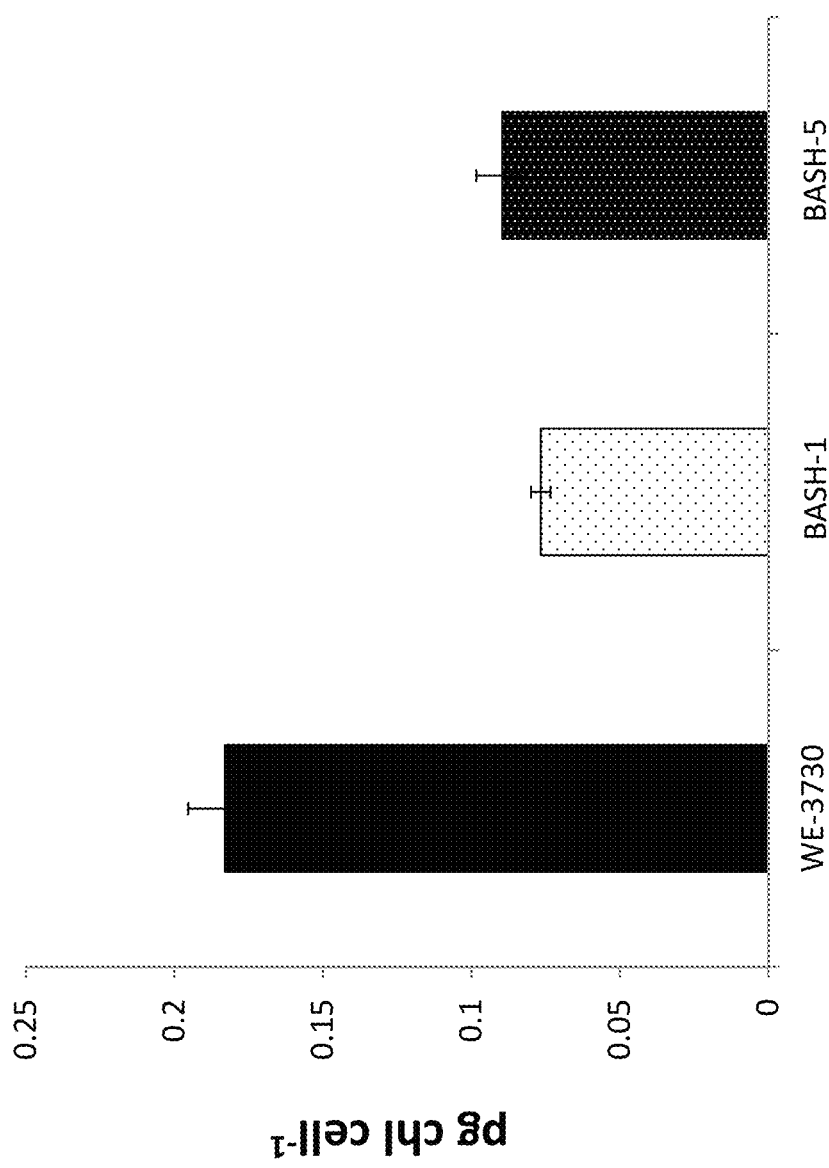
FIG. 10 is a bar chart showing chlorophyll content of two Bromo-1091 knockdown strains, GE-13027 (BASH-1) and GE-13132 (BASH-5) compared to wild type strain WT-3730 (WT).

The results of the analysis are provided in FIG. 10, where it can be seen that the GE-13027 and GE-13032 Bromo-1091 gene attenuation mutants had an approximately 55% reduction in total chlorophyll per cell.

TABLE 16

Chlorophyll content of Bromo-1091 Knockdown Strains Compared to Wild Type strain in Semi-continuous Assay with $NO_3$-only Culture Medium

| Sample | avg pg chl/cell | % difference |
|---|---|---|
| WE-3730 | 0.183 (0.012) | 0% |
| HAT BASH-1 GE-13027 | 0.077 (0.003) | −58% |
| HAT BASH-4 GE-13030 | 0.105 (0.003) | −43% |
| HAT BASH-5 GE-13032 | 0.090 (0.009) | −51% |

Example 11. Transcriptomic Analysis of LION Mutants

To determine what genes were regulated by the Bromo-1091 polypeptide, as well as the ZnCys regulator disclosed in commonly-owned and co-pending U.S. patent application Ser. No. 15/210,845 filed Jul. 14, 2016, a transcriptomic analysis was performed of GE-13032, the Bromo-1091 5' BASH-5 mutant, the ZnCys-2845 knockout mutant GE-8564 (US Provisional application filed Jul. 14, 2015), and a nitrate reductase (NR) loss-of-function (knockout) mutant. GE-13032 and GE-8564 are referred to herein as Lipid Induced on Nitrate or "LION" mutants. GE-8564 is given the designation LION1, referring to mutants relating to attenuation, disruption, or mutation in the ZnCys-2845 gene disclosed in U.S. patent application Ser. No. 15/210, 845 and orthologs of other species, and GE-13032 is given the designation LION2, referring to mutants relating to attenuation, disruption, or mutantion in the Bromo gene disclosed herein and orthologs of other species. The GE-13032 and GE-8564 strains and appropriate parental controls were grown in batch assay using PM074 medium containing only nitrate as the nitrogen source. Samples were harvested during the $5^{th}$ day of the 7 day assay and RNA was extracted and sequenced using the NextSeq platform available in-house. Pairwise correlation, principal component and replicate clustering analyses of total reads obtained from the NextSeq (quantified as fragments per kilobase of exon per million reads mapped, FPKM) indicated that the biological replicates clustered together, thus validating the experimental setup. As expected, the parental controls (Cas9 Editor strains and wild type) displayed one transcriptional pattern and the mutants displayed a distinct transcriptional pattern. Interestingly, the ZnCys-2845 knockout mutant, the Bromo-1091 5' bash mutant, and the nitrate reductase mutant each showed a distinct pattern.

Figures 11A, 11B:
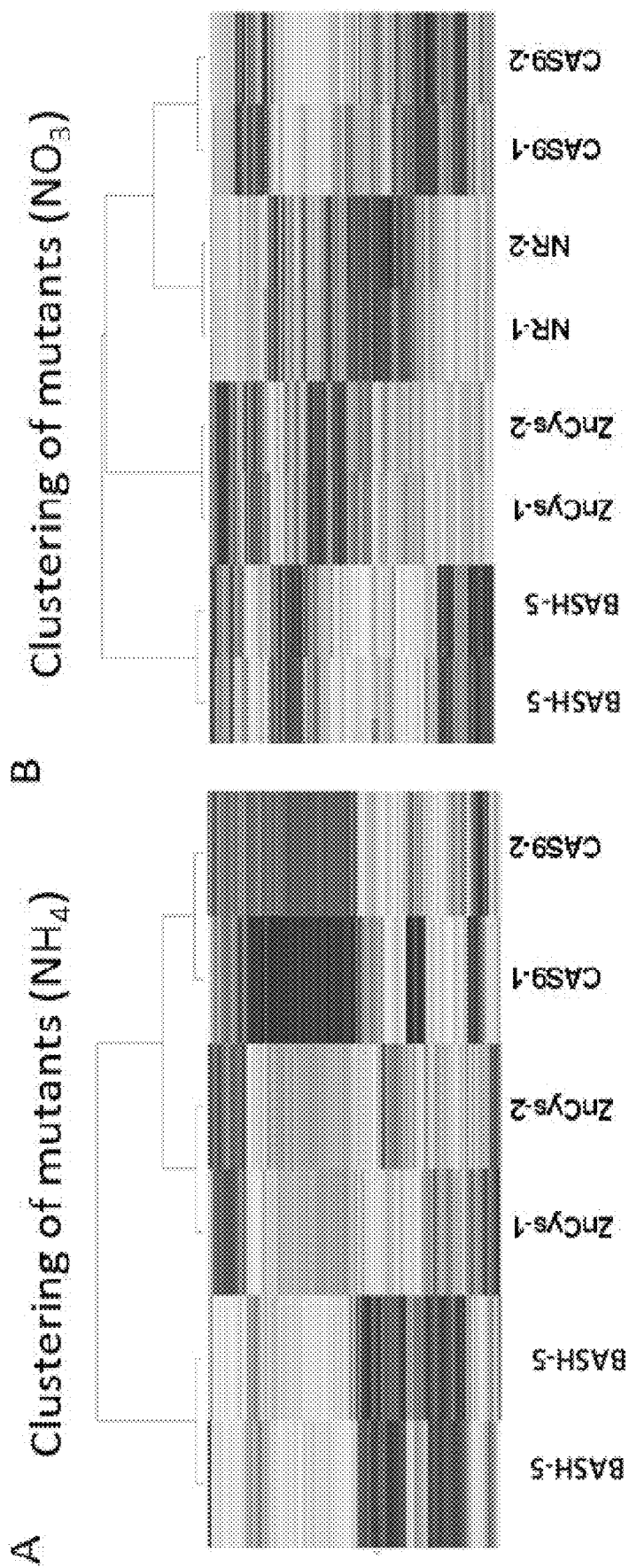
FIGS. 11A-11B depicts a transcriptomics "heat map" in which the darkness of the bands, each of which represents a gene, is correlated with the level of expression of the gene (assessed by FPKM value).

FIGS. 11A-11B provides a "heat map" diagram of transcriptional profiling of the ZnCys-2845 knockout, the Bromo-1091 5' bash promoter disruption mutant, and nitrate reductase loss-of-function mutants (ZnCys-KO, Bromo-5' Bash, and NR-KO, respectively) grown in batch assay on nitrate-based medium. Genes were hierarchically clustered based on their abundance (measured as FPKM) using Pearson's correlation. The color intensity corresponds to the FPKM value, with darker bands representing higher values and lighter bands representing lower values, respectively. Biological replicates clustered together for each mutant line, thus validating the experimental setup. As expected, the parental controls (Cas9 enabled strains) grouped into a "wild-type" Glade and the mutants formed distinct separate clades. Interestingly, within the mutant Glade, both the ZnCys-2845 knockout and the Bromo-1091 mutants demonstrated a different gene expression pattern from the nitrate reductase mutant, and differed significantly from one another in their gene expression patterns. The Bromo-1091 knockout mutant was observed to upregulate 1895 genes at least 2-fold with respect to the Cas9 parental strain while 1025 genes were observed to be down-regulated at least 2-fold with respect to the Cas9 parental strain (FDR<0.01).

What is claimed is:

1. A mutant heterokont microorganism having attenuated expression of a gene encoding a polypeptide that includes a TAZ zinc finger domain and a Bromo domain, wherein the mutant heterokont microorganism produces at least 20% more lipid than a control heterokont microorganism and at least 45% of the amount of biomass accumulated by the control heterokont microorganism when the mutant heterokont microorganism and control heterokont microorganism are cultured under identical conditions under which the control is heterokont microorganism accumulating biomass, wherein the polypeptide has at least 80% identity to an amino acid sequence selected from the group consisting of SEQ ID NO:2, SEQ ID NO:4, SEQ ID NO:6, SEQ ID NO:8, and SEQ ID NO:12, wherein the control microorganism is the same as the mutant heterokont microorganism with the proviso that expression the gene encoding a polypeptide that includes a TAZ zinc finger domain and a Bromo domain is not attenuated.

2. A mutant heterokont microorganism according to claim 1, wherein the control heterokont microorganism is a wild type heterokont microorganism.

3. A mutant heterokont microorganism according to claim 1, wherein the polypeptide has at least 80% identity to an amino acid sequence of SEQ ID NO:2.

4. A mutant heterokont microorganism according to claim 3, wherein the mutant heterokont microorganism is *Nannochloropsis*.

5. A mutant heterokont microorganism according to claim 1, wherein the mutant heterokont microorganism produces at least 30% more lipid than the control heterokont microorganism and at least 80% of the amount of biomass accumulated by the control heterokont microorganism when the mutant heterokont microorganism and control heterokont microorganism are cultured under identical conditions under which the control heterokont microorganism is accumulating biomass.

6. A mutant heterokont microorganism according to claim 1, wherein the mutant heterokont microorganism is present in a culture medium that is nutrient replete with respect to the control heterokont microorganism.

7. A mutant heterokont microorganism according to claim 6, wherein the culture medium comprises less than 2 mM ammonium.

8. A mutant heterokont microorganism according to claim 6, wherein the culture medium comprises nitrate.

9. A mutant heterokont microorganism according to claim 8, wherein the concentration of nitrate in the culture medium is at least 2 mM.

10. A mutant heterokont microorganism according to claim 1, wherein the mutant heterokont microorganism has a knockout mutation in the gene encoding a polypeptide that includes a TAZ zinc finger domain and a Bromo domain.

11. A mutant heterokont microorganism according to claim 1, wherein the mutant heterokont microorganism has a knockdown mutation in the gene encoding a polypeptide that includes a TAZ zinc finger domain and a Bromo domain.

12. A mutant heterokont microorganism according to claim 11, wherein the mutant heterokont microorganism comprises an RNAi construct, an antisense construct, or includes an insertional mutation in the gene encoding a polypeptide that includes a TAZ zinc finger domain and a Bromo domain.

13. A mutant heterokont microorganism according to claim 12, wherein the mutant heterokont microorganism includes a Cas/CRISPR-mediated insertion into the 5' or 3' end of the gene.

14. A mutant heterokont microorganism according to claim 1, wherein the attenuated expression of a gene encoding a polypeptide that includes a TAZ zinc finger domain and a Bromo domain is achieved using a nucleic acid molecule construct for expression of an antisense RNA, shRNA, or microRNA, comprising a nucleotide sequence complementary to at least fifteen nucleotides of a naturally-occurring gene encoding a polypeptide having an amino acid sequence with at least 80% identity to SEQ ID NO:2, SEQ ID NO:4, SEQ ID NO:6, SEQ ID NO:8, or SEQ ID NO:12.

15. A mutant heterokont microorganism according to claim 1, wherein the attenuated expression of a gene encoding a polypeptide that includes a TAZ zinc finger domain and a Bromo domain is achieved using a guide RNA of a CRISPR system, wherein the guide RNA includes a sequence complementary to a target sequence selected from the group consisting of SEQ ID NO:61, SEQ ID NO:68, SEQ ID NO:70, and SEQ ID NO:72.

16. A method of producing lipid, comprising culturing a microorganism according to claim 1 to produce lipid.

17. A method according to claim 16, further comprising isolating the lipid from the culture.

18. A method according to claim 16, wherein the culturing is under photoautotrophic conditions.

\* \* \* \* \*